United States Patent
Gammie et al.

(10) Patent No.: US 11,045,224 B2
(45) Date of Patent: Jun. 29, 2021

(54) APPARATUS AND METHOD FOR SEPTAL PUNCH

(71) Applicants: University of Maryland, Baltimore, Baltimore, MD (US); University of Maryland Medical System LLC, Linthicum, MD (US); Protaryx Medical Inc., Baltimore, MD (US)

(72) Inventors: James S. Gammie, Stevenson, MD (US); Philip J. Haarstad, Chanhassen, MN (US); David Blaeser, Brooklyn Park, MN (US); Ryan Bauer, Plymouth, MN (US); Stephen Roller, Rockville, MD (US); Rachael Quinn, Abingdon, MD (US); Chetan Pasrija, Baltimore, MD (US); Edwin Hlavka, Minneapolis, MN (US)

(73) Assignees: University of Maryland, Baltimore, Baltimore, MD (US); University of Maryland Medical System LLC, Linthicum, MD (US); Protaryx Medical Inc., Baltimore, MD (US)

( * ) Notice: Subject to any disclaimer, the term of this patent is extended or adjusted under 35 U.S.C. 154(b) by 0 days.

(21) Appl. No.: 16/858,015

(22) Filed: Apr. 24, 2020

(65) Prior Publication Data
US 2020/0246046 A1    Aug. 6, 2020

Related U.S. Application Data

(63) Continuation-in-part of application No. PCT/US2019/052714, filed on Sep. 24, 2019.
(Continued)

(51) Int. Cl.
*A61B 17/34* (2006.01)
*A61B 17/00* (2006.01)

(52) U.S. Cl.
CPC .......... *A61B 17/3478* (2013.01); *A61B 2017/00247* (2013.01); *A61B 2017/3486* (2013.01); *A61B 2017/3488* (2013.01)

(58) Field of Classification Search
CPC ........ A61B 17/3478; A61B 2017/3288; A61B 2017/00247; A61B 2017/3488;
(Continued)

(56) References Cited

U.S. PATENT DOCUMENTS

| 5,370,675 A | 12/1994 | Edwards et al. |
| 5,520,685 A | 5/1996 | Wojciechowicz |

(Continued)

FOREIGN PATENT DOCUMENTS

| WO | WO 2005/063321 | 7/2005 |
| WO | WO 2009/061848 | 5/2009 |

(Continued)

OTHER PUBLICATIONS

Invitation to Pay Additional Fees and Partial International Search Report for International Application No. PCT/US2019/052714, dated Dec. 5, 2019, 14 pages.
(Continued)

*Primary Examiner* — Sarah A Simpson
(74) *Attorney, Agent, or Firm* — Cooley LLP

(57) ABSTRACT

In some embodiments, a method includes a shaft having a side catheter guide attached thereto via a guide coupler into an inferior vena cava and a superior vena cava such that the guide coupler is disposed in a right atrium, and applying a distal force to a proximal portion of the side catheter guide such that a distal end of the side catheter guide deflects laterally about the guide coupler towards a septum. The method further includes extending a side catheter that is disposed within the side catheter guide distally from the side catheter guide towards and into contact with the septum. The
(Continued)

method further includes, with the side catheter in contact with the septum, extending a septum penetrator that is slidably disposed within the side catheter distally from the side catheter such that the septum penetrator pierces the septum.

6 Claims, 73 Drawing Sheets

Related U.S. Application Data

(60) Provisional application No. 62/735,410, filed on Sep. 24, 2018, provisional application No. 62/994,751, filed on Mar. 25, 2020.

(58) Field of Classification Search
CPC .. A61B 2017/3486; A61B 2017/22061; A61B 2017/00336
See application file for complete search history.

(56) References Cited

U.S. PATENT DOCUMENTS

| | | | |
|---|---|---|---|
| 6,314,962 B1 | 11/2001 | Vaska et al. | |
| 6,645,225 B1 | 11/2003 | Atkinson | |
| 7,112,197 B2 * | 9/2006 | Hartley | A61B 18/1492 600/485 |
| 7,553,625 B2 | 6/2009 | Hoon et al. | |
| 7,635,353 B2 | 12/2009 | Gurusamy et al. | |
| 7,976,551 B1 * | 7/2011 | Gutfinger | A61B 5/0215 606/129 |
| 7,993,909 B2 | 8/2011 | Hoon et al. | |
| 8,000,809 B2 | 8/2011 | Elencwajg | |
| 8,019,404 B2 | 9/2011 | Kapadia | |
| 8,029,470 B2 | 10/2011 | Whiting et al. | |
| 8,084,246 B2 | 12/2011 | Hoon et al. | |
| 8,114,110 B2 | 2/2012 | Bednarek et al. | |
| 8,235,916 B2 | 8/2012 | Whiting et al. | |
| 8,317,810 B2 | 11/2012 | Stangenes et al. | |
| 8,333,687 B2 | 12/2012 | Farnan et al. | |
| 8,343,029 B2 | 1/2013 | Farnan et al. | |
| 8,388,549 B2 | 3/2013 | Paul et al. | |
| 8,394,010 B2 | 3/2013 | Farnan | |
| 8,460,168 B2 | 6/2013 | Farnan | |
| 8,491,619 B2 | 7/2013 | Breznock | |
| 8,694,077 B2 | 4/2014 | Kapadia | |
| 8,784,291 B2 | 7/2014 | Farnan et al. | |
| 8,821,366 B2 | 9/2014 | Farnan et al. | |
| 8,831,707 B2 | 9/2014 | Tekulve et al. | |
| 8,900,193 B2 | 12/2014 | Paul et al. | |
| 8,940,008 B2 | 1/2015 | Kunis | |
| 8,961,550 B2 | 2/2015 | Lenker et al. | |
| 8,979,750 B2 | 3/2015 | Van Bladel et al. | |
| 8,986,264 B2 | 3/2015 | Kimmel et al. | |
| 8,996,135 B2 | 3/2015 | Elencwajg | |
| 9,022,916 B2 | 5/2015 | Farnan et al. | |
| 9,028,393 B2 | 5/2015 | Farnan | |
| 9,050,064 B2 | 6/2015 | Kassab et al. | |
| 9,095,363 B2 | 8/2015 | Van Bladel et al. | |
| 9,173,711 B2 | 11/2015 | Butler et al. | |
| 9,173,712 B2 | 11/2015 | Annest et al. | |
| 9,198,756 B2 | 12/2015 | Aklog et al. | |
| 9,211,367 B2 | 12/2015 | Farnan et al. | |
| 9,220,417 B2 | 12/2015 | Paul et al. | |
| 9,289,577 B2 | 3/2016 | Gurley et al. | |
| 9,301,759 B2 | 4/2016 | Spivey et al. | |
| 9,314,595 B2 | 4/2016 | Gurley | |
| 9,320,513 B2 | 4/2016 | Van Bladel et al. | |
| 9,326,756 B2 | 5/2016 | Stangenes et al. | |
| 9,358,039 B2 | 6/2016 | Kimmel et al. | |
| 9,415,148 B2 | 8/2016 | Farnan | |
| 9,445,836 B2 | 9/2016 | Breznock | |
| 9,486,206 B2 | 11/2016 | Annest et al. | |
| 9,492,623 B2 | 11/2016 | Kapadia et al. | |
| 9,498,584 B2 | 11/2016 | Kapadia et al. | |
| 9,498,585 B2 | 11/2016 | Kapadia et al. | |
| 9,545,265 B2 * | 1/2017 | Maisano | A61B 17/3478 |
| 9,597,146 B2 | 3/2017 | Davies et al. | |
| 9,662,212 B2 | 5/2017 | Van Bladel et al. | |
| 9,700,351 B2 | 7/2017 | Maisano et al. | |
| 9,707,007 B2 | 7/2017 | Lenker et al. | |
| 9,788,858 B2 | 10/2017 | Maisano et al. | |
| 9,937,043 B2 | 4/2018 | Van Bladel et al. | |
| 9,962,184 B2 | 5/2018 | Paul et al. | |
| 10,004,879 B2 | 6/2018 | Gurley | |
| 10,016,210 B2 | 7/2018 | Lenker et al. | |
| 10,034,686 B2 | 7/2018 | Breznock | |
| 10,092,726 B2 | 10/2018 | Gurley et al. | |
| 10,179,049 B2 | 1/2019 | Van Bladel et al. | |
| 10,208,290 B2 | 2/2019 | Zhu et al. | |
| 10,219,904 B2 | 3/2019 | Butler et al. | |
| 10,220,134 B2 | 3/2019 | Kunis | |
| 10,307,569 B2 | 6/2019 | Kunis | |
| 10,314,641 B2 | 6/2019 | Paul et al. | |
| 10,398,503 B2 | 9/2019 | Sapir et al. | |
| 10,485,569 B2 | 11/2019 | Lenker et al. | |
| 10,500,371 B2 | 12/2019 | Sapir et al. | |
| 2005/0010203 A1 | 1/2005 | Edwards et al. | |
| 2005/0119670 A1 | 6/2005 | Kerr | |
| 2005/0153309 A1 | 7/2005 | Hoon et al. | |
| 2006/0020276 A1 | 1/2006 | Saadat et al. | |
| 2006/0079769 A1 | 4/2006 | Whiting et al. | |
| 2006/0079787 A1 | 4/2006 | Whiting et al. | |
| 2006/0196137 A1 * | 9/2006 | Brenzel | A61B 90/39 52/506.02 |
| 2007/0021767 A1 | 1/2007 | Breznock | |
| 2007/0043318 A1 | 2/2007 | Sogard et al. | |
| 2007/0083168 A1 | 4/2007 | Whiting et al. | |
| 2007/0173757 A1 | 7/2007 | Levine et al. | |
| 2007/0270751 A1 | 11/2007 | Stangenes et al. | |
| 2010/0114184 A1 | 5/2010 | Degtyar et al. | |
| 2011/0022057 A1 | 1/2011 | Eigler et al. | |
| 2011/0087261 A1 | 4/2011 | Wittkampf et al. | |
| 2011/0238102 A1 | 9/2011 | Gutfinger et al. | |
| 2011/0245800 A1 | 10/2011 | Kassab et al. | |
| 2012/0041422 A1 | 2/2012 | Whiting et al. | |
| 2012/0078061 A1 | 3/2012 | Calafiore et al. | |
| 2013/0085388 A1 | 4/2013 | Stangenes et al. | |
| 2013/0304036 A1 | 11/2013 | Kimmel et al. | |
| 2013/0304051 A1 | 11/2013 | Kimmel et al. | |
| 2014/0148828 A1 | 5/2014 | Ewers et al. | |
| 2014/0171870 A1 | 6/2014 | Kapadia | |
| 2014/0206961 A1 | 7/2014 | Hoon et al. | |
| 2014/0236205 A1 | 8/2014 | Jabba et al. | |
| 2014/0309679 A1 | 10/2014 | Maisano et al. | |
| 2015/0165159 A1 | 6/2015 | Elencwajg | |
| 2015/0238729 A1 | 8/2015 | Jenson et al. | |
| 2016/0007896 A1 | 1/2016 | Hoon et al. | |
| 2016/0058489 A1 * | 3/2016 | Fischell | A61B 18/1492 604/510 |
| 2016/0095600 A1 | 4/2016 | Annest et al. | |
| 2016/0100859 A1 | 4/2016 | Sapir et al. | |
| 2016/0193449 A1 | 7/2016 | Sarabia et al. | |
| 2016/0270837 A1 | 9/2016 | Cheng et al. | |
| 2017/0001000 A1 * | 1/2017 | Beach | A61M 39/105 |
| 2017/0105761 A1 | 4/2017 | Sapir et al. | |
| 2017/0303961 A1 | 10/2017 | Sapir et al. | |
| 2018/0000516 A1 | 1/2018 | Maisano et al. | |
| 2018/0263658 A1 * | 9/2018 | Drasler | A61F 2/2466 |
| 2018/0317949 A1 | 11/2018 | Lenker et al. | |
| 2018/0333170 A1 | 11/2018 | Breznock | |
| 2019/0046236 A1 | 2/2019 | Kassab et al. | |
| 2019/0209808 A1 | 7/2019 | Gurley et al. | |
| 2019/0274833 A1 | 9/2019 | Van Bladel et al. | |
| 2019/0298411 A1 | 10/2019 | Davies et al. | |
| 2019/0336163 A1 | 11/2019 | McNamara et al. | |

(56) References Cited

U.S. PATENT DOCUMENTS

2020/0155132 A1  5/2020  Gammie et al.
2020/0229805 A1  7/2020  Gammie et al.

FOREIGN PATENT DOCUMENTS

| WO | WO 2016/009337 | 1/2016 |
| WO | WO 2017/139463 | 8/2017 |
| WO | WO 2018/175743 | 9/2018 |

OTHER PUBLICATIONS

International Search Report and Written Opinion for International Application No. PCT/US2019/052714, dated Jan. 29, 2020, 19 pages.
International Search Report and Written Opinion for International Application No. PCT/US2018/023800, dated Jun. 1, 2018, 12 pages.
Office Action for U.S. Appl. No. 16/787,747, dated May 26, 2020, 23 pages.

* cited by examiner

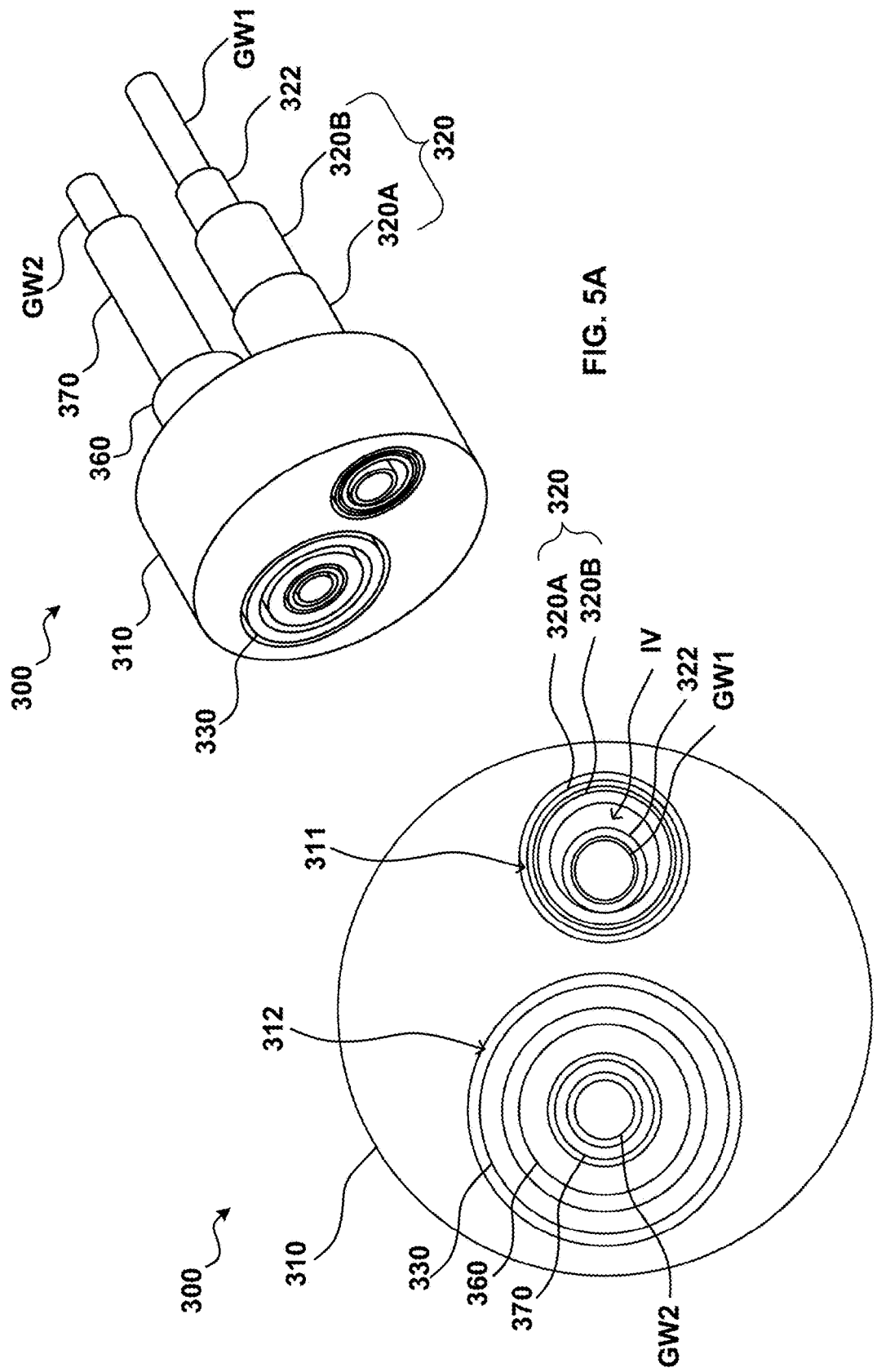

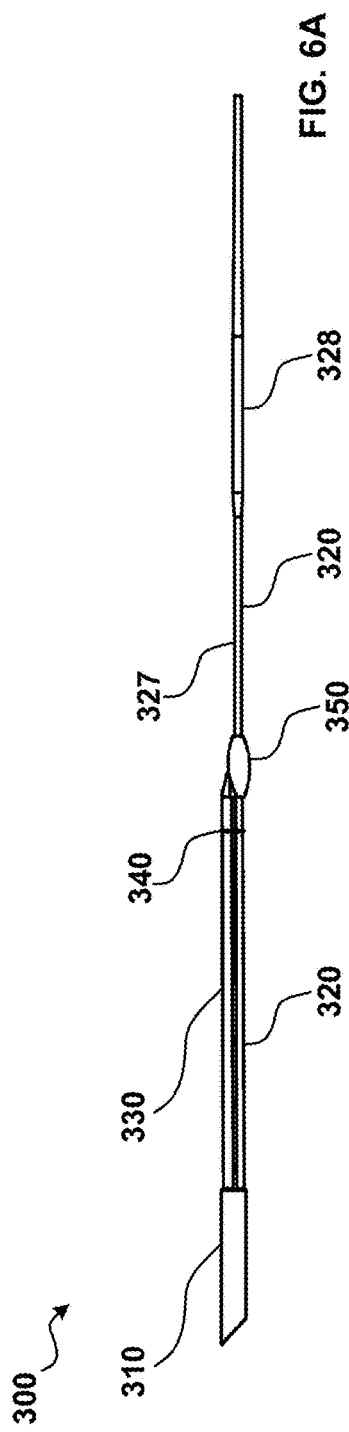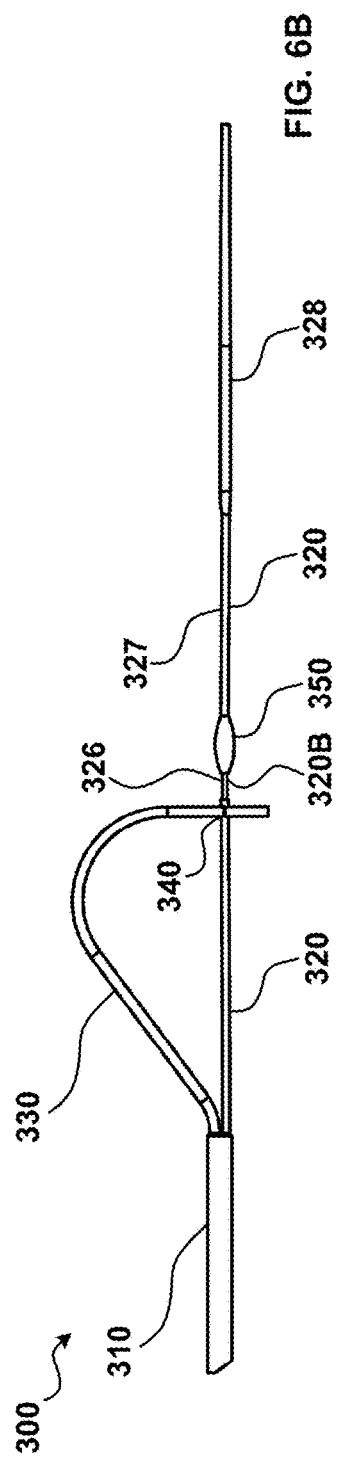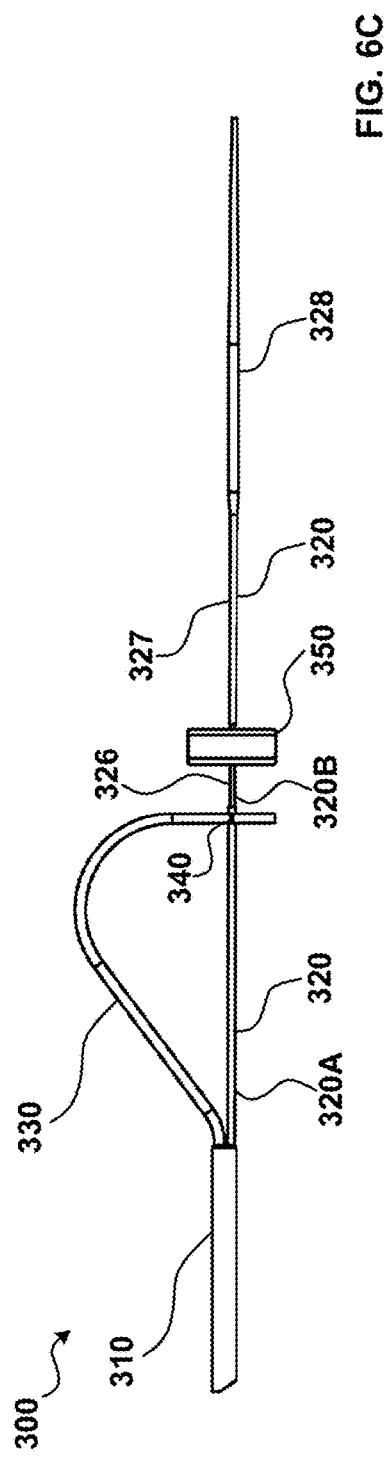

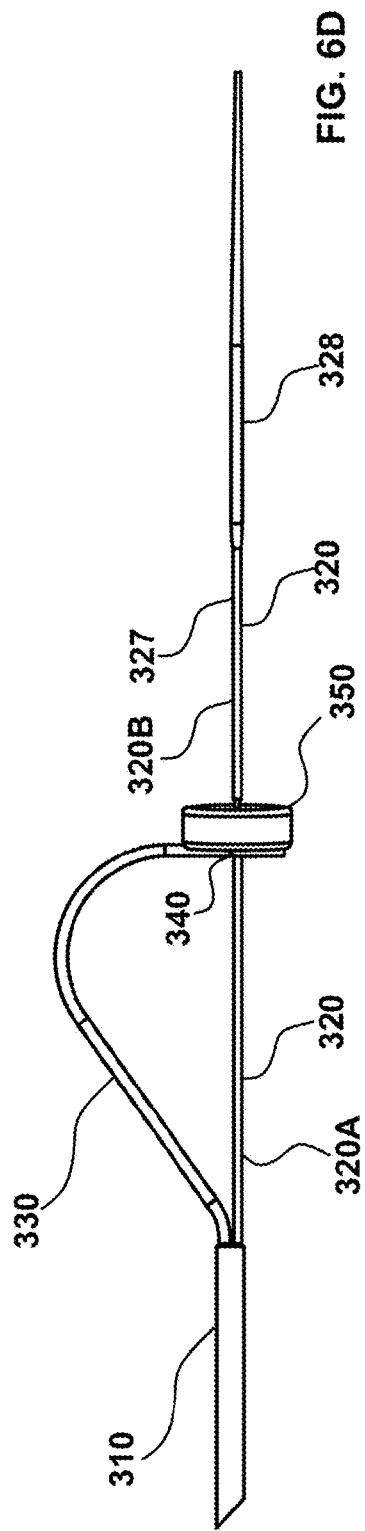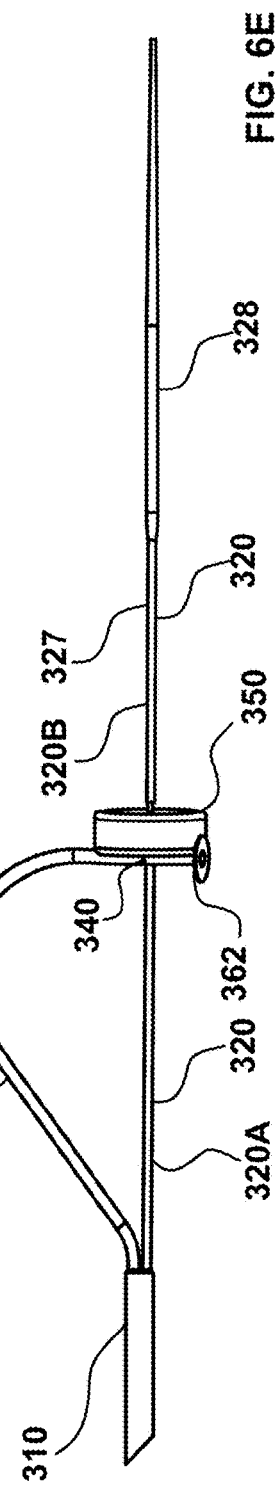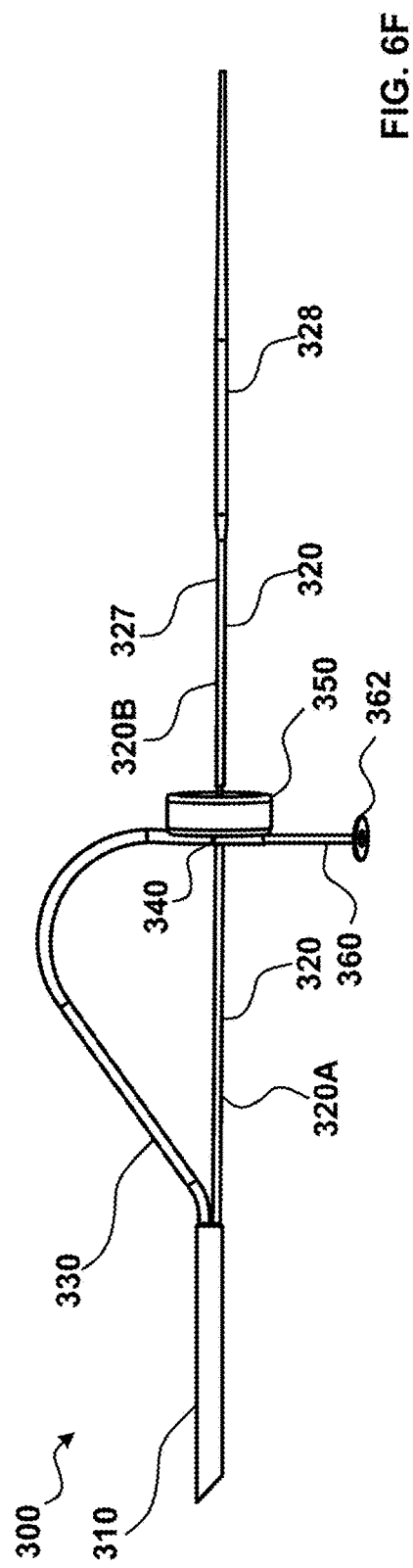

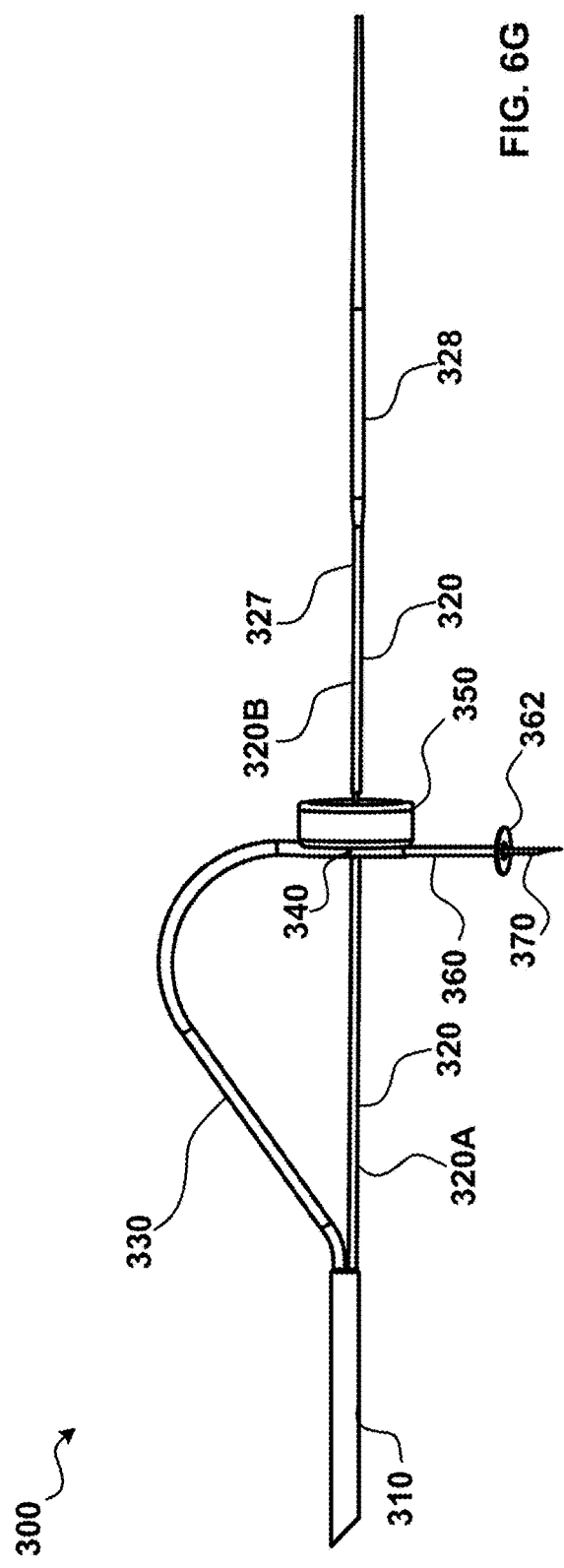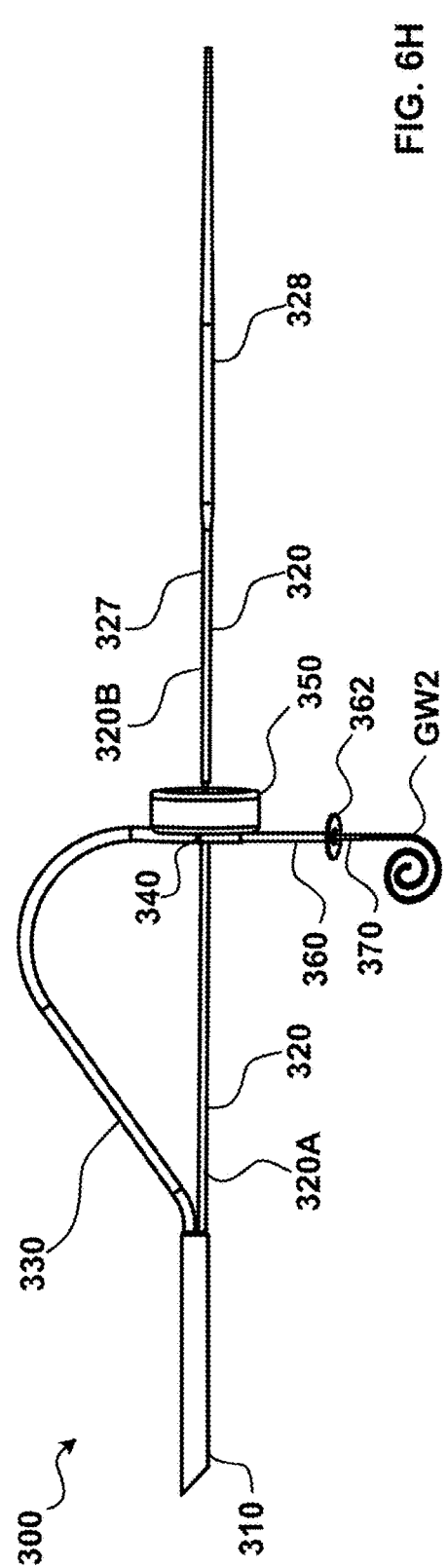

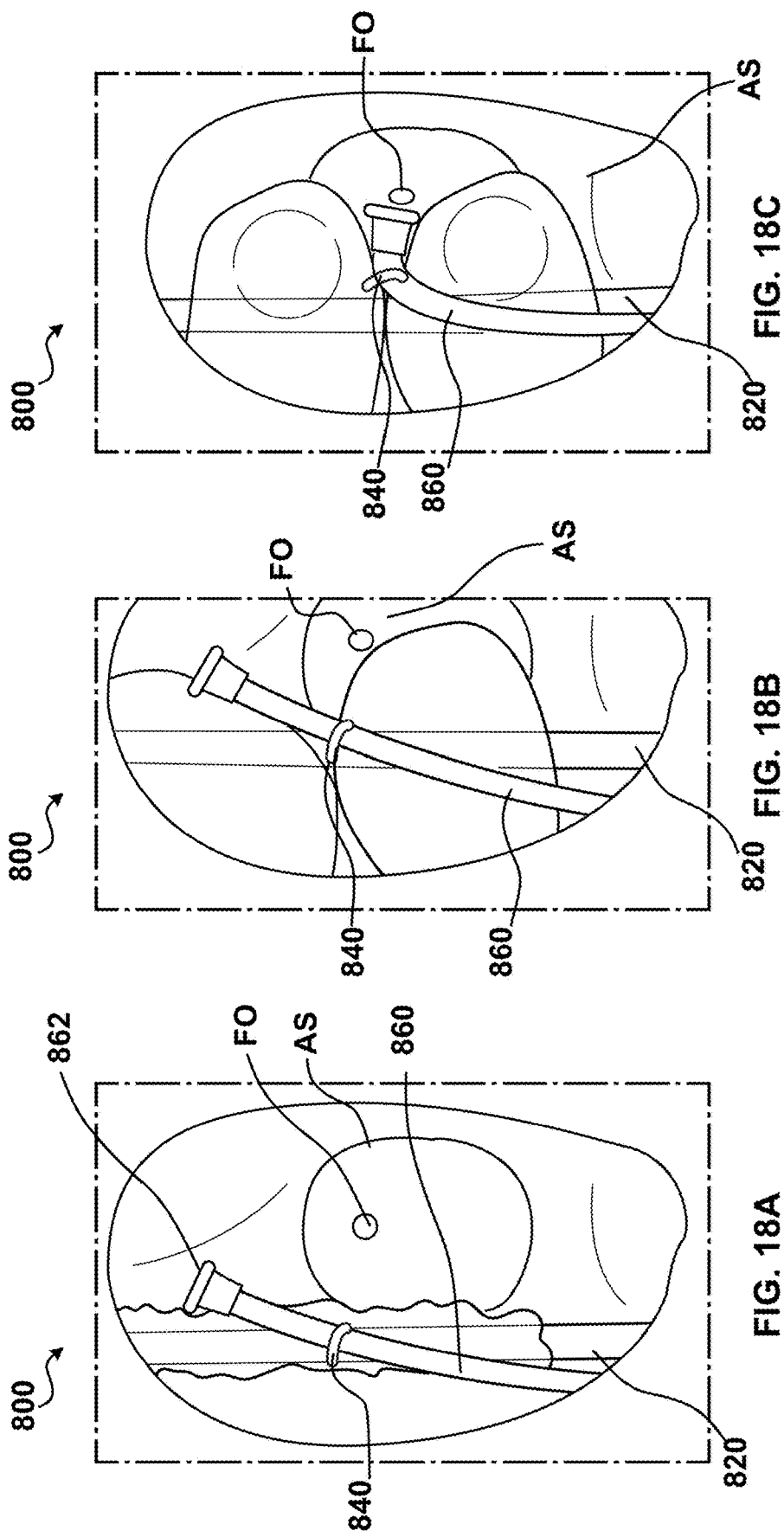

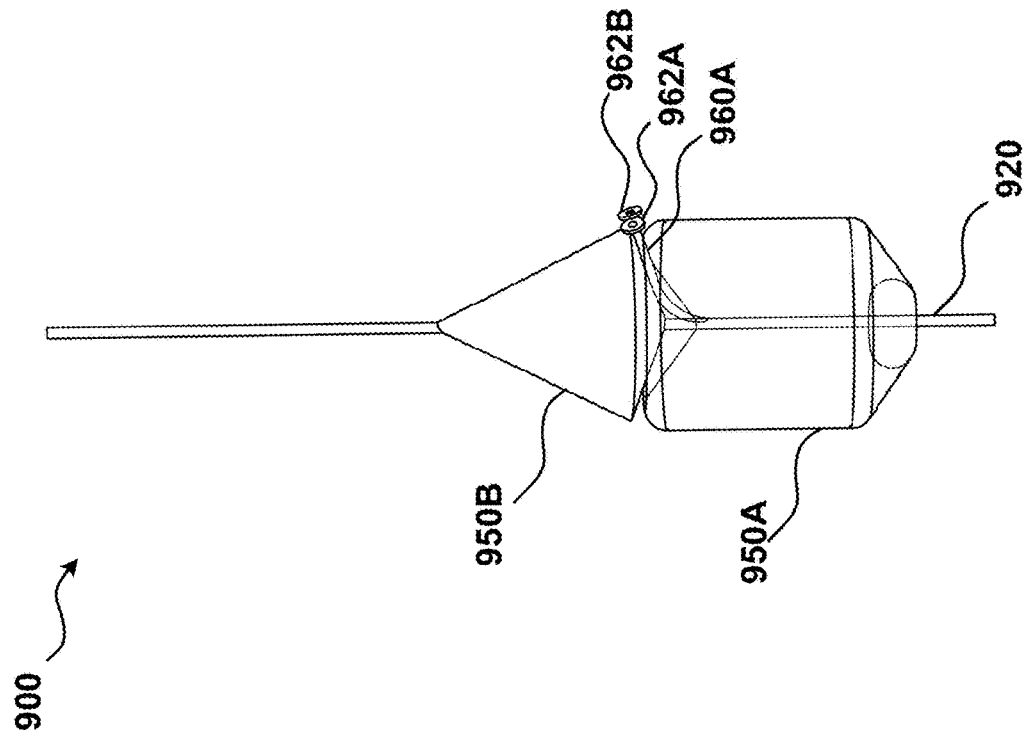
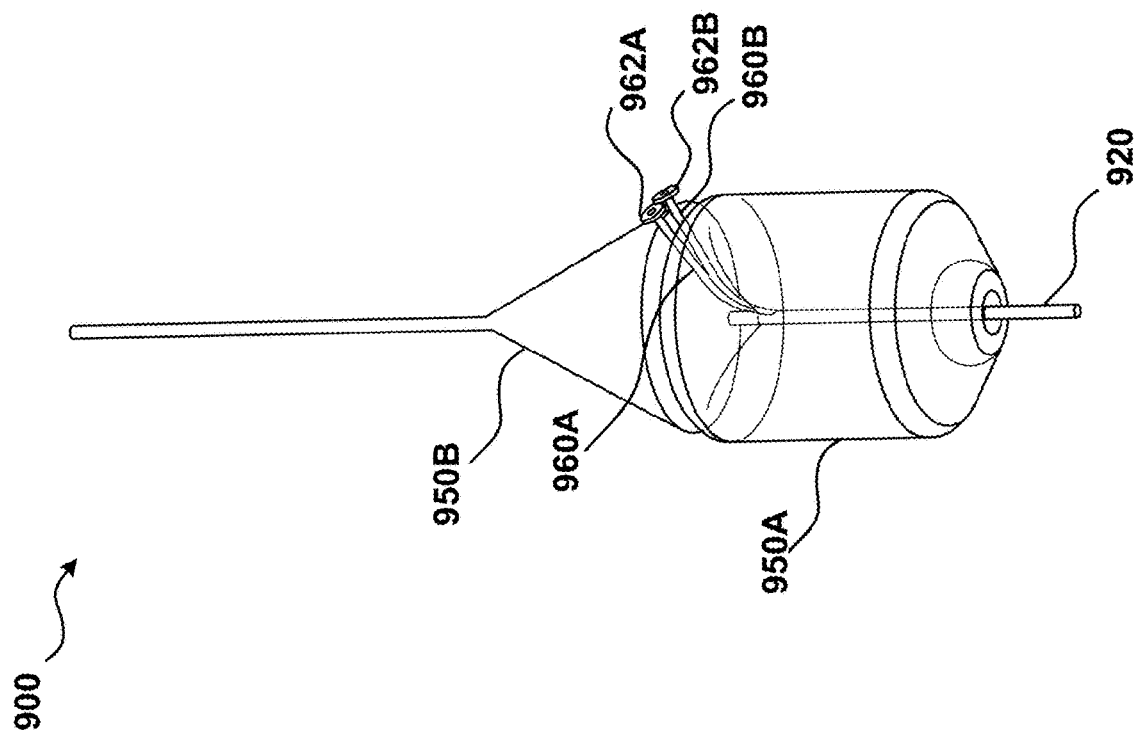

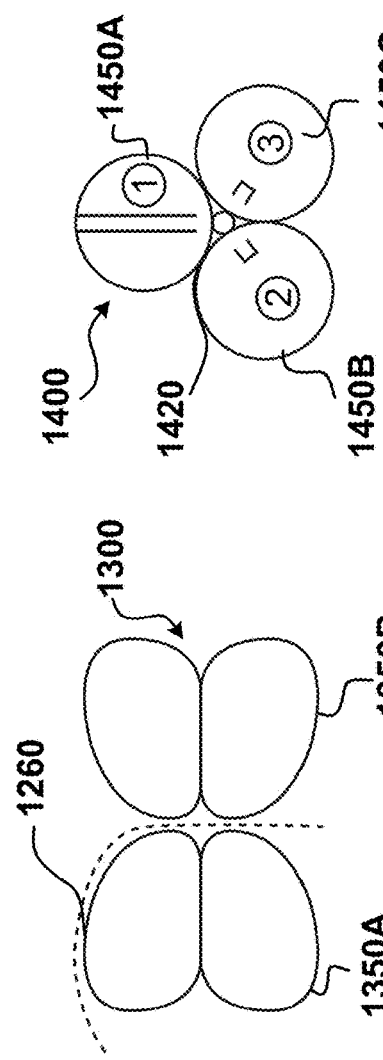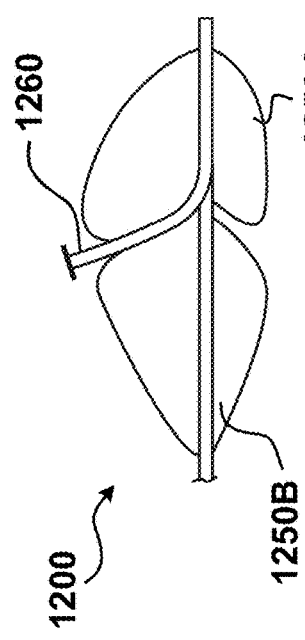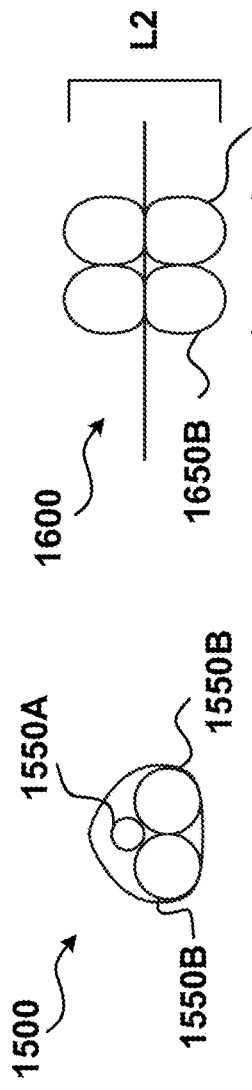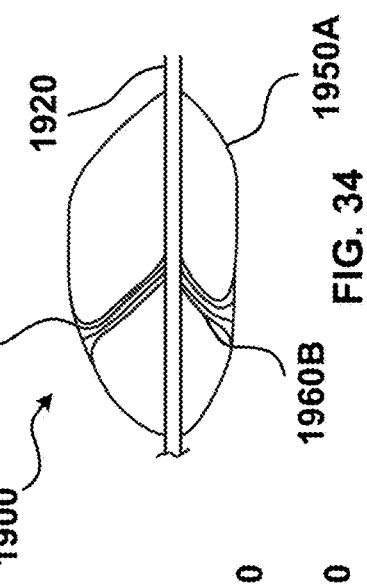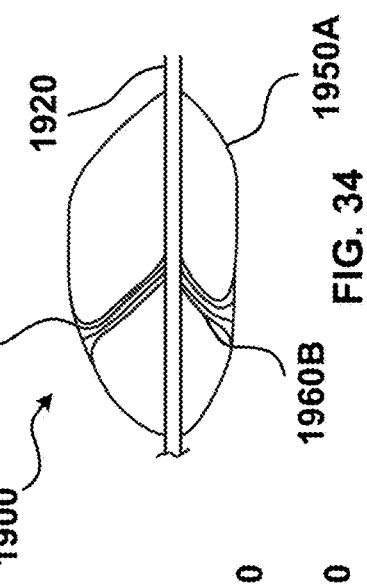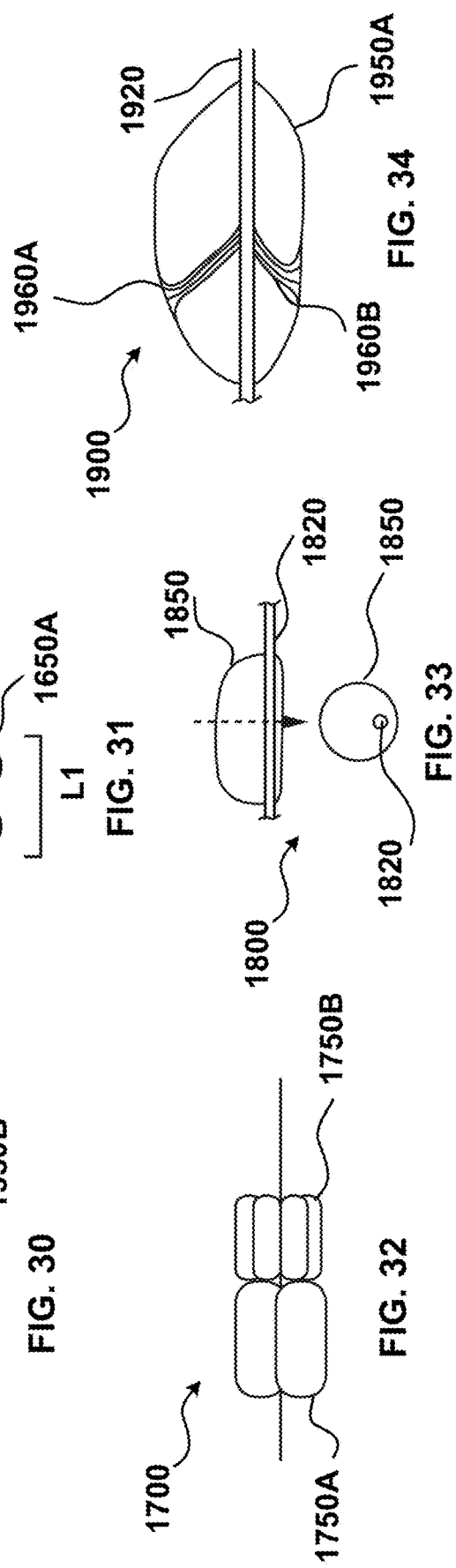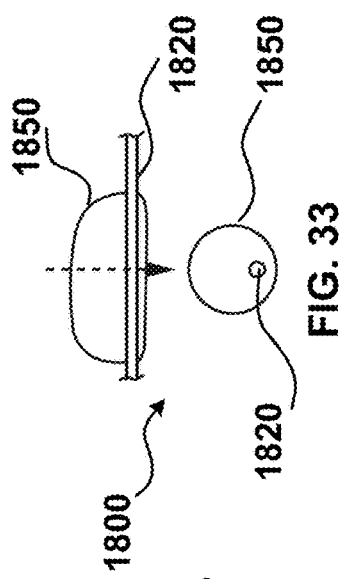

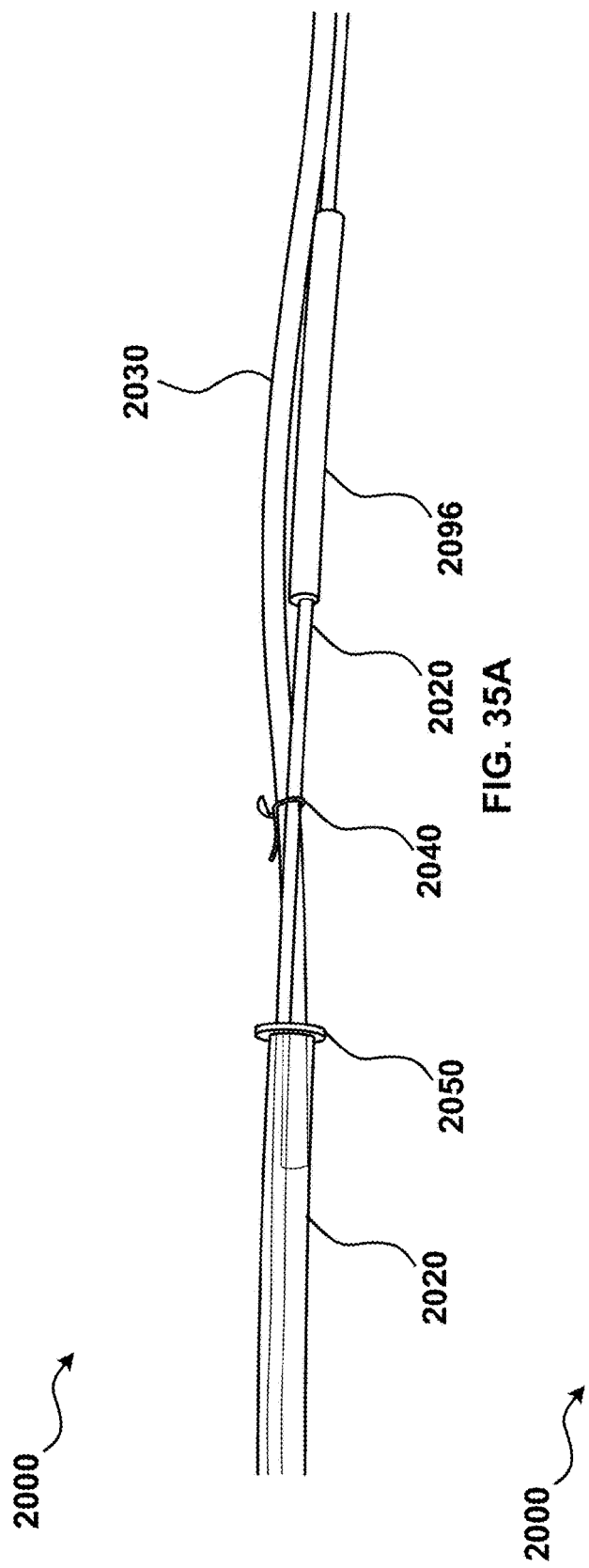
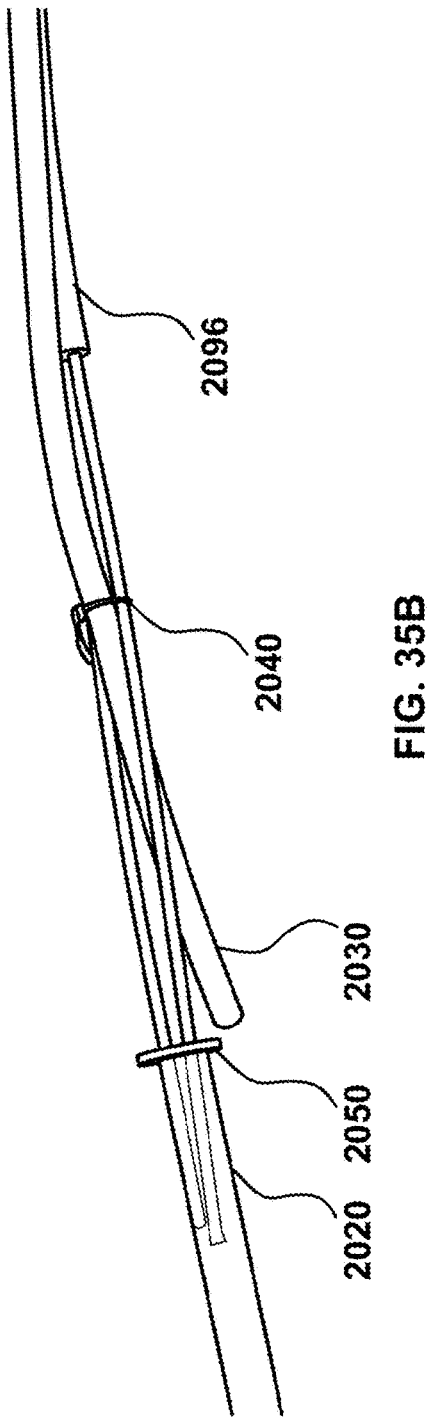

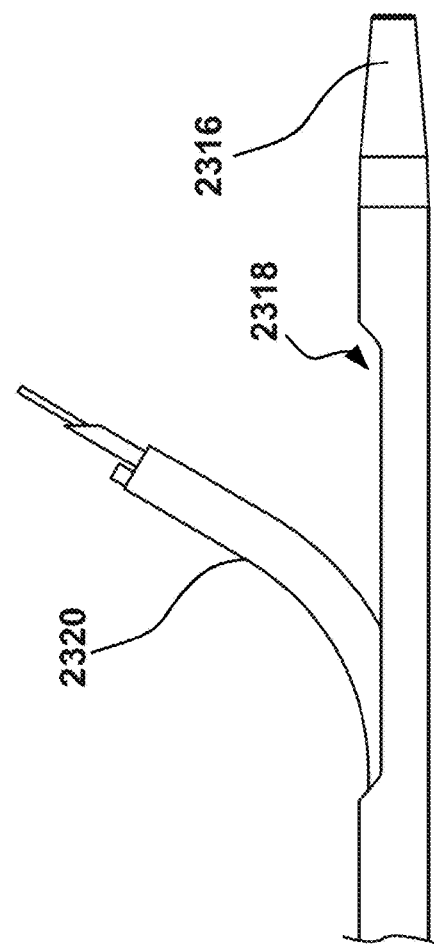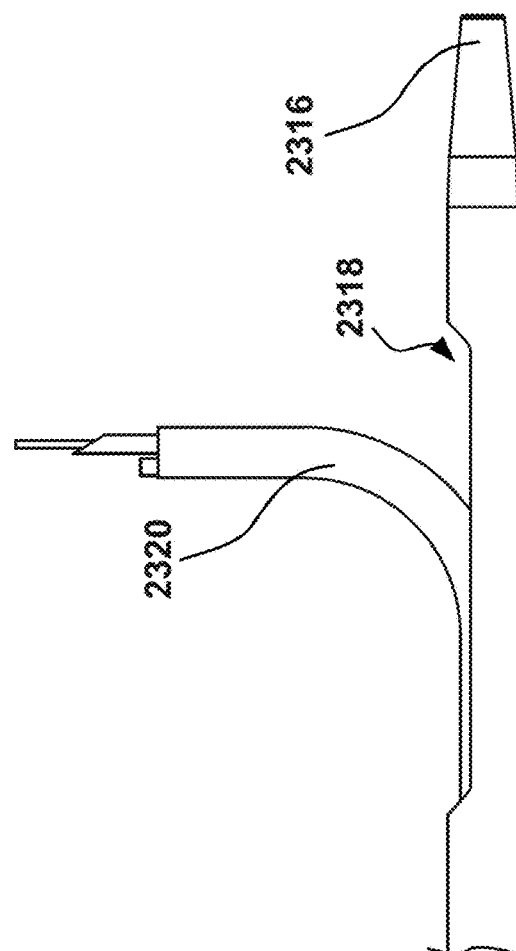

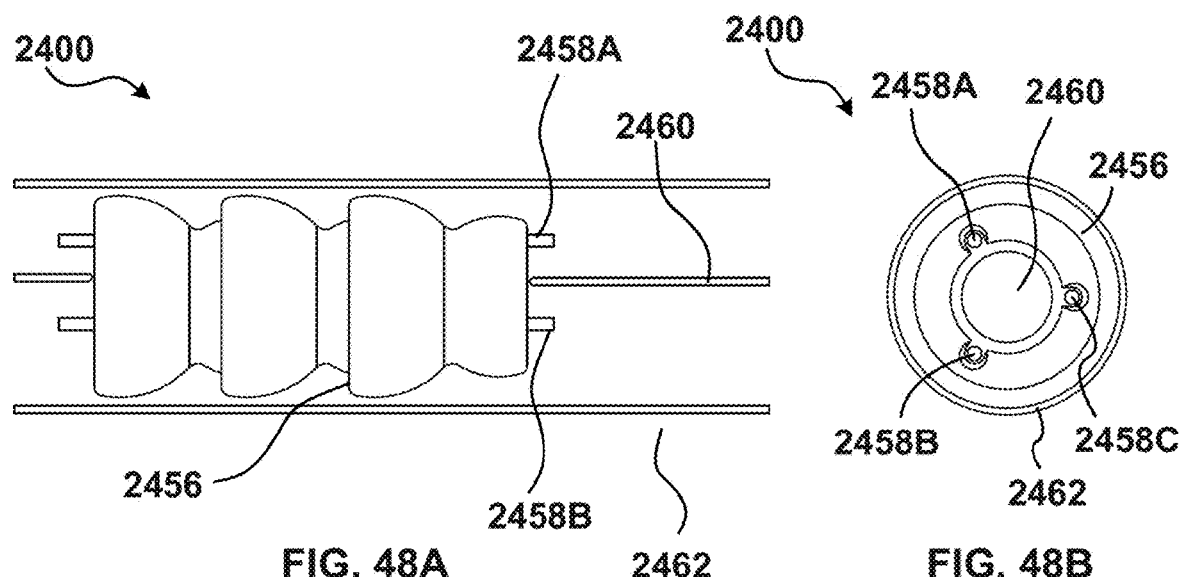
FIG. 48A
FIG. 48B
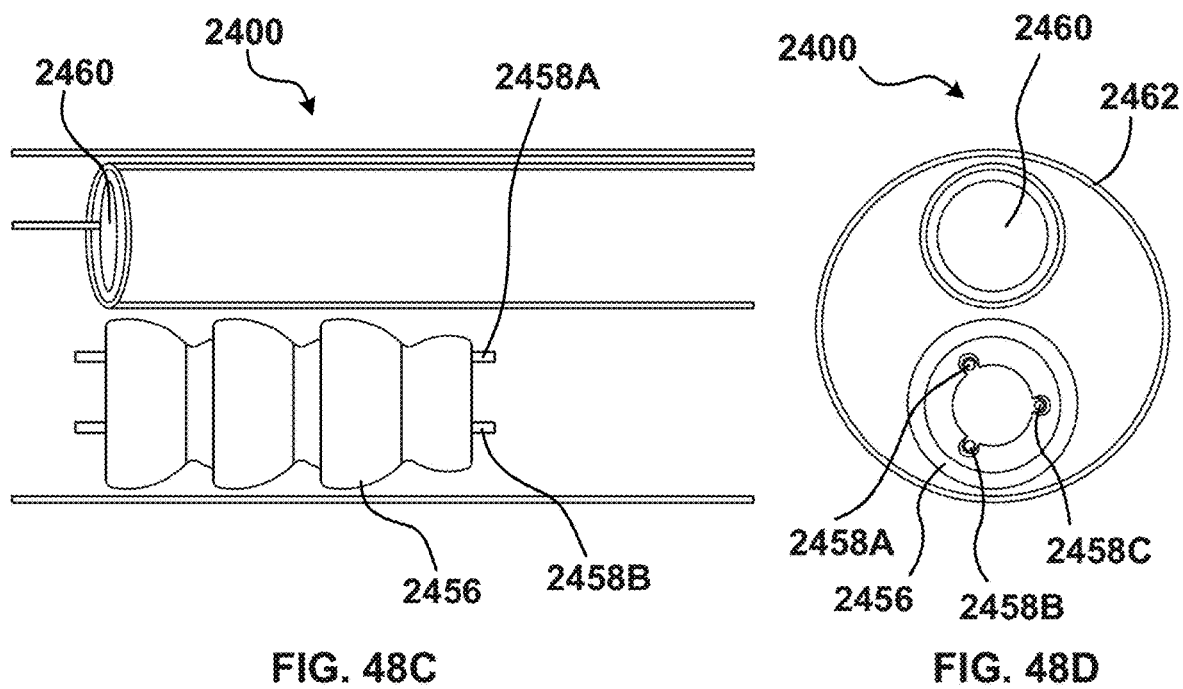
FIG. 48C
FIG. 48D

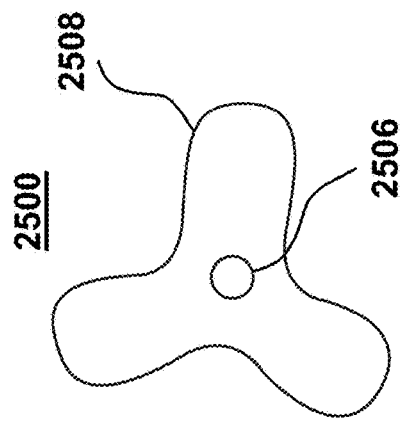
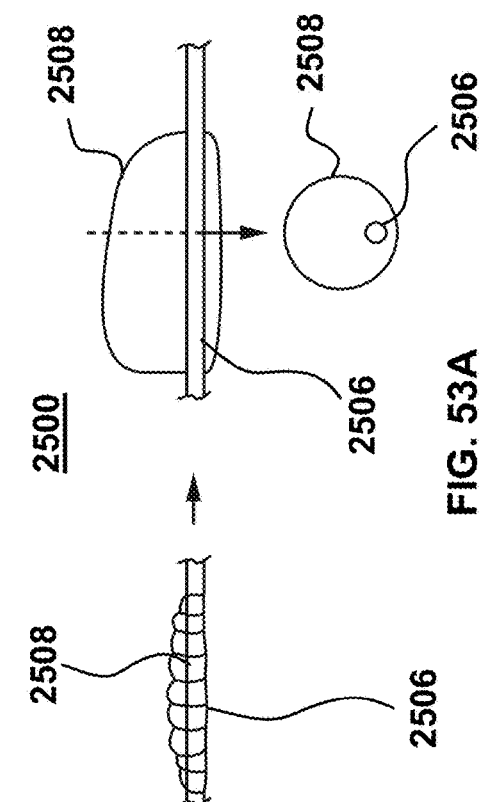
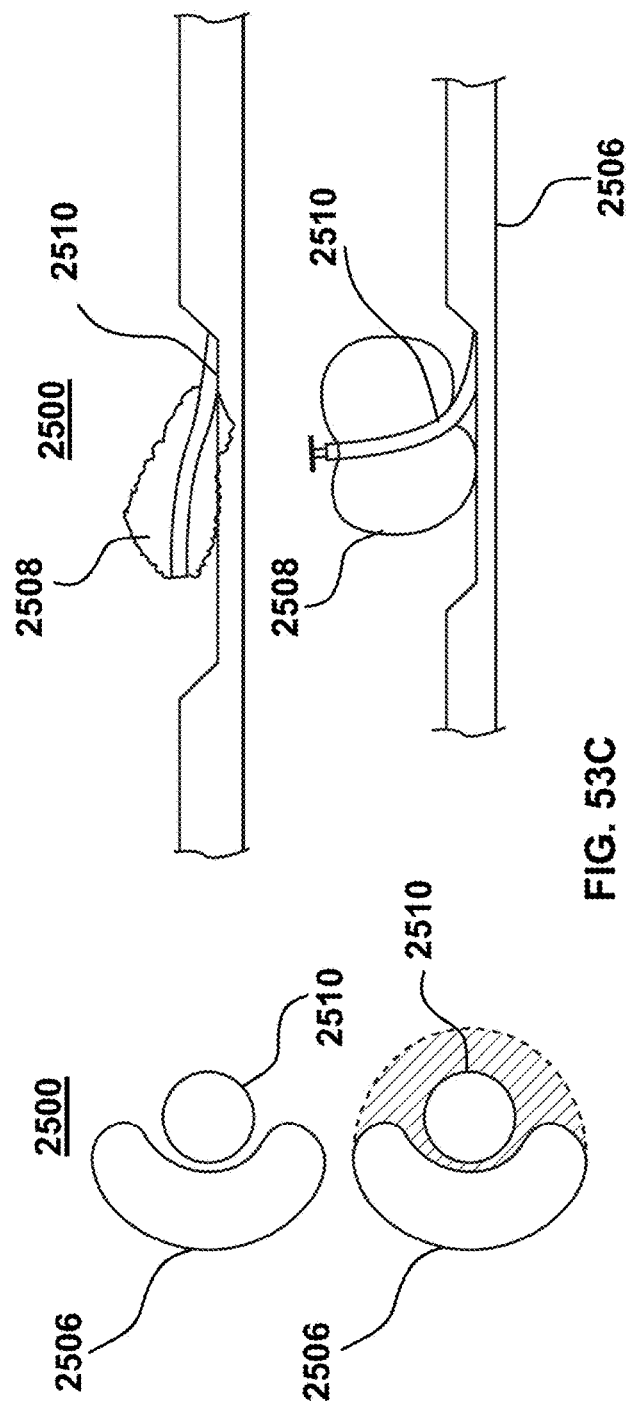
FIG. 53A
FIG. 53B
FIG. 53C

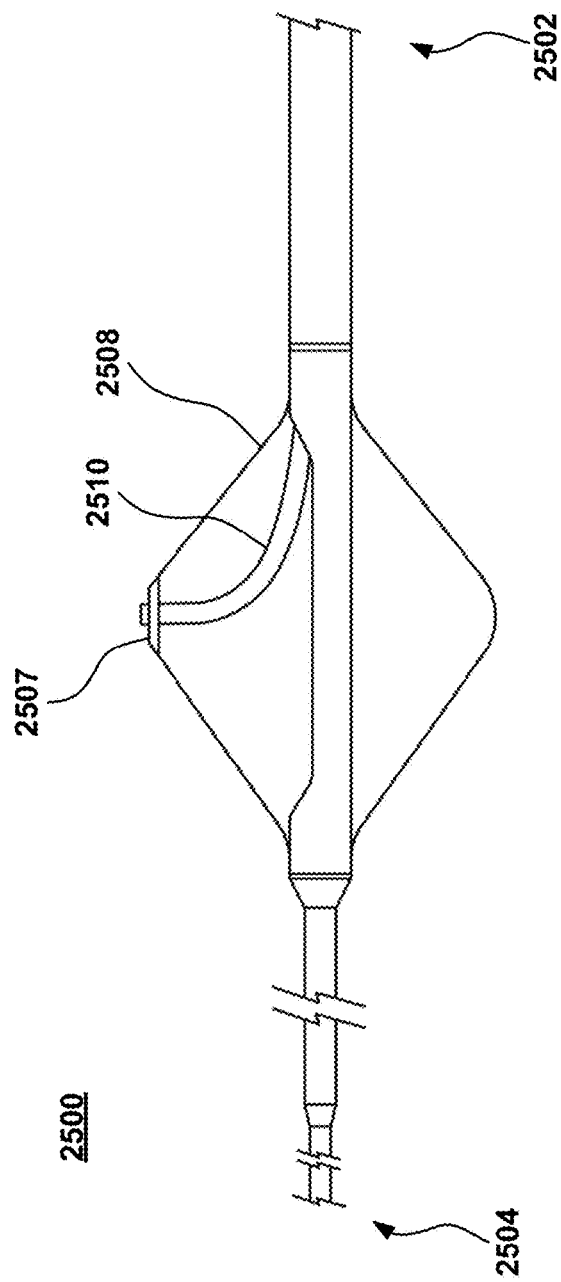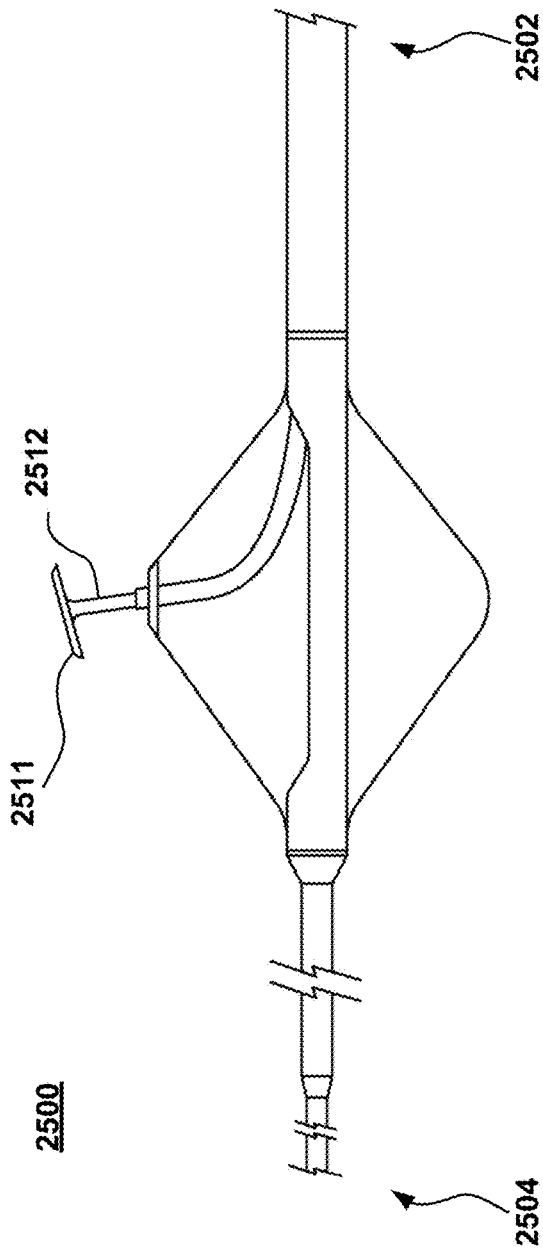
FIG. 59A
FIG. 59B

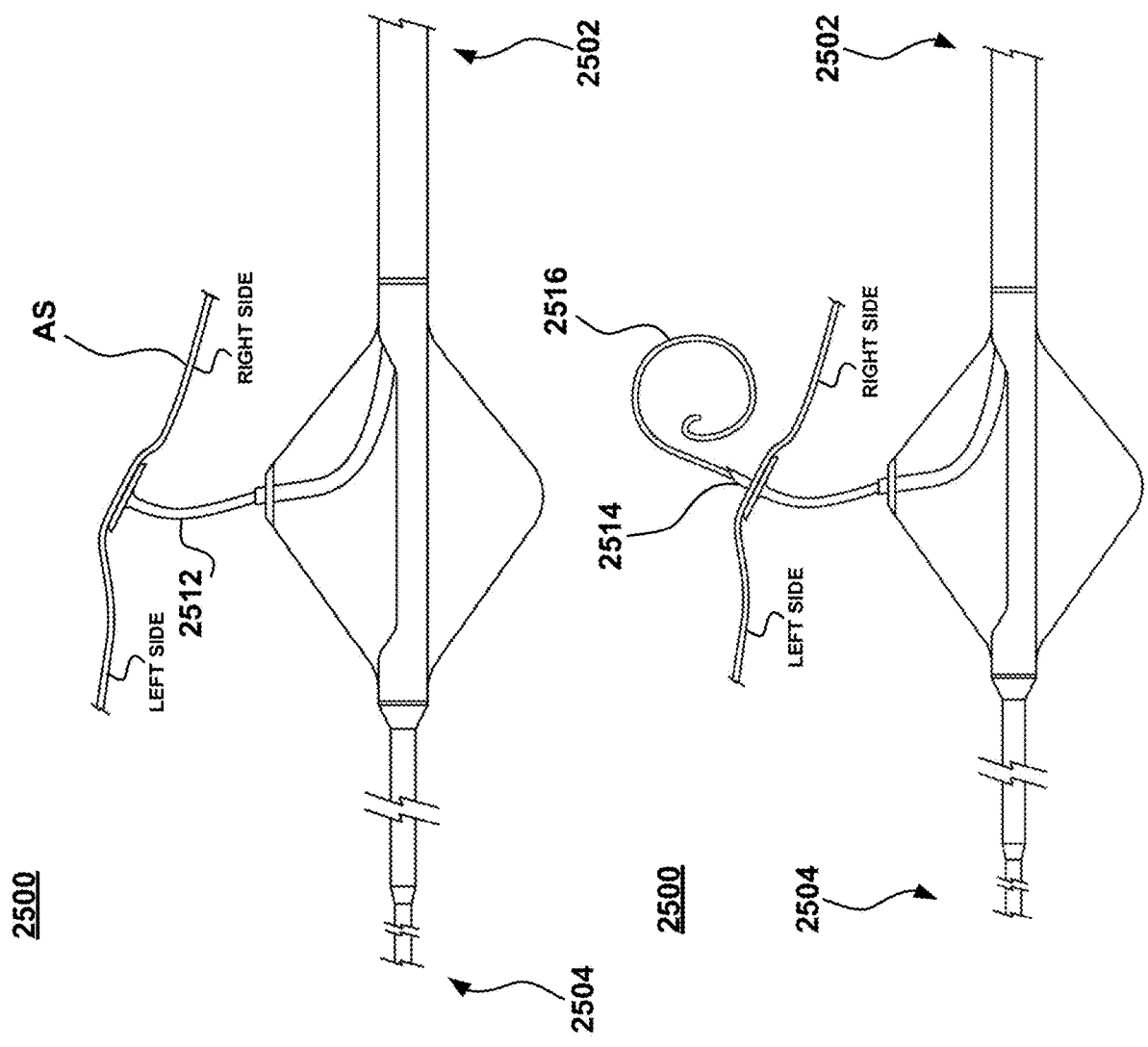

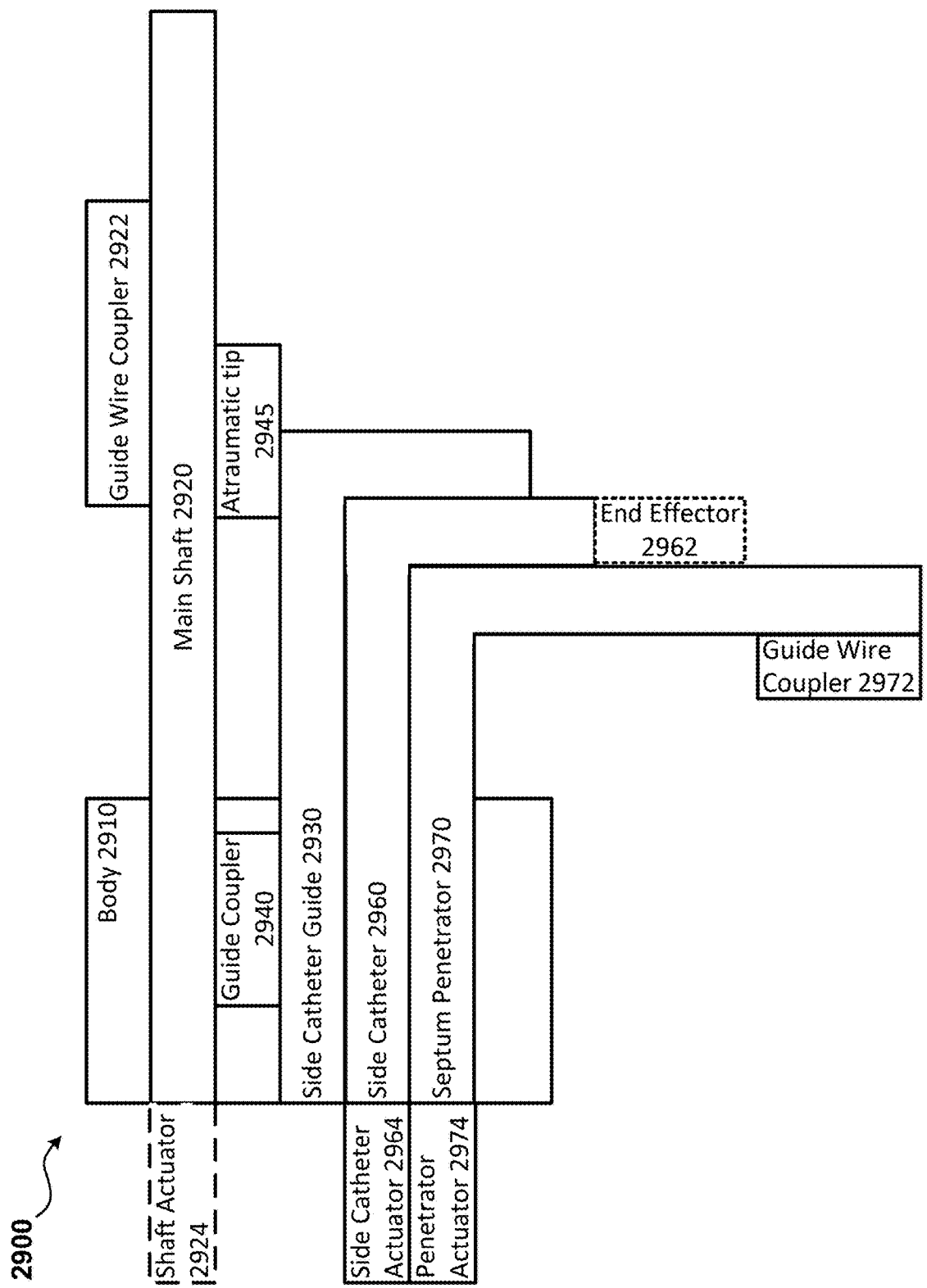

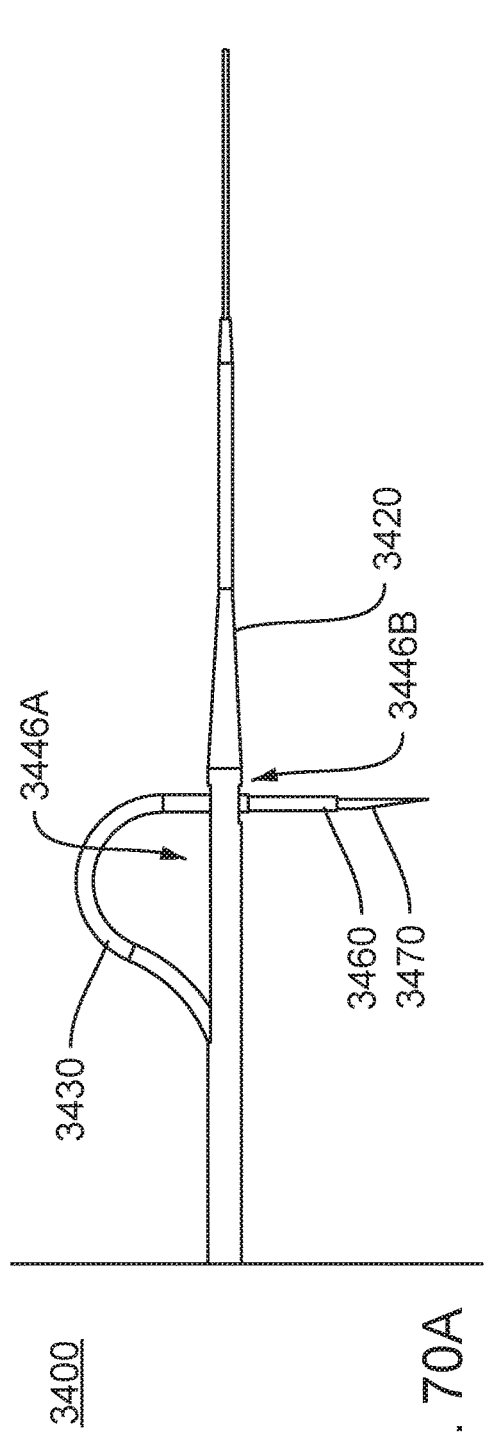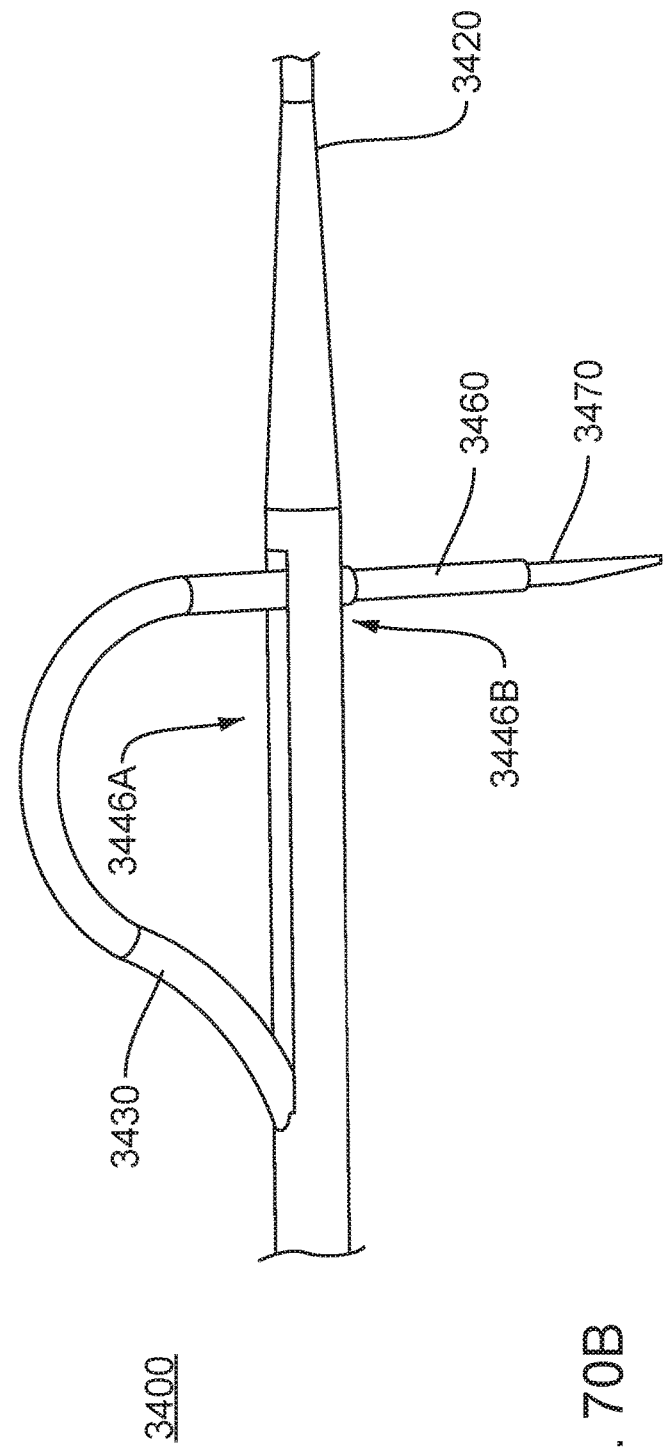

APPARATUS AND METHOD FOR SEPTAL PUNCH

CROSS REFERENCE TO RELATED APPLICATIONS

This application is a continuation-in-part of International Application No. PCT/US2019/052714, filed Sep. 24, 2019, entitled "Apparatus and Method for Septal Punch," which claims priority to U.S. Provisional Application No. 62/735,410, filed Sep. 24, 2018, entitled "Device for Transseptal Puncture," the disclosures of each of which are hereby incorporated by reference in their entirety.

This application claims priority to and the benefit of U.S. Provisional Application No. 62/994,751, filed Mar. 25, 2020, entitled "Apparatus and Method for Septal Punch," the disclosures of which is hereby incorporated by reference in its entirety.

BACKGROUND

Embodiments are described herein that relate to devices and methods for use in accessing the left side of the heart.

Many diseases and disorders, such as, for example, heart failure, atrial fibrillation, mitral valve disease, and others, specifically impact or are addressable in the left side of the heart. Accordingly, many interventional percutaneous cardiac procedures require access to the left side of the heart, including, for example, electrophysiological procedures, left atrial appendage occlusion procedures, mitral valve repair and replacement procedures, atrial shunt procedures, and many more. In additional to therapeutic interventional procedures, indications for access to the left side of the heart also include diagnostic procedures, including, for example, hemodynamic measurements (e.g., left atrial pressure, transmitral pressure gradient, etc.). Minimally-invasive access to the left side of the heart is challenging and not without significant risk.

Some catheter-based procedures access the left side of the heart by puncturing the atrial septum ("AS") of the heart, which separates the left atrium ("LA") of the heart from the right atrium ("RA") of the heart. Such procedures use a catheter containing a sheathed needle, which is advanced from the femoral vein in the groin of the patient to the superior vena cava ("SVC") through the RA of the heart. The sheathed needle is often a long, stiff-wire needle that has a bend of approximately twenty degrees near its tip. With the catheter assembly disposed within the SVC, the catheter assembly is then slowly withdrawn inferiorly from the SVC and into the RA until its tip rests within the fossa ovalis ("fossa", "FO", or "F"). The FO is a thumbprint-sized depression in the wall of the RA, and is the thinnest portion of the interatrial septum (i.e., the wall between the RA and LA). Once the operator visualizes contact between the tip of the catheter assembly and the F, the needle is advanced such that it punctures the F. With the needle extending from the LA into the RA, a guidewire is advanced through the catheter and into the RA. The needle is then removed from the LA, and a device (e.g., an AF ablation device, a catheter, percutaneous mitral valve repair delivery system or catheter, as examples) can be inserted into the LA.

Alternative procedures include the use of a blunt needle, electrified by radiofrequency, to puncture or perforate the atrial septum.

The above procedure has significant limitations. It is difficult to learn, time intensive, and prone to premature, misaligned, and inadvertent puncturing of the FO. Further, precisely and accurately locating the F with the tip of the device is difficult, and if the catheter assembly is withdrawn from the SVC too far, time-intensive procedural steps must be repeated because such a device cannot be moved cephalad. Moreover, the shape of the needle may need to be customized or adjusted based on a patient's particular anatomy, thereby further complicating the process.

Furthermore, such catheters are typically very flexible and not very stable within the SVC, and thus easily inadvertently maneuvered out of an ideal position, particularly during normal dynamic cardiac activity. Even more, the needle is not fixed to the catheter, thereby resulting in accidental needle exposure, and possibly inadvertent cardiac puncture, which can be lethal. Further complicating this procedure is potentially distorted or abnormal anatomy due to, for example, aortic or mitral valve disease, leading to changes in the location of the FO and obfuscation of typical anatomical landmarks. Yet even more, for patients undergoing a repeat procedure, the FO may be thickened or scarred, necessitating application of greater puncturing force and increased risk of unintended damage to nearby anatomy.

It can be crucial for many left-heart procedures that the septal puncture is performed in a specific location within the FO. For delivering a replacement mitral valve, for example, it may be important to puncture an inferior portion of the FO, while for a native valve leaflet clip implant procedure, it may be important to puncture a post/mid portion of the FO. Existing systems do not provide for sufficient accurate and precise targeting of an intended puncture site, such as a particular region within the FO. Failure to puncture the septum in a proper location can result in prolonged, unsuccessful, or canceled procedures.

Thus, a need exists for improved devices and methods for faster, more stable, safer, more accurate, and more precise access to the LA.

SUMMARY

Devices and methods are described herein for use in minimally-invasively accessing various portions of a patient's anatomy, such as, for example, accessing a left atrium of a heart through a transseptal puncture. In some embodiments, a method includes inserting a shaft having (1) a side catheter guide attached thereto via a guide coupler, and (2) a guide stabilizer/actuator ("GSA") in a delivery configuration and slidably attached thereto, into an inferior vena cava of a heart of a patient and a superior vena cava of the heart such that the GSA is disposed in a right atrium of the heart. The method further includes applying a distal force to the side catheter guide such that a distal end of the side catheter guide deflects laterally about the guide coupler towards a septum of the heart. The method further includes, with the GSA in its delivery configuration in the right atrium of the heart, actuating the guide stabilizer/actuator to transition the GSA from its delivery configuration to a deployed configuration. After initiating the applying the distal force and with the guide stabilizer/actuator in its deployed configuration, disposing the GSA in contact with the side catheter guide to laterally stabilize the side catheter guide relative to the shaft. The method further includes with the distal end of the side catheter guide laterally deflected about the guide coupler towards the septum and laterally stabilized by the GSA, extending a side catheter that is disposed within the side catheter guide distally from the side catheter guide towards and into contact with the septum. The method further includes, with the distal end of the side catheter in contact with the septum, extending a septum penetrator that is slidably disposed within the side catheter distally from the side catheter such that the septum penetrator pierces the septum.

BRIEF DESCRIPTION OF THE DRAWINGS

FIGS. 5A and 5B illustrate in cross-sectional view a portion of the septum puncture device 300 of FIGS. 4A and 4B, in perspective view and front view, respectively.

FIGS. 6A-6H illustrate in side view a deployment sequence of and at a distal end portion of the septum puncture device 300, according to an embodiment.

FIGS. 18A-18C illustrate a first a guide stabilizer/actuator ("GSA") 850A and a second GSA 850B, of a septum puncture device 800, in a deflated, delivery configuration, a partially inflated, partially deployed configuration, and an inflated, deployed configuration, respectively, according to an embodiment.

FIGS. 19-21 illustrate a septum puncture device 900 in perspective view, front view, and detailed, partial perspective view, respectively, that includes two side catheters, according to an embodiment.

FIG. 27 illustrates a septum puncture device 1200 having a GSA with a concave shape and a GSA with a convex shape, according to an embodiment.

FIG. 28 illustrates a septum puncture device 1300 having a GSA with a particular curvature, according to an embodiment.

FIG. 29 illustrates in top view a septum puncture device 1400 having a tri-lobed GSA, according to an embodiment.

FIG. 30 illustrates in top view a septum puncture device 1500 having a GSA with multiple lobes, according to an embodiment.

FIG. 31 illustrates in side view a septum puncture device 1600 having GSAs configured to limit blood flow occlusion, according to an embodiment.

FIG. 32 illustrates in side view a septum puncture device 1700 having GSAs rotatably offset and interlocked with each other, according to an embodiment.

FIG. 33 illustrates in side view and top view a septum puncture device 1800 having an asymmetric GSA, according to an embodiment.

FIG. 34 illustrates in side view a septum puncture device 1900 defining two pathways between GSAs, according to an embodiment.

FIGS. 35A-35D illustrate a deployment sequence of a septum puncture device 2000, according to an embodiment.

FIGS. 42A-42D illustrate an example deployment sequence of the septum puncture device 2300, according to an embodiment.

FIGS. 47A-48D illustrate a segmented septum puncture device 2400, according to an embodiment.

FIGS. 53A-53C illustrate various implementations of the septum puncture device 2500.

FIGS. 59A-59D illustrate an example deployment sequence of a septum puncture device, according to an embodiment.

FIG. 65B is a schematic illustration of the septum puncture device of FIG. 65A, disposed in a deployed configuration.

FIG. 70A illustrates a portion of a septum puncture device in side view, disposed in a deployed configuration, according to an embodiment.

FIG. 70B illustrates the septum puncture device of FIG. 70A in side perspective view.

DETAILED DESCRIPTION

Figure 1A:
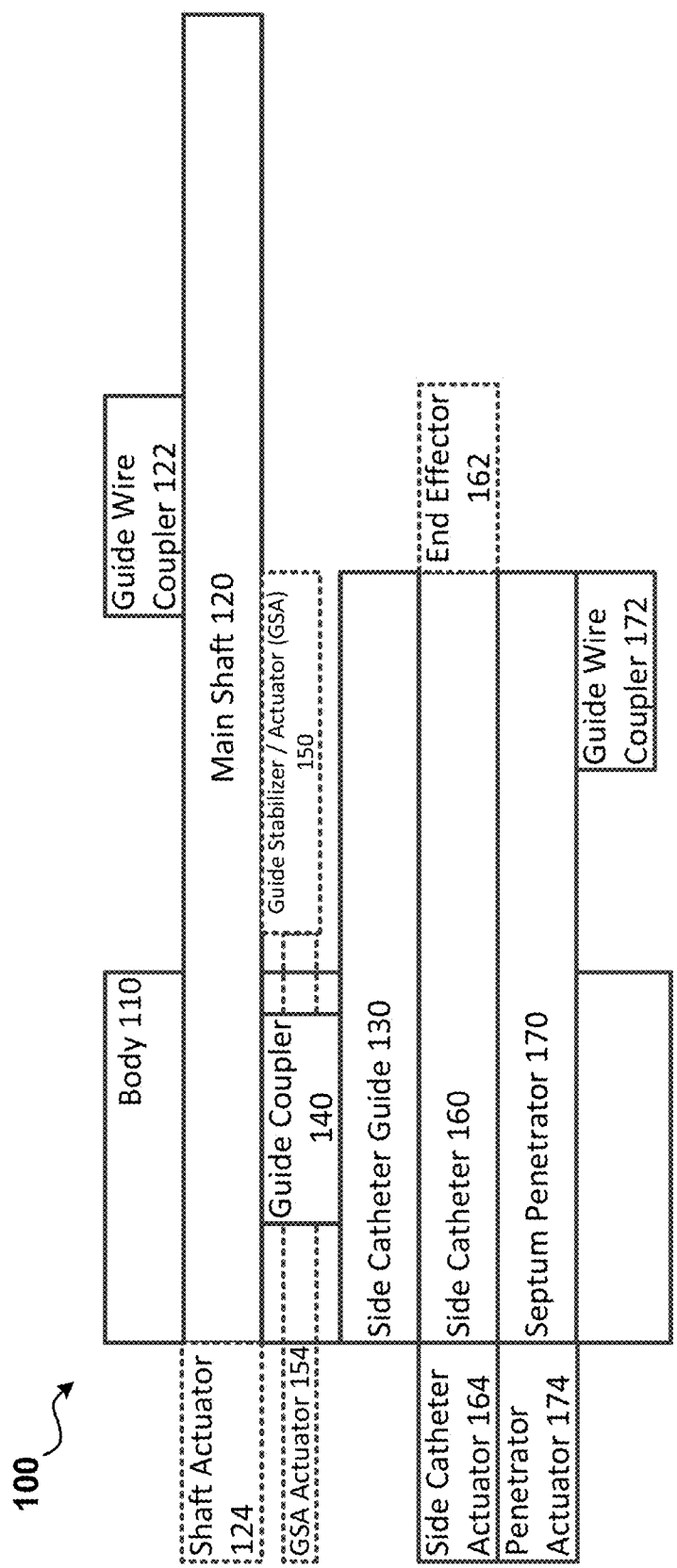
FIG. 1A is a schematic illustration of a septum puncture device, disposed in a delivery configuration, according to an embodiment.

Devices and methods are described herein for use in accessing the left side of the heart (e.g., LA) from the right side of the heart (e.g., RA) without requiring open-heart surgery. The methods described herein are minimally invasive and utilize a septum puncture device to access the left side of the heart in a safe (e.g., atraumatic), efficient, timely, accurately and precisely located and repeatable manner. This is accomplished, in part, by providing a steerable (e.g., translatable and rotatable) stable platform between the IVC and SVC from which a puncture member can be extended laterally and into a target puncture location (e.g., the FO) of the atrial septum.

In some embodiments, a method includes inserting a shaft having (1) a side catheter guide attached thereto via a guide coupler, and (2) a guide stabilizer/actuator ("GSA") in a delivery configuration and slidably attached thereto, into an inferior vena cava of a heart of a patient and a superior vena cava of the heart such that the guide stabilizer/actuator is disposed in a right atrium of the heart. The method further includes applying a distal force to the side catheter guide such that a distal end of the side catheter guide deflects laterally about the guide coupler towards a septum of the heart. The method further includes, with the guide stabilizer/actuator in its delivery configuration in the right atrium of the heart, actuating the guide stabilizer/actuator to transition the guide stabilizer/actuator from its delivery configuration to a deployed configuration. After initiating the applying the distal force and with the guide stabilizer/actuator in its deployed configuration, disposing the side catheter guide in contact with the side catheter guide to laterally stabilize the side catheter guide relative to the shaft. The method further includes with the distal end of the side catheter guide laterally deflected about the guide coupler towards the septum and laterally stabilized by the guide stabilizer/actuator, extending a side catheter that is disposed within the side catheter guide distally from the side catheter guide towards and into contact with the septum. The method further includes, with the distal end of the side catheter in contact with the septum, extending a septum penetrator that is slidably disposed within the side catheter distally from the side catheter such that the septum penetrator pierces the septum.

In some embodiments, a method includes a shaft having a side catheter guide attached thereto via a guide coupler into an inferior vena cava of a heart of a patient and a superior vena cava of the heart such that the guide coupler is disposed in a right atrium of the heart. The method further includes applying a distal force to a proximal portion of the side catheter guide such that a distal end of the side catheter guide deflects laterally about the guide coupler towards a septum of the heart. The method further includes, with the distal end of the side catheter guide laterally deflected about the guide coupler towards the septum, extending a side catheter that is disposed within the side catheter guide distally from the side catheter guide towards and into contact with the septum. The method further includes, with the side catheter in contact with the septum, extending a septum penetrator that is slidably disposed within the side catheter distally from the side catheter such that the septum penetrator pierces the septum.

In some embodiments, a method includes inserting a shaft having a guide stabilizer/actuator in a delivery configuration and slidably attached thereto, into an inferior vena cava of a heart of a patient and a superior vena cava of the heart such that the guide stabilizer/actuator is disposed in a right atrium of the heart, a side catheter guide being coupled to the guide stabilizer/actuator. The method further includes, with the guide stabilizer/actuator in its delivery configuration in the right atrium of the heart, actuating the guide stabilizer/actuator to transition the guide stabilizer/actuator from its delivery configuration to a deployed configuration such that a distal end of the side catheter guide is laterally deflected about the shaft towards the septum of the heart and laterally stabilized in part by the guide stabilizer/actuator being in its deployed configuration. With the guide stabilizer/actuator in its deployed configuration, the side catheter guide extends proximally from its distal end that is disposed beyond a first side of the shaft, across the shaft, and to a second side of the shaft opposite the first side of the shaft, and then turns and extends proximally towards a proximal end of the shaft. The method further includes, with the distal end of the side catheter guide laterally deflected about the shaft towards the septum and laterally stabilized in part by the guide stabilizer/actuator, extending a side catheter that is disposed within the side catheter guide distally from the distal end of the side catheter guide towards and into contact with the septum. The method further includes, with the side catheter in contact with the septum, extending a septum penetrator that is slidably disposed within the side catheter distally from the side catheter such that the septum penetrator pierces the septum.

In some embodiments, an apparatus includes a body that defines a first lumen and a second lumen. The apparatus further includes a shaft that has a first section fixedly coupled to the body and extends distally from the first lumen of the body, and a second section disposed partially within and telescopable with respect to the first section of the shaft. The apparatus further includes a guide wire coupler that is coupled to the body and extends distally from within a lumen defined by the shaft. The guide wire coupler defines a guide wire lumen configured to slidably receive a first guide wire. The apparatus further includes a side catheter guide that is coupled to the body and extends distally from within the second lumen of the body. The side catheter guide is coupled to the first section of the shaft via a guide coupler. The side catheter guide is configured to be transitioned between a delivery configuration and a deployed configuration in which a distal end of the side catheter guide is laterally deflected about the guide coupler when transitioned from its delivery configuration to its deployed configuration. The apparatus further includes a guide stabilizer/actuator that is coupled to the second section of the shaft and configured to transition between a delivery configuration and a deployed configuration to cause the distal end of the side catheter guide to further laterally deflect about the guide coupler and laterally stabilize. The side catheter guide defines a lumen that is configured to slidably receive a side catheter. The side catheter defines a lumen configured to slidably receive a puncture member. The puncture member is configured to puncture tissue of a patient.

In some embodiments, an apparatus includes a body that defines a first lumen and a second lumen. The apparatus further includes a shaft that has a first section fixedly coupled to the body and extends distally from the first lumen of the body, and a second section disposed partially within and telescopable with respect to the first section of the shaft. The apparatus further includes a guide wire coupler that is coupled to the body and extends distally from within a lumen defined by the shaft. The guide wire coupler defines a guide wire lumen configured to slidably receive a first guide wire. The apparatus further includes a side catheter guide that is coupled to the body and extends distally from within the second lumen of the body. The side catheter guide is coupled to the first section of the shaft via a guide coupler. The side catheter guide is configured to be transitioned between a delivery configuration and a deployed configuration in which a distal end of the side catheter guide is laterally deflected about the guide coupler when transitioned from its delivery configuration to its deployed configuration. The side catheter guide defines a lumen that is configured to slidably receive a side catheter. The side catheter defines a lumen configured to slidably receive a puncture member. The puncture member is configured to puncture tissue of a patient.

In some embodiments, an apparatus includes a shaft having a proximal end and a distal end, and a lumen extending therethrough. The shaft defines (1) a first aperture, and (2) a second aperture and a third aperture both disposed distal to the first aperture. The apparatus further includes a first guide stabilizer/actuator ("GSA") and a second GSA both (1) circumferentially disposed about the shaft, and (2) configured to transition between a delivery configuration and a deployed configuration. The apparatus further includes a side catheter guide coupled to the shaft and extending distally into the lumen at the proximal end of the shaft, exiting the shaft through the first aperture, and extending distally between the first GSA and the second GSA and into the second aperture, and then exiting the shaft through the third aperture. The first GSA and the second GSA are configured such that transition from the delivery configuration to the deployed configuration causes a distal end of the side catheter guide to (1) laterally deflect about, and (2) stabilized relative to, a central axis of the shaft. The side catheter guide defines a lumen configured to slidably receive a side catheter. The side catheter defines a lumen configured to slidably receive a puncture member that is configured to puncture tissue of a patient.

As used herein, the terms "proximal" and "distal" refer to the direction closer to and away from, respectively, an operator (e.g., a surgeon, physician, nurse, technician, etc.) who would insert the septum puncture device into the patient, with the tip-end (i.e., distal end) of the device inserted inside a patient's body first. Thus, for example, the end of a main shaft described herein first inserted inside the patient's body would be the distal end, while the opposite end of the main shaft (e.g., the end of the main shaft being manipulated by the operator) would be the proximal end of the main shaft.

As used herein, the terms "advance," "advanced," and "advancing" each refer to distal movement. Advancing a device within a patient's vasculature, for example, refers to moving at least a portion of the device distally within the patient's vasculature. Similarly, as used herein, the terms "withdraw," "withdrawn,", and withdrawing" each refer to proximal movement. Withdrawing a device within a patient's vasculature, for example, refers to moving at least a portion of the device proximally within the patient's vasculature. In some instances, advancing and withdrawing can refer to relative movement of the device itself. Advancing a side catheter, for example, can refer to moving a side catheter distally relative to a side catheter guide to which the side catheter is movably coupled. Similarly, withdrawing the side catheter, for example, can refer to moving the side catheter proximally relative to the side catheter guide to which the side catheter is movably coupled.

The septum puncture device 100 can be used to access a left side of the heart (e.g., left atrium) from the right side of the heart (e.g., right atrium) and to deliver a guidewire to the left side of the heart. As shown in FIG. 1A, the septum puncture device 100 includes a body 110 coupled to a main shaft 120, a side catheter guide 130, a side catheter 160, and a septum penetrator 170. The main shaft 120 is coupled to the side catheter guide 130 via a guide coupler 140, the side catheter guide 130 is coupled to the side catheter 160, and the side catheter 160 is coupled to the septum penetrator 170, as shown in FIG. 1A. The side catheter guide 130 is configured to define a pathway through or across which the side catheter 160 can travel (e.g., be advanced and/or withdrawn). Said another way, and as described in further detail herein, the side catheter guide 130 can be manipulated (e.g., actuated from a delivery state to a deployed state) to guide the side catheter 160 in a desired direction (the actuated or deployed state of the side catheter guide 130 is shown in FIG. 1B), e.g., towards the left atrium.

Figure 1B:
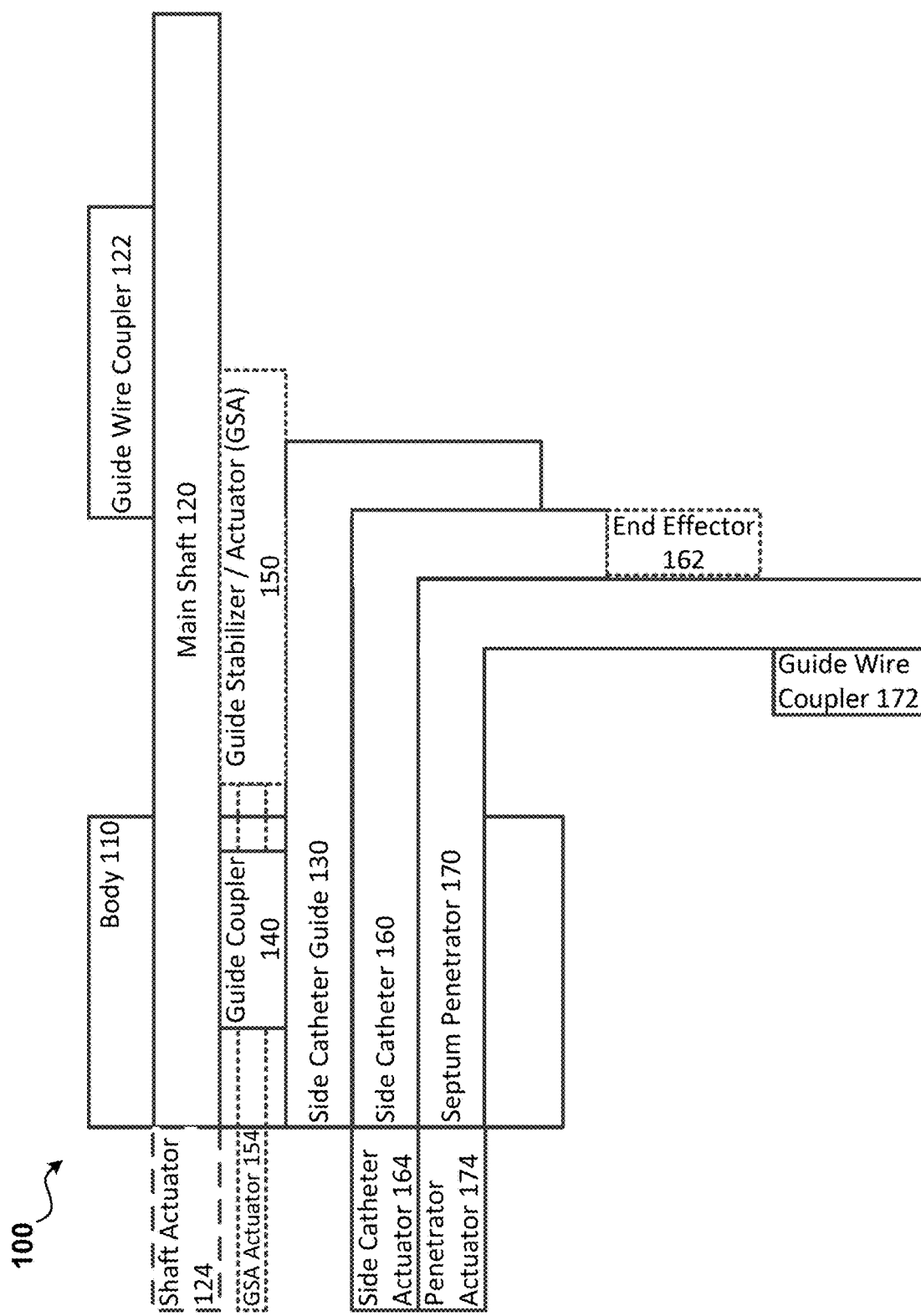
FIG. 1B is a schematic illustration of the septum puncture device of FIG. 1A, disposed in a deployed configuration.

As described in further detail herein, the guide coupler 140 can couple the side catheter guide 130 to the main shaft 120 to minimize or prevent relative translational movement between the main shaft 120 and the side catheter guide 130, but to allow relative rotational movement between the main shaft 120 and the side catheter guide 130, as illustrated schematically in FIG. 1B. In this manner, the guide coupler 140 can facilitate transition of the side catheter guide 130 from a delivery configuration (e.g., parallel to or substantially parallel to the main shaft 120), e.g., for insertion through the patient's vasculature and into the RA, to a deployed configuration such that a distal end of the side catheter guide 130 is deflected laterally (e.g., perpendicular or substantially perpendicular) relative to the main shaft 120, e.g., towards the patient's left atrium (e.g., the FO of the atrial septum). In some embodiments, the guide coupler 140 can be a hinge to facilitate lateral deflection of the side catheter guide 130 relative to the main shaft 120, as described in further detail herein. In such embodiments, for example, a distal force can be applied to a proximal end portion of the side catheter guide 130, thereby causing the hinge to rotate and cause a distal end portion of the side catheter guide (i.e., a portion of the side catheter guide 130 that extends distal to the guide coupler 140) to laterally deflect. In some implementations, the amount of lateral deflection or the defined between the side catheter guide 130 and the main shaft 120 after such lateral deflection is adjustable by the operator intra-procedure, i.e., in real-time, such that, for example, the operator has procedural flexibility when locating the target puncture location.

In some implementations, one or more of the main shaft 120, the side catheter guide 130, or the side catheter 160 can have a circular cross-sectional shape, while in other implementations, one or more of the main shaft 120, the side catheter guide 130, or the side catheter 160 can have a non-circular cross-sectional shape. In some instances, for example, the main shaft 120 and the side catheter guide 130 can have circular cross-sectional shapes, and can be operably coupled together, as discussed in further detail herein, such that the main shaft 120 and the side catheter guide 130 are at least partially disposed side-by-side (e.g., during delivery). In other instances, for example, the main shaft 120 may have a non-circular cross-section (e.g., a half-moon shape, c-shape a convex or concave shape, or any other suitable noncircular cross-sectional shape) such that when coupled to the side catheter guide 130, a portion of the side catheter guide 130 can be nestled within a space defined at least in part by the non-circular curvature of the main shaft 120. In this manner, the collective cross-sectional area, footprint, diameter, etc. of the main shaft 120 and side catheter guide 130 can be reduced. In some instances, a similar relationship can be had by the main shaft 120 and the side catheter 160 (e.g., in embodiments in which a septum puncture device does not have a side catheter guide).

In some embodiments, the septum puncture device 100 includes a side catheter guide stabilizer/actuator ("GSA") 150 (also referred to herein as "guide stabilizer/actuator"), and a GSA actuator 154 operably coupled to the GSA 150 and configured to actuate the GSA 150. In some implementations, the GSA 150 can be configured to stabilize (e.g., laterally, axially (proximally or distally), e.g., with respect to the main shaft 120) the side catheter guide 130 to facilitate the side catheter's 160 engagement with the FO and the septum penetrator's 170 penetration of the FO. In this manner, the guide coupler 140 can laterally deflect the side catheter guide 130, and the GSA 150 can stabilize the side catheter guide 130 (and in turn the side catheter 160, optional end effector 162, and septum penetrator 170) to optimize subsequent penetration of the septum and access to the left atrium. In some implementations, in addition to or instead of stabilizing the side catheter guide 130, the GSA 150 can be configured to laterally deflect (e.g., laterally deflect in addition to the lateral deflection caused or facilitated by the guide coupler 140, as described above) the side catheter guide 130 (and in turn the side catheter 160 and septum penetrator 170, given their coupling to the side catheter guide 130). In this manner, in some implementations, the guide coupler 140 and the GSA 150 can collectively laterally deflect and stabilize the side catheter guide 130 (and in turn the side catheter 160, optional end effector 162, and septum penetrator 170) to optimize subsequent penetration of the septum and access to the left atrium.

The GSA 150 can be manipulatable in any manner suitable to provide the above-described functionality. In some embodiments, for example, the GSA 150 can be a balloon, and as such, it can be configured to be inflatable and deflatable. In such embodiments, the GSA 150 can be fluidically coupled to a lumen extending from the GSA 150 to the GA actuator 154 such that the GA actuator 154 can selectively deliver fluid to the GA actuator 154 to inflate the GSA 150 (i.e., deploy the GSA 150), and selectively withdraw fluid from the GSA 150 to deflate the GSA 150 for removal of the GSA 150 from the heart (e.g., after left atrium access has been achieved).

In embodiments in which the GSA 150 is a balloon, the balloon can have any shape and size suitable to perform the desired functions described herein. In some embodiments, for example, the balloon can be cone-shaped, while in other embodiments, it can be at least partially concave, convex, circular, oval, or the like. Further, in some embodiments, the balloon can have one or more lobes, e.g., it can be bi-lobed or tri-lobed, to, for example, allow blood flow along the balloon and past the device. Further, the balloon can have additional features configured to improve stabilization of the side catheter guide 130 (e.g., improve coupling between the balloon and the side catheter guide 130). In some embodiments, for example, a balloon can have dimples, protrusions, ridges, adhesives, etc.

The balloon can be formed of any material or combination of materials suitable to perform its functionality described herein. In some embodiments, for example, the balloon can be formed of one or more of Polyethylene, Polyethylene terephthalate ("PET"), a polymer, a thermoplastic polymer, an elastomer, nylon, polyurethane, any non-compliant material, etc. The balloon can be configured to be inflated to any suitable pressure, e.g., from about 2 ATM to about 20 ATM, as an example. In some instances, higher inflation pressures can result in greater or improved rigidity of the balloon, thereby providing better stabilization of the side catheter guide, side catheter, septum penetrator, etc.

The GSA 150 can be formed of any material suitable to perform its functions described herein. In some embodiments the GSA 150 can include or be formed of shape memory material (e.g., Nitinol) and configured to be transitioned between a delivery/withdrawal configuration in which the GSA 150 is constrained, compressed, or otherwise placed in a relatively small arrangement, and a deployed configuration in which the GSA 150 is unconstrained, expanded, or otherwise placed in a larger arrangement sufficient to laterally deflect or stabilize the side catheter guide 130 as described in further detailed herein.

Similar to the guide coupler 140, in some embodiments, the GSA 150 can include or be formed of radiopaque material to assist the operator in locating that portion of the septum puncture device 100 before, during, or after deployment. In this manner, the operator can in real time selectively position the septum penetrator 170 in a position suitable to penetrate the FO upon actuation of the septum penetrator 170. In embodiments in which the GSA 150 is a balloon, for example, in some instances the GSA 150 can be inflated with a contrast agent (or a combination of a contrast agent and another fluid, such as saline) to provide visualization (e.g., under any suitable imaging modality) for the operator when the GSA 150 is disposed within the patient.

As described in further detail herein, with the side catheter guide 130 laterally deflected and stabilized at a suitable angle relative to the FO or the main shaft 120, and with (1) one or more landmark portions of the septum puncture device 100 and (2) a desired puncture location (e.g., the FO) on the septum visible to the operator from outside the patient, the operator can manipulate the main shaft 120 translationally or rotationally in any suitable manner to align the side catheter guide 130 with the FO.

Further as shown in FIG. 1A, the septum puncture device 100 includes a guide wire coupler 122 configured to couple the main shaft 120 to a guide wire (not shown in FIG. 1A) to facilitate delivery of the septum puncture device 100 into a patient (e.g., through the vasculature of the patient) and to the patient's heart, and a guide wire coupler 172 configured to couple a guide wire (not shown in FIG. 1A) to the septum penetrator 170, to facilitate delivery of that guide wire to the left side of the heart (e.g., the left atrium).

Further as shown in FIG. 1A, the septum puncture device 100 optionally includes a shaft actuator 124 operably coupled to the main shaft 120 and configured to actuate the main shaft 120 to advance or withdraw the main shaft 120 relative to the body 110. The septum puncture device 100 further includes (1) a side catheter actuator 164 operably coupled to and configured to actuate the side catheter 160 to advance or withdraw the side catheter 160, thereby transitioning the side catheter 160 between a delivery configuration and a deployed configuration (the side catheter 160 shown in an actuated or deployed configuration in FIG. 1B), and a (2) a septum penetrator actuator (or "penetrator actuator") 174 to actuate the septum penetrator 170 to advance or withdraw the septum penetrator 170, thereby transitioning the septum penetrator 170 between a delivery configuration and a deployed configuration (the septum penetrator 170 shown in an actuated or deployed configuration in FIG. 1B), as described in further detail herein.

Further as shown in FIG. 1A, the septum puncture device 100 optionally includes a GSA ("GA") 150 coupled to the main shaft 120. The optional GSA 150 is operably coupled to a GA actuator 154 that is configured to actuate the GSA 150, as described in further detail herein.

Further as shown in FIG. 1A, the septum puncture device 100 optionally includes an end effector 162 coupled to and extending distally from the side catheter 160. The end effector 162 is configured to facilitate subsequent puncture through a target puncture location, such as, for example, the FO of the septum of the heart. The end effector 162 can be configured, for example, to contact or tent the FO, as described in further detail herein. Such contact or tenting of the FO can, for example, reduce or minimize the force required to penetrate the FO and/or provide for improved force distribution to the FO. The end effector 162 can be configured to prevent inadvertent puncturing of and/or damage to the FO with the end effector 162.

In some embodiments, the end effector 162 is formed of or includes a radiopaque material such that the end effector 162 can be visualized when within the heart from outside the patient under any suitable imaging modality (e.g., fluoroscopy, echocardiography, etc.), to facilitate an operator in deploying the end effector 162, e.g., locating the end effector 162 within the heart or relative to the FO in preparation for deploying the septum penetrator 170.

In some embodiments, the end effector 162 can include multiple configurations, e.g., a delivery or withdrawal configuration, in which the end effector 162 is configured to be routed through the patient's vasculature, and a deployed configuration in which the end effector 162 is configured to facilitate subsequent penetration of the FO, as described in further detail herein. In such embodiments, for example, the end effector 162 can be delivered to the heart in a compressed, deflated, or otherwise relatively small configuration, and then transitioned into a deployed configuration in which it is expanded, inflated, or otherwise increased in size to then contact or tent the FO. Further, in some embodiments, after deployment of the end effector 162, the end effector 162 can be transitioned to a withdrawal configuration (which can be the same as or similar to its delivery configuration) in which the end effector 162 is in a compressed, deflated, or otherwise small configuration to assist in removal of the end effector 162 from the patient.

The end effector 162 can be formed of any suitable material(s) to facilitate its functionality described herein. In some embodiments, for example, the end effector 162 can be formed of shape memory material(s) (e.g., Nitinol) or a polymer, or a combination thereof (e.g., Nitinol coated with a polymer), such that it can be transitioned between a constrained or compressed arrangement (e.g., delivery or withdrawal configuration) and an unconstrained or expanded arrangement (deployed configuration). In some embodiments, for example, the end effector 152 can be or include a balloon such that it can be delivered to the heart in a deflated arrangement and then inflated (e.g., via an inflation lumen fluidically coupled to and extending proximally from the end effector 162, not shown) to a deployed configuration. Various further embodiments of an end effector are described in further detail below.

Each of the main shaft 120, the guide wire coupler 122, the side catheter guide 130, the guide coupler 140, the optional GSA 150, the side catheter 160, the septum penetrator 170, and the guide wire coupler 172 are translatable (e.g., distally advanceable and/or extendable, and proximally withdrawable and/or retractable) relative to the body 110. The side catheter 160 is translatable relative to the side catheter guide 130, and the septum penetrator 170 is translatable relative to the side catheter 160, as described in further detail herein.

The septum penetrator 170 can be sized, shaped, and formed of any material suitable to effectively penetrate and traverse a target tissue such as the FO. In some embodiments, for example, the septum penetrator 170 can be a needle. In some embodiments, the septum penetrator 170 can be a non-coring needle (e.g., a needle with a sharp tip that has a cutting edge, such as, for example, a Quincke-type needle). In some embodiments, the septum penetrator 170 can have variable material properties. In such embodiments, for example, a distal portion of the septum penetrator 170 can have a stiffness greater than a stiffness of a portion proximal to that distal portion. In this manner, the stiffer distal portion can be configured for penetration through the septum, while the portion proximal can be configured for delivery through the patient's vasculature. In some embodiments, the septum penetrator 170 can be solid-tipped and can be electrified with radiofrequency ("RF") energy to puncture the FO.

The septum penetrator 170 can have any suitable length, for example, any length suitable to reach the LA. In some embodiments, for example, the septum penetrator 170 can have an effective length (i.e., the length extendable from the distal end of the side catheter 160 (or from the distal end of the end effector 162) of about 5 mm to about 25 mm. In some instances, an effective length of the septum penetrator 170 can be about 8 mm or about 10 mm, or any length therebetween. In some embodiments, the septum penetrator 170 can contain or be configured to receive a stylet to limit or minimize tissue coring. In some embodiments, the septum penetrator 170 can include a pressure transducer (not shown) configured to monitor pressure through a lumen of the septum penetrator 170. In some embodiments, a port or leuer lock can be incorporated into the septum puncture device 100 to flush the septum penetrator 170.

Figure 2A:
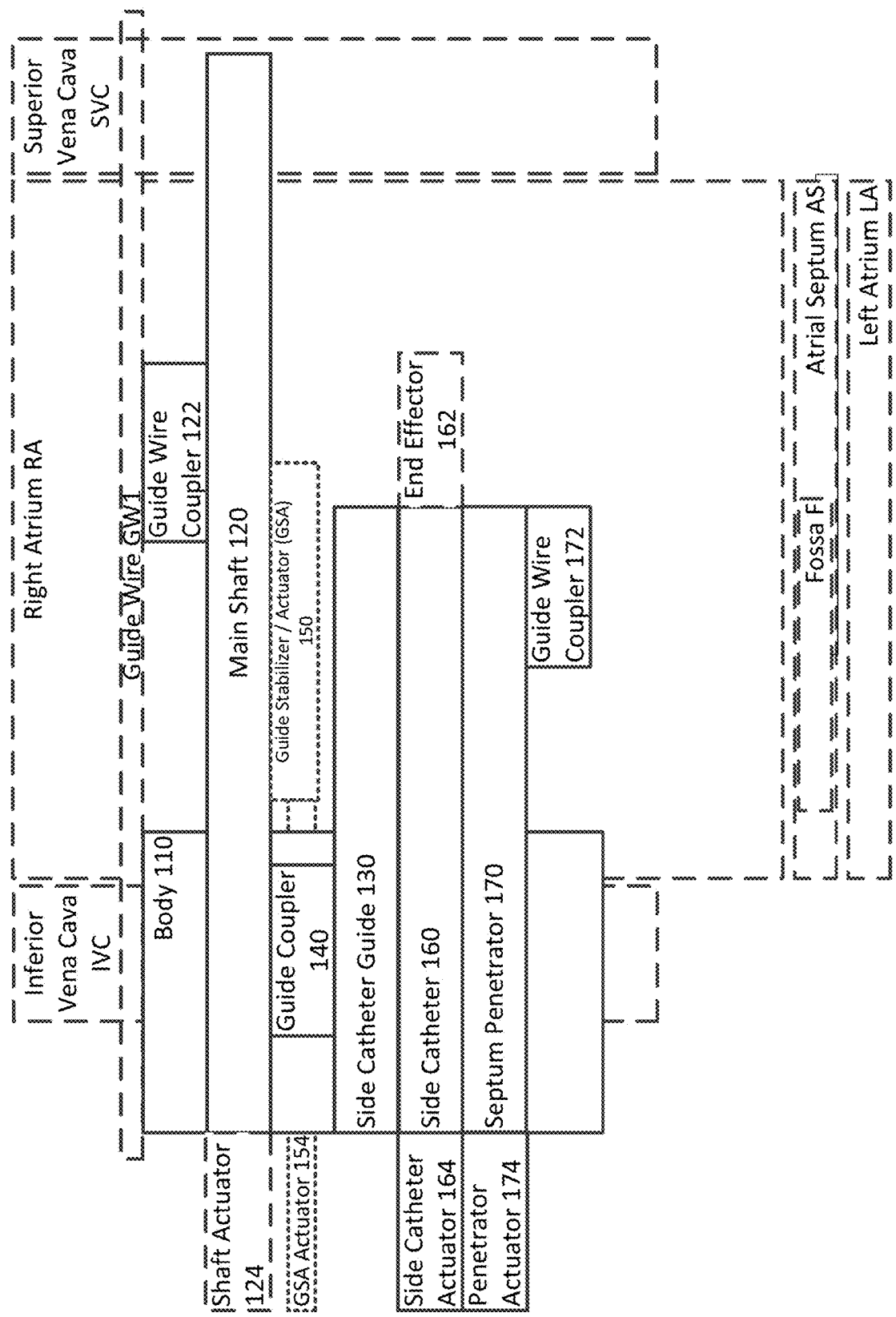
FIG. 2A is a schematic illustration of the septum puncture device of FIG. 1A, disposed in the delivery configuration within a right atrium ("RA") of a heart of a patient, and coupled to a first guide wire extending from an inferior vena cava ("IVC") of the heart across the RA and into a superior vena cava ("SVC") of the heart.
Figure 2B:
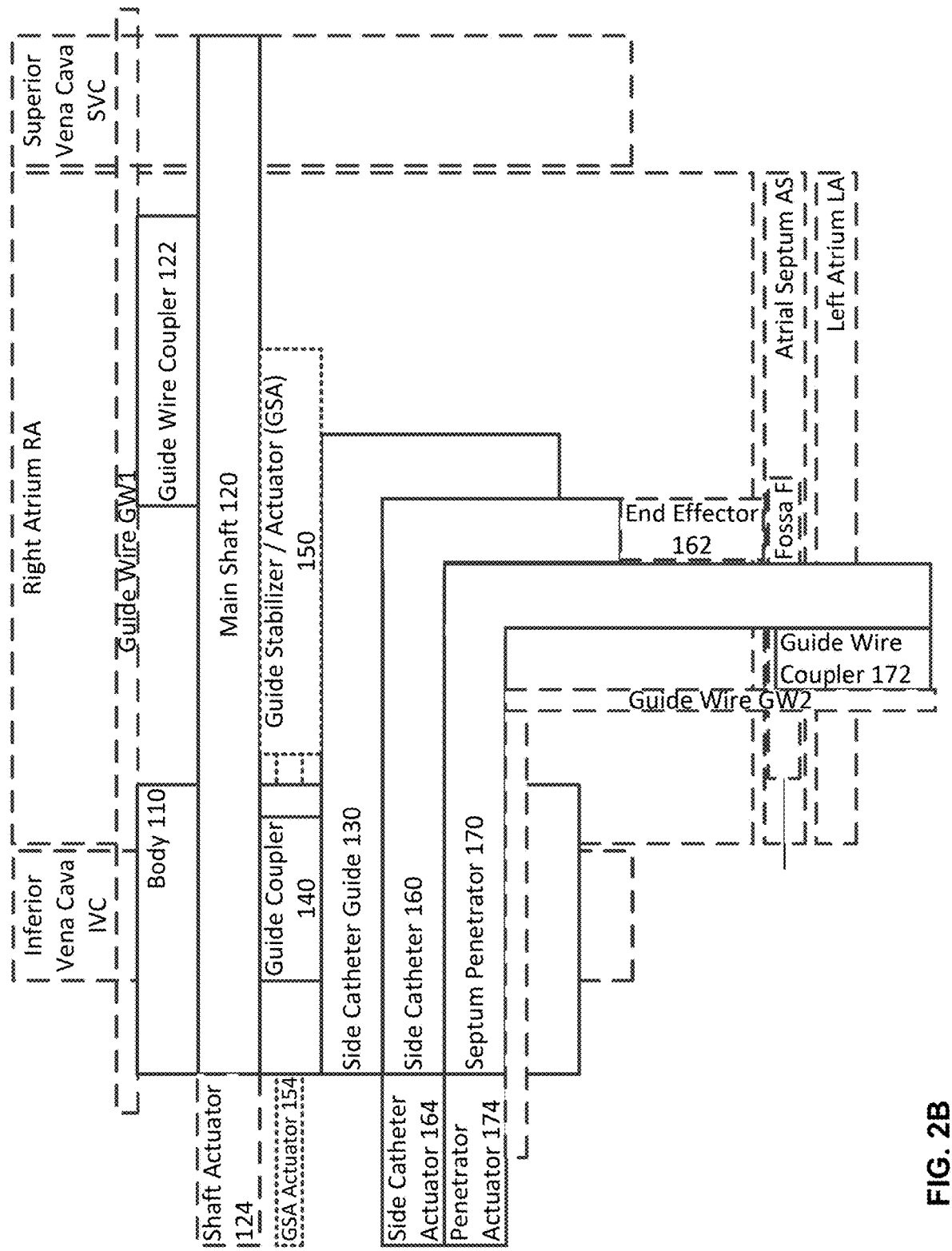
FIG. 2B is a schematic illustration of the septum puncture device of FIG. 1A, disposed in the deployed configuration and such that it has accessed and delivered to the LA a second guide wire.

Turning to FIGS. 2A and 2B to describe the septum puncture device 100 (1) in context with the anatomy of a patient and (2) in a sample procedure to access the LA of the patient, FIG. 2A is a schematic illustration of the septum puncture device 100 disposed in a delivery configuration within the RA of the heart and coupled to a first guide wire GW1 extending from the IVC across the RA and into a SVC and FIG. 2B is a schematic illustration of the septum puncture device 100 disposed in a deployed configuration and such that it has accessed and delivered to the LA a second guide wire that can be used to provide subsequent access to the LA.

In use, prior to introducing into the patient the septum puncture device 100, a guide wire GW1 can be inserted through an entry site of the patient (e.g., femoral vein puncture site) (not shown) and advanced through the patient's vasculature across the IVC and RA, and into the SVC using known, suitable techniques for guidewire delivery. With the guide wire GW1 disposed in such a manner, the septum puncture device 100 can be movably coupled to the guide wire GW1 via the guide wire coupler 122 and advanced from the entry site of the patient towards the heart. In some embodiments, the guide wire coupler 122 can be a lumen defined by the main shaft 120 through which the guide wire GW1 can be disposed and such that the main shaft 120 can be slidably disposed about the guide wire GW1. The guide wire GW1 can be any suitable size. In some embodiments, for example, the guide wire GW1 can have a diameter of about 0.014 inches to about 0.035 inches in diameter. In some embodiments, the guide wire GW1 can be about 0.025 inches diameter. With the guide wire coupler 122 movably coupled to the delivered guide wire GW1, the septum puncture device 100 can be advanced along the guide wire GW1 into the heart, as shown in FIG. 2A. More specifically, with the main shaft 120 coupled to (1) the body 110 and (2) the side catheter guide 130 via the guide coupler 140, the body 110, the main shaft 120, the guide coupler 140, the side catheter guide 130, the side catheter 160, the septum penetrator 170, and the guide wire coupler 172 all can be advanced into the heart of the patient as shown in FIG. 2A, such that body 110 extends through the IVC and into the RA, and the main shaft 120 extends into the SVC. With the main shaft 120 spanning the IVC, RA, and SVC, the main shaft 120 can provide a foundation or backstop against which the side catheter guide 130, side catheter 160, and septum penetrator 170 can be deployed and advanced towards the septum, as described in further detail herein.

In some instances, a distal end of the (1) main shaft 120, (2) side catheter guide 130, (3) side catheter 160, and septum penetrator 170 (and accompanying couplers, e.g., the guide wire coupler 122 and the guide wire coupler 172), can be disposed within the body 110 (e.g., within one or more lumens (not shown) defined by the body 110). In this manner, during delivery, the patient's anatomy can be protected or shielded by the body 110 to avoid inadvertent trauma to or contact with the patient's anatomy from such components. With a distal end of the body 110 disposed in or near the RA, the body 110 can be withdrawn (and/or one or more of the components movably coupled thereto can be advanced), thereby exposing the side catheter guide 130 and guide coupler 140 within the RA.

With the side catheter guide 130 exposed within the RA and translationally fixedly coupled to the main shaft 120 via the guide coupler 140, the side catheter guide 130 can be actuated to laterally deflect the distal end of the side catheter guide 130 (and as a result, also the side catheter 160, the septum penetrator 170, and the guide wire GW2 if disposed in the side catheter guide 130 during its lateral deflection), as shown in FIG. 2B. The side catheter guide 130 can be laterally deflected at any angle suitable to direct the side catheter 160 and septum penetrator 170, which are movably attached to the side catheter guide 130, towards the target penetration site, e.g., the FO, as shown in FIG. 2B. In some instances, an optimal angle of entry to the FO is 90 degrees or substantially 90 degrees relative to a surface line tangent to the FO, which can be about a similar angle relative to a central axis of the main shaft 120. Such a perpendicular (or substantially perpendicular) angle of entry can minimize the force required to penetrate the FO because the entire or substantially entire force vector is directed at the plane of the FO (rather than a tangential approach). Additionally, such a perpendicular (or substantially perpendicular) angle of entry, given the nature of a patient's anatomy, directs the septum penetrator 170 to a relatively large open space within the LA, thereby minimizing risk of inadvertent puncture within the LA (e.g., inadvertent puncture of a wall of the LA).

In other instances, the angle of entry relative to the FO or relative to the central axis of the main shaft 120 can be anywhere within a range of about 50 degrees to about 90 degrees. In some instances, the preferred angle of entry can be selected based on a particular therapy planned for the left side of the heart. The angle of entry, for example, defines the trajectory for the subsequent therapeutic device to enter the left side of the heart, and so in some instances an optimal angle and location of entry through the FO is based on a particular therapeutic device or procedure.

Note that the guide wire GW2 can be delivered in any suitable manner. In some instances, for example, the guide wire GW2 is disposed within the side catheter guide 130 during delivery of the side catheter guide 130, while in other instances the guide wire GW2 is inserted at a later time during the procedure, e.g., after the septum penetrator 170 has penetrated the FO and reached the LA.

With the side catheter guide 130 transitioned to its deployed configuration, in which the side catheter guide 130 is laterally deflected towards the FO, the side catheter actuator 164 can be actuated to advance the side catheter 160 along a path defined at least in part by the side catheter guide 130 and towards the FO. In some instances the side catheter 160 is advanced until it's distal end tents or otherwise contacts the FO. For embodiments that include the end effector 162, the side catheter 160 can be advanced until the end effector 162 extending from the distal end of the side catheter 160 tents or otherwise contacts the FO.

In embodiments in which the end effector 162 is expandable and compressible, the end effector 162 can be delivered to the Right Atrium RA in a compressed or relatively small configuration, and then transitioned to a deployed configuration in which the end effector 162 is expanded to a relatively larger configuration, and then advanced to engage with the FO. After sufficient penetration of the Atrial Septum AS with the septum penetrator 170, as described in further detail herein, the end effector 162 can be transitioned to its retracted or compressed configuration suitable to be withdrawn from the patient. In embodiments in which the side catheter 160 is slidably disposed within a lumen defined by the side catheter guide 130, the end effector 162 can similarly be slidably disposed within the lumen defined by the side catheter guide 130 such that the side catheter guide 130 contains the end effector 162 in its constrained or compressed configuration during delivery, and then as the side catheter actuator 164 is actuated to advance the side catheter 160 distally from the distal end of the side catheter guide 130, the end effector 162 can transition to its expanded or unconstrained configuration as or after it exits the lumen of the side catheter guide 130.

With the side catheter 160 (or end effector 162) in sufficient contact with the FO, the penetrator actuator 174 can be actuated to advance the septum penetrator 170 relative to and along a path defined at least in part by the side catheter 160. The septum penetrator 170 can be advanced through the FO and across the Atrial Septum AS and into the Left Atrium LA. In some embodiments, the side catheter 160 defines a lumen through which the septum penetrator 170 is slidably disposed such that actuating the penetrator actuator 174 advances the septum penetrator 170 through the lumen of the side catheter 160. The septum penetrator 170 can be advanced in this manner to penetrate the FO and to extend into the left atrium LA. During such penetration, the main shaft 120 can provide lateral or axial stability to the septum penetrator 170.

As the distal end of the septum penetrator 170 is advanced across the Atrial Septum AS and into the Left Atrium LA, the guide wire GW2 can follow via the guide wire coupler 172 and the septum penetrator 170 in instances in which the guide wire GW2 is coupled to the side catheter guide 130 during delivery of the side catheter guide 130. In other instances, the guide wire GW2 can be inserted at a later time during the procedure, e.g., after the septum penetrator 170 has penetrated the FO and reached the LA In some embodiments, the guide wire coupler 172 is a lumen defined by the septum penetrator 170 and through which the guide wire GW2 can be slidable disposed. In such embodiments, the guide wire GW2 can be disposed within the lumen of the septum penetrator 170 during delivery and deployment of the septum penetrator 170 into the Left Atrium LA.

With the septum penetrator 170 and the guide wire GW2 disposed within the Left Atrium LA, the guide wire GW2 can be further advanced into the Left Atrium LA by manipulation of the guide wire GW2 at its proximal end, and/or the septum penetrator 170 can be withdrawn from the Left Atrium LA, across the puncture or entry site of the FO, leaving the guide wire GW2 within the Left Atrium LA.

With the guide wire GW2 delivered to the Left Atrium LA, and extending proximally from the Left Atrium LA across the puncture or entry site of the FO, into the Right Atrium RA, the IVC, and through the vasculature of the patient to the entry point of the patient (for subsequent access to the Left Atrium AS), the septum puncture device 100 can be withdrawn from the heart proximally over guide wire GW2 and from the patient.

The guide wire GW2 can be any guide wire suitable to provide desirable subsequent access to the Left Atrium LA. In some embodiments, for example, the guide wire GW2 can be a pigtail, atraumatic guide wire or other suitable guide wire conventionally used in transseptal procedures. For example, the guide wire GW2 can have a flexible, spiral tip, pigtail, and can be configured to anchor the septum puncture device 100 to the LA, thereby limiting or preventing the guide wire GW2 from being inadvertently withdrawn or removed from the LA in response to or while the septum puncture device 100 is being withdrawn along the guide wire GW2 and from the patient. Another example guide GW2 can be a ProTrack™ Pigtail Wire from Baylis Medical Company, Inc.

The septum puncture device 100 can be configured to be withdrawn from the patient in any suitable sequence (e.g., after the guide wire GW2 has been delivered to the Left Atrium LA). With the guide wire GW2 disposed within the Left Atrium LA, for example, the portions of the septum penetrator 170 and guide wire coupler 172 disposed within the Left Atrium LA can be withdrawn relative to the guide wire GW2 and through the puncture site in the FO and into the Right Atrium RA. In embodiments in which the side catheter 160 defines a lumen through which the septum penetrator is slidably disposed, the septum penetrator 170 can be withdrawn relative to and into the lumen defined by the side catheter 160. In this manner, the septum penetrator 170, and particular it's distal that is designed to penetrate tissue, can be sheathed or shielded by the side catheter 160 to facilitate safe withdrawal from the patient and avoid inadvertent contact with the patient's heart or vasculature during removal of the septum puncture device 100 from the patient.

Similarly, the side catheter 160 can be withdrawn relative to the side catheter guide 130. For example, in embodiments in which the side catheter guide 130 defines a lumen through which the side catheter 160 is slidably disposed, the side catheter 160 can be withdrawn into the lumen of the side catheter guide 130. In embodiments in which the septum puncture device 100 includes an end effector 162, the side catheter guide 160 can be withdrawn relative to and into the lumen of the side catheter guide 130 such that the end effector 162 is also withdrawn into the lumen of the side catheter guide 130. In embodiments in which the end effector 162 has a deployed configuration with a diameter larger than an internal diameter of the side catheter guide 130, the end effector 162 can be configured to be transitioned from its deployed configuration to its withdrawal (or delivery) configuration. For example, if the end effector 162 is a balloon, it can be deflated and then withdrawn into the lumen of the side catheter guide 130. As another example, if the end effector 162 includes or is formed of shape memory material, the end effector 162 can be compressed, constrained, or otherwise transitioned to a smaller arrangement such that it can be withdrawn into the side catheter guide 130. In some instances, withdrawal of the end effector 162 into the side catheter guide 130 can cause the end effector 162 to transition to its constrained or compressed configuration.

Further, the side catheter guide 130 can be configured to transition from its deployed configuration in which its distal portion is laterally deflected relative to the main shaft 120 to its withdrawal (or delivery) configuration in which the side catheter guide 130 is at least substantially linear and parallel to the main shaft 120. In some embodiments, for example, a proximal force can be applied to a proximal end portion of the side catheter guide 130 to withdraw the side catheter guide 130 relative to the main shaft.

With the septum puncture device 100 disposed as shown in FIG. 2A, for example, after delivering the guide wire GW2, the septum puncture device 100 can be withdrawn from the heart and from the patient. For example, the body 110, and all of the components coupled thereto, can be withdrawn from the heart, through the patient's vasculature, and out through the initial entry site into the patient (e.g., a the femoral puncture site).

Although embodiments described herein refer to introducing a guide wire and septum puncture device into the patient's vasculature, and across the IVC and RA, and into the SVC, access to the RA for purposes of deploying a septum penetrator, can be accomplish in a variety of ways. In some embodiments, for example, the guide wire and septum puncture device can be inserted into a patient's jugular vein (e.g., right internal jugular vein), and then advanced into and across the SVC and RA, and into the IVC, such that a distal end of the septum puncture device is disposed in the IVC (or beyond).

Although embodiments described herein refer to a single FO puncture to deliver a single guide wire to the LA, it should be understood that the septum puncture devices described herein can be used to perform multiple punctures and to deliver multiple guide wires. In some instances, for example, a double puncture and delivery of two guide wires may be desirable, e.g., in connection with an atrial fibrillation ablation procedure. In such instances, the septum puncture devices described herein can be deployed twice to puncture the septum twice, with each puncture providing access to deliver a guide wire, as described herein. In some procedures that require multiple punctures and guide wires delivered to the LA, for example, it can be crucial that the punctures are in a particular location and located a particular distance from each other, and as described through this disclosure, the septum puncture devices described herein provide just that.

Further, instead of using a septum puncture device described herein to administer multiple punctures in series (e.g., with a single penetrator, single side catheter, single side catheter guide, etc.), in some embodiments, any of the septum puncture devices described herein can be modified to incorporate additional components. For example, in some instances, a septum puncture device can include a body and a main shaft (similar to septum puncture device 100), but also include two side catheter guides, two side catheters, two end effectors, two septum penetrators, and two guide couplers (for the guide wires being delivered), and optionally one or two guide couplers and one or two guide stabilizer/ actuators. In this manner, two side catheter guides can be deployed (i.e., laterally deflected and stabilized) simultaneously, and then two side catheters (optionally with end effectors) can be advanced, optionally simultaneously, to contact the septum, and then two septum penetrators can be advanced, optionally simultaneously, to penetrate the septum. With two punctures in the septum, two guide wires can then be delivered, optionally simultaneously. In such instances, the preferred distance between the two punctures can be selectively defined by the distance between the side catheters from which the septum penetrators are advanced.

Figure 3:
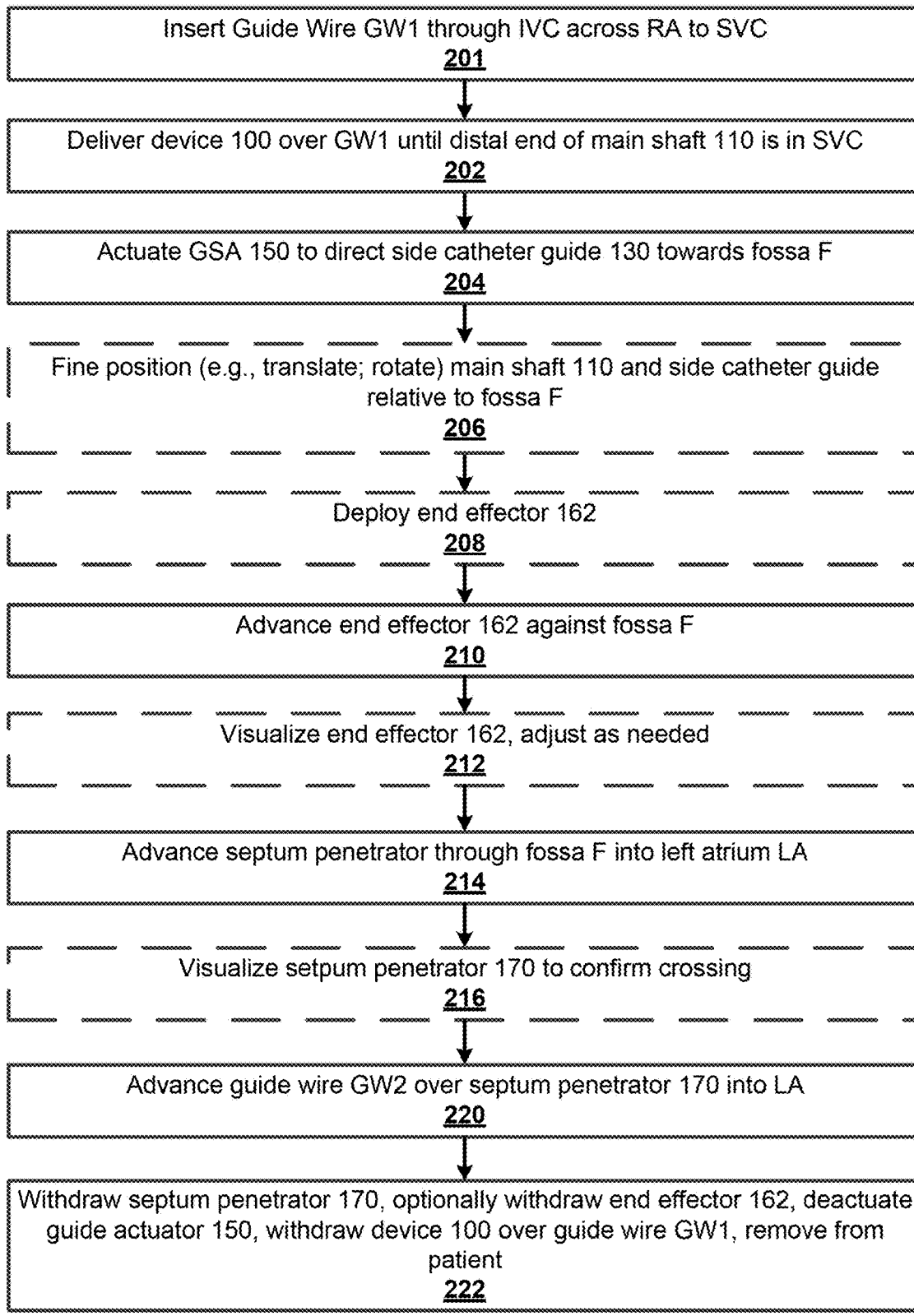
FIG. 3 is a flowchart illustrating a method of using a septum puncture device to access a left atrium of a heart of a patient, according to an embodiment.

FIG. 3 illustrates a method 200 of using the septal puncture device 100 to access a left atrium of a heart of a patient, according to an embodiment. At 201, the guide wire GW1 is inserted through the IVC, across the RA, and into SVC of the heart (e.g., via a femoral vein puncture and through the patient's vasculature disposed between the femoral vein puncture site and the IVC). At 202, the septal puncture device 100 is delivered over the guide wire GW1 until a distal end of a main shaft 110 is disposed within the SVC. At 204, the GSA 150 is actuated to laterally deflect and direct the side catheter guide 130 towards the FO. Optionally, at 206, the main shaft 110 and the side catheter guide 130 are selectively positioned (e.g., translated or rotated) relative to the FO. Optionally, at 208, the end effector 162 is deployed. At 210, the end effector 162 (or distal end of side catheter) is advanced against and into contact with the FO (e.g., to tent the FO). Optionally, at 212, the end effector 162 (or distal end of side catheter 130) is visualized from outside the patient, and if necessary, the main shaft 110 or the side catheter guide 130 are adjusted to selectively reposition the end effector 162 (or distal end of side catheter 130) relative to the FO.

At 214, the septum penetrator 170 is advanced through the FO and into the LA. Optionally, at 216, visualization techniques are used to confirm crossing of the septum penetrator 170 into the LA. At 220, the guide wire GW2 is advanced relative to the septum penetrator 170 and into the LA or the septum penetrator 170 is withdrawn relative to the septum penetrator 170, thereby leaving a portion of the guide wire GW2 in the LA. At 222, the septum penetrator 170 is withdrawn, the end effector 162 is optionally withdrawn, the main shaft 120 is withdrawn, the guide actuator 150 is deactuated, and the device 100 is withdrawn over the guide wire GW1 and removed from the patient.

Although not shown, in some embodiments, any of the main shafts described herein can define a channel through which an intra-cardiac echo can be disposed or slidably coupled to assist in navigation through the patient.

Figure 4A:
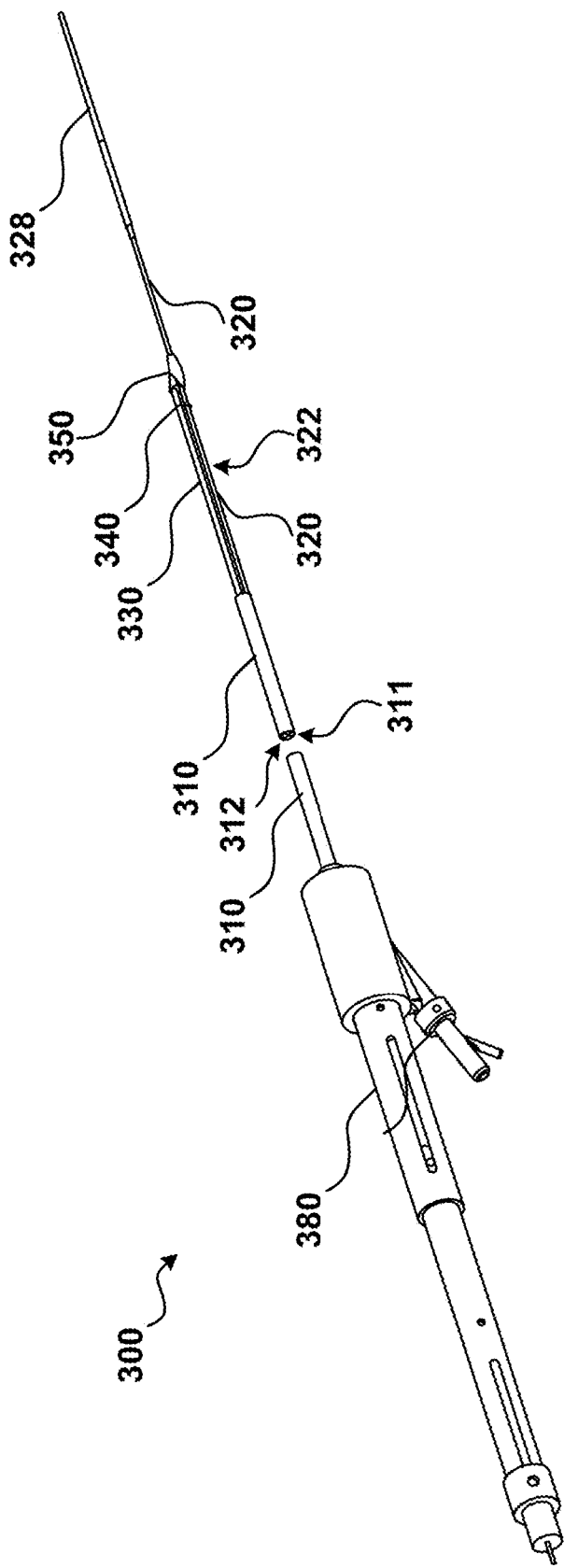
FIGS. 4A and 4B illustrate in perspective and partially exploded view a septum puncture device 300 in a delivery configuration and a deployed configuration, respectively. The septum puncture device 300 is shown partially exploded to illustrate the lumens defined by the body 310.
Figure 4B:
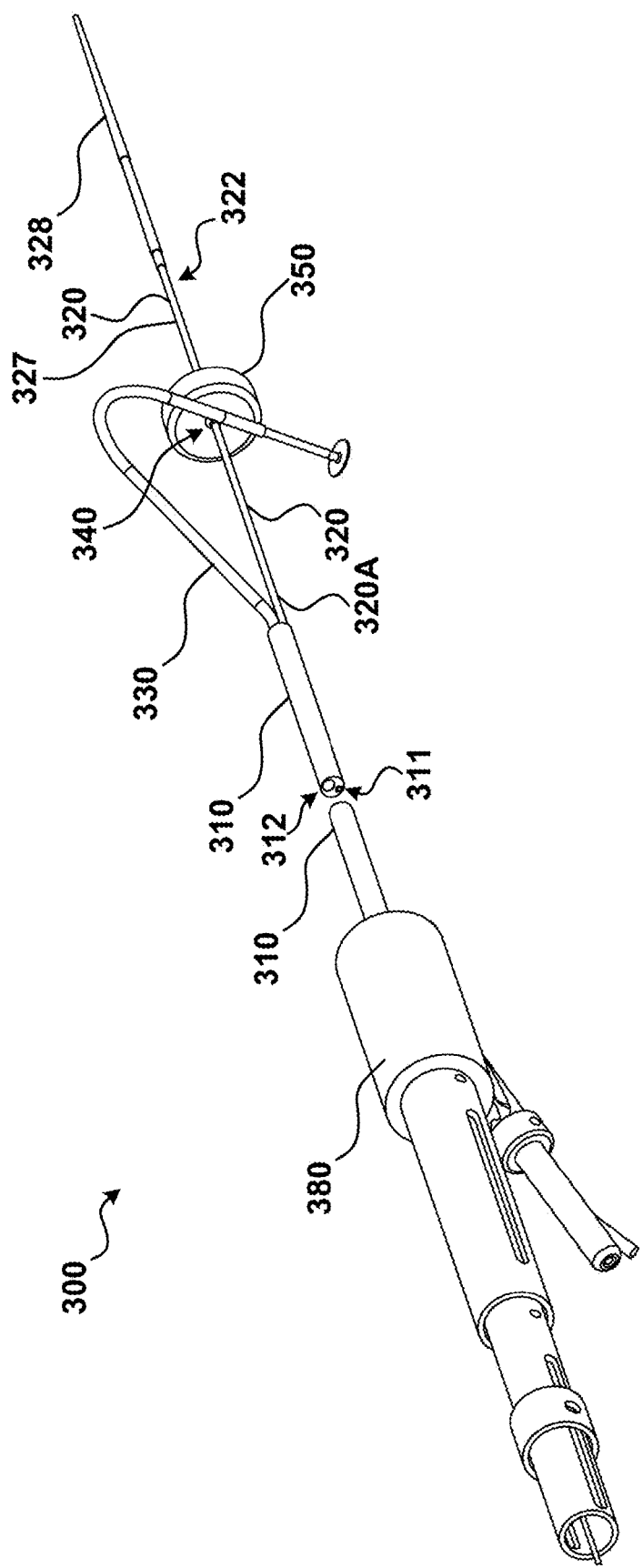

FIGS. 4A and 4B illustrate in perspective view a septum puncture device 300 in a delivery configuration and a deployed configuration, respectively; FIGS. 5A and 5B illustrate a cross-sectional view of a portion of the septum puncture device 300, in perspective view and front view, respectively; and FIGS. 6A-6H illustrate a deployment sequence at a distal end portion of the septum puncture device 300, according to another embodiment.

Similar to or the same as described with respect to the septum puncture device 100, the septum puncture device 300 can be used to access a left side of the heart (e.g., left atrium) from the right side of the heart (e.g., right atrium) and to deliver a guidewire to the left side of the heart. The septum puncture device 300 can be constructed the same as or similar to, and can function the same as or similar to, the septum puncture device 100. Thus, portions of the septum puncture device 300 are not described in further detail herein.

In this embodiment, the septum puncture device 300 includes a body 310 defining a first lumen 311 and a second lumen 312, through which various portions of the septum puncture device 300 are disposed or slidably disposed, as described in further detail herein. Coupled to the body 310 are a main shaft 320 and a side catheter guide 330, and the main shaft 320 is coupled to the side catheter guide 330 via a guide coupler 340. As shown in FIGS. 5A and 5B, a proximal end portion of the side catheter guide 330 is disposed within the second lumen 312 of the body 310. The side catheter guide 330 defines a lumen through which a side catheter 360 is slidable disposed, the side catheter 360 defines a lumen through which a septum penetrator 370 is slidably disposed, and the septum penetrator 370 defines a lumen through which a guide wire GW2 can be slidably disposed (as shown in FIGS. 5A, 5B, and 6H). Extendable from a distal end portion of the side catheter 360 is an end effector 362.

The main shaft 320 is telescopable, i.e., capable of being expanded/extended/advanced and contracted/withdrawn in sections. The main shaft 320 includes a proximal section 320A, and an inflation section 320B disposed partially within and telescopable distally with respect to the proximal section 320A. Although not shown, in some embodiments, the septum puncture device 300 can include a lock operably coupled to the inflation section 320B of the main shaft 320 and configured to translationally fix the inflation section 320B with the proximal section 320A to at least temporarily limit or prevent relative movement therebetween. In this manner, an operator can selectively enable and disable the telescopable feature of the main shaft 320, as described in further detail herein.

The proximal section 320A of the main shaft 320 is coupled to and disposed within the first lumen 311 of the body 310, and extends distally from a distal end of the body 310. In some implementations of this embodiment, the proximal section 320A of the main shaft 320 is fixedly coupled to the body 310 (e.g., welded within the first lumen 311 of the body). Disposed circumferentially about and fluidically coupled to the inflation section 320B of the main shaft 320 (the inflation section 320B being fluidically and slidably coupled to the proximal section 320A) is a guide stabilizer/actuator ("GSA") 350. In this embodiment, the GSA 350 is a balloon configured to be inflated for deployment and deflated for delivery or withdrawal. To inflate, the GSA 350 is configured to receive one or more fluids (e.g., one or more of saline, air, or a contrast agent for visualization) via the inflation section 320B. In use, for example, one or more fluids can be conveyed from a lumen defined by the proximal section 320A to a lumen defined by the inflation section 320B and into a volume defined by the GSA 350. The same fluid(s) can be withdrawn from the GSA 350 (e.g., via the same pathway used to deliver the fluid(s)) to deflate the GSA 350 such that the GSA 350 can be withdrawn from the patient. The balloon can be any size suitable to perform that desired functionality disclosed herein, for example, in some embodiments, the balloon can be about 10 mm to about 60 mm in diameter when inflated. In some embodiments, for example, the balloon can be 20 mm or about 20 mm in diameter when inflated. In some implementations of this embodiment, the septum puncture device 300 can include a GA actuator (not shown, but e.g., disposed at or operably coupled to the handle 380) configured to inflate or deflate the GSA 350.

As shown, the inflation section 320B includes an inflation portion 326, circumferentially about which the GSA 350 is disposed, and a distal portion 327 extending distally from the GSA 350. In use, for example, with the GSA 350 deployed within the right atrium of the heart of the patient, the distal portion 327 extends into the SVC of the patient to provide stability between the IVC and SVC for subsequent puncture of the FO. Although not shown, in some embodiments, the distal portion 327 can have a diameter greater than a diameter of the inflation portion 326. In this manner, the cross-sectional area or footprint collectively assumed within the atrium of the heart by the GSA 350 and the inflation portion 326 about which the GSA 350 is coupled can be minimized while the diameter of the distal portion 327 can be relatively larger to provide additional stability (e.g., by having relatively greater stiffness) to ensure a stable platform bridged between the IVC and SVC. In other embodiments, for a similar purpose, other design considerations (e.g., thickness, material, etc.) can be employed to increase the stiffness or stability of the distal portion 327, relative to the inflation portion 326.

Disposed within the first lumens defined by the main shaft 320 is a guide wire coupler 322. The guide wire coupler 322 extends distally from the body 310 and is configured in use to extend from the body 310 to the SVC of the patient. The guide wire coupler 322 defines a lumen through which the guide wire GW1 can be routed and slidably disposed. In some implementations of this embodiment, the guide wire coupler 322 is fixedly coupled (e.g., welded) to an inner surface of the main shaft 320. As shown best in FIG. 5B, an inflation volume IV (e.g., a crescent-shaped void or volume) is defined between an external surface a portion of the guide wire coupler 322 and an inner surface of the main shaft 320. This volume is fluidically coupled to the GSA 350 disposed about the main shaft 320 such that it provides a conduit through which fluid can be delivered from outside the patient to the interior of the GSA 350 when the GSA 350 is disposed within the heart of the patient.

In this embodiment, the guide coupler 340 is formed from a single thread of suture (although in other embodiments a guide coupler 340 could be formed from any suitable number of sutures, e.g., two or more). Any suture suitable to translationally fixedly couple the main shaft 320 with the side catheter guide 330, but allow relative rotationally movement between the main shaft 320 and the side catheter guide 330, can be used. In some embodiments, for example, a polymer such as Dacron, can be used.

To couple the guide coupler 340 with the main shaft 320 and side catheter guide 330, the suture can be circumferentially wrapped around each of the side catheter guide 330 and main shaft 320 separately and can be circumferentially wrapped around the side catheter guide 330 and main shaft 320 collectively. For additional securement, in some embodiments, an adhesive can be applied between the guide coupler 340 and the main shaft 320, between the guide coupler 340 and the side catheter guide 330, or between the side catheter guide 330 and the main shaft 320, or any combination thereof.

As with many minimally-invasive surgical procedures in the cardiac space, it can be important to minimize the size, and in particular the cross-sectional footprint, of the device(s) inserted into the patient. Forming the guide coupler 340 with suture addresses this goal by allowing for flush or substantially flush contact (e.g., direct or substantially direct contact) between the main shaft 320 and the side catheter guide 330. In some embodiments, for example, the suture can be wrapped around each of the main shaft 320 and the side catheter guide 330 such that the distance between an external surface of the main shaft 320 and an external surface of the side catheter guide 330 is equal to or substantially equal to an external diameter of the thread of suture. In such embodiments, using, for example, a suture having a United States Pharmacopeia ("USP") of 4-0 having an external diameter of 0.15 mm can allow for a distance between the main shaft 320 and the side catheter guide 330 of 0.15 mm. In some implementations, other suture sizes could be used, such as, for example, USP 2-0, USP 3-0, USP 5-0, USP 6-0, or USP 7-0.

Although in this embodiment the guide coupler 340 is formed of suture, in other embodiments, a guide coupler can be formed, additionally or alternatively, of other materials, such as, for example, a textile, polymer, fine wire, metal, or braided material. As another example, in some embodiments a guide coupler can be a sleeve (e.g., a textile sleeve), and in some implementations, the sleeve could serve in conjunction with a suture (e.g., formed into a cow hitch), and the free ends of the suture can be stabilized with an adhesive coating.

Further, in this embodiment, and as shown FIG. 4B, the side catheter guide 330, from top view, is disposed to the right of the main shaft 320. Offsetting the side catheter guide 330 relative to the central axis of the main shaft 320 in this manner in many instances aligns the distal end of the side catheter guide 330 with the FO, given the common anatomical location of the FO relative to the IVC, SVC, and RA. The FO is often offset from a central axis defined from the IVC to the SVC, so aligning the side catheter guide 330 to be offset from the central axis of the main shaft 320, may in some instances, place the side catheter guide 330 in a more suitable position for subsequent puncture. In this manner, the arrangement of the side catheter guide 330 and the main shaft 332 can optimize the time and number of steps required of the operator to locate the FO with the side catheter 360 (or end effector 362), for subsequent puncturing of the FO with the septum penetrator 370.

Similar to as described elsewhere herein, in this embodiment, the septum puncture penetrator 370 has variable stiffness. More specifically, a distal end portion of the septum penetrator 370 is configured to be stiffer/more rigid than a proximal end portion of the septum penetrator 370, with the distal end portion being optimized to penetrate the FO and the proximal end portion being optimized to advance (with flexibility) through the curved side catheter guide 330. Accommodating a rigid septum penetrator 370 suitable to puncture the septum and be able to make a suitable turn from the central axis of the main shaft 320 within the RA and towards the FO, can be challenging given the anatomical spatial constraints within the heart.

To address such constraints, as shown in FIG. 4B, the side catheter guide 330, when deployed, assumes a curved shape as it extends distally from the body 310. More specifically, in front view, the side catheter guide 330 extends proximally from its distal end and from below the central axis of the main shaft 320, across the central axis of the main shaft 320 and above the central axis of the main shaft 320, and then curves left and towards and into the second lumen 312 of the body 310. In this manner, a linear section at the distal end portion of the side catheter guide 360, when deployed, can have a length sufficient to slidably contain or house the septum penetrator 370. That length, for example, can be greater than a thickness of the FO. In some embodiments, that length can be about 5 mm to about 15 mm, or greater. In this embodiment, that length is greater than a diameter of the GSA 350 when deployed. Further, this curved configuration allows for a more gradual lateral deflection/turn towards the FO than would otherwise be attainable, e.g., rather than the lateral deflection towards the FO being initiated from a linear axis parallel to the central axis of the main shaft 320.

In use, for example, when advancing the main shaft 320 from entry into the patient, through the patient's vasculature, and into the IVC, RA, and SVC, it is desirable to avoid any traumatic contact with the patient's anatomy. To limit or prevent undesirable trauma to the patient from the septum puncture device 300, in this embodiment the septum puncture device 300 includes a flexible, atraumatic distal component 328 coupled to and extending from the main shaft 320. Although this embodiment illustrates the atraumatic distal component 328 as a separate component that is coupled to the main shaft 320, in other embodiments a distal end portion (e.g., a distal tip) of the main shaft 320 can be configured to be atraumatic (e.g., flexible, soft, or any other design features configured to avoid undesirable trauma to the patient). The atraumatic distal component 328, in some implementations, can be tapered such that its proximal end portion has a cross-sectional area greater than its distal end portion. In some instances, the portion of the atraumatic distal component 328 having the greatest cross-sectional area, diameter, or width, can have the same, about the same, or larger cross-sectional area, diameter, or width of the GSA 350 (when the GSA 350 is in its delivery configuration). In this manner, the atraumatic distal component 328 can facilitate a smooth delivery through the patient.

Further, as shown, the septum puncture device 300 includes a handle 380 coupled to the body 310 and configured to be manipulatable by the operator to deliver and deploy the septum puncture device 300 as described in more detail herein. The handle 380 can include or be coupled to one or more shaft actuators (when included, not shown), the GA actuator 354, a side catheter actuator (not shown), and a penetrator actuator (not shown). Further, the handle can be manipulatable to actuate one or more of the actuators.

Turning now to an exemplary deployment sequence, FIGS. 6A-6H illustrate in side view an exemplary deployment sequence of and at a distal end portion of the septum puncture device 300, according to an embodiment.

FIG. 6A illustrates a portion of the septum puncture device 300 prior to deployment. It is in this configuration that the septum puncture device 300 can be inserted into the patient (e.g., via a femoral vein puncture), through the patient's vasculature, and into the heart of the patient such that the main shaft 320 extending distally from the body 310 spans the IVC, RA, and SVC to provide a stable platform against which the septum puncture device 300 can be deployed to puncture the FO. As shown, during delivery the septum puncture device 300 is in its delivery configuration in which the main shaft 320 and the side catheter guide 330 are parallel or substantially parallel to each other. In this manner, for example, the cross-sectional footprint of the septum puncture device 300 can be minimized or optimized for minimally-invasive delivery through the patient.

As shown in FIG. 6A, during delivery the distal end of the side catheter guide 330 is in physical contact with a proximal side of the GSA 350. In some instances, for example, the proximal side of the GSA 350 and the distal end of the side catheter guide 330 can be in such close contact that a portion of the distal end of the side catheter guide 330 can be nestled partially within, or covered partially by the proximal side of the GSA 350. In this manner, the GSA 350 can shield the distal end of the side catheter guide 330 from inadvertent contact with the patient's anatomy. In such instances, a subsequent step can include telescoping the main shaft 320, including advancing the inflation section 320B of the main shaft 320 to separate the distal end of the side catheter guide 330 from the GSA 350 or unshield the distal end of the side catheter guide 330. In other instances, the septum puncture device 300 can be delivered with separation between the side catheter guide 330 and the GSA 350 such that the unshielding step is unnecessary.

With the main shaft 320 extended from the IVC to the SVC, and the GSA 350 and guide coupler 340 disposed within the RA, the side catheter guide 330 can be deployed, as shown in FIG. 6B. More specifically, a distal force is applied to a proximal end portion of the side catheter guide 330 such that the force is transferred to the guide coupler, causing the guide coupler 340 to rotate or deflect, resulting in rotation or deflection of a portion of the side catheter guide 330 extending distally from the guide coupler 340 about the guide coupler 340. In this embodiment, as shown in FIG. 6B, the deflection occurs such that the distal end portion of the side catheter guide 330 laterally deflects about 90 degrees and about perpendicular to the central axis of the main shaft 320. In alternative embodiments, the lateral deflection may be less than about 90 degrees, such as, for example, about 15 degrees, about 30 degrees, about 45 degrees, about 60 degrees, about 75 degrees, or any degrees therebetween. In some instances, the lateral deflection may be about 75 degrees to about 85 degrees, e.g., about 80 degrees. In even further embodiments, the lateral deflection may be greater than about 90 degrees, such as, for example, about 105 degrees, about 120 degrees, about 135 degrees, or any degrees therebetween. Although in this embodiment actuation of the side catheter guide 330 is sufficient to laterally deflect a portion of the side catheter guide 330 such that that portion is about perpendicular to the central axis of the main shaft 320, in other embodiments, for example, in which the lateral deflection is less than about 90 degrees, additional lateral deflection/rotation can be applied by the GSA 350, as discussed in further detail herein.

Next, the GSA 350 is actuated, i.e., in this embodiment, inflated, as shown in FIG. 6C. More specifically, fluid is administered to the GSA 350 to inflate the GSA 350. With the GSA 350 inflated, the inflation section 320B about which the GSA 350 is disposed is telescoped proximally, including withdrawn relative to the proximal section 320A such that the proximal side of the GSA 350 is brought into physical contact with the side catheter guide 350, as shown in FIG. 6D. The inflation section 320B can be withdrawn relative to the proximal section 320A any distance and with any safely-administrable amount of force suitable to sufficiently contact or stabilize the side catheter guide 330. In some instances, such withdrawal can apply a force to the side catheter guide 350 to further laterally deflect the side catheter guide 350 (although as shown and described in this embodiment, the side catheter guide 350 is laterally deflected about 90 degrees prior to being physically contacted by the GSA 350), resulting in the distal end portion of the side catheter guide 350 being, for example, perpendicular or about perpendicular to the central axis of the main shaft 320 or a surface line tangent to the FO or main shaft 320. Further, such withdrawal force causes the GSA 350 to contact or abut the distal end portion of the side catheter guide 350 to stabilize (e.g., laterally, axially (proximally or distally)) relative to the main shaft 320. Although not shown, in some instances, the withdrawal force can be sufficient to cause the GSA 350 to become indented with an impression of the side catheter guide 330 or envelop a portion of the side catheter guide 330. In this manner, the side catheter guide 330 can be sufficiently stabilized and temporarily sufficiently coupled to the GSA 350. In some embodiments, the GSA 350 can be configured to possess variable amounts of compliance. In some embodiments, for example, a proximal portion of the GSA 350 that is configured to contact the side catheter guide 330 can have a first level of compliance while another portion of the GSA 350 can have a second level of compliance that is different from the first level of compliance. Further, in some embodiments, the proximal side of the GSA 350 can include features configured to further stabilize the side catheter guide 330 relative to the GSA 350. These features can include, for example, dimples, protrusions, adhesives, or the like.

With the GSA 350 actuated and in sufficient contact with the side catheter guide 330 and providing sufficient stabilization of the side catheter guide 330 relative to the main shaft 320, the end effector 362 is deployed, as shown in FIG. 6E. To deploy the end effector 362, the side catheter 360 from which the end effector 362 distally extends is advanced relative to the side catheter guide 330 such that the end effector 362 is allowed to expand to its expanded/deployed configuration as it is released from its constrained configuration within the lumen of the side catheter guide 330.

With the end effector 362 deployed, the end effector 362 can be advanced towards and into contact with the FO to tent the FO. As described elsewhere herein, both the end effector and the tenting of the FO (or other portion of the septum) are visible to the operator from outside the patient via various imaging technologies, such as, for example, ultrasound or related suitable imaging technologies. To advance the end effector 362 towards and into contact with the FO, the side catheter 360 can be advanced (e.g., by actuating the side catheter actuator, not shown) relative to the side catheter guide 330) or by manipulating (i.e., translating or rotating) the main shaft 320.

In instances in which the operator is not satisfied with the location on the septum contacted or tented by the end effector 362, e.g., if the end effector 362 is misaligned with the FO, the end effector 362 can be withdrawn from contact with the FO or septum (e.g., by withdrawing the side catheter 360 relative to the side catheter guide 330 or by manipulating the main shaft 320), and then the operator can make another approach at landing the end effector 362 on the FO in a manner sufficient for subsequent puncturing of the FO. This process can be repeated until the operator is satisfied.

With the FO properly tented by the end effector 362, the septum penetrator 370 can be advanced relative to the side catheter 360 and the end effector 362, and shown in FIG. 6G, and through the FO and into the LA. With the FO sufficiently penetrated by the septum penetrator 370, and a distal end of the septum penetrator 370 disposed within the LA, the guide wire GW2 is advanced relative to and through the lumen defined by the septum penetrator 370 such that at least a distal end portion of the guide wire GW2 exits the distal end of the septum penetrator 370 (as shown in FIG. 6H) and advances into the LA, which can be confirmed by the operator under imaging technologies. Once confirmed that the GW2 is sufficiently disposed within the LA, the septum penetrator 370 can be withdrawn relative to and into the lumen of the side catheter 360, the GSA 350 can be deflated (e.g., into its delivery configuration), and the side catheter guide 330 can be withdrawn into its linear, pre-deployed, delivery configuration, suitable for removal from the patient. Further, in some instances, the end effector 362 can be withdrawn relative to and into the lumen defined by the side catheter 360.

With the septum penetrator 370 withdrawn from the LA, the operator can manipulate the septum puncture device 300

(e.g., the handle 380, the body 310, or the main shaft 320) to withdraw the entire septum puncture device 300 along the guide wire GW2 until the septum puncture device 300 exits the patient.

Figure 7B:
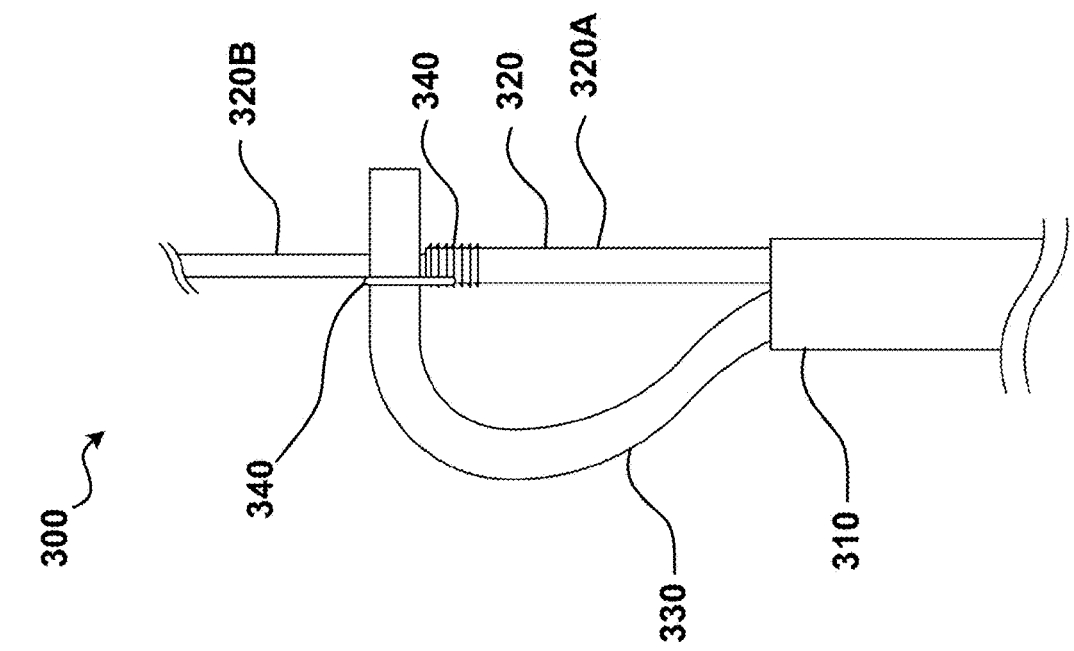
FIGS. 7A and 7B illustrate a portion of the septum puncture device 300 in its delivery configuration and its deployed configuration, respectively.
Figure 7A:
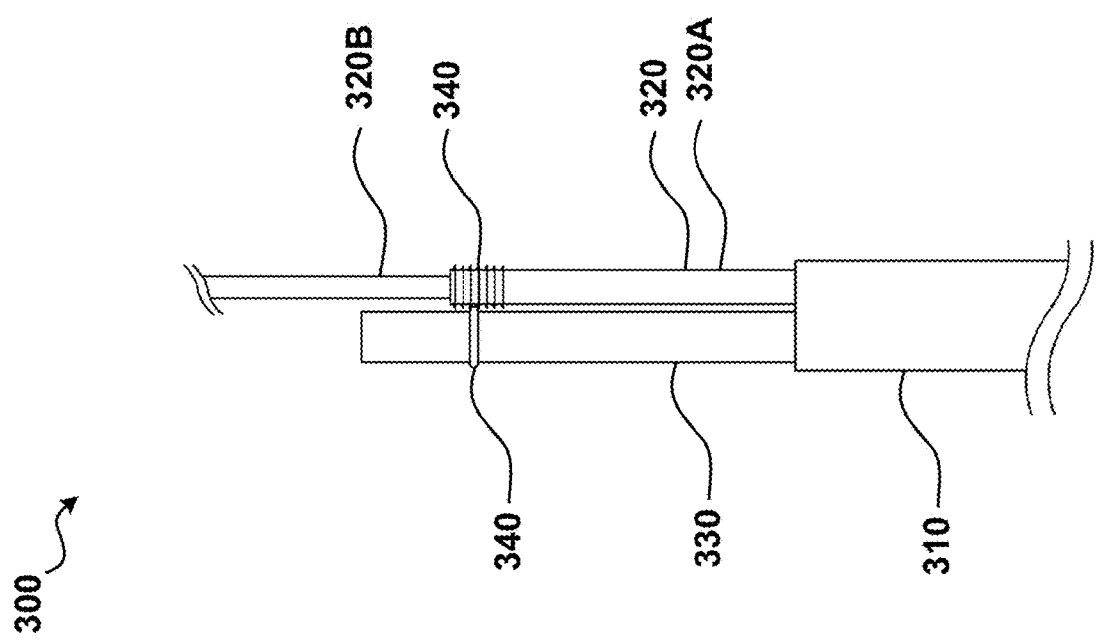

FIGS. 7A and 7B further illustrate actuation of or transition of the side catheter guide 340 and the guide coupler 340 between their respective delivery (FIG. 7A) and deployed configurations (FIG. 7B). As shown in FIG. 7A, with the septum puncture device 300 disposed in its delivery configuration, the main shaft 320 and the side catheter guide 330 extend distally and relatively parallel or about parallel from the body 310, and are coupled to each other via the guide coupler 340. More specifically, the guide coupler 340 is coupled to and between the side catheter guide 330 and the proximal section 320A of the main shaft 320. With the guide coupler 340 coupled to the proximal section 320A of the main shaft 320, the inflation section 320B of the main shaft 320 can be advanced relative to the proximal section 320A, in some instances, for example, without disturbance to or by the guide coupler 340.

As described in further detail herein, the side catheter guide 340 can be configured to transition its delivery configuration (FIG. 7A) to its deployed configuration (FIG. 7B) in response to a distal force applied to a portion of the side catheter guide 340 that is disposed proximal to the guide coupler 340 (e.g., a distal force applied at the handle 380). With a portion of the side catheter guide 340 translationally fixed but rotationally movably coupled to the proximal section 320A of the main shaft 320 via the guide coupler 340, the side catheter guide 330 is configured to deform as shown in FIG. 7B, and such that the portion of the side catheter guide 330 that is disposed distal to the guide coupler 340 rotates clockwise about the guide coupler 340.

Further, the distal force applied to the side catheter guide 340 causes the portion of the guide coupler 340 disposed about the side catheter guide 340 to rotate about the portion of the guide coupler 340 that is disposed about the main shaft 320, as shown in FIG. 7B. Said another way, the distal force applied to the side catheter guide 340 is transferred at least in part to the guide coupler 340 such that the hinging feature of the guide coupler 340 is activated to allow the side catheter guide 330 to transition from its delivery configuration to its deployed configuration.

In this embodiment the guide coupler 340 is formed of suture, and is threaded or routed about and between both the main shaft 320 and the side catheter guide 330 to limit or prevent relative translational movement but allow rotational relative movement between the main shaft 320 and the side catheter guide 330, as described in further detail herein. The suture can be threaded or routed about and between the main shaft 320 and the side catheter guide 330 in any manner suitable to provide it's intended functionality. In some implementations, a fastener can be added to the suture to improve its fixation to the main shaft 320 and the side catheter guide 330. The fastener, can be, for example, an adhesive, which in some instances, is used to bond the wraps/loops of suture and the loose ends of the suture.

Figure 8:
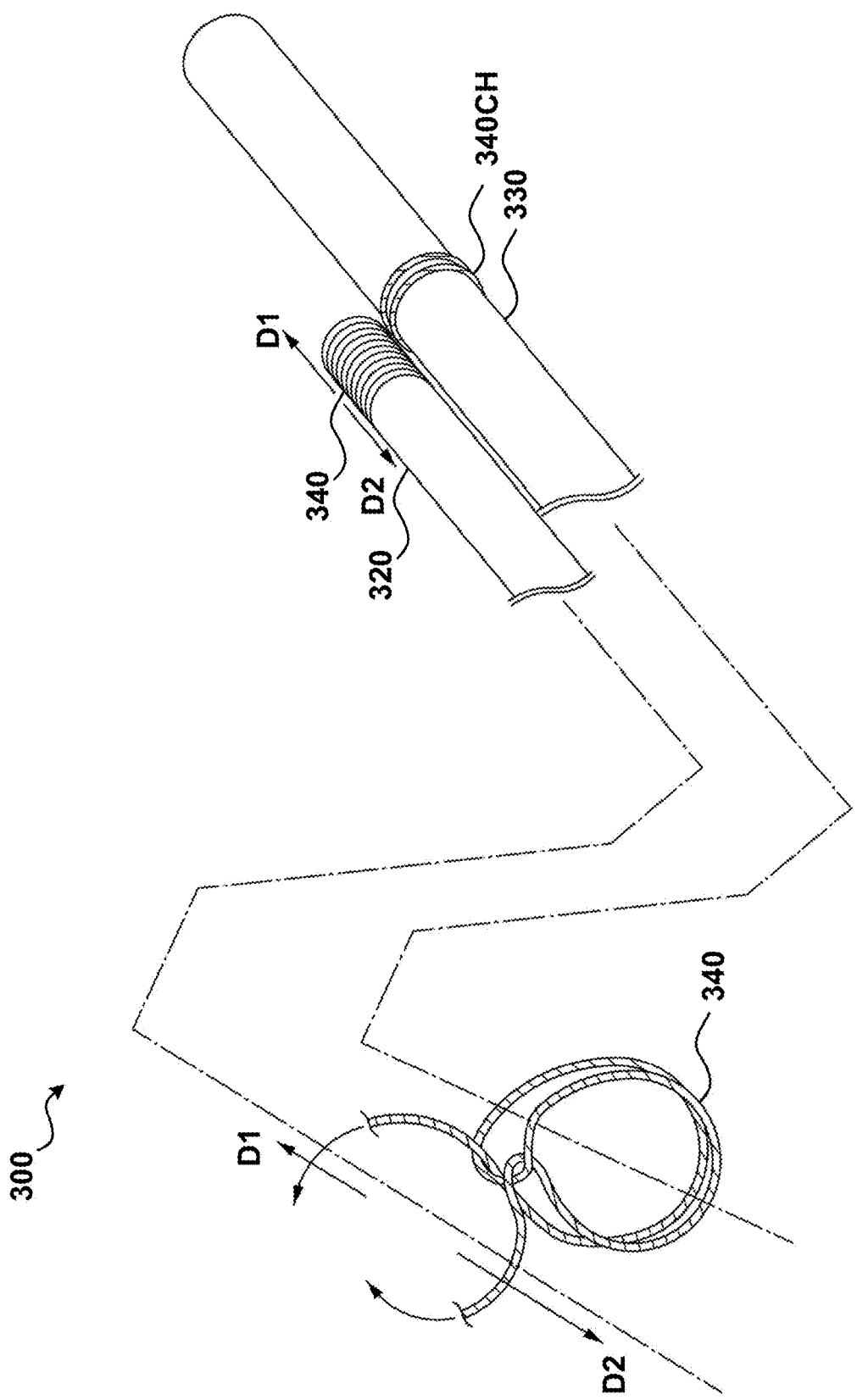
FIG. 8 illustrates the guide coupler 340 of the septum puncture device 300 coupled to and between the main shaft 320 and the side catheter guide 330 in an assembled arrangement (at right), and in detailed, partially assembled, arrangement (at left).

FIG. 8 illustrates an example arrangement of the suture (the guide coupler 340). As shown (at left of FIG. 8), the suture is initiated with a cow hitch 340CH about the side catheter guide 330, and then a first working end of the suture is routed in a first direction D1 about the main shaft 320, spiraling or looping about the main shaft 320, and a second working end of the suture is routed in a second direction D2 (opposite the first direction D1) about the main shaft 320, spiraling or looping about the main shaft 320 in a manner similar to the first working end. Each end of the suture can be secured by being tucked under, between, or threaded through one or more of the loops, or the suture can be secured by an additional fastener, such as, for example, an adhesive coating.

Figure 9:
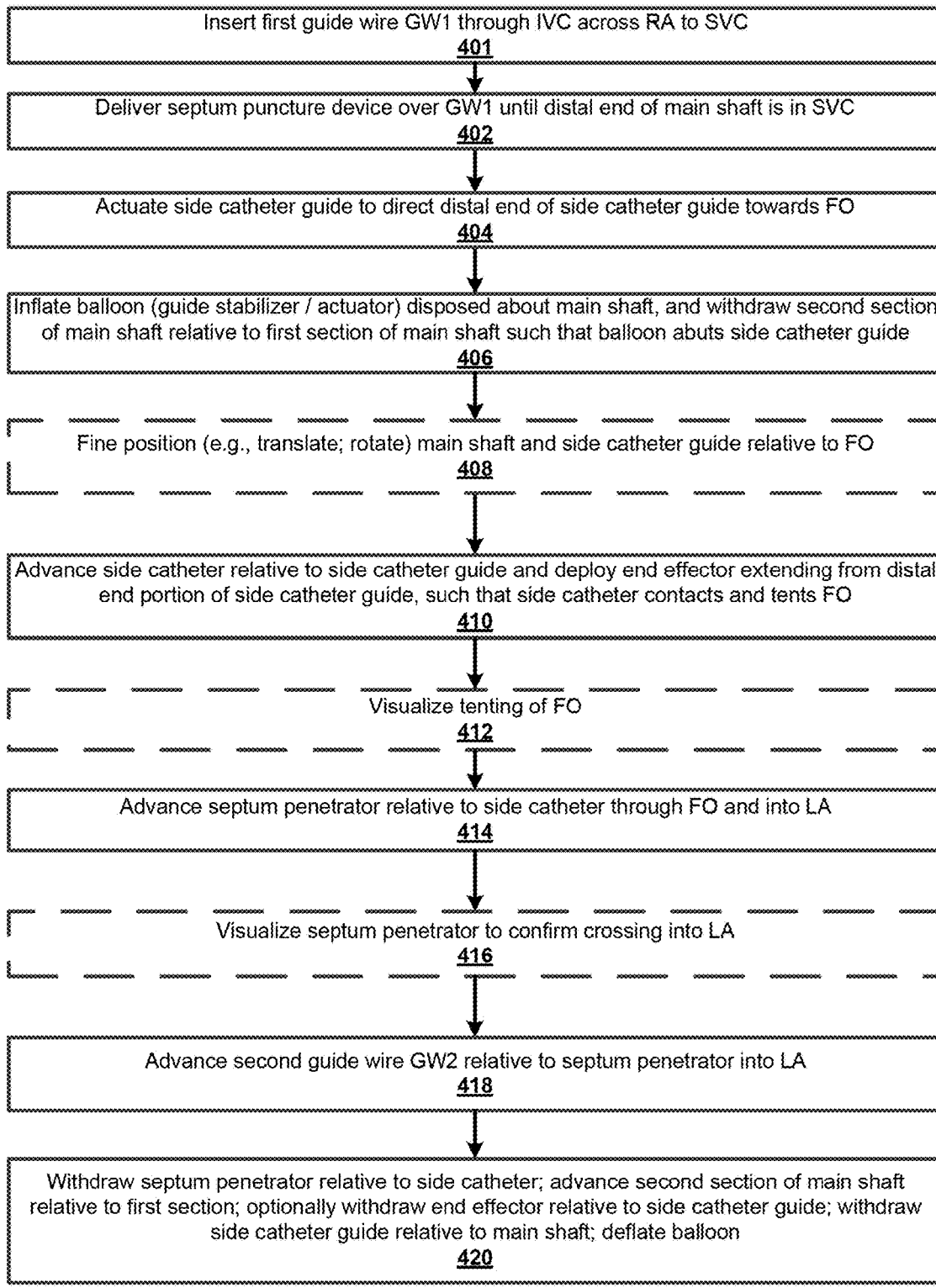
FIG. 9 is a flowchart illustrating a method of using a septum puncture device to access a left atrium of a heart of a patient, according to an embodiment.

FIG. 9 illustrates a method 400 of using the septum puncture device 300 to access a left atrium of a heart of a patient, according to an embodiment. At 401, the guide wire GW1 is inserted through the IVC, across the RA, and into SVC of the heart (e.g., via a femoral vein puncture and through the patient's vasculature disposed between the femoral vein puncture site and the IVC). At 402, the septum puncture device 300 is delivered over the guide wire GW1 until the distal end of a main shaft 320 is disposed within the SVC. In some instances, the guide wire GW1 can be advanced or wedged into the uppermost aspect of the SVC (e.g., the bifurcation of the SVC into the right and left brachiocephalic (innominate) veins, to provide additional stability for the main shaft 520 and associated components (e.g., side catheter guide 530). At 404, the side catheter guide 330 is actuated to direct a distal end of the side catheter guide 330 towards a FO of a septum of the heart. At 406, the balloon 550 that is disposed about the main shaft 320 is inflated, and the inflation section 320B of the main shaft 320 is withdrawn relative to the proximal section 320B of the main shaft 320 such that the balloon 350 abuts the side catheter guide 330.

At 408, optionally, the main shaft 320 and the side catheter guide 330 are fine positioned (e.g., translated, rotated, etc.) relative to the FO. At 410, the side catheter 360 is advanced and the end effector 362 is deployed from a distal end portion of the side catheter guide 330 such that the side catheter 360 contacts and tents the FO. At 412, optionally, an operator visualizes the tenting of the FO. At 414, the septum penetrator 370 is advanced relative to the side catheter 360 through the FO and into the LA. At 416, optionally, an operator visualizes the septum penetrator 370 to confirm that the septum penetrator 370 crossed into the LA. At 418, the second guide wire GW2 is advanced relative to the septum penetrator 370 into the LA. At 420, the septum penetrator 370 is withdrawn relative and into a lumen defined by the side catheter 360, the inflation section 320B of the main shaft 320 is advanced relative to the proximal section 320A, the side catheter guide 330 is withdrawn relative to the main shaft 320, and the balloon 350 is deflated. Optionally, at 420, the end effector 362 is withdrawn relative to the side catheter guide 330. In some instances, withdrawing the end effector 362 relative to the side catheter guide 330 includes withdrawing the end effector 362 into the lumen defined by the side catheter guide 330 to place the end effector 362 back into its delivery configuration.

Although the septum puncture device 300 is shown and described as having the GSA 350, in alternative embodiments, for example, a septum puncture device could be similar to the septum puncture device 300, but not include a GSA. In such embodiments, the septum puncture device could, for example, rely on the guide coupler for both lateral deflection and stabilization of the side catheter guide, side catheter, and septum penetrator. FIGS. 7A and 7B can be referred to as an illustrative example of such an alternative embodiment, given that these figures show only a portion of the septum puncture device 300, not including the GSA 350.

Figure 10:
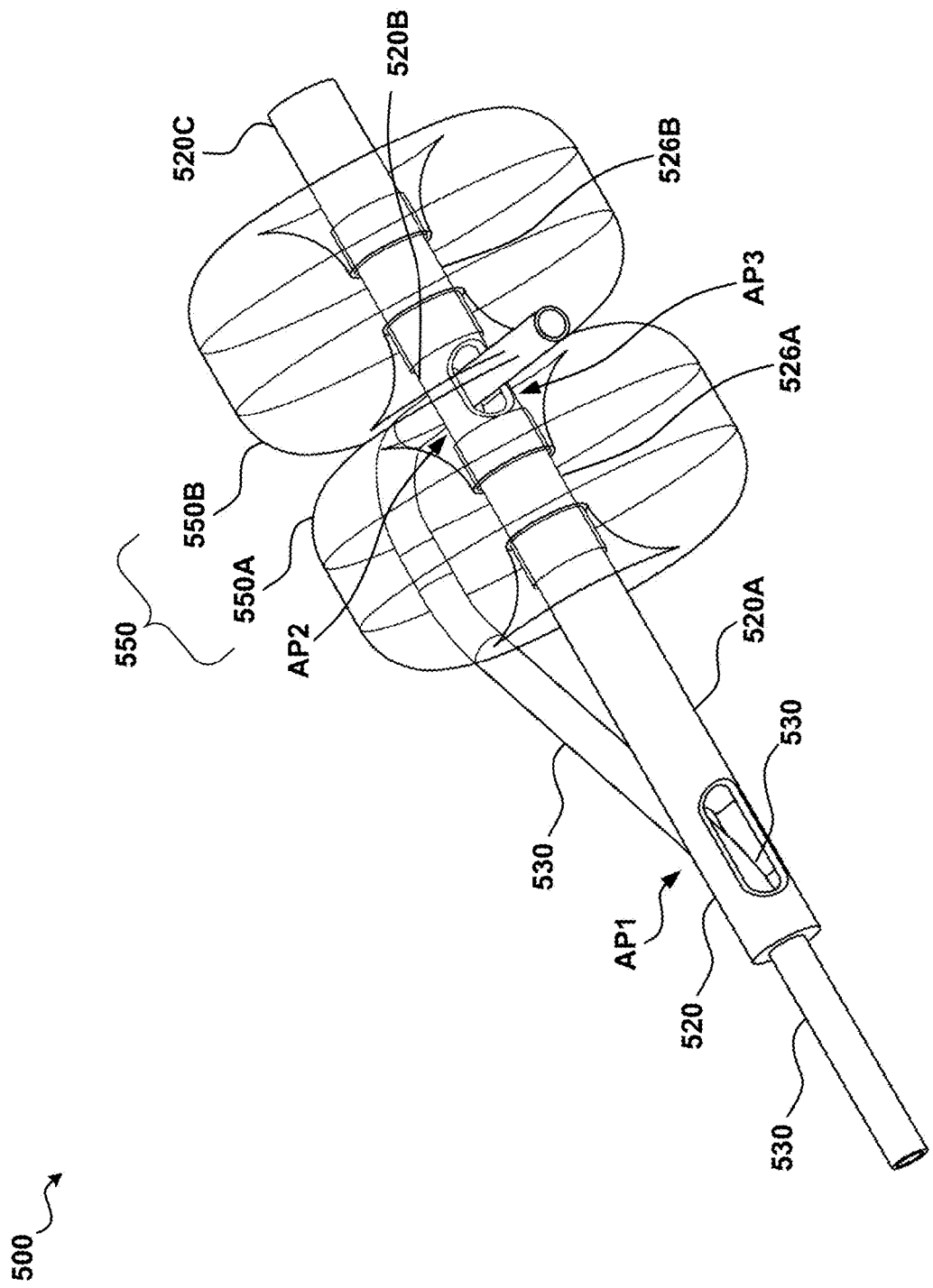
FIGS. 10-12 illustrate in perspective bottom view, perspective side view, and side view, respectively, a portion of a septum puncture device 500 in a deployed configuration, according to another embodiment.
Figure 11:
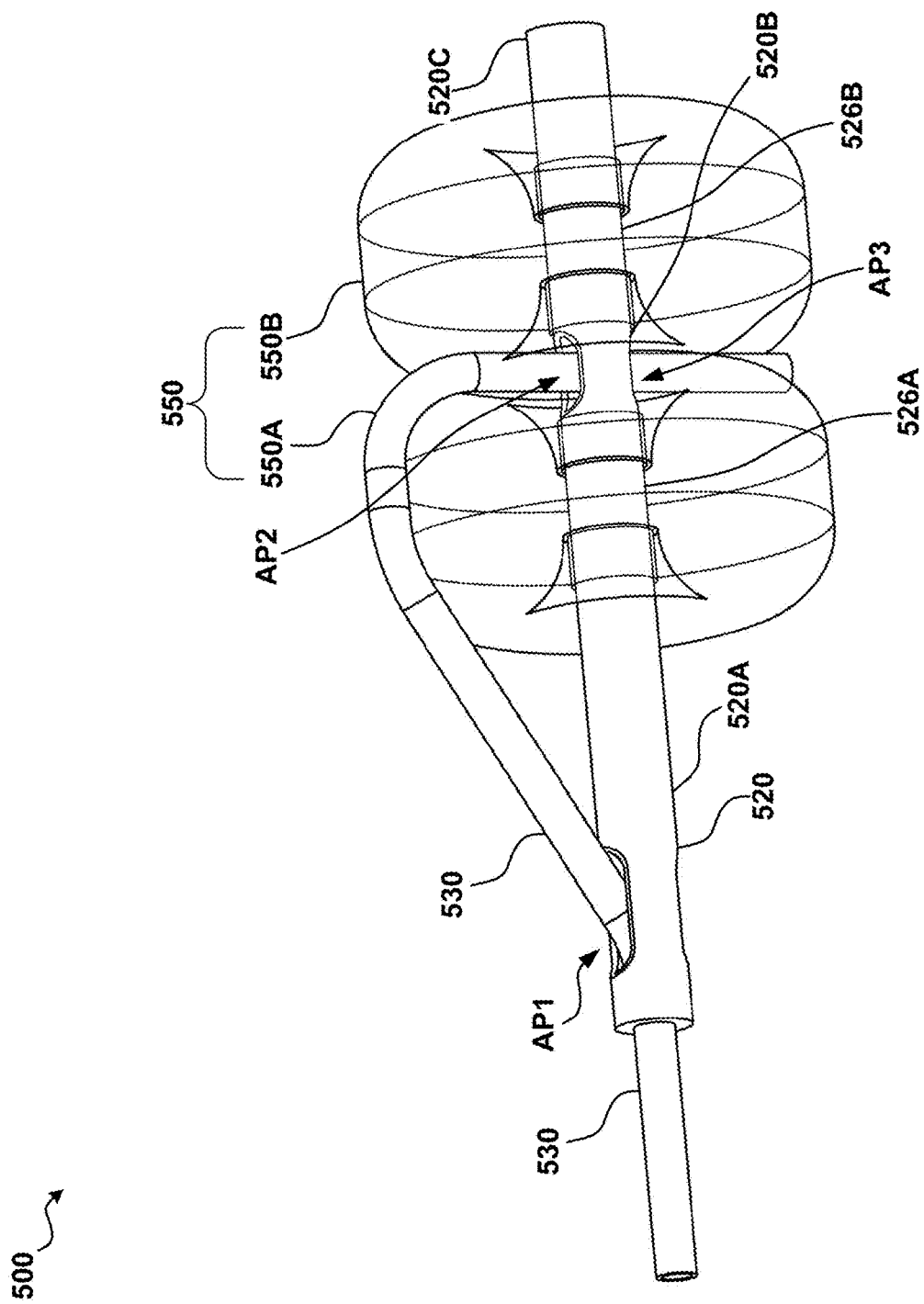
Figure 12:
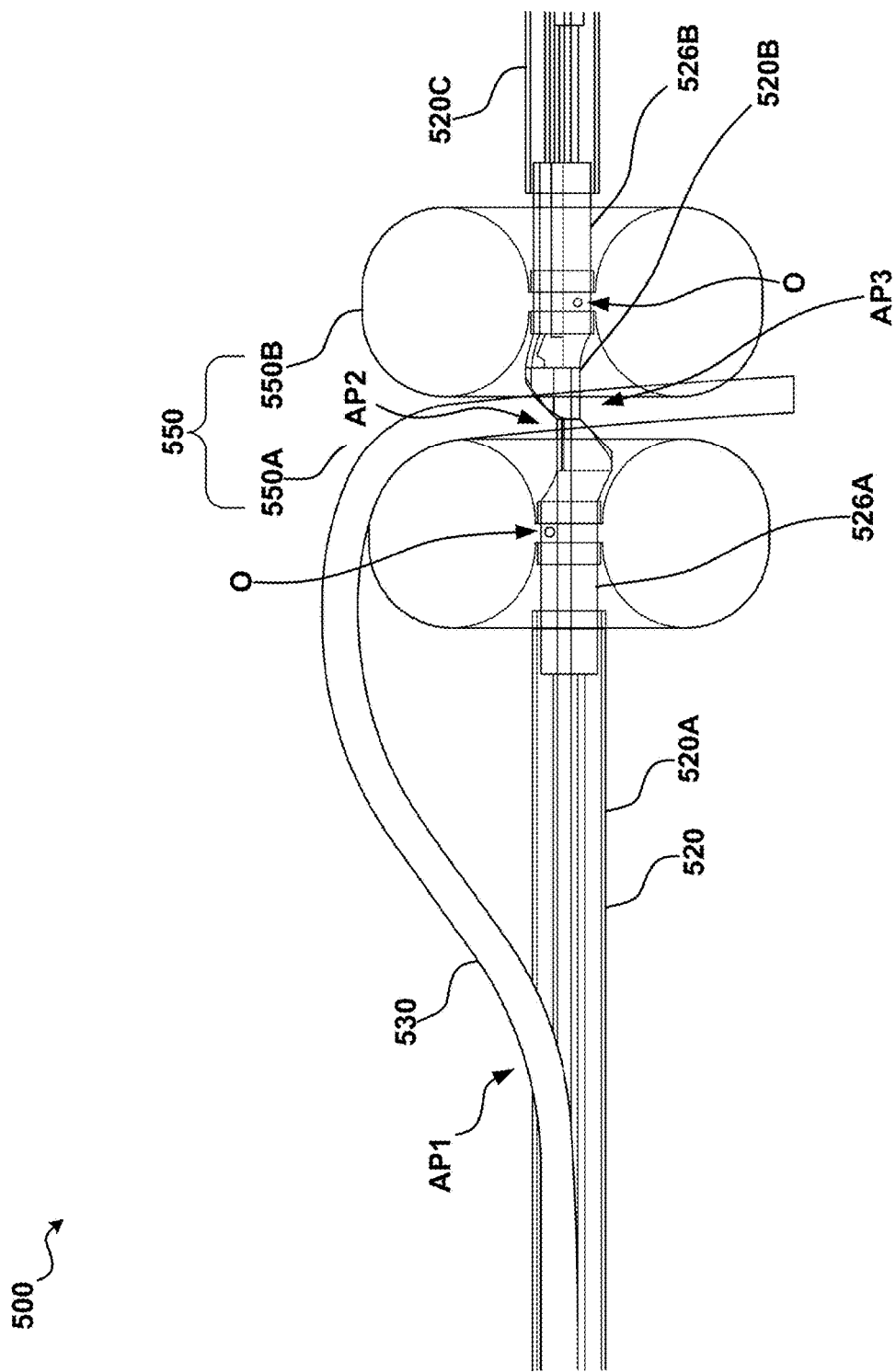

FIGS. 10-12 illustrate in perspective bottom view, perspective side view, and side view, respectively a portion of a septum puncture device 500 in a deployed configuration, according to another embodiment. Similar to or the same as described with respect to other septum puncture devices described herein (e.g., septum puncture device 100, septum puncture device 300, etc.), the septum puncture device 500 can be used to access a left side of the heart (e.g., left atrium) from the right side of the heart (e.g., right atrium) and to deliver a guidewire to the left side of the heart. The septum puncture device 500 can be constructed the same as or similar to, and can function the same as or similar to, any of the septum puncture devices described herein. Thus, portions of the septum puncture device 500 are not described in further detail herein.

In this embodiment, as shown, the septum puncture device 500 includes a main shaft 520 that defines a lumen therethough (e.g., through which a guide wire can be routed). The main shaft 520 includes a proximal section 520A at its proximal end, a distal section 520C at its distal end, and an inflation section 520B disposed therebetween. The proximal section 520A defines a first aperture AP1, and the inflation section 520B defines a second aperture AP2 and a third aperture AP3 disposed opposite the second aperture AP2, both in fluid communication with the lumen of the main shaft 520. As shown best in FIG. 12, in this embodiment, a proximal end of the inflation section 520B is inserted into the proximal section 520A, and a distal end of the inflation section 520B is inserted into the distal section 520C. In alternative embodiments, however, other main shaft designs suitable to provide stability for lateral puncture can be used. In some embodiments, for example, two or three of the proximal section, inflation section, distal section can be monolithically formed, rather than formed separated and then coupled together.

The septum puncture device 500 further includes a side catheter guide 530 that extends distally into the lumen of the main shaft 520 at a proximal end of the proximal section 520A of the main shaft 520, out the first aperture AP1 (see e.g., FIG. 11), towards and into the second aperture AP2, and out the third aperture AP3, as shown.

The inflation section 520B of the main shaft 520 defines (1) a first inflation portion 526A about which a first stabilizer/actuator guide ("GSA") 550A is disposed, and (2) a second inflation portion 526B about which a second stabilizer/actuator guide ("GSA") 550B is disposed. In this embodiment, the first GSA 550A and the second GSA 550B are balloons disposed circumferentially about the main shaft 520. A distal portion of the side catheter guide 530 can be translationally coupled (relative to the main shaft 520) directly to the main shaft 520 between the first GSA 550A and the second GSA 550B (e.g., using any suitable fastener), or the distal portion of the side catheter guide 530 can be translationally fixed relative to the main shaft 520 by way of contact, abutment, interference fit, etc., from the distal side surface of the first GSA 550A and the proximal side surface of the second GSA 550B. In some implementations, the distal portion of the side catheter guide 530 can be fastened to one or both of the first GSA 550A or second GSA 550B.

The first GSA 550A and the second GSA 550B are configured to be inflated for deployment and deflated for delivery or withdrawal. To inflate, the first GSA 550A is configured to receive one or more fluids (e.g., one or more of saline, air, or a contrast agent for visualization) from and through an opening O (FIG. 12) defined by the first inflation portion 526A; and similarly, the second GSA 550B is configured to receive one or more fluids from and through an opening O (FIG. 12) defined by the second inflation portion 526B. In use, for example, one or more fluids can be conveyed through the lumen of the main shaft 320 and into a volume defined by the first GSA 550A (via the opening O in the first inflation portion 526A) and into a volume defined by the second GSA 550B (via the opening O in the second inflation portion 526B). The same fluid(s) can be withdrawn from the first GSA 550A and the second GSA 550B (e.g., via the same pathway used to deliver the fluid(s)) to deflate the first GSA 550A and the second GSA 550B such that the cross-sectional area or footprint of the first GSA 550A and the second GSA 550B is reduced to facilitate removal from the patient. The balloons can be any size suitable to perform that desired functionality disclosed herein, for example, in some embodiments, the balloons can be 20 mm or about 20 mm in diameter when inflated. In some implementations of this embodiment, the septum puncture device 500 can include a GSA actuator (not shown, but e.g., disposed at or operably coupled to a handle of the septum puncture device, which is also not shown) configured to inflate or deflate the first GSA 550A and the second GSA 550B.

As shown, and similar to other embodiments described herein, routing the side catheter guide 530 distally around the first GSA 550A and then through a pathway defined by and between the first GSA 550A and the second GSA 550B, the side catheter guide 530 assumes a curve such that a length of the side catheter guide 530 extends from beyond a first side of the main shaft 520 to beyond a second side of the main shaft 520 (e.g., at least a distance equal to a diameter of the first GSA 550A or the second GSA 550B, when inflated), thereby providing a suitable straight or substantially straight length (e.g., about 3 cm to about 4 cm in some instances) to house a septum penetrator (or a rigid portion of the septum penetrator), as described in further detail herein with respect to other embodiments.

As recited above, some components of the septum puncture device 500 are similar to or the same as (in form or function) components from other septum puncture devices described herein, and some of those components are not described or illustrated again with respect to the septum puncture device 500. For example, in some embodiments, the septum puncture device 500 includes a body, a handle, a side catheter (with or without an end effector extending therefrom), a septum penetrator, guide wire coupler(s), or actuators (e.g., shaft actuator, GSA actuator, side catheter actuator, penetrator actuator), none of which are illustrated in FIGS. 10-12. The following example method of using the septum puncture device 500 refers to some of those components.

In use, for example and similar to as described herein with respect to other embodiments, the septum puncture device 500 can be inserted into the patient (e.g., via a femoral vein puncture), through the patient's vasculature, and into the heart of the patient such that the main shaft 520 spans the IVC, RA, and SVC to provide a stable platform against which the septum puncture device 300 can be deployed to puncture the FO. In some instances, the septum puncture device 500 can be inserted over a guide wire (not shown) that is routed through the lumen of the main shaft 520 (or in some instances, through a guide wire coupler, not shown). During such delivery, the septum puncture device 500 is in its delivery configuration in which the first GSA 550A and the second GSA 550B deflated (not shown). In this manner, for example, the cross-sectional area or footprint of the septum puncture device 500 can be minimized or optimized for minimally-invasive delivery through the patient.

With the main shaft 520 extended from the IVC to the SVC, and the first GSA 550A, the second GSA 550B, and the distal end portion of the side catheter guide 530 disposed within the RA, the first GSA 550A and the second GSA 550B can be inflated to deploy the side catheter guide 530, as shown in FIGS. 10-12. Inflating the first GSA 550A and the second GSA 550B in this manner causes the distal end portion of the side catheter 530 (1) to laterally deflect to a preferred angle and towards the FO, and (2) to stabilize the distal end portion of the side catheter 530, to facilitate subsequent tenting or puncturing of the FO. In this embodiment, as shown in FIG. 11, the deflection occurs such that the distal end portion of the side catheter guide 530 laterally deflects to perpendicular or about perpendicular to a central axis of the main shaft 520 or to a surface line tangent to the FO or the main shaft 520. In alternative embodiments, as described with respect to other embodiments, the lateral deflection may selectively be less than about or greater than about 90 degrees. Although not shown, in some instances, the first GSA 550A or the second GSA 550B can be inflated such that the first GSA 550A or the second GSA 550B become indented with an impression of the distal end portion of the side catheter guide 530 or envelop a portion of the same. In this manner, the side catheter guide 530 can be sufficiently stabilized and temporarily sufficiently coupled to the first GSA 550A or the second GSA 550B. In some embodiments, the GSA 550A or the GSA 550B can be configured to possess variable amounts of compliance. In some embodiments, for example, a distal portion of the first GSA 550A and a proximal portion of the second GSA 550B can have a first level of compliance while another portion of the first GSA 550A and another portion of the second GSA 550B can have a second level of compliance that is different from the first level of compliance. Further, in some embodiments, the distal side of the first GSA 550A and the proximal side of the second GSA 550B can include features configured to further stabilize the side catheter guide 530 relative to the GSA 550. These features can include, for example, dimples, protrusions, adhesives, or the like.

With the first GSA 550A and the second GSA 550B actuated and in sufficient contact with the side catheter guide 530 and providing sufficient stabilization of the side catheter guide 530 relative to the main shaft 520, an end effector (not shown) can be deployed from the side catheter guide 530, similar to or the same as described in other embodiments. To deploy the end effector, for example, a side catheter (not shown) from which the end effector distally extends can be advanced relative to the side catheter guide 530 (e.g., through a lumen defined by and extending through the side catheter guide 530) such that the end effector is allowed to expand to its expanded/deployed configuration as it is released from its constrained or delivery configuration within the lumen of the side catheter guide 530.

With the end effector deployed, the end effector can be advanced towards and into contact with the FO to tent the FO. As described elsewhere herein, both the end effector and the tenting of the FO (or other portion of the septum) are visible to the operator from outside the patient via various imaging technologies, such as, for example, ultrasound or related suitable imaging technologies. To advance the end effector towards and into contact with the FO, the side catheter can be advanced (e.g., by actuating a side catheter actuator, not shown) relative to the side catheter guide 530) or by manipulating (i.e., translating or rotating) the main shaft 520.

In instances in which the operator is not satisfied with the location on the septum contacted or tented by the end effector, e.g., if the end effector is misaligned with the FO, the end effector can be withdrawn from contact with the FO or septum (e.g., by withdrawing the side catheter relative to the side catheter guide 530 or by manipulating the main shaft 520), and then the operator can make another approach at landing the end effector on the FO in a manner sufficient for subsequent puncturing of the FO. This process can be repeated until the operator is satisfied.

With the FO properly tented by the end effector, the septum penetrator (not shown) can be advanced relative to the side catheter (e.g., through a lumen defined by and extending through the side catheter) and the end effector, and through the FO and into the LA. With the FO sufficiently penetrated by the septum penetrator, and a distal end of the septum penetrator disposed within the LA, a second guide wire can advanced relative to and through a lumen defined by and extending through the septum penetrator such that at least a distal end portion of the guide wire exits the distal end of the septum penetrator and advances into the LA, which can be confirmed by the operator under imaging technologies.

Once confirmed that the second guide wire is sufficiently disposed within the LA, the septum penetrator can be withdrawn relative to and into the lumen of the side catheter, the first GSA 550A and the second GSA 550B can be deflated, in preparation for removal of the septum puncture device 500 from the patient. Further, in some instances, the end effector can be withdrawn relative to and into the lumen defined by the side catheter.

With the septum penetrator withdrawn from the LA, the operator can manipulate the septum puncture device 500 (e.g., the handle, the body, or the main shaft 520) to withdraw the entire septum puncture device 500 along the second guide wire until the septum puncture device 500 exits the patient, leaving the second guide wire within the patient for subsequent access to the left atrium (e.g., without further penetration of the FO).

Figure 13A:
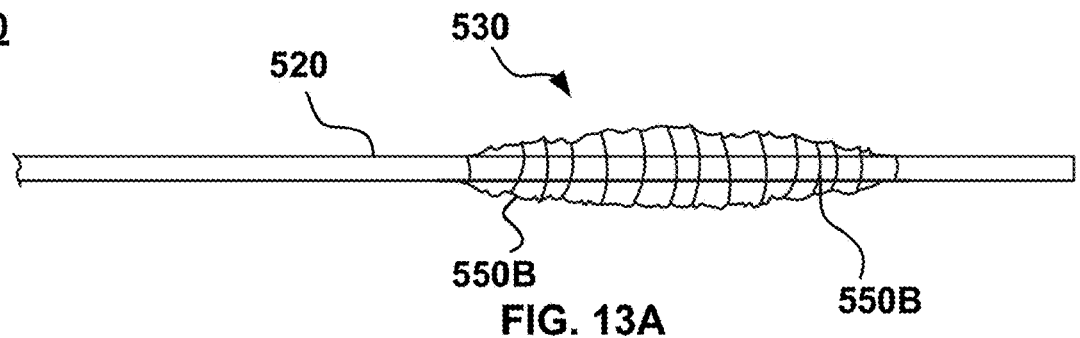
FIGS. 13A-13F illustrate a partial delivery and deployment sequence using the septum puncture device 500 of FIGS. 10-12, according to an embodiment.
Figure 13B:
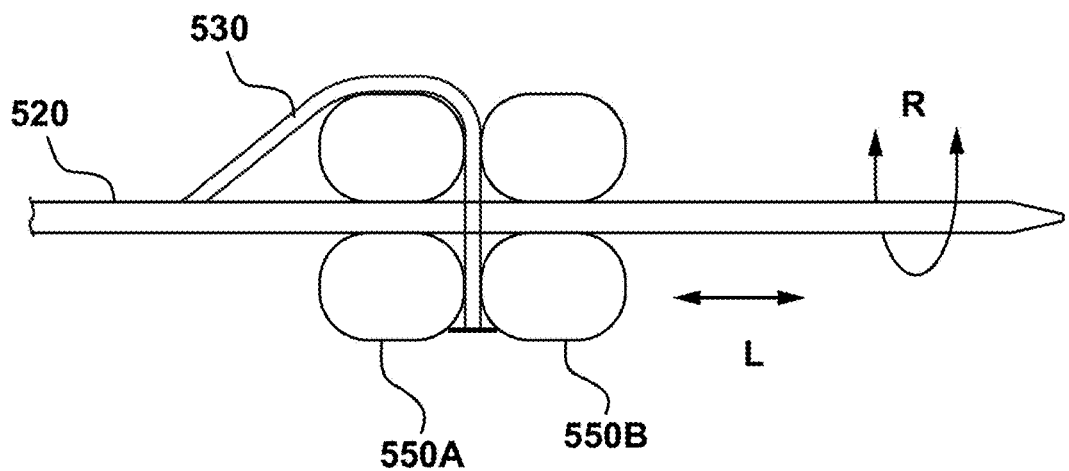

In some implementations, during delivery, the side catheter guide 530 (or any components disposed therein) can be protected from deploying or advancing prematurely or from inadvertently undesirably contacting the patient's anatomy. In some instances, for example, the side catheter guide 530 (or side catheter and end effector extending or protruding from the distal end of the side catheter guide 530) can be at least partially encased within the first GSA 550A and the second GSA 550B, in their delivery, or deflated configurations. As an example illustration, FIGS. 13A-13F show a partial delivery and deployment sequence. FIG. 13A shows the septum puncture device 500 in a delivery configuration in which the first GSA 550A and the second GSA 550B are deflated and disposed circumferentially about the side catheter guide 530. FIG. 13B shows the first GSA 550A and the second GSA 550B in deployed, inflated configurations, in which the side catheter guide 530 is laterally deflected relative to the main shaft 520 such that a distal end of the side catheter guide 530 is directed towards the FO, and extends proximally in a linear fashion between the first GSA 550A and the second GSA 550B, towards and beyond the main shaft 520. Arrow L and arrow R represent a linear axis and an angular axis, respectively, along which the main shaft 520 can be adjusted by the operator to align the distal end of the side catheter guide (or end effector of the side catheter) with the FO.

Figure 13C:
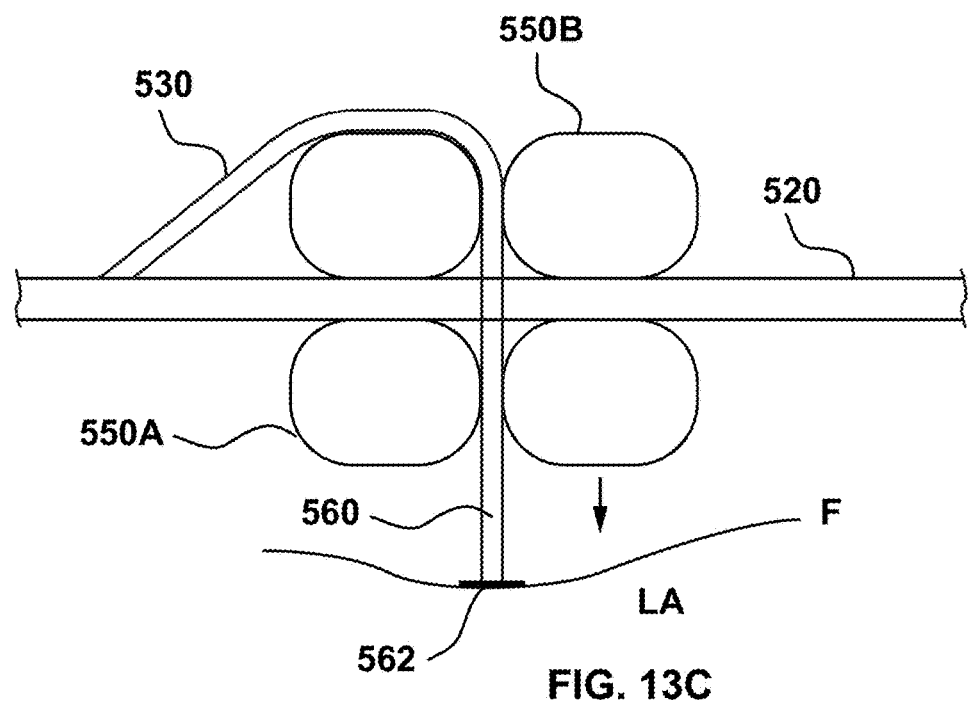

FIG. 13C shows the side catheter 560 with end effector 562 advanced from the side catheter guide 530 and in contact with and tenting the FO. The side catheter 560 can be advanced any suitable distance to probe the FO. In some instances, for example, the side catheter 560 can advance about 1 cm to about 4 cm from the side catheter guide 530. In other instances, as another example, the side catheter 560 can advance about 2 cm to about 3 cm from the side catheter guide 530.

Figure 13D:
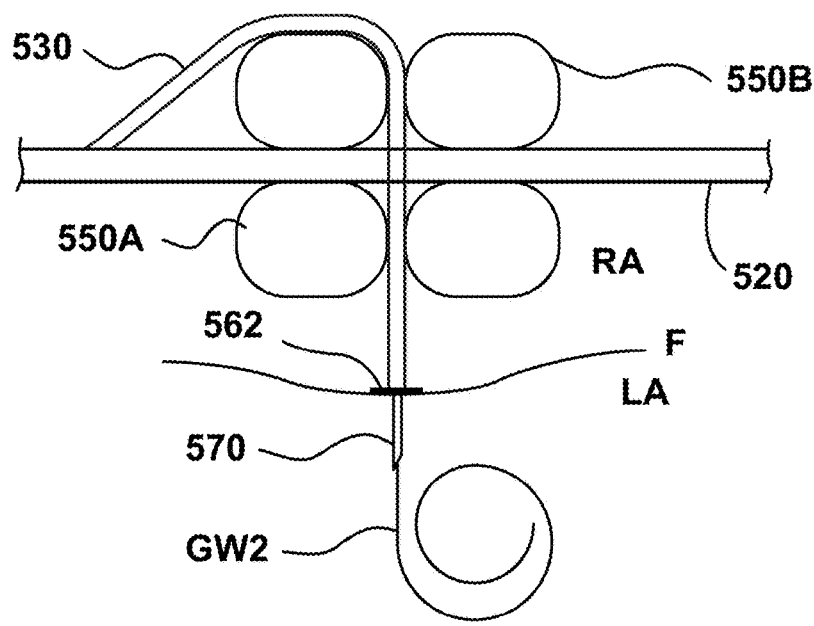

FIG. 13D shows the septum penetrator 570 advanced from the side catheter 560, through the FO and into the LA, and a guide wire GW2 (with a pigtail configuration) advanced from the septum penetrator 570 through the FO and into the LA. The septum penetrator 570 can be advanced any suitable distance from the side catheter 560 to penetrate the FO and enter the LA. In some instances, for example, the septum penetrator 570 can be advanced about 0.5 cm to about 1 cm from the side catheter 560.

Figure 13E:
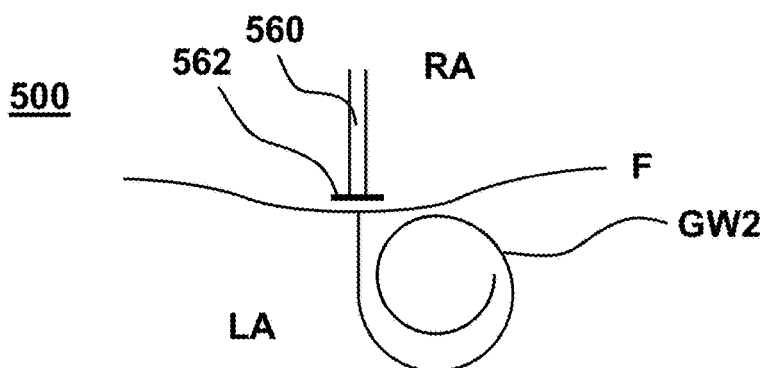
Figure 13F:
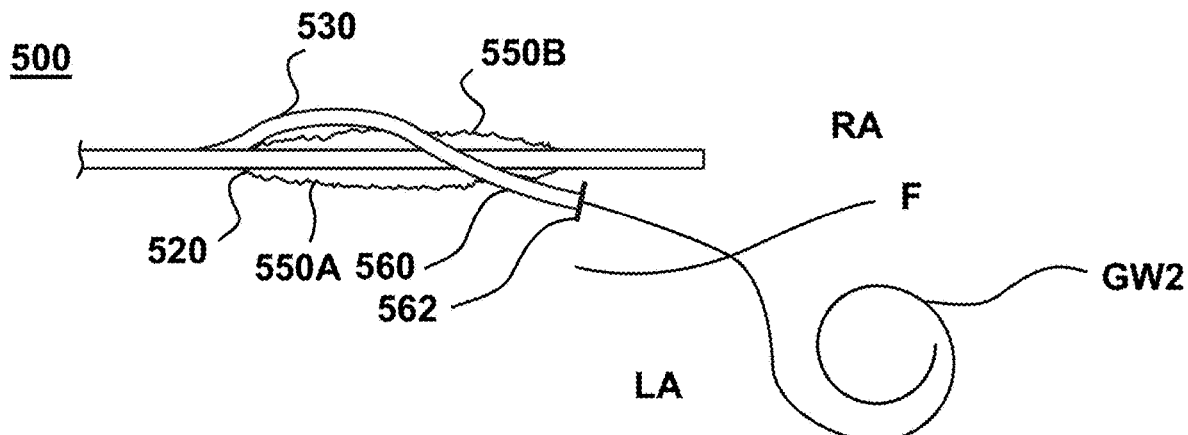

With the guide wire GW2 disposed within the LA, the septum penetrator 570 can be withdrawn from the LA, as described in more detail herein, and as shown in FIG. 13E. Further, as shown in FIG. 13F, the first GSA 550A and the second GSA 550B can be deflated, and the septum puncture device 500 can be withdrawn relative to and along the guide wire GW2, leaving the guide wire GW2 extending from within the LA, through the puncture in the FO, into the LA, and through the patient's vasculature and out of the patient, for subsequent minimally-invasive access to the LA.

Although the septum puncture device 500 is shown and described as having the second aperture AP2 and third aperture AP3 in the main shaft 520 through which the side catheter guide 530 can be disposed, in other embodiments, a similar septum puncture device could include a side catheter guide that extends or is routed along an exterior surface of the main shaft, rather than through the main shaft. In such embodiments, for example, the septum puncture device can include a guide coupler that is similar to or the same as, in form or function, to any of the guide couplers described herein with respect to other embodiments. The guide coupler, for example, can be disposed between a first GSA and a second GSA, and used to couple (e.g., translationally fixedly couple, and rotatably couple) the side catheter guide to the main shaft, such that the side catheter guide can laterally deflect about the guide coupler in response to the inflation/deployment of the first GSA and the second GSA. The guide coupler, in some implementations, can be a hinge, such as a hinge formed of suture, similar to or the same as described herein in other embodiments.

Although the septum puncture device 500 is shown and described as having a side catheter guide 530 through which the side catheter 560 (and end effector 562), septum penetrator 570, and guide wire GW2 can be slidably disposed, in alternative embodiments, a septum puncture device can, for example, not include a side catheter guide. FIGS. 14A-14K illustrate such an alternative embodiment. More specifically, FIGS. 14A-14K illustrate an example deployment sequence of and at a distal end portion of a septum puncture device 600, according to an embodiment.

Similar to or the same as described with respect to other septum puncture devices described herein, the septum puncture device 600 can be used to access a left side of the heart (e.g., left atrium) from the right side of the heart (e.g., right atrium) and to deliver a guidewire to the left side of the heart. The septum puncture device 600 can be constructed the same as or similar to, and can function the same as or similar to, any of the septum puncture devices described herein. Thus, portions of the septum puncture device 600 are not described in further detail herein.

Figure 14A:
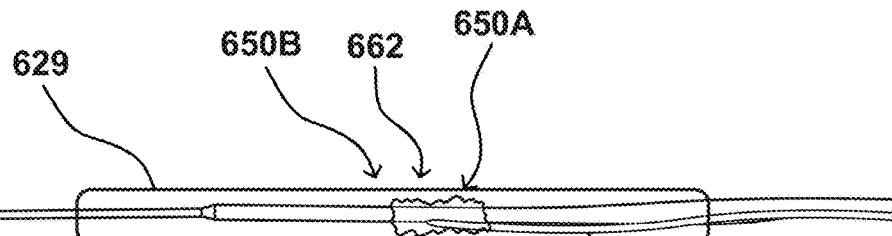
FIGS. 14A-14K illustrate an illustrate an example deployment sequence of a septum puncture device 600, according to an embodiment.

In this embodiment, as shown in FIG. 14A, prior to deployment, the septum puncture device 600 has a protective sleeve 629 coupled to and circumferentially disposed about a portion of the main shaft 620, the first GSA 650A, the second GSA 650B, and a portion of the side catheter 660. The protective sleeve 629, for example, can shield the aforementioned components of the septum puncture device 600 prior to use of the septum puncture device 600. In such instances, the protective sleeve 629 could be removed prior to insertion of the septum puncture device 600 into the patient. Further, in some instances, the protective sleeve 629 can shield the aforementioned components of the septum puncture device 600 during delivery of the septum puncture device 600 into and through the patient. As an example, the septum puncture device 600 could be inserted into the patient's vasculature, through the IVC and into the RA, similar to as described herein with respect to other embodiments. In such instances, the protective sleeve 629 can be configured to prevent inadvertent contact or trauma to the patient's surrounding tissue. Additionally, or alternatively, the protective sleeve 629 can be configured to constrain the first GSA 650A, the second GSA 650B, or the side catheter 660 to define a cross-sectional profile or footprint suitable to be delivered through the patient. In this manner, the protective sleeve 629, and components disposed therein, could be delivered to the RA of the heart, and then the protective sleeve 629 can be withdrawn along the main shaft 620 (or in some instances advanced along the main shaft 620) to expose the first GSA 650A, the second GSA 650B, and a portion of the side catheter 660.

Figure 14B:
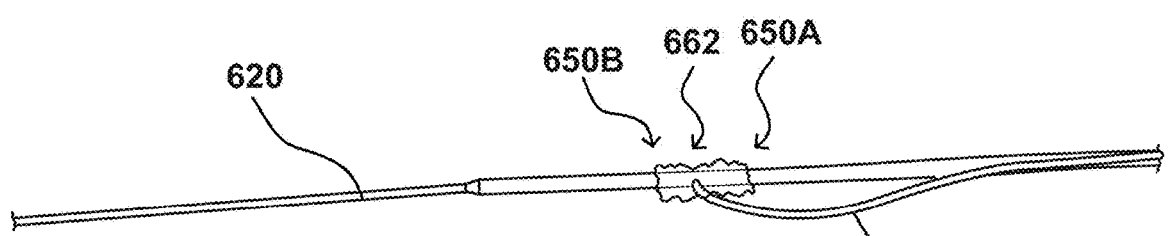
Figure 14C:
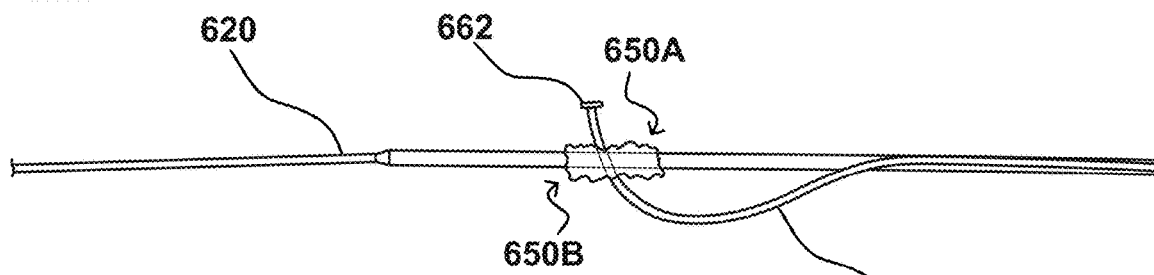

With the protective sleeve 629 withdrawn or advanced, the side catheter 630 can assume it's curved orientation, as described herein in other embodiments and as shown in FIG. 14B. Further, as shown in FIG. 14B, in some instances the end effector 662 can be disposed between the first GSA 650A and the second GSA 650B such that the end effector 662 is at least partially shielded. Said another way, the end effector 662 is spaced a distance from the central axis of the main shaft 620 that is less than a radius of the first GSA 650A and the second GSA 650B. Further, the side catheter 660 is slidably disposed relative to the main shaft 620 and the first GSA 650A and the second GSA 650B. As such, the side catheter 660 (and end effector 662) can be advanced relative to the main shaft 620 to provide sufficient space within which the first GSA 650A and the second GSA 650B can expand or inflate, as shown in FIG. 14C.

Figure 14D:
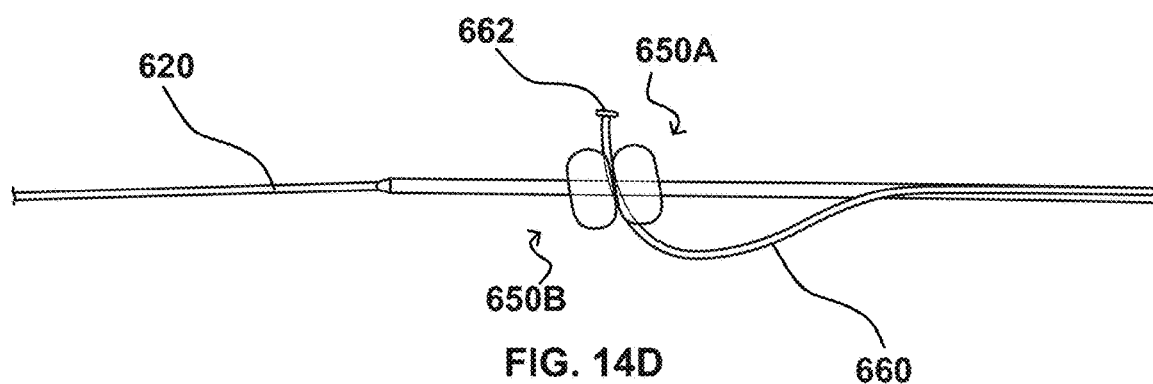
Figure 14E:
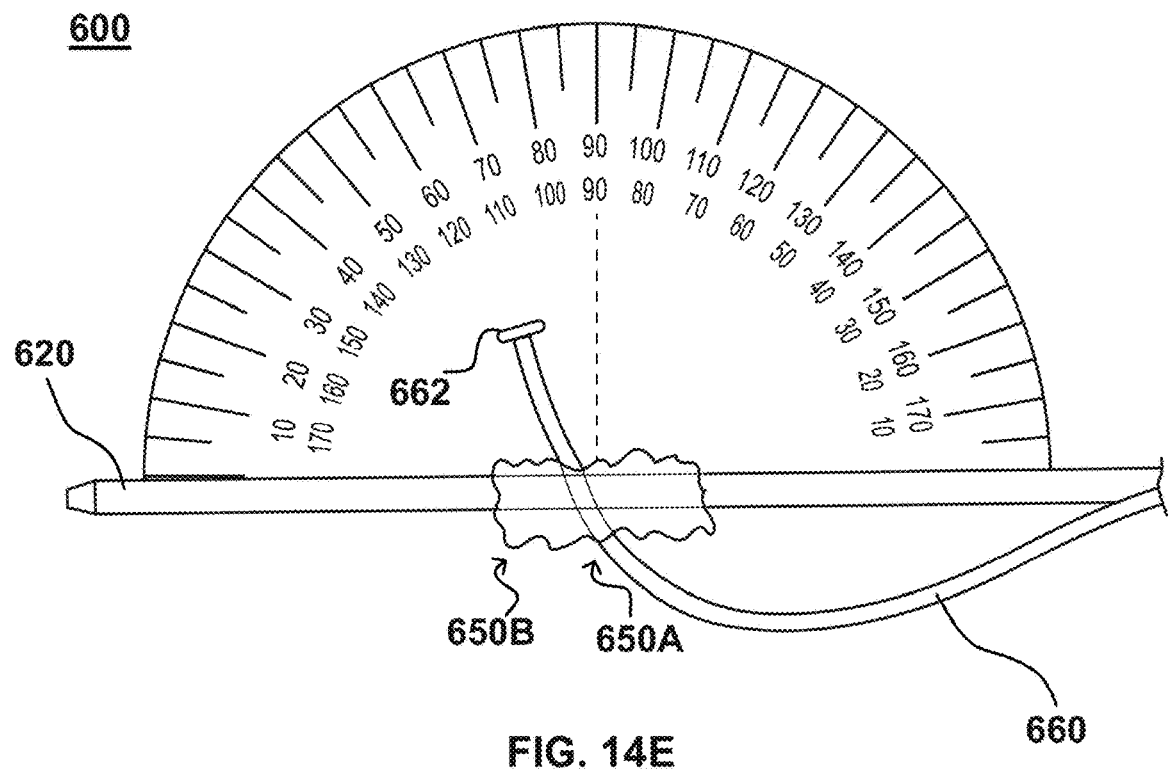
Figure 14F:
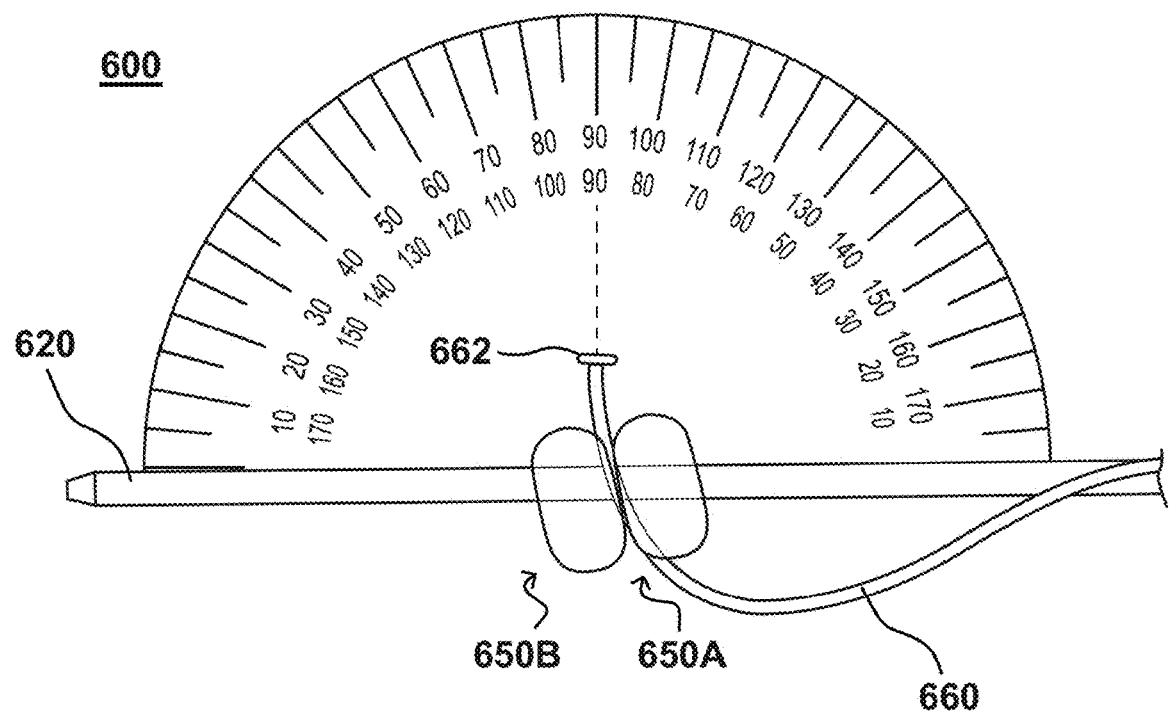

With the end effector 662 advanced in this manner, the first GSA 650A and the second GSA 650B are inflated, as shown in FIG. 14D. Also, as shown, inflation of the first GSA 650A and the second GSA 650B causes the distal end portion of the side catheter 660 to laterally deflect and to stabilize with respect to the main shaft 620. The lateral deflection was measured during an experiment, and the measurement is shown in FIGS. 14E and 14F as an illustrative example. As shown in FIG. 14E, prior to inflation of the first GSA 650A and the second GSA 650B, an angle between (1) a central axis of the portion of the side catheter 660 extending distally from (a) the central axis of the main shaft 620 and (b) the first GSA 650A and the second GSA 650B, and (2) the central axis of the main shaft 620, is between about 65 to about 70 degrees. Upon inflation of the first GSA 650A and the second GSA 650B, that angle changes to about 90 degrees, as shown in FIG. 14F.

Figure 14G:
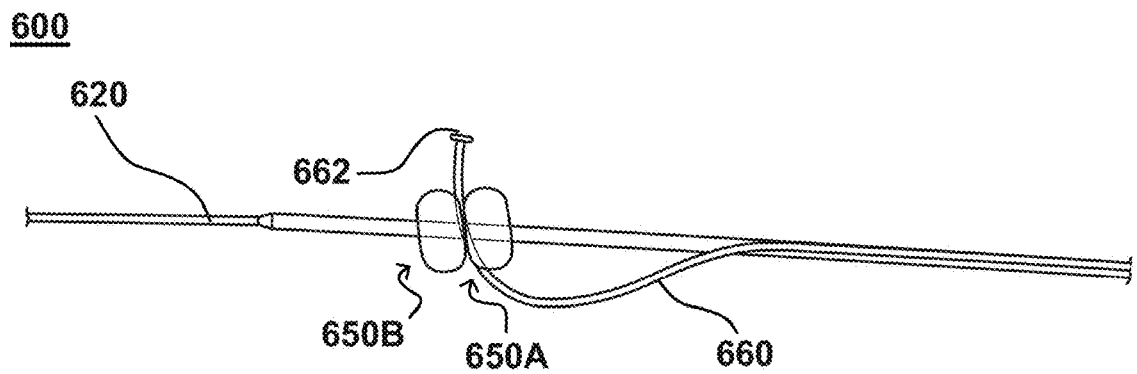
Figure 14H:
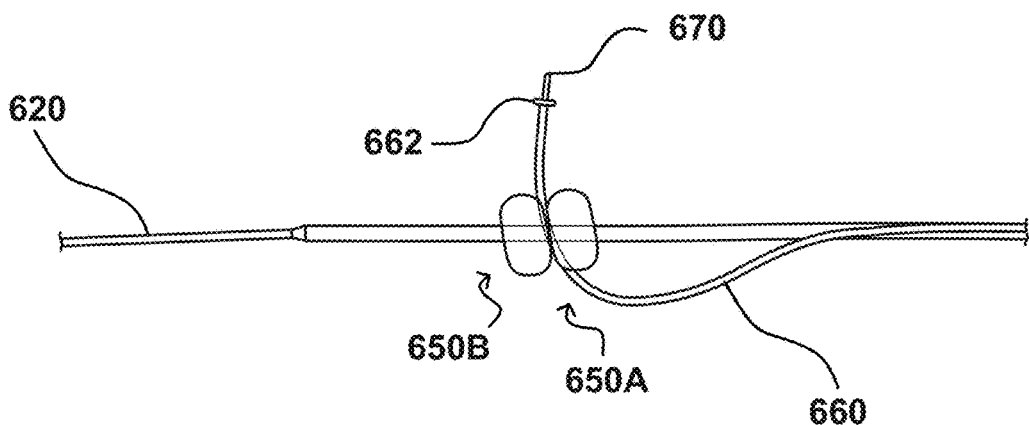
Figure 14I:
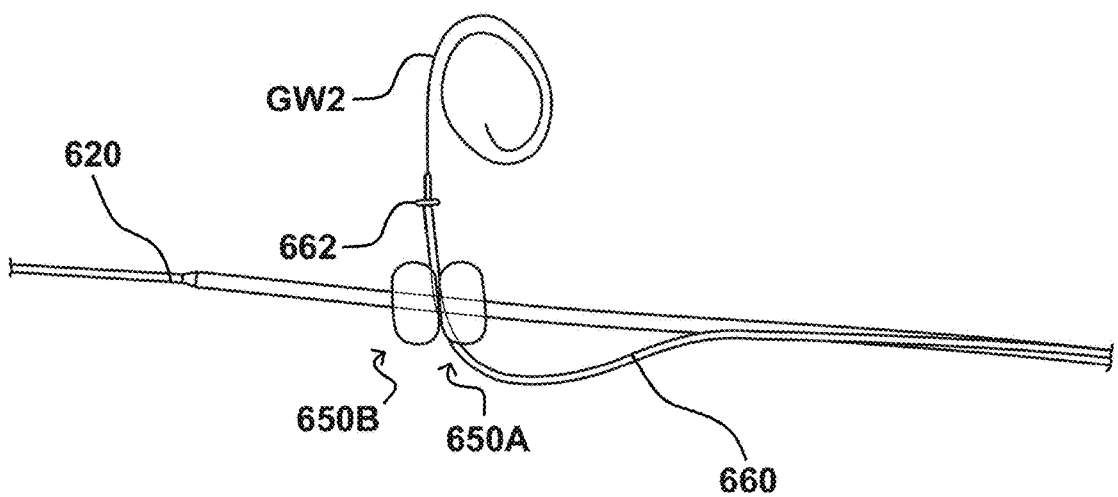

With the side catheter 660 laterally deflected in this manner, the side catheter 660 optionally can be advanced further relative to the main shaft 620 such that the effective length (e.g., the length of the side catheter extending distally from the closest external surfaces of the first and second GSA 650A, 650B) is increased to a desirable amount for tenting of the FO, as shown in FIG. 14G. Next, the septum penetrator 670 can be advanced relative to the end effector 662, as shown in FIG. 14H, to, for example, penetrate the FO. Further, and as described herein in other embodiments, a guide wire GW2 can be advanced through a lumen defined by the septum penetrator 670 and relative to the end effector 662, as shown in FIG. 14I.

Figure 14J:
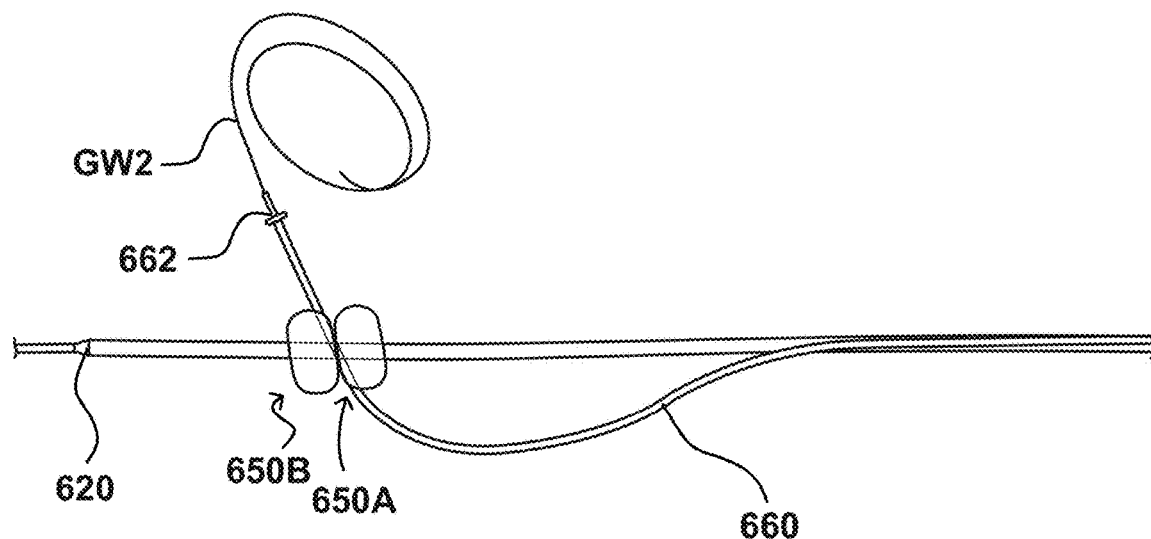
Figure 14K:
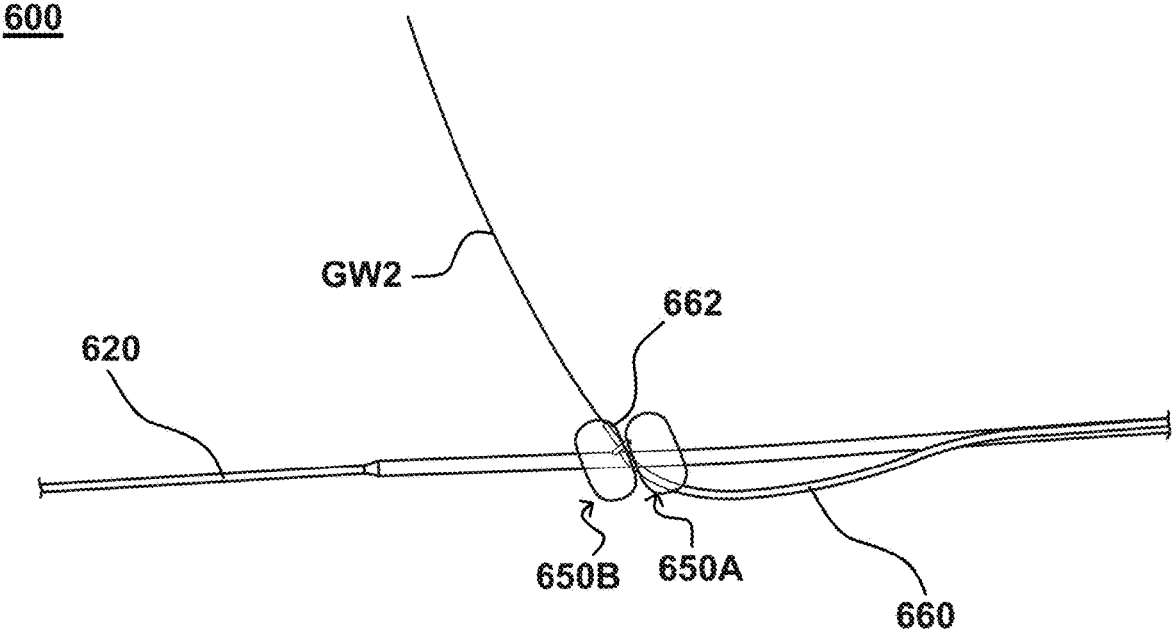

With the guide wire GW2 sufficiently advanced, the septum penetrator 670 can be withdrawn into the lumen defined by the side catheter 670 (e.g., to prevent any inadvertent contact (and risk of damage) between a sharp edge of the septum penetrator 670 and the guide wire GW2, and the sharp edge of the septum penetrator 670 and the patient's surrounding anatomy, as shown in FIG. 14J. Further, as shown in FIG. 14J, the first GSA 650A and the second GSA 650B can be deflated, and the side catheter (and end effector 662) can be withdrawn about the guide wire GW2, relative to the main shaft 620, and towards its delivery position, as shown in FIG. 14K.

Although (1) the septum puncture device 500 is shown and described as having a side catheter guide 530 routed through a lumen defined by the main shaft 520 (or a central axis of the main shaft 520), or more specifically, into the second aperture AP2 and out of the third AP3 of the main shaft 520, and (2) the septum puncture device 600 is shown and described as having a side catheter 660 routed through a lumen or central axis of the main shaft 620, in other embodiments, a side catheter guide or side catheter can be routed along an external surface of the main shaft, i.e., offset from the central axis of the main shaft. The side catheter guide or side catheter, from top view, for example, can be disposed to one side of the main shaft. Offsetting the side catheter guide or side catheter relative to the central axis of the main shaft in this manner in many instances better aligns the distal end of the side catheter guide or side catheter with the FO, given the common anatomical location of the FO relative to the IVC, SVC, and RA (e.g., measured laterally from a central longitudinal axis from the IVC to the SVC). The FO is often offset from a central axis defined from the IVC to the SVC by about 4 mm to about 6 mm, so aligning the side catheter guide a comparable distance offset from the central axis of the main shaft, may in some instances, place the side catheter guide or side catheter in a more suitable position for subsequent puncture. In this manner, the arrangement of the side catheter guide or side catheter with the main shaft can optimize the time and number of steps required of the operator to locate the FO with the side catheter (or end effector), for subsequent puncturing of the FO with the septum penetrator.

Figure 15:
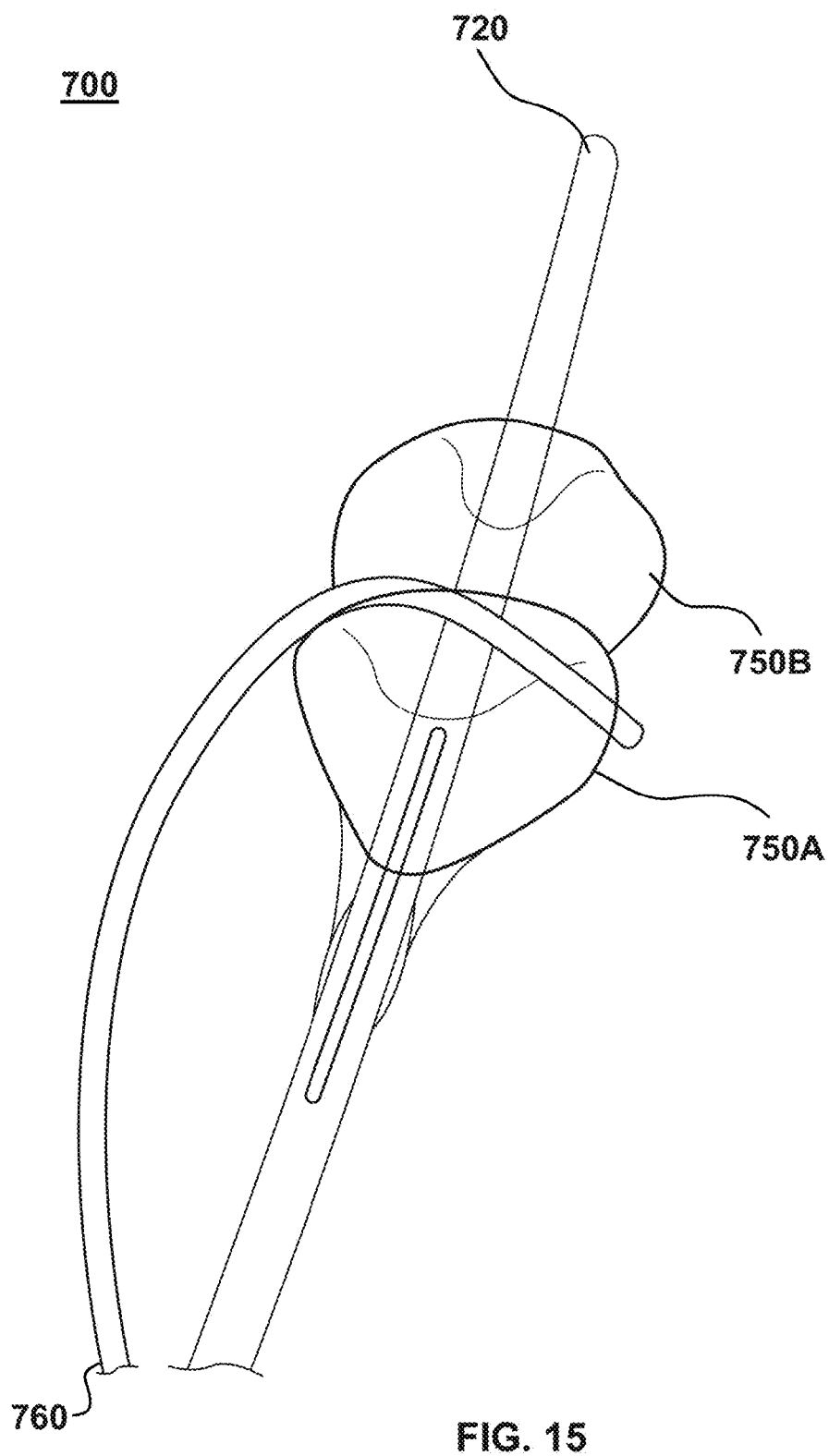
FIGS. 15-17 illustrate a septum puncture device 700 in perspective view, front view, and side view, respectively, according to an embodiment.
Figure 16:
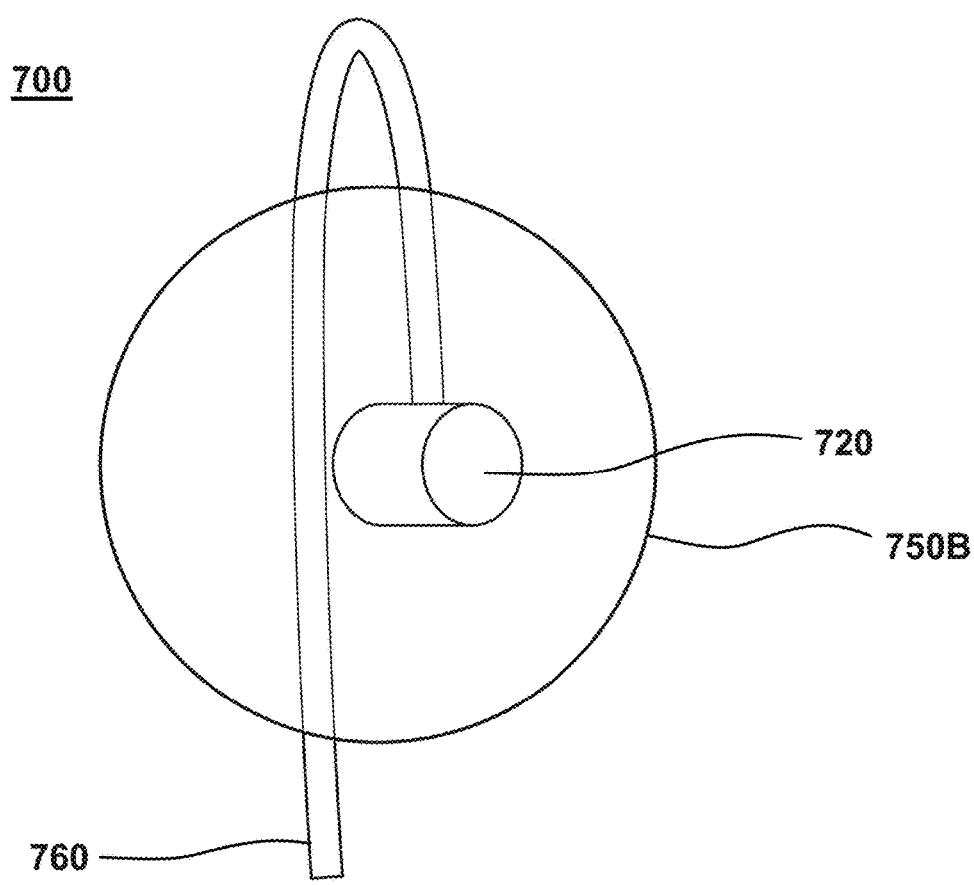
Figure 17:
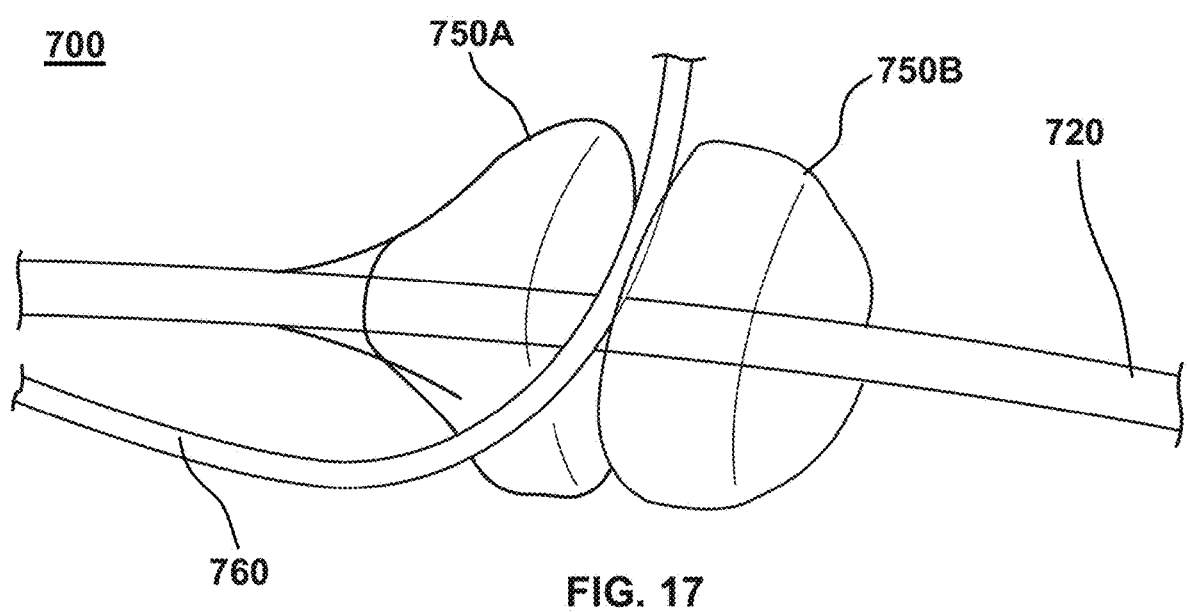

One such example is illustrated in FIGS. 15-17, which show a septum puncture device 700 in a perspective view, front view, and side view, respectively, according to an embodiment. Similar to or the same as described with respect to other septum puncture devices described herein, the septum puncture device 700 can be used to access a left side of the heart (e.g., left atrium) from the right side of the heart (e.g., right atrium) and to deliver a guidewire to the left side of the heart. The septum puncture device 700 can be constructed the same as or similar to, and can function the same as or similar to, any of the septum puncture device described herein. Thus, portions of the septum puncture device 700 are not described in further detail herein.

In this embodiment, the septum puncture device 700 includes a main shaft 720, a first GSA 750A, a second GSA 750B, and a side catheter 760 routed around or about the first GSA 750A and then between the first GSA 750A and the second GSA 750B, and along an external surface of the main shaft 720 (and offset from the central axis of the main shaft 720), as shown. In this manner, in some instances, the side catheter 760 can be better aligned with the FO of the patient. Although not shown in FIGS. 15-17, in some implementations, the side catheter 760 can be slidably attached via a guide coupler (not shown) to the main shaft 720. The guide coupler, for example, can be configured to slidably and rotatably attach the side catheter 760 to the main shaft 720 to prevent the side catheter 760 from separating from the main shaft 720 or from between the first GSA 750A and the second GSA 750B. In other implementations, for example, the guide coupler can be attached to, part of, or extend from the first GSA 750A or the second GSA 750B. An illustrated example of a guide coupler 840 of a septum puncture device 800 is shown in FIGS. 18A-18C, according to an embodiment.

Similar to or the same as described with respect to other septum puncture devices described herein, the septum puncture device 800 can be used to access a left side of the heart (e.g., left atrium) from the right side of the heart (e.g., right atrium) and to deliver a guidewire to the left side of the heart. The septum puncture device 800 can be constructed the same as or similar to, and can function the same as or similar to, any of the septum puncture device described herein. Thus, portions of the septum puncture device 700 are not described in further detail herein.

FIGS. 18A-18C illustrate the first GSA 850A and the second GSA 850B in a deflated, delivery configuration (in which the side catheter 860 is at least partially axially aligned with the main shaft 820), a partially inflated, partially deployed configuration (in which the side catheter 860 has been laterally deflected a first number of degrees), and an inflated, deployed configuration (in which the side catheter 860 has been laterally deflected a second number of degrees that is greater than the first number of degrees, stabilized, and directed towards the representative model of a FO), respectively.

As shown, the guide coupler 840 in this embodiment extends from the main shaft 820 and circumferentially surrounds or engages the side catheter 860. More specifically, the guide coupler 840 defines an eyelet through which the side catheter 860 is threaded. In this manner, the side catheter 860 has freedom to translate (advance or be withdrawn) through the eyelet. In some implementations, the eyelet can be sized to have at least a partial interference fit, thereby providing some friction between the guide coupler 840 and the side catheter 860 such that the side catheter 860 isn't inadvertently translated. Further, the guide coupler 840 is configured to rotate about the main shaft 820 in response to inflation of the first GSA 850A and the second GSA 850B, to allow the side catheter 860 to laterally deflect towards its target location (e.g., the FO), as shown in FIG. 18C. After delivery of a guide wire GW2 (not shown), as discussed herein with respect to other embodiments, the first GSA 850A and the second GSA 850B can be deflated and the guide coupler 840 can be rotated in a direction opposite to the direction it rotated during deployment.

Figure 21:
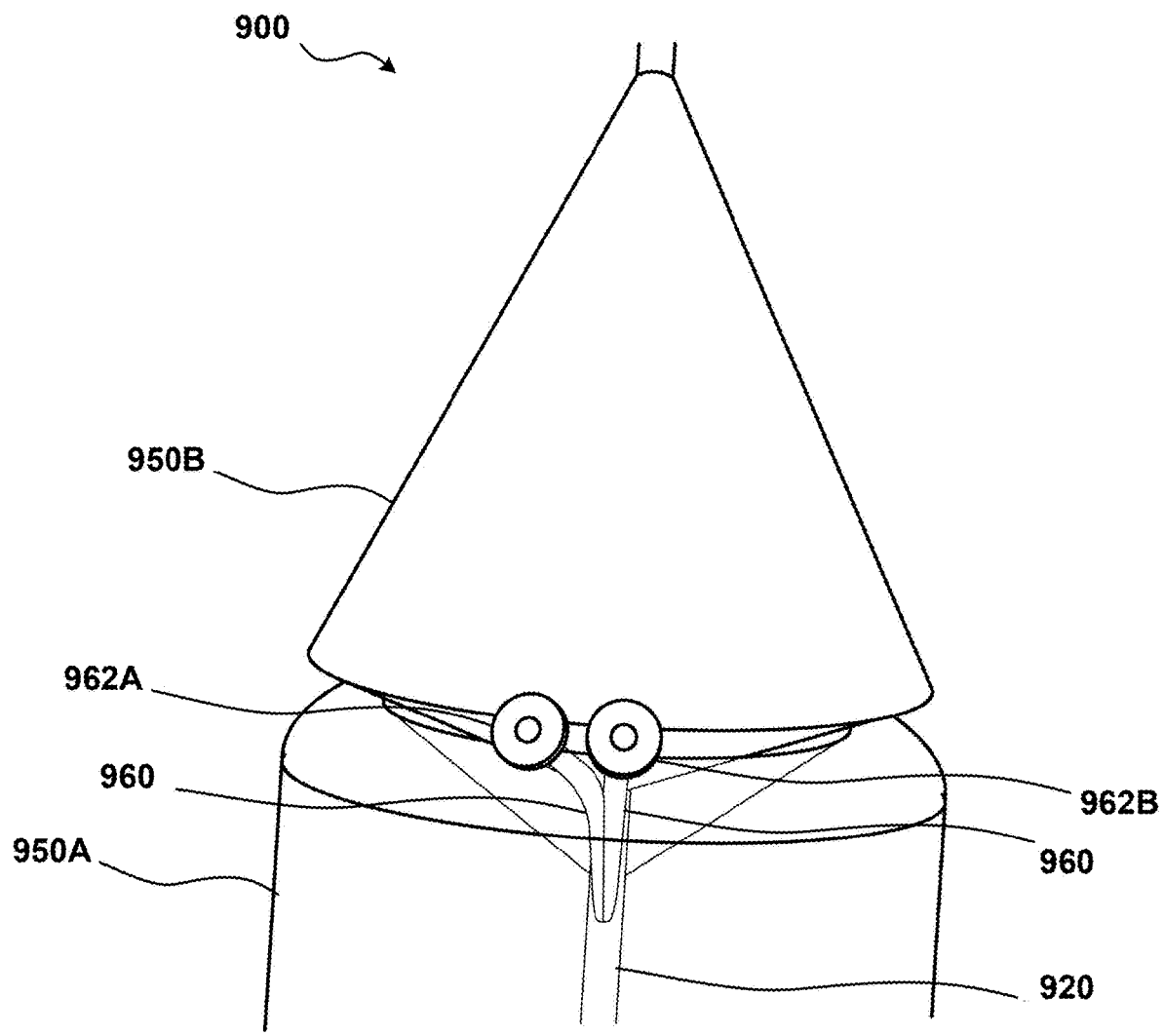

Although various embodiments of septum puncture devices described herein disclose having a single side catheter guide or single side catheter (with single end effector), in some embodiments, a septum puncture device can include two side catheter guides or two side catheters (with or without the side catheter guide(s)). Such an embodiment is illustrated in FIGS. 19-21. FIGS. 19-21 illustrate a septum puncture device 900 in perspective view, front view, and detailed, partial perspective view, respectively, that includes a two side catheters.

Similar to or the same as described with respect to other septum puncture devices described herein, the septum puncture device 900 can be used to access a left side of the heart (e.g., left atrium) from the right side of the heart (e.g., right atrium) and to deliver a guidewire to the left side of the heart. The septum puncture device 900 can be constructed the same as or similar to, and can function the same as or similar to, any of the septum puncture device described herein. Thus, portions of the septum puncture device 900 are not described in further detail herein.

In this embodiment, the septum puncture device 900 includes a first side catheter 960A and second side catheter 960B, each being configured to be delivered and deployed within a patient, as described herein with respect to other embodiments. The septum puncture device 900 further includes a first end effector 962A extending from the first side catheter 960A and a second end effector 962B extending from the second side catheter 960B. As shown, the main shaft 920 defines a lumen through which the first side catheter 960A and the second side catheter 960B can be slidably disposed, and an aperture AP through which the first side catheter 960A and the second side catheter 960B can be advanced or withdrawn. The septum puncture device 900 further includes a first GSA 950A disposed circumferentially about the main shaft 920 and proximal to the aperture AP, and a second GSA 950B disposed circumferentially about the main shaft 920 and distal to the aperture AP. In this manner, the first side catheter 960A and the second side catheter 960B can extend distally from the AP and through a pathway defined between the first GSA 950A and the second GSA 950B.

In use, similar to as described herein with respect to other embodiments, the first GSA 950A and the second GSA 950B can be inflated to laterally deflect and stabilize (e.g., laterally, axially (proximally, distally)) the first side catheter 960A and the second side catheter 960B, such that a first and second septum penetrator (not shown) can be advanced or withdrawn there through, and a first and second guide wire (not shown), can be advanced and withdrawn via the first and second septum penetrator. In accessing the LA, for example, with the first GSA 950A and the second GSA 950B disposed within the RA in inflated, deployed configurations, and the first side catheter 960A and the second side catheter 960B directed towards the septum, the first side catheter 960A and the second side catheter 960B can be advanced to tent the FO, and then the first and second septum penetrators can be advanced (optionally simultaneously) to pierce the FO, or other target location(s) of the septum. The puncture sites can be separated by a predefined distance, set by a distance between the side catheter lumens. With two punctures in the septum, two guide wires can then be advanced (optionally simultaneously) into the LA, one through each puncture.

Figure 23:
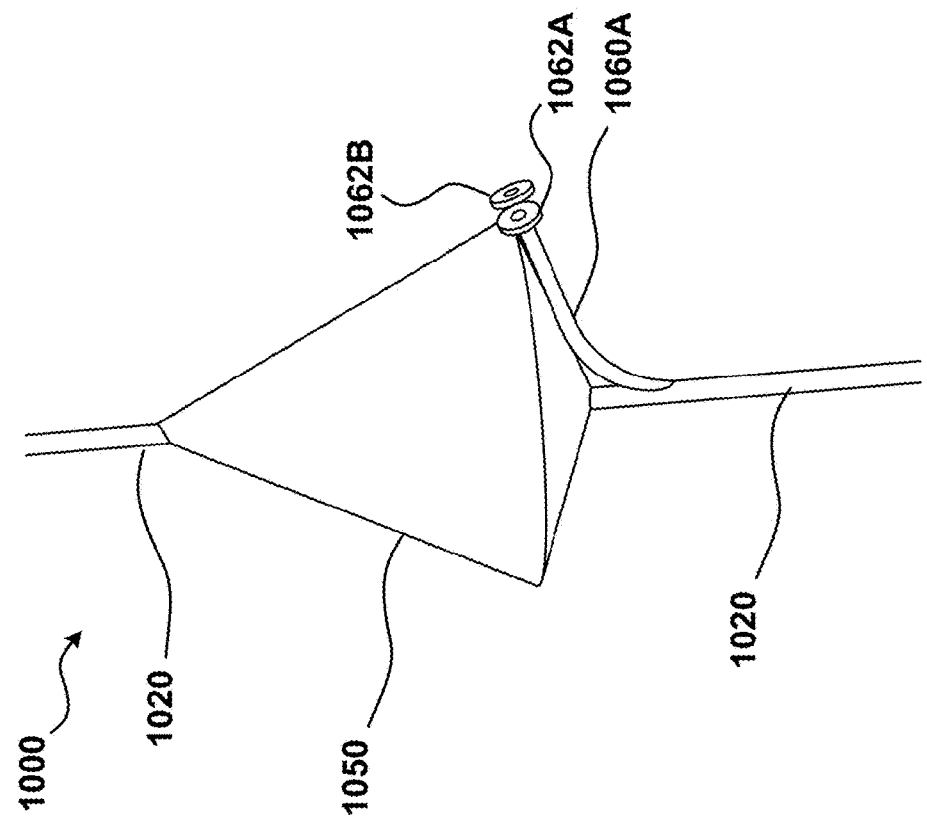
FIGS. 22 and 23 illustrate a septum puncture device 1000, in front view and perspective view, respectively, having a single GSA and two side catheters, according to an embodiment.
Figure 22:
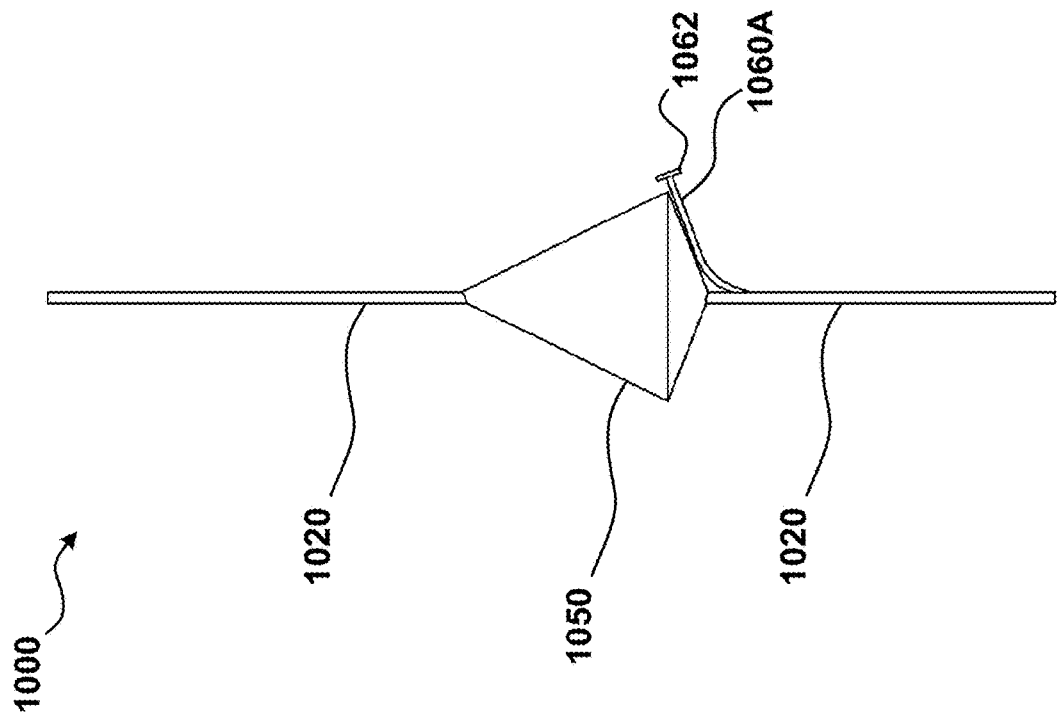

Although the septum puncture device 900 is shown and described as having two GSAs, in other embodiments, a septum puncture device can be similar to or the same as the septum puncture device 900, but include only a single GSA. An example embodiment is shown in FIGS. 22 and 23, in which a septum puncture device is shown in front view and perspective view, respectively. Similar to or the same as described with respect to other septum puncture devices described herein, the septum puncture device 1000 can be used to access a left side of the heart (e.g., left atrium) from the right side of the heart (e.g., right atrium) and to deliver two guidewires to the left side of the heart. The septum puncture device 1000 can be constructed the same as or similar to, and can function the same as or similar to, any of the septum puncture device described herein. Thus, portions of the septum puncture device 1000 are not described in further detail herein.

In this embodiment, the septum puncture device 1000 includes a first side catheter 1060A and second side catheter 1060B, each being configured to be delivered and deployed within a patient, as described herein with respect to other embodiments. The septum puncture device 1000 further includes a first end effector 1062A extending from the first side catheter 1060A and a second end effector 1062B extending from the second side catheter 1060B. As shown, the main shaft 1020 defines a lumen through which the first side catheter 1060A and the second side catheter 1060B can be slidably disposed, and an aperture AP through which the first side catheter 1060A and the second side catheter 1060B can be advanced or withdrawn. The septum puncture device 1000 further includes a GSA 1050 disposed circumferentially about the main shaft 1000 and distal to the aperture AP. In this manner, the first side catheter 1060A and the second side catheter 1060B can extend distally from the AP and along a proximal end surface of the GSA 1050, as shown.

Although not shown, with the GSA 1050 in its deflated, delivery configuration, the first side catheter 1060A and the second side catheter 1060B can be orientated in a more delivery-friendly position, e.g., about parallel to the central axis of the main shaft 1020, along an external surface of the deflated GSA 1050. As described in further detail herein with respect to other embodiments, the GSA 1050 can be configured to be inflated or deployed to laterally deflect the first side catheter 1060A and the second side catheter 1060B relative to the main shaft 1020, as shown in FIGS. 22 and 23. As described in further detail herein with respect to other embodiments, the GSA 1050 can also be configured to stabilize the first side catheter 1060A and the second side catheter 1060B relative to the main shaft 1020. In some implementations, for example, the GSA 1050 can include dimples, protrusions, ridges, adhesives, etc., configured to improve stabilization of the first side catheter 1060A and the second side catheter 1060B.

With the first side catheter 1060A and the second side catheter 1060B laterally deflected and stabilized in this manner, the first side catheter 1060A and the second side catheter 1060B can be advanced relative to the main shaft 1020 and towards a target tissue (e.g., the septum, or FO), and a first septum penetrator, a second septum penetrator, a first guide wire, and a second guide wire (none of which are shown in FIGS. 19 and 20) can be deployed, e.g., to penetrate the septum and delivery the first guide wire and the second guide wire.

Figure 25:
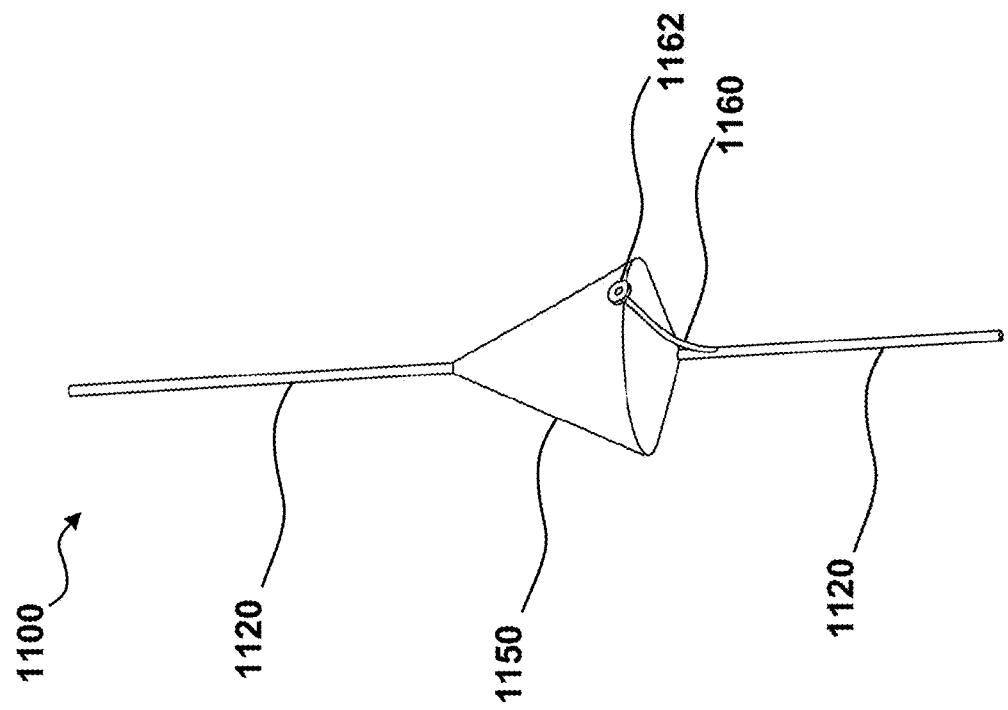
FIGS. 24 and 25 illustrate a septum puncture device 1100, in perspective front view and perspective side view, respectively, having a single GSA and a single side catheter, according to an embodiment.
Figure 24:
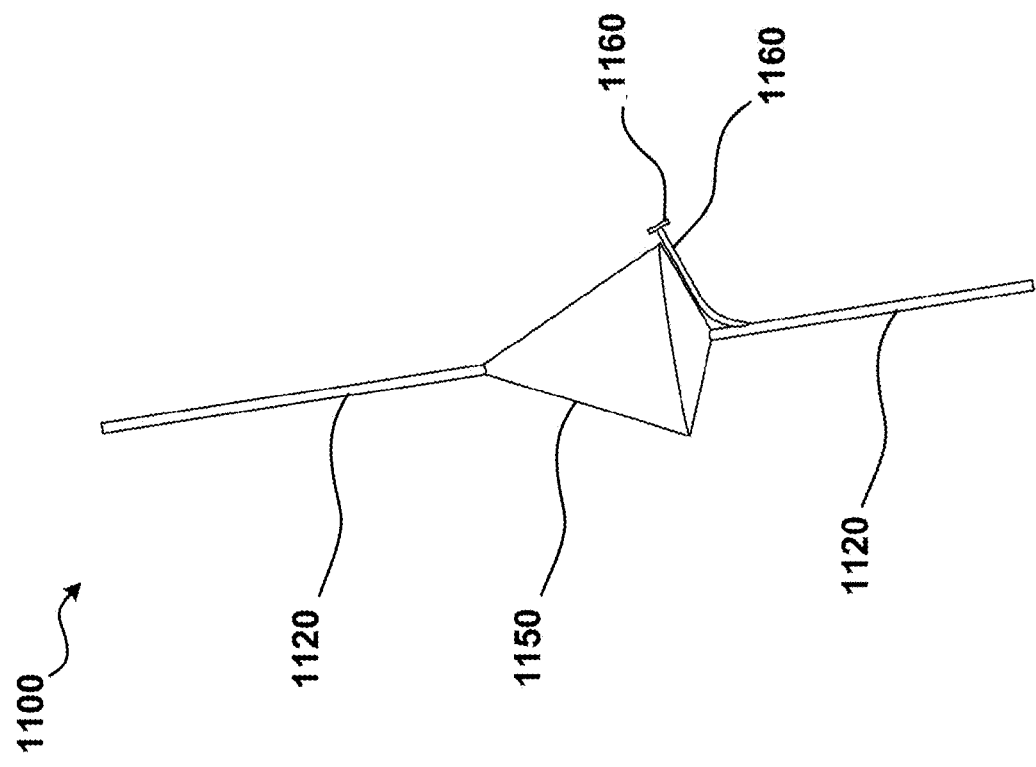

Although the septum puncture device 1000 is shown and described as having two side catheters, in other embodiments, a septum puncture device can be similar to or the same as the septum puncture device 1000, but include only a single GSA. An example embodiment is shown in FIGS. 24 and 25, in which a septum puncture device is shown in perspective front view and perspective side view, respectively. Similar to or the same as described with respect to other septum puncture devices described herein, the septum puncture device 1100 can be used to access a left side of the heart (e.g., left atrium) from the right side of the heart (e.g., right atrium) and to deliver two guidewires to the left side of the heart. The septum puncture device 1100 can be constructed the same as or similar to, and can function the same as or similar to, any of the septum puncture device described herein. Thus, portions of the septum puncture device 1100 are not described in further detail herein.

In this embodiment, the septum puncture device 1100 includes a side catheter configured to be delivered and deployed within a patient, as described herein with respect to other embodiments. The septum puncture device 1100 further includes an end effector 1162 extending from the side catheter 1160. As shown, the main shaft 1120 defines a lumen through which the side catheter 1160 and the second side catheter 1160 can be slidably disposed, and an aperture AP through which the side catheter 1160 and the second side catheter 1160 can be advanced or withdrawn. The septum puncture device 1100 further includes a GSA 1150 disposed circumferentially about the main shaft 1100 and distal to the aperture AP. In this manner, the side catheter 1160 can extend distally from the AP and along a proximal end surface of the GSA 1150, as shown.

Although not shown, with the GSA 1150 in its deflated, delivery configuration, the side catheter 1160 can be orientated in a more delivery-friendly position, e.g., about parallel to the central axis of the main shaft 1120, along an external surface of the deflated GSA 1150. As described in further detail herein with respect to other embodiments, the GSA 1150 can be configured to be inflated or deployed to laterally deflect the side catheter 1160 relative to the main shaft 1120, as shown in FIGS. 24 and 25. As described in further detail herein with respect to other embodiments, the GSA 1150 can also be configured to stabilize the side catheter 1160 relative to the main shaft 1120. In some implementations, for example, the GSA 1150 can include dimples, protrusions, ridges, adhesives, etc., configured to improve stabilization of the first side catheter 1160.

With the side catheter 1160 laterally deflected and stabilized in this manner, the side catheter can be advanced relative to the main shaft 1120 and towards a target tissue (e.g., the septum, or FO), and a first septum penetrator, a second septum penetrator, a first guide wire, and a second guide wire (none of which are shown in FIGS. 24 and 25) can be deployed, e.g., to penetrate the septum and delivery the first guide wire and the second guide wire.

Figure 26B:
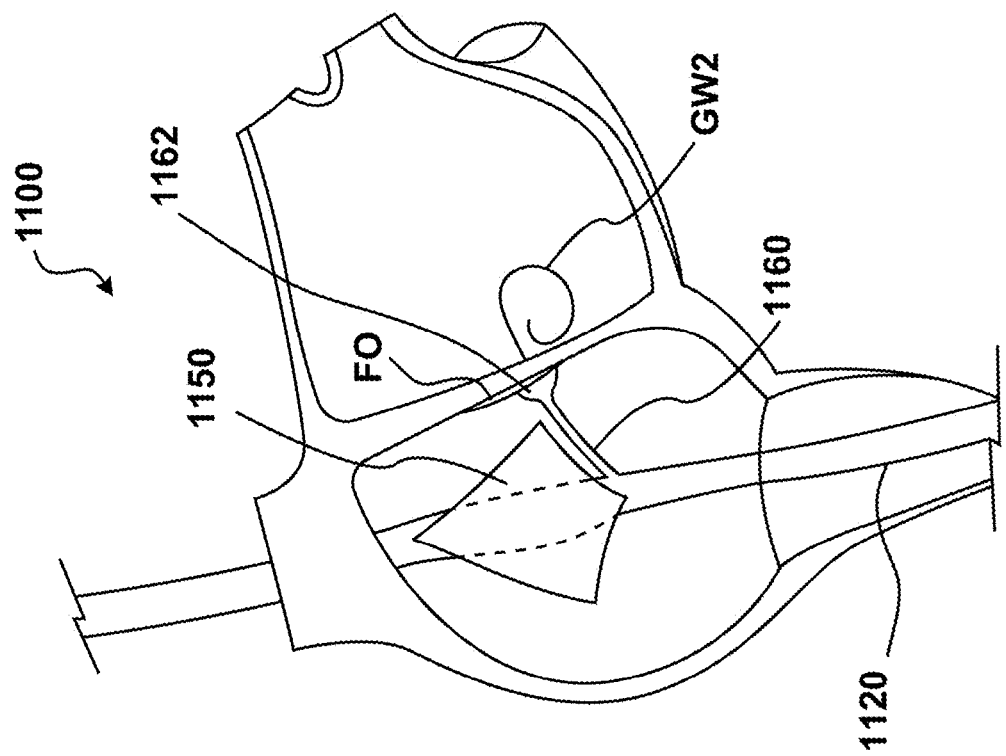
FIGS. 26A and 26B illustrate an example delivery and deployment sequence of the septum puncture device 1100 in the context of a heart of a patient, according to an embodiment.
Figure 26A:
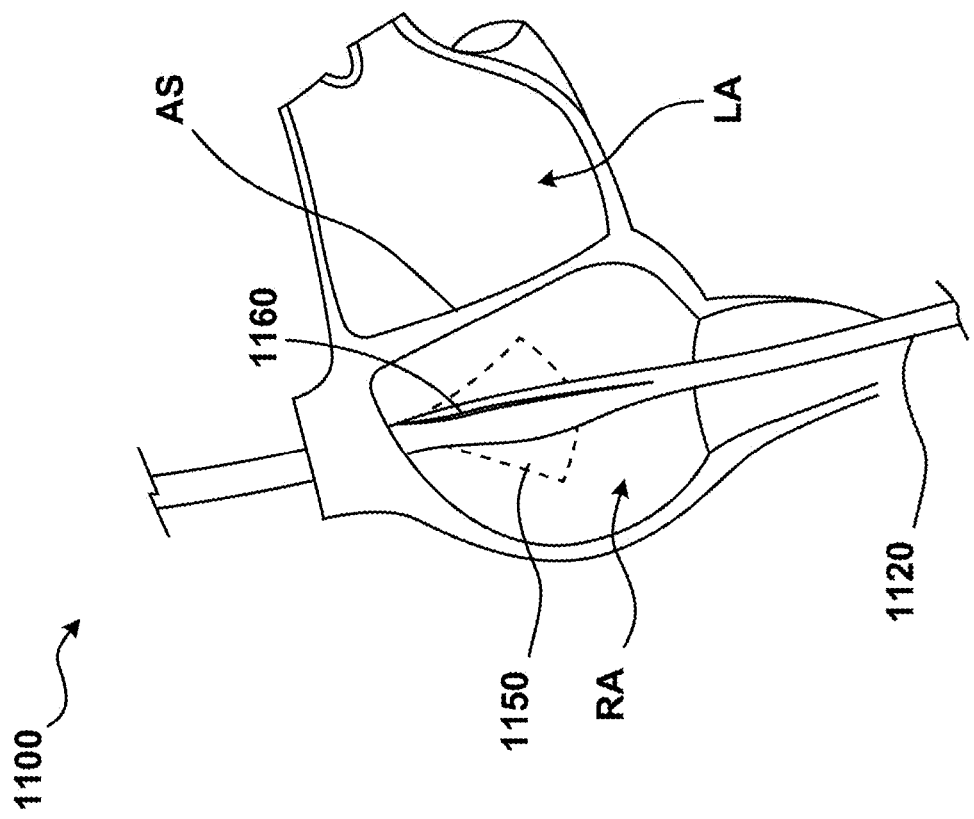

An example delivery and deployment of the septum puncture device 1100 in the context of a heart of a patient is shown in FIGS. 26A and 26B. As shown in FIG. 26A, the septum puncture device 1100 can be disposed within the RA of the heart, such that the main shaft 1120 spans the IVC, RA, and SVC, and the GSA 1150 and the side catheter 1160 are disposed within the RA. As described in further detail herein with respect to other embodiments, the GSA 1150 can be inflated into its deployed configuration to laterally deflect and stabilize the side catheter 1160 relative to the main shaft 1120 and towards the FO, as shown in FIG. 26B. Further as shown in FIG. 26B, the side catheter 1160 can be advanced such that the end effector 1162 contacts or tents the FO, after which the septum penetrator 1170 can be advanced relative to and distally from the end effector 1162, and the guide wire GW2 can be advanced into the LA.

Although various embodiments of septum puncture devices are described herein as having one or more GSAs, some of which can be a balloon, having a particular shape, size, etc., any of the embodiments described herein can be modified to have one or more GSAs having any shape, size, inflation volume, material(s), surface feature(s), etc. suitable to be inflatably and deflatably coupled to a main shaft, and to laterally deflect and stabilize one or more side catheter guides or one or more side catheters (and any components disposed therein, such as, for example, end effectors, septum penetrators, and guide wires). Various embodiments of GSAs, as illustrative examples, are described below with respect to FIGS. 27-34, and referred to as being part of septum puncture devices 1200-1900, all of which can be the same has or similar to, and function the same as or similar to, other septum puncture devices described herein. Thus, portions of the septum puncture devices 1200-1900 are not described in further detail herein.

In some embodiments, for example, a GSA can have a concave or a convex shape. One such embodiment is illustrated in FIG. 27, which shows a portion of a septum puncture device 1200 including a first GSA 1250A having a concave shape at its distal end, and a second GSA 1250B, disposed distal to the first GSA 1250A, and having a convex shape at its proximal end. As shown, such a combination of shapes can define a pathway through which the side catheter 1260 can be slidably disposed (or through which a side catheter guide can be disposed, in alternative embodiments).

In another embodiment, a GSA can be configured to define an optimal pathway along which a side catheter guide or side catheter can extend from a proximal end of the GSA to a distal end of the GSA. One such embodiment is illustrated in FIG. 28, which shows a portion of a septum puncture device 1300 including a first GSA 1350A having a particular curve C along which the side catheter 1360 (or side catheter guide in other implementations) can extend and engage with the first GSA. As shown, in this embodiment, the curve C is different from the corresponding section of the second GSA 1350B.

In some embodiments, a septum puncture device can include one or more GSAs with multiple lobes (bi-lobed, tri-lobed, etc.). Multiple lobes, for example, can reduce or limit the footprint of the GSAs, thereby reducing the risk of undesirable occlusion within the patient. In instances in which the GSAs are disposed within a patient's RA, for example, it may be advantageous to minimize the cross-sectional area or footprint of the GSAs to allow blood to flow in line with normal functioning of the heart. A tri-lobed GSA, for example, is shown in FIG. 29, in top view. As shown, the main shaft 1420 (of a septum puncture device 1400) extends axially between a first lobe GSA 1450A, a second lobe GSA 1450B, and a third lobe GSA 1450C, with the first lobe GSA 1450A defining a pathway through which a side catheter or side catheter guide can be routed.

In some embodiments, a septum puncture device can include GSAs with multiple lobes in which at least two of the multiple lobes are dissimilar in size or shape, as illustrated in FIG. 30, in top view. As shown in FIG. 30, the septum puncture device 1500 includes a first lobe GSA 1550A, a second lobe GSA 1550B, and a third lobe GSA 1550C, in which the first lobe GSA 1550A has a size different from a size of the second lobe GSA 1550B.

In some embodiments, to further reduce the risk of blood flow occlusion, one or more GSAs can have a particular aspect ratio. For example, a portion of a septum puncture device 1600 is in FIG. 31, in side view, in which a first GSA 1650A and a second GSA 1650A have a collective height of L1. Minimizing L1, in some instances, can help limit any risk of blood flow occlusion. In this implementation, for example, L1 is less than a collective width or collective diameter of the first GSA 1650A and the second GSA 1650B, as illustrated by L2.

In some embodiments, a septum puncture device can include interlocked GSAs. For example, as shown in FIG. 32, in side view, a first tri-lobed GSA 1750A and a second tri-lobed GSA 1750B of a septum puncture device 1700 are rotatably offset about the main shaft 1750 and relative to each other, and then brought into engagement and interlocked. In some implementations, for example, the first tri-lobed GSA 1750A can be rotated about 60 degrees about the main shaft 1750 and relative to the second tri-lobed GSA 1750B, and then interlocked. In other implementations, other degrees of rotations can be used.

In some embodiments, a septum puncture device can include an asymmetric GSA. For example, as shown in FIG. 33, in side view and top view, a septum puncture device 1800 includes an asymmetric GSA 1850 circumferentially disposed about a main shaft 1820.

In some embodiments, a septum puncture device can include two side catheters (or side catheter guides) extending and disposed between GSAs in different or opposite directions such that the main shaft can be rotated to selectively align one, but not the other, side catheter (or side catheter guide) with a target location to be penetrated. For example, as shown in FIG. 34, in side view, a septum puncture device 1900 includes a first GSA 1950A and a second GSA 1950B, collectively defining two pathways therebetween in an opposite directions. In this manner, as shown, a first side catheter 1960A can be disposed in or routed through the first pathway defined between the first GSA 1950A and the second GSA 1950B, and a second side catheter 1960B can be disposed in or routed through the second pathway defined between the first GSA 1950A and the second GSA 1950B. In use, for example, an operator can rotate the main shaft 1920 about its central axis to selectively align only one (at a time) of the first GSA 1950A or the second GSA 1950B with a target location (e.g., the septum, or FO).

In some embodiments, a septum puncture device can include a guide coupler that is configured to couple a side catheter guide or side catheter (without the side catheter guide in some embodiments) to a main shaft such that the guide coupler is slidable with the side catheter and relative to the main shaft. An exemplary embodiment is shown in FIGS. 35A-35D, in which a septum puncture device 2000 in shown in various stages of a deployment sequence.

Similar to or the same as described with respect to other septum puncture devices described herein, the septum puncture device 2000 can be used to access a left side of the heart (e.g., left atrium) from the right side of the heart (e.g., right atrium) and to deliver a guidewire to the left side of the heart. The septum puncture device 2000 can be constructed the same as or similar to, and can function the same as or similar to, any of the septum puncture device described herein. Thus, portions of the septum puncture device 2000 are not described in further detail herein.

Figure 35C:
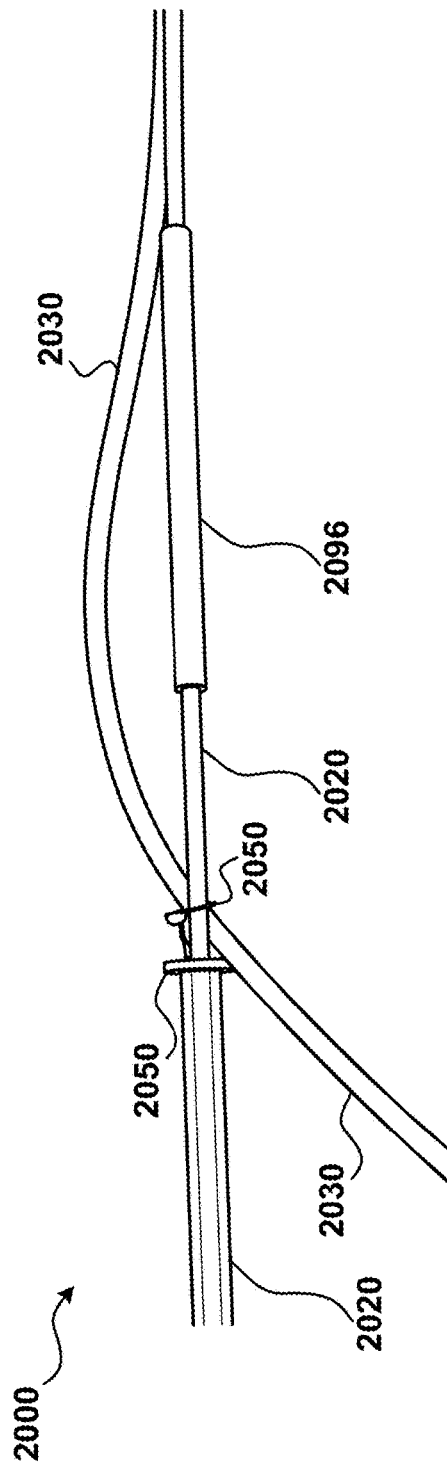
Figure 35D:
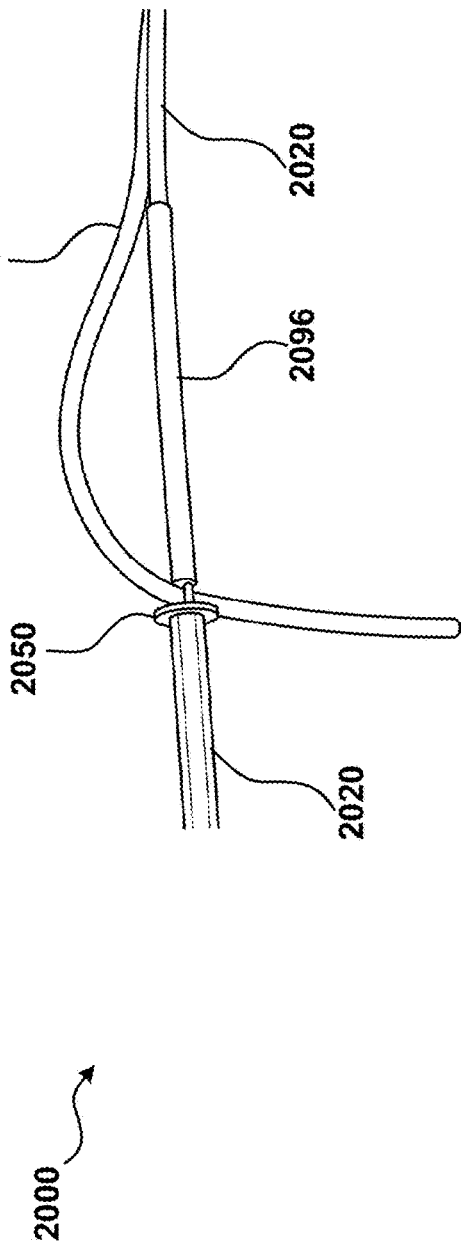

In this embodiment, the septum puncture device 2000 includes a body (not shown) slidably disposed about a side catheter guide 2030 and a telescopable main shaft 2020. The side catheter guide 2030 is coupled to the main shaft 2020 via a guide coupler 2040, as shown in FIG. 35A. The guide coupler 2040 is slidable relative to the main shaft 2020. Disposed distal to the body (not shown) is a pusher 2096 slidably and circumferentially disposed about the main shaft 2020. The main shaft 2020 includes a GSA 2050 disposed distal to the guide coupler 2040. The pusher 2096 is configured to be advanced relative to the main shaft 2020 and into contact with the guide coupler 2040 to push/advance the guide coupler 2040, and attached side catheter guide 2030, towards and into contact with the GSA 2050, such that a distal end portion of the side catheter guide 2030 laterally deflects about the guide coupler 2040 and the GSA 2050, similar to as described herein in other embodiments, and as shown across FIGS. 35A-35D.

Figure 36:
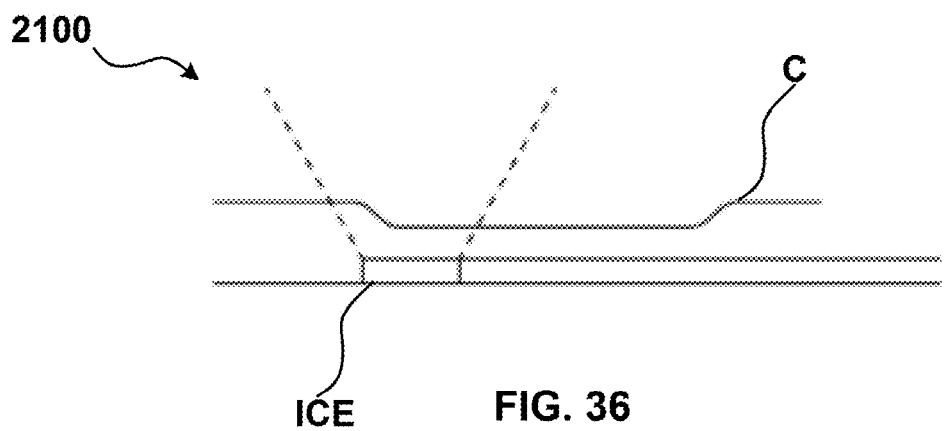
FIG. 36 illustrates a portion of a septum puncture device 2100 having an intracardiac echo ("ICE") sensor, according to an embodiment.

In some procedures involving a septum puncture device it may be desirable to sense various parameters, such as pressure, flow, temperature, oxygen, etc., at or near the septum puncture device, e.g., within a heart of a patient. In a procedure to access the LA of the heart, for example, it may be desirable to determine a pressure within the heart, such as within the RA or the LA. Accordingly, in any of the embodiments described herein, a sensor can be coupled to the septum puncture device. In some implementations, for example, a septum puncture device can include an intracardiac echo ("ICE") sensor configured to enhance visualization capabilities for the operator during the procedure. An illustrative example is shown in FIG. 36. FIG. 36 illustrates a portion of a septum puncture device 2100 having an ICE sensor disposed within a catheter C. The catheter can be representative of a main shaft, a side catheter guide, a side catheter, or a septum penetrator. In this manner, the ICE sensor can provide visualization from various orientations and positions within the patient, depending on, for example, a location within the septum puncture device within which the ICE is disposed.

Figure 37:
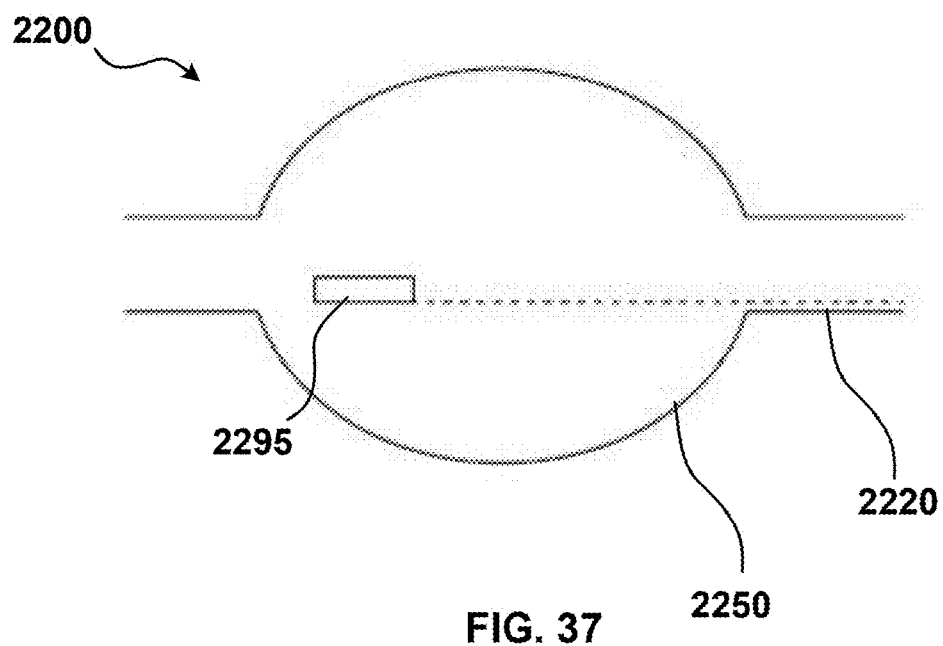
FIG. 37 illustrates a portion of a septum puncture device 2200 having a camera, according to an embodiment.

In some embodiments, in addition to or instead of the ICE sensor or other suitable sensors, a septum puncture device can include a camera. An illustrative example is shown in FIG. 37. FIG. 37 illustrates a portion of a septum puncture device 2200 having a camera 2295 disposed within a GSA 2250. The camera 2295 can in some implementations be configured to communicate wirelessly, while in other implementations the camera 2295 can have a physical connection (e.g., wires, fiber optics, etc.) extending proximally from the camera 2295 through the main shaft 2220 of the septum puncture device 2200 and out of the patient. The camera 2295 can be disposed in various positions within the GSA 2250, such as, for example, in contact with and coupled to an internal wall of the GSA 2250, or attached to a catheter disposed within the GSA 2250 (as described herein with respect to various embodiments). With the camera 2295 disposed within the GSA 2250, the camera 2295 can provide direct visualization of the procedure, e.g., of the septum or FO before, during, or after puncture.

In some procedures involving a septum puncture device it may be desirable to flush an area adjacent to a septum penetrator, side catheter, or end effector, e.g., prior to, during, or after puncturing. To this end, any of the septum puncture devices described herein could include a flusher (not shown) having an outlet near the septum penetrator, side catheter, or end effector, and being configured to flush (e.g., with saline) an area at or adjacent to its location before, during, or after puncturing. The septum puncture device can also include a pressure transducer configured to measure pressure, e.g., within the RA or LA, before or after puncturing, e.g., to verify a successful puncture.

Figure 38:
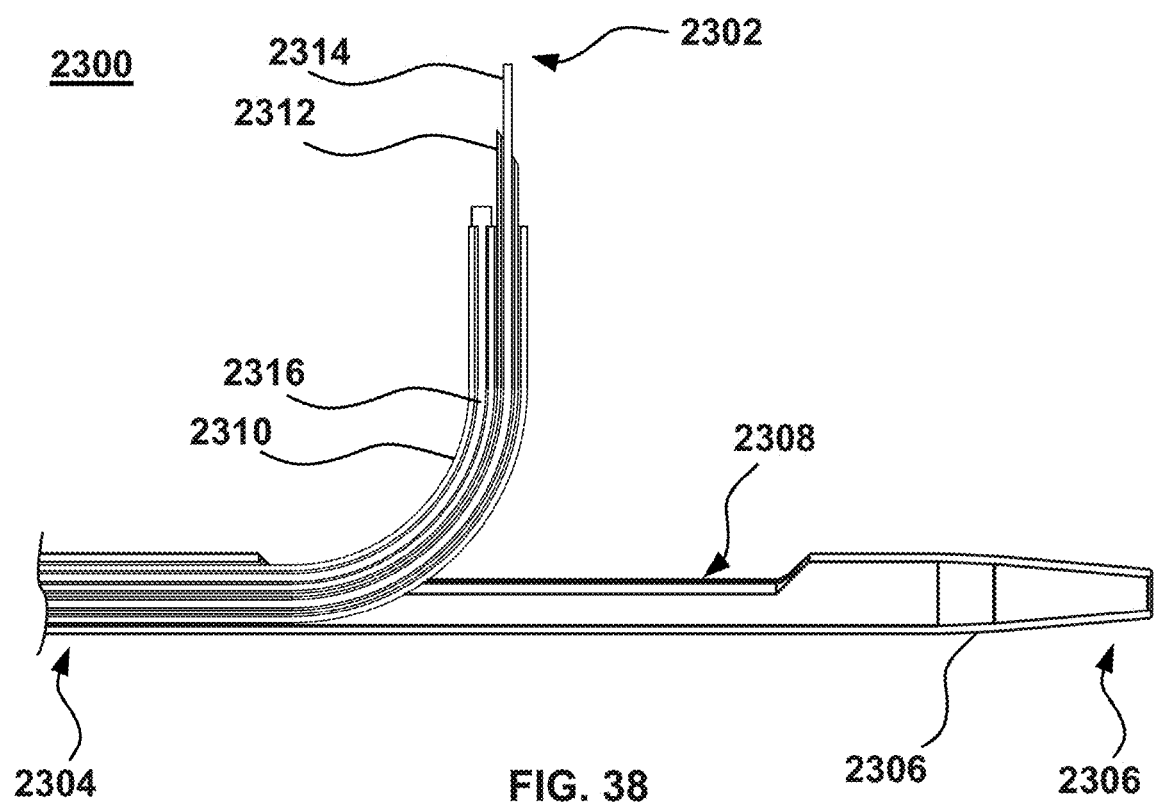
FIGS. 38 and 39 illustrate in cross-sectional side view and front view, respectively, a portion of a septum puncture device 2300, according to an embodiment.
Figure 39:
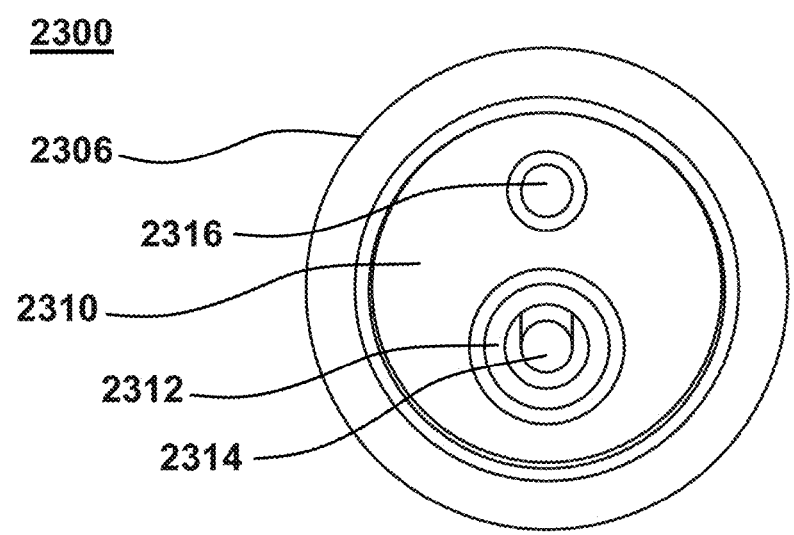

Referring now to FIGS. 38 and 39, an exemplary septum puncture device (also referred to herein as "device") 2300 is depicted. In contrast to many of the embodiments described above, rather than having a body that contains a main shaft and a side catheter side-by-side, this embodiment, the includes a cannula 2306 with a central lumen, and a stylus) 2310 disposed in the lumen of cannula 2306. Cannula 2306 extends from a distal end 2302 to a proximal end 2304. Cannula 2306 has an elongate hollow tubular shape having a lumen running throughout. Cannula 2306 includes an opening at its distal end 2302 and at least one elongate window 2308 adjacent to its distal end 2302, wherein both the opening and the at least one window 2308 are fluidly connected to the lumen of cannula 2306. Cannula 2306 can have any suitable dimensions. For example, cannula 2306 can have an outer diameter of between about 14 and 22 French (about 5 mm to 7 mm). In some implementations, cannula 2306 can have one or more surface coatings. Suitable surface coatings can reduce friction or irritation, and can include anticoagulants such as heparin, ethylenediamine tetraacetic acid (EDTA), oxalate, or the like.

Figure 40A:
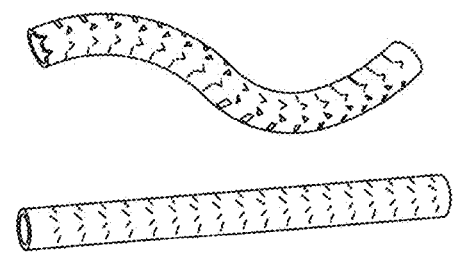
FIGS. 40A and 40B illustrate the stylus 2310, according to an embodiment.
Figure 40B:
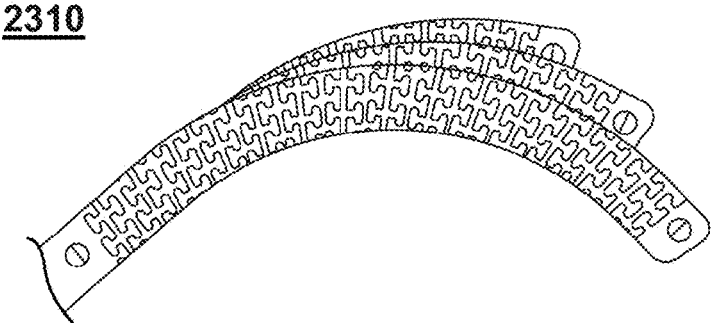

Device 2300 further includes an elongate, flexible, tubular stylus 2310 sized to fit within the lumen of cannula 2306. Stylus 2310 corresponds functionally to the combination of the side catheter guide and side catheter in the embodiments described above. In some implementations, stylus 2310 has an articulated construction, such as in FIGS. 40A and 40B. The articulation can extend for the entire length of stylus 2310, or only for a section of stylus 2310. In some implementations, stylus 2310 is articulated for a length of between about 2 cm to 4 cm from distal end 2302. Stylus 2310 includes a first lumen sized to fit a hollow needle 2312, which corresponds to the septum penetrator in the embodiments described above. Hollow needle 2312 also has a guidewire lumen (corresponding to the guide wire coupler in the embodiments described above) sized to fit any suitable guidewire 2314, such as, for example, a 0.035" guidewire. In some implementations, stylus 2310 includes one or more additional lumen, each additional lumen sized to fit a cable 2316.

Figure 41:
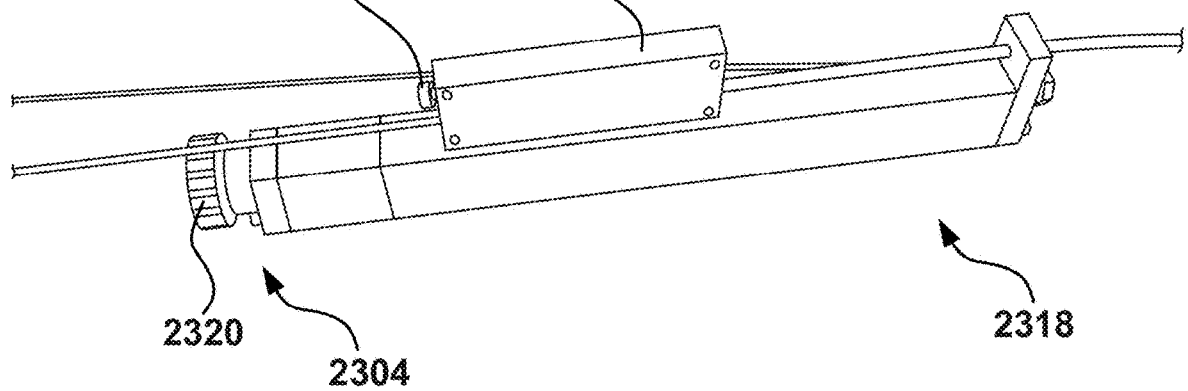
FIG. 41 illustrates handle 2318, according to an embodiment.

Device 2300 further includes handle 2318 at its proximal end 2304 (see e.g., FIG. 41). Handle 2318 includes an extension knob 2320 and at least one angulation screw 2322. Extension knob 2320 is connected to the proximal end of stylus 2310 and is actuatable to extend and retract stylus 2310 within cannula 2306. Each of the at least one angulation screw is connected to the proximal end of a cable 2316 and is actuatable to extend and retract a connected cable 2316 within stylus 2310. In some implementations, handle 2318 further includes one or more actuatable knobs or screws connectable to needle 2312 and guidewire 2314, such that extension and retraction of needle 2312 and guidewire 2314 within stylus 2310 may be achieved with precision.

Figure 42A:
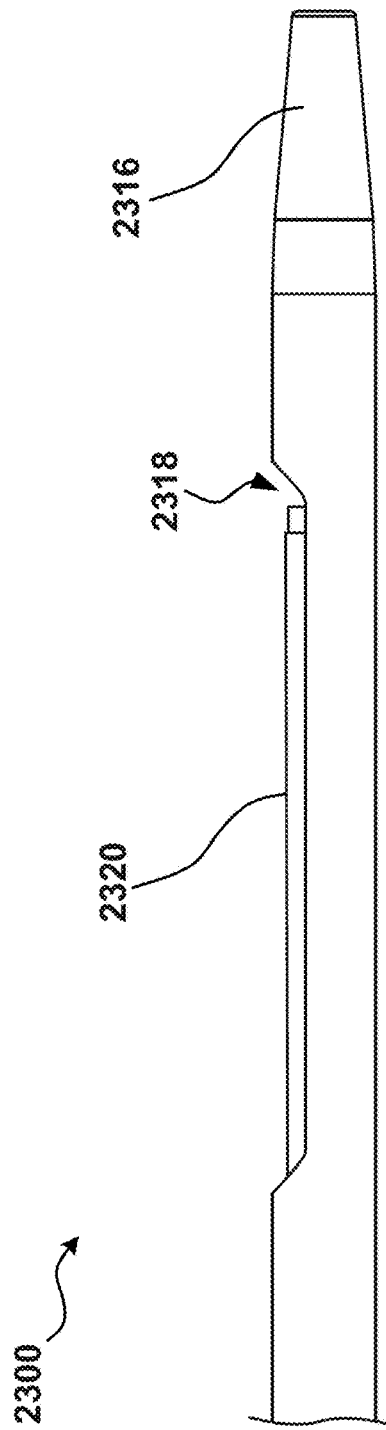

Referring now to FIGS. 42A-42D, a device 2300 is shown in several stages of stylus 2320 deployment. In FIG. 42A, stylus 2320 lies flush within cannula 2316 and does not protrude out of window 2318. In this configuration (a delivery configuration), cannula 2316 may be manipulated to a desired location without being impeded by stylus 2320. For example device 2300 can be delivered to the desired location over a first, deliver guidewire (not shown, disposed in the guidewire lumen of hollow needle 2322. After delivery to the desired location, the delivery guidewire can be withdrawn from device 2300, and a second guidewire can be disposed through device 2300 and the guidewire lumen of hollow needle 2322.

Figure 42B:
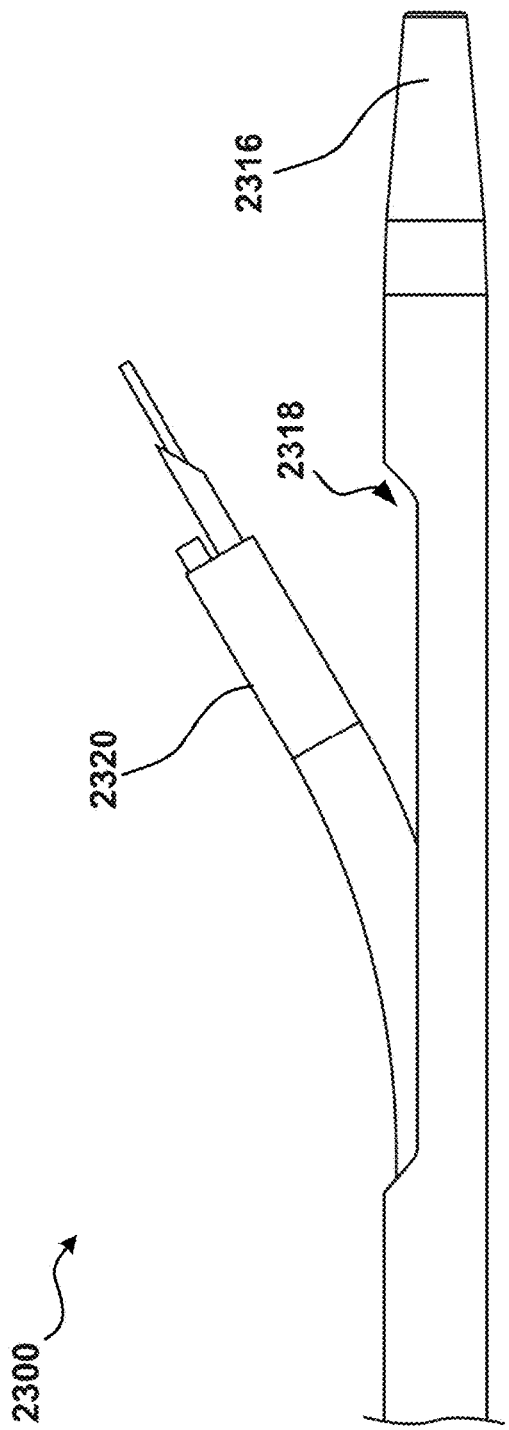

In FIG. 42B through FIG. 24D, a cable 2326 is retracted within stylus 2320, such as by way of a connected angulation screw 2332 on handle 2328. Retracting a cable 3226 causes stylus 20 to angulate out of window 2318 in the direction of the retracted cable 2326, towards a deployed configuration. For example, a stylus 2320 having two or more cables 2326 can have its distal tip angulated in the direction of any of the cables 2326 by retracting one or more cable 2326. The degree of angulation can be varied between about 0 degrees and 90 degrees relative to the axis of the cannula 2316 by adjusting the amount of retraction of a cable 2326 at a connected angulation screw 2332. In various implementations, stylus 2320 can be repositioned within cannula 2316 by adjusting extension knob 2330, such as in FIG. 42D. The combination of angulation control and positional control of stylus 2320 relative to cannula 2316 enables device 2300 to accurately aim needle 2322 towards the FO. In certain implementations, device 2300 can be aimed at a specific location of the FO. The FO can be divided into quadrants, wherein a puncture in each quadrant is advantageous for a specific procedure. For example, device 2300 can be aimed to puncture slightly superior, posterior, and 3.5 cm-4.5 cm above the mitral valve for typical MitraClip devices, and is further configured to puncture posterior and slightly inferior within the FO for typical left atrial appendage occlusion devices.

In various implementations, device 2300 can further comprise one or more modifications to enhance its performance. For example, in some embodiments device 2300 can include one or more additional instruments positioned within a lumen of stylus 2320, such as an endoscope assembly, an ultrasound transducer, a temperature sensor, an oxygen probe, a flow sensor, a cauterizer, and the like. In another example, device 2310 can comprise one or more radiopaque or echo-bright markers positioned on cannula 2316, stylus 2320, or both. The markers enable the position of device 2310 to be monitored via fluoroscopy or echocardiography, and can be placed at or near structures of interest, including but not limited to the distal tips of cannula 2316 and stylus 2320 and the at least one window 2318.

Figure 43A:
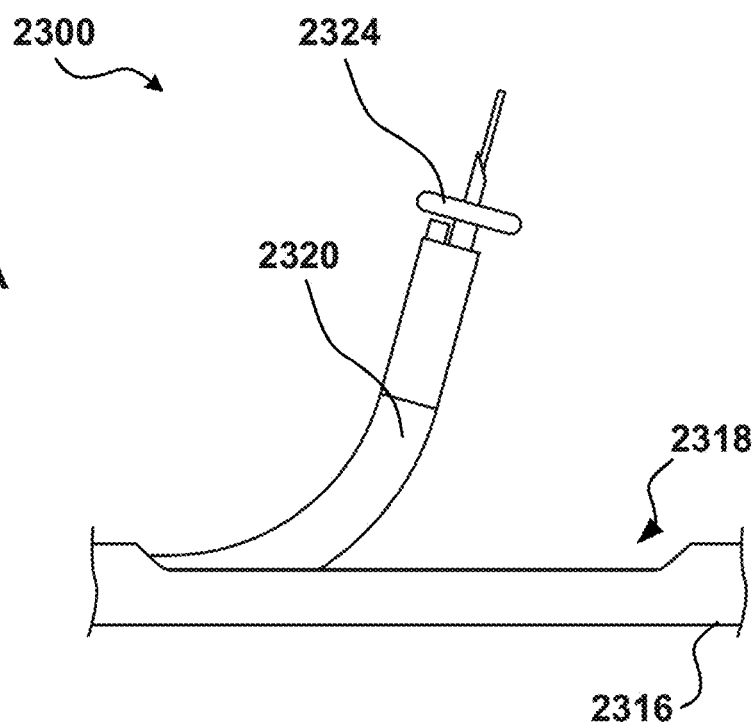
FIGS. 43A and 43B illustrate in side view and cross-sectional side view, respectively, a portion of the septum puncture device 2300.
Figure 43B:
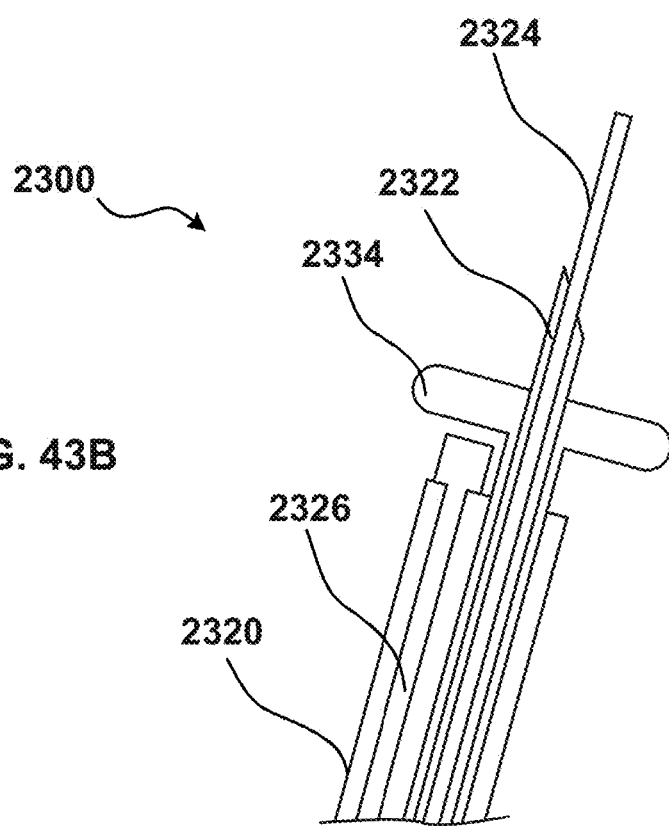
Figure 44:
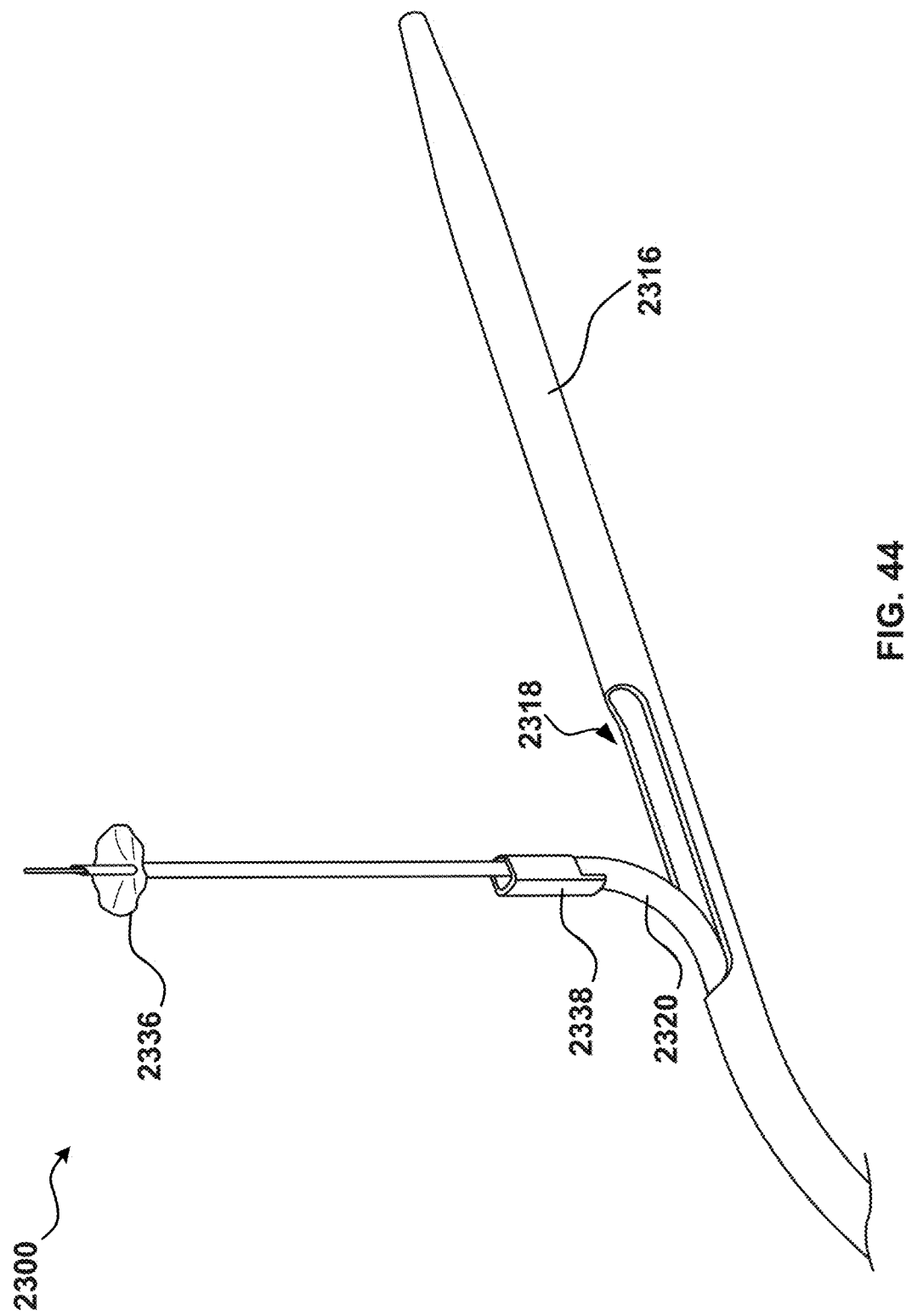
FIG. 44 illustrates in perspective view a portion of the septum puncture device 2300 including an end effector.
Figure 45A:
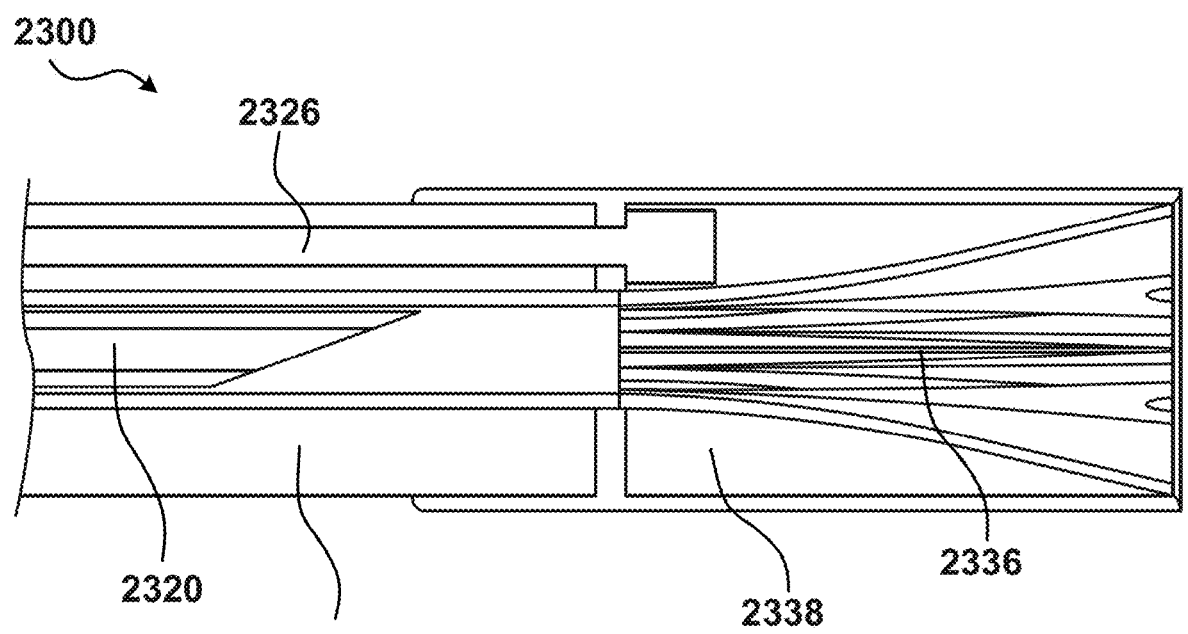
FIGS. 45A-45D illustrate the end effector of FIG. 44.
Figure 45B:
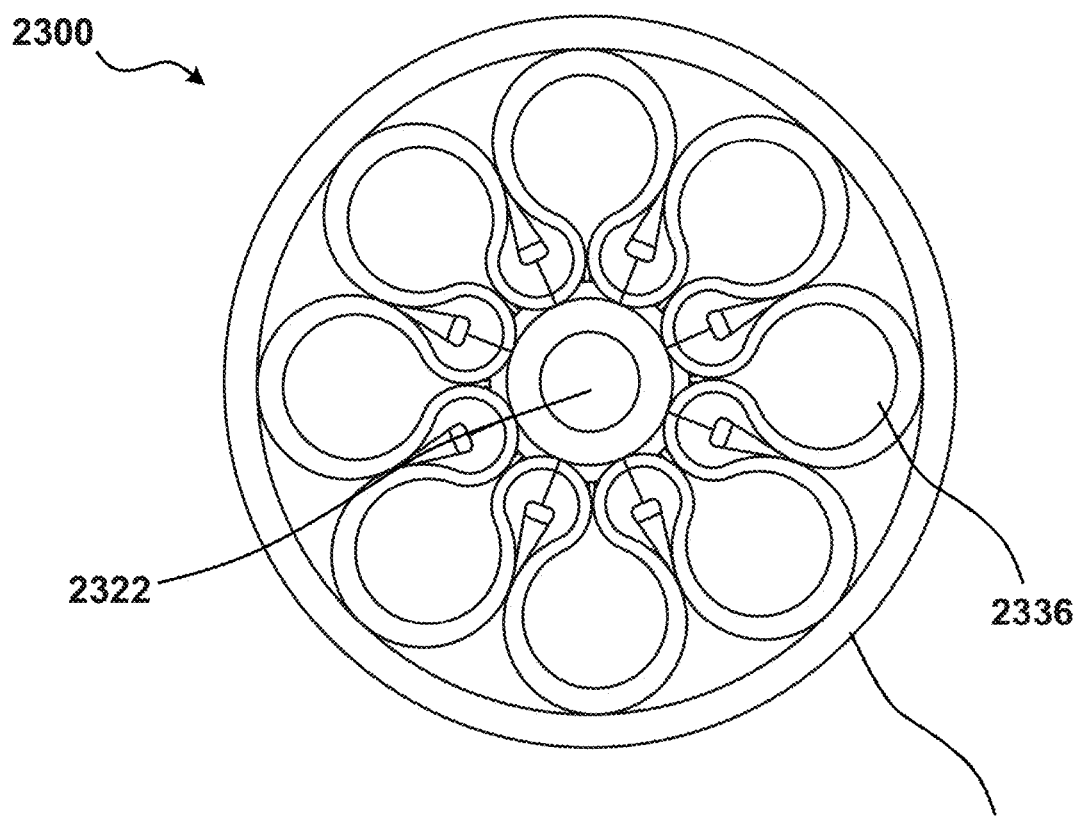
Figure 45C:
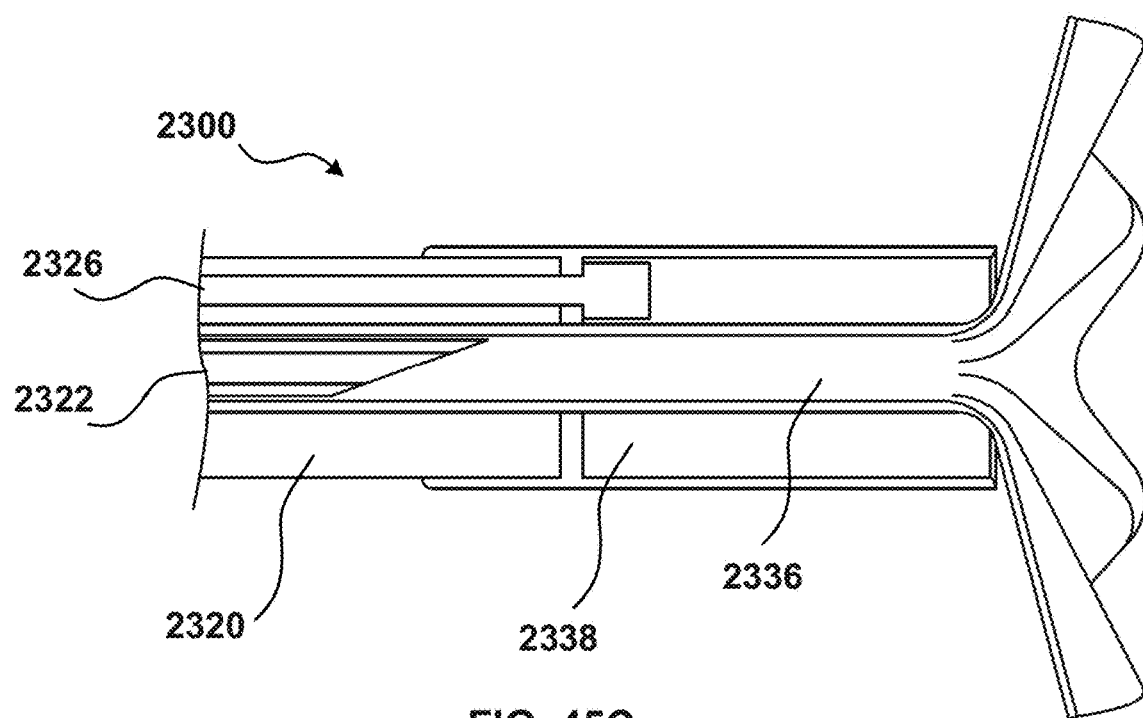
Figure 45D:
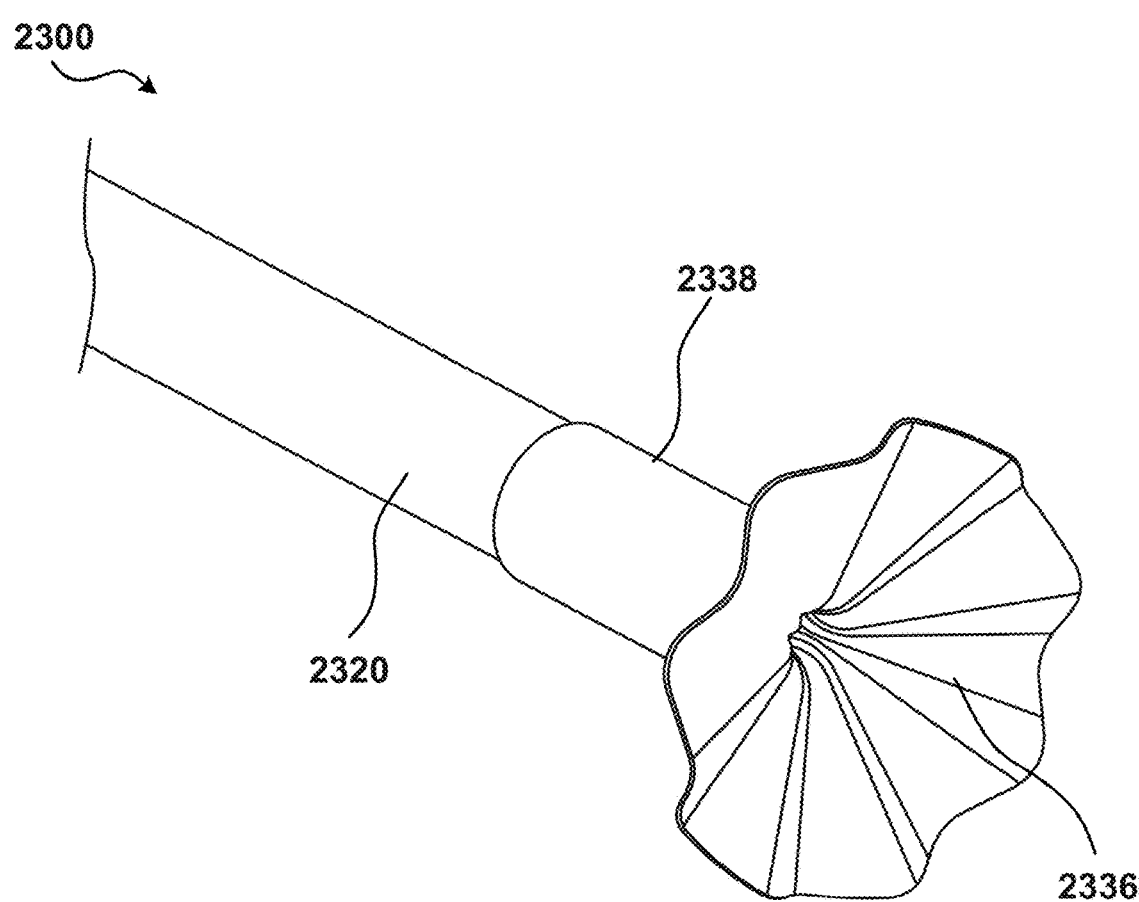

In some embodiments, device 2300 can include an atraumatic support 2334 as shown in FIGS. 43A and 43B. Atraumatic support 2334 has an elongate tubular shape and can fit within the first lumen of stylus 2320 around needle 2322. Atraumatic support 2334 further comprises a blunt tip at its distal end. In some implementations the blunt tip includes an inflatable balloon. In still another implementation, the blunt tip is a flattened end-effector. In still yet another implementation, the blunt tip is a ring-like end-effector. The blunt tip of atraumatic support 2334 provides the distal end of stylus 2320 with a greater surface area to minimize injury and increase stability by providing uniform pressure when placed against a tissue surface, such as the FO. In FIG. 44, device 2310 is depicted having atraumatic support 2336 with a bell-tip configured to be collapsible and withdrawable into a sheath 2338 attached to the distal end of stylus 2320. Similar to atraumatic support 2334, atraumatic support 2336 is generally configured to increase the surface area of stylus 2320 that is in contact with the FO tissue (prior to puncturing the FO) to decrease the pressure on the tissue and to reduce or prevent the likelihood of premature puncture or damage. A collapsible design enables device 2310 to support a wide bell-tip, such as width of between about 8 mm and 15 mm, within the confines of cannula 2316. Referring now to FIGS. 45A-45D, the geometry of atraumatic support 2336 is shown in detail. Atraumatic support 2336 comprises a bell-tip at its distal end having a plurality of undulating folds. Withdrawing atraumatic support 2336 into sheath 2338 causes the bell-tip to bunch together in a controlled manner to fit within sheath 2338 while maintaining a space for the passage of needle 2322. Needle 2322 is thereby capable of being extended and retracted past the bell-tip of atraumatic support 2336 regardless of whether the bell-tip is in a collapsed or an open configuration.

In some implementations, device 2300 can include a stiffening element configured to modify the rigidity of a section of device 2323. Increasing the stiffness of a section of device 2300, such as a section of cannula 2316 comprising at least one window 2318, provides device 2300 with a stable backbone against which an extended stylus 2320 and needle 2322 can push against to penetrate a tissue.

Figure 46A:
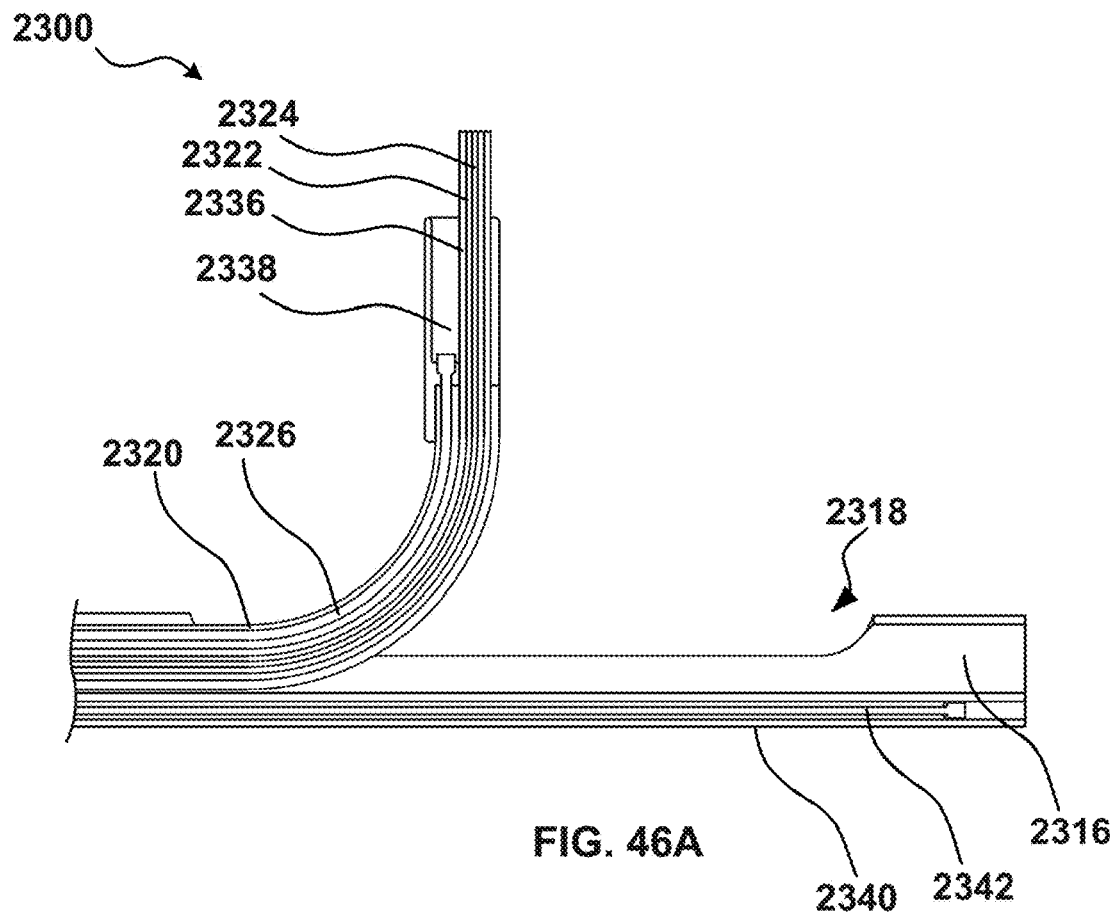
FIGS. 46A and 46B illustrate in cross-sectional side view and front view, respectively, a portion of the septum device 2300, including a stiffening element.
Figure 46B:
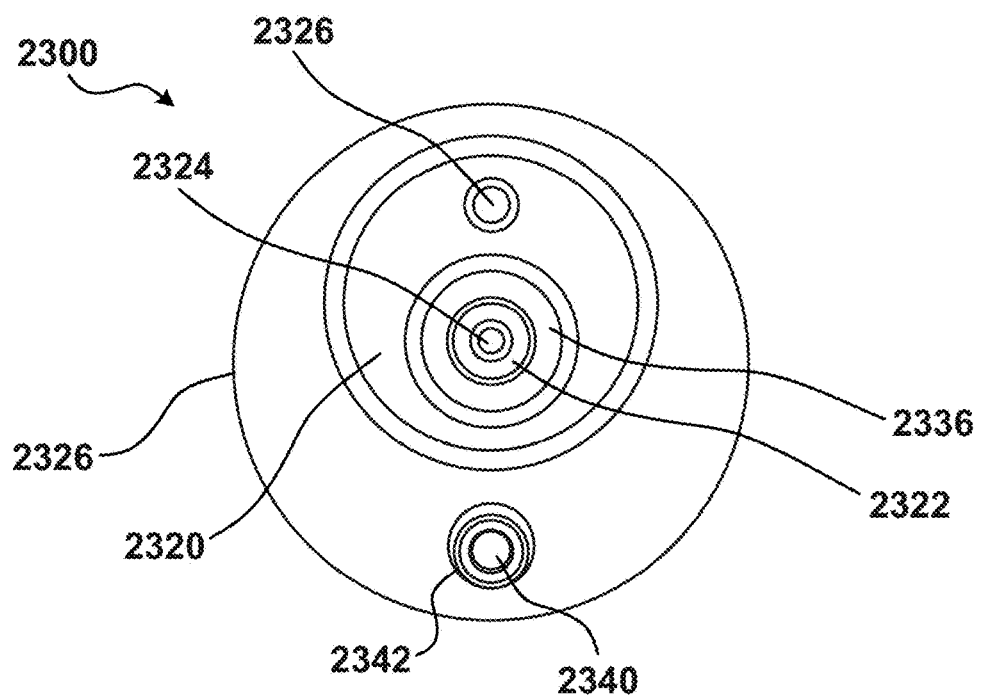
Figure 47A:
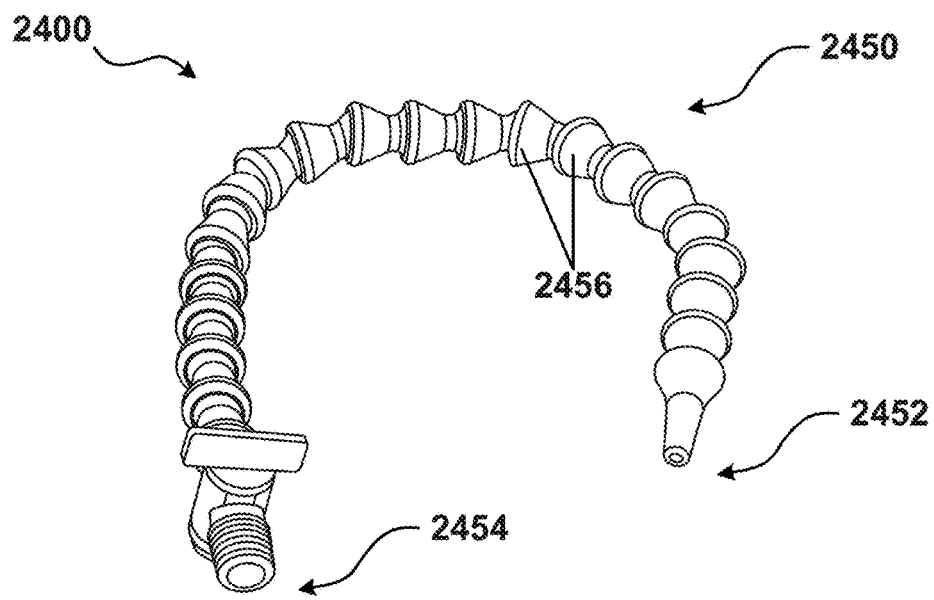
Figures 47B, 47C:
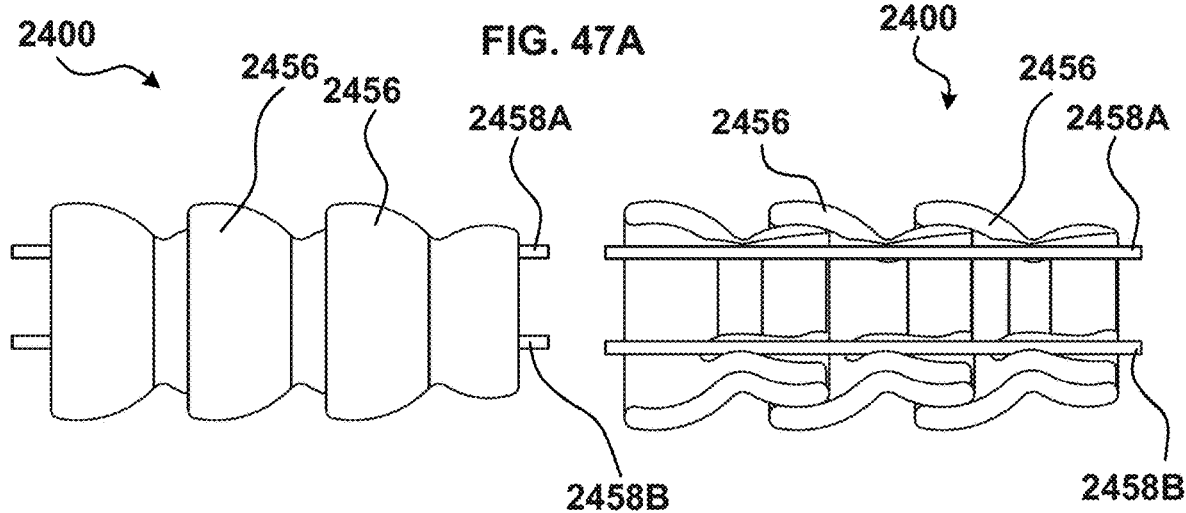
Figure 47D:
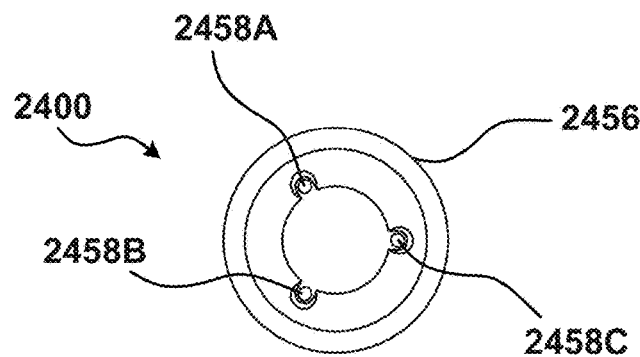
Figure 49:
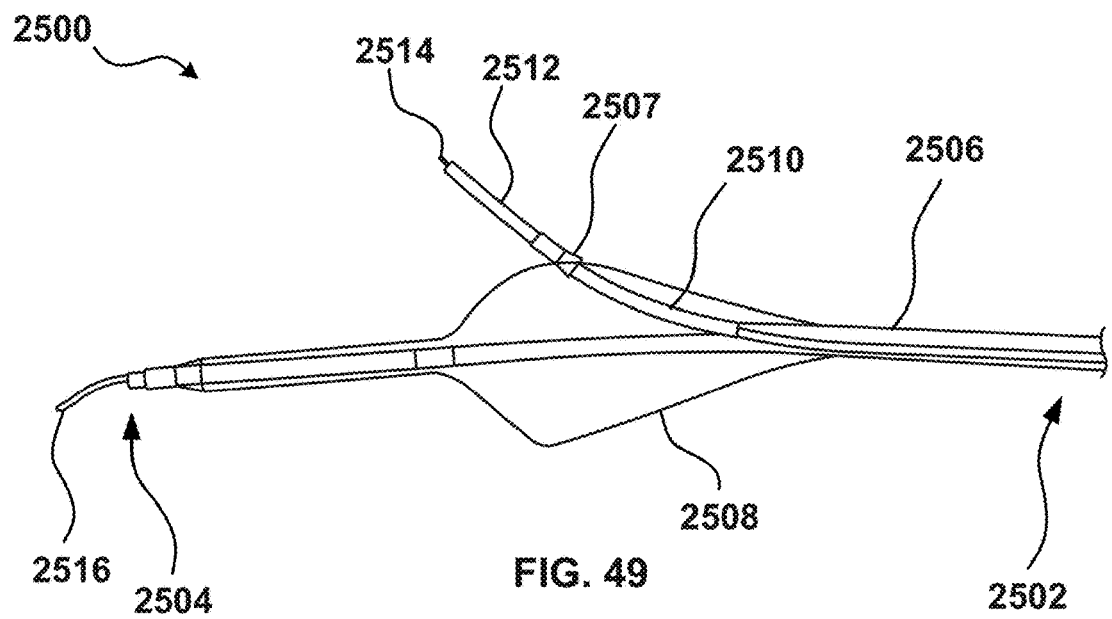
FIGS. 49-52 illustrate a septum puncture device 2500, according to an embodiment.

Referring now to FIGS. 46A and 46B, device 2300 is depicted with a stiffening element comprising spine 2340 and cable 2342. Spine 2340 is positioned within a second lumen of cannula 2316 and extends to at least the location of the at least one window 2318. Spine 2340 is constructed such that it is flexible when loose and stiff when compacted. For example, in some implementations, spine 2340 is an elongate tubular member constructed from a compressible polymer. In other implementations, spine 2340 is made from a long chain of interlocking segments or from a series of hollow tubules loosely positioned next to one another, constructed, for example, from either a plastic or a metal. Cable 2342 runs through the entire length of spine 2340 and comprises a tip at its distal end that is wider than spine 2340. Retracting cable 2342 presses its tip against the distal end of spine 2340, thereby compacting the entire length of spine 2340 and stiffening spine 2340 and the length of cannula 2316 that spine 2340 resides in. Extending cable 2342 relieves the pressure that its tip exerts on the distal end of spine 2340, which relaxes spine 2340 and the length of cannula 2316 that spine 2340 resides in.

Referring now to FIGS. 47A-47D, an exemplary segmented septum puncture device 2400 is depicted. Device 2400 comprises a plurality of interlocking segments 2456 between a distal end 2452 and a proximal end 2454. Interlocking segments 2456 can have any suitable construction to form an elongate, flexible member. For example, in some implementations, tach interlocking segment 2456 comprises a first end having a small hollow spherical shape and a second end having a large hollow spherical shape, such that the first end of one interlocking segment 2456 fits flush within the second end of another interlocking segment 2456 to form a ball joint. A plurality of interlocking segments 2456 connected in this manner thereby forms an elongate, articulating series of ball joints. In other implementations, interlocking segments 2456 can form a gooseneck member, a snake chain member, and the like. Device 2400 further comprises at least a first cable 2458a, a second cable 2458b, and a third cable 2458c running throughout its entire length, each cable 2458a, 2458b, and 2458c being arranged equidistantly from each other in a radial pattern. Each cable 2458a, 2458b, and 2458c is attached to the distal-most interlocking segment 2456, such that retracting any one or two of cable 2458a, 2458b, or 2458c causes distal end 2452 of device 50 to curl in the direction of the retracted cables. Retracting all of the cables 2458a, 2458b, and 2458c with the same amount of force causes device 2450 to stiffen and retain its instant shape.

Referring now to FIGS. 48A-48D, two exemplary configurations of device 2450 are shown. In FIGS. 48A-48D, device 2450 fits within the lumen of a cannula 2462 and comprises a needle 2460 running throughout its hollow interior. In FIGS. 48C and 48D, device 2450 fits within a first lumen of cannula 2462 and needle 2460 fits within a second lumen of cannula 2462. In this configuration, the hollow interior of device 2450 can be used to house an additional instrument, such as an endoscope assembly, an ultrasound transducer, any number of sensor probes (including temperature probes, oxygen sensors, flow sensors), or the like.

Referring now to FIGS. 49-52, an exemplary septum puncture device 2500 is depicted. Similar to other septum puncture devices described herein, device 2500 comprises a cannula 2506 (corresponding to the main body of embodiments described above) extending from a proximal end 2502 to a distal end 2504. Cannula 2506 has an elongate hollow tubular shape having a lumen running between an opening at its proximal end 2502 and its distal end 2504. In some embodiments, cannula 2506 can be described as having two segments, a proximal cannula 206a and a distal cannula 2506b. Near distal end 2504 and positioned between proximal cannula 2506a and distal cannula 2506b, device 2500 comprises a balloon 2508 (corresponding to the GSA in embodiments described above) that is inflatable from a relaxed state to an expanded state. Balloon 2508 is elastic and can be waterproof. Balloon 2508 may be inflatable to a pressure of between about 2 and 20 atmospheres using any suitable fluid, including liquids (such as saline) and gases (such as air). Higher inflation pressures generally increase the rigidity of balloon 2508 for increased stabilization (i.e., vertical and lateral). In some embodiments, balloon 2508 can be supported by one or external arms or enveloped in a mesh for additional stabilization, such as during inflation or tissue puncture. Balloon 2508 can be inflated to any desired diameter. In some embodiments, the inflated diameter of balloon 2508 is contextual to the anatomical space within which it is positioned. For example, balloon 2508 can be inflated to have a diameter that presses or does not press against the walls of a right atrium or the inferior vena cava, for example, to provide further stability for extending stylus 2512 to puncture a FO (in some cases generally reducing the image guidance requirements).

Figure 50:
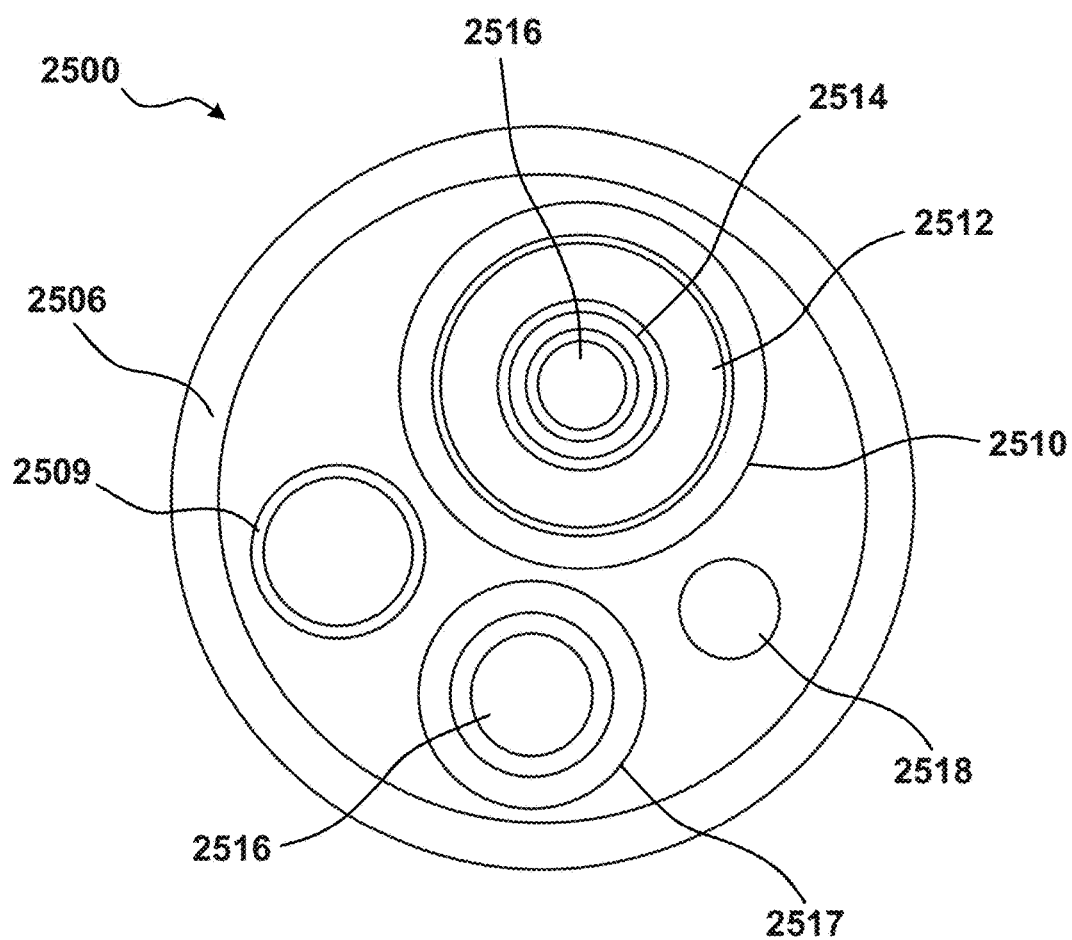
Figure 51:
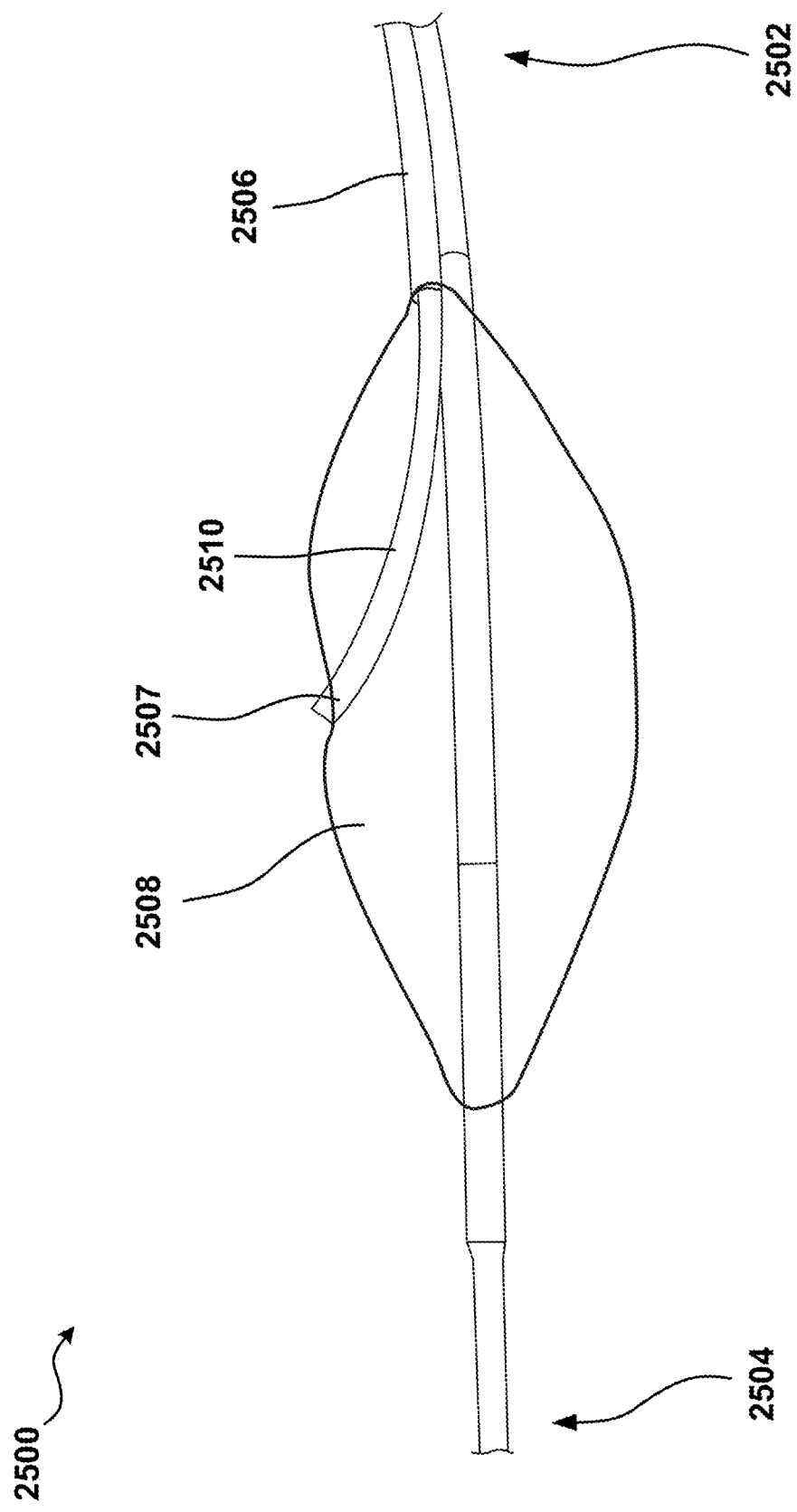

An exemplary internal arrangement of device 2500 is shown in FIG. 50 in a cross-sectional view of device 2500 taken proximal to balloon 2508. The lumen of cannula 2506 is sized to fit an elongate tubular sheath 2510 (corresponding to the side catheter guide of embodiments described above), which has a lumen sized to fit an elongate tubular stylus 2512 (corresponding to the side catheter of embodiments described above), which in turn has a lumen sized to fit hollow needle 2514 (corresponding to the septum penetrator of embodiments described above), which in turn has a lumen sized to fit a guidewire 2516 (e.g., the guidewire to be delivered through the septum, corresponding to guidewire GW2 in embodiments described above). Cannula 2506 further comprises a second guidewire lumen 2517 sized to fit a second guidewire GW1 (e.g. the guidewire over which device 2500 is to be delivered to the desired location, corresponding to guidewire GW1 in embodiments described above). Guidewire 2516 can be any suitable guidewire, such as a 0.035" guidewire, a 0.025" guidewire, a curlycue wire (e.g., a Baylis left atrial wire), and the like. Inflation tube 209 is provided within the lumen of cannula 2506, wherein inflation tube 2509 has an internal lumen fluidly connected to balloon 2508 for inflation and deflation. In some embodiments, cannula 2506 can include one or more stiffening rods 2518 having a selected length to provide device 2500 with greater stiffness in desired sections.

A distal tip of sheath 2510 is secured to an exterior surface of balloon 2508 by balloon grommet 2507. In this configuration, balloon 2508 can be inflated and deflated without leaking out of balloon grommet 2507 or sheath 2510, and sheath 5210 can provide access to the exterior of balloon 2508. Grommet 2507 can include a smooth interior surface (or other surface treatment) to reduce friction between stylus 2512 and grommet 2507, such as when inflating or deflating balloon 2508 or when advancing or retracting stylus 2512 through sheath 2510. Grommet 2507 may be constructed from any suitable material, including a plastic, a metal, a composite, a ceramic, and the like. Grommet 2507 can be further configured to have a particular shape or edging, such that the interior surface has a bevel or chamfer. In one embodiment, grommet 2507 is positioned at a widest radial point or circumference on balloon 208, although grommet 2507 is not limited by placement in other locations.

In some implementations, stylus 2512 has an atraumatic end effector 2511 positioned at a distal tip (e.g., similar to or the same as depicted in FIG. 59B), wherein end effector 2511 has a disc-shape configured to tent a tissue (such as the FO) and apply pressure without inadvertent puncturing. End effector 2511 can have a bell-tip configured to be collapsible and withdrawable into sheath 2510. A collapsible design enables device 2500 to support a wide bell-tip, such as width of between about 8 mm and 15 mm, within sheath 2510. End effector 2511 can comprise a bell-tip having a plurality of undulating folds. Withdrawing end effector 2511 into sheath 2510 causes the bell-tip to bunch together in a controlled manner to fit within sheath 2510 while maintaining a space for the passage of needle 2514. Needle 2514 is thereby capable of being extended and retracted past the tip of end effector 2511 regardless of whether the tip is in a collapsed or an open configuration. In some embodiments, the lumen of stylus 1510 can accept a radiofrequency probe having a rounded metal tip, wherein the metal tip can be electrified with a current (e.g., radio ablation) to puncture tissue in lieu of a needle.

Figure 52:
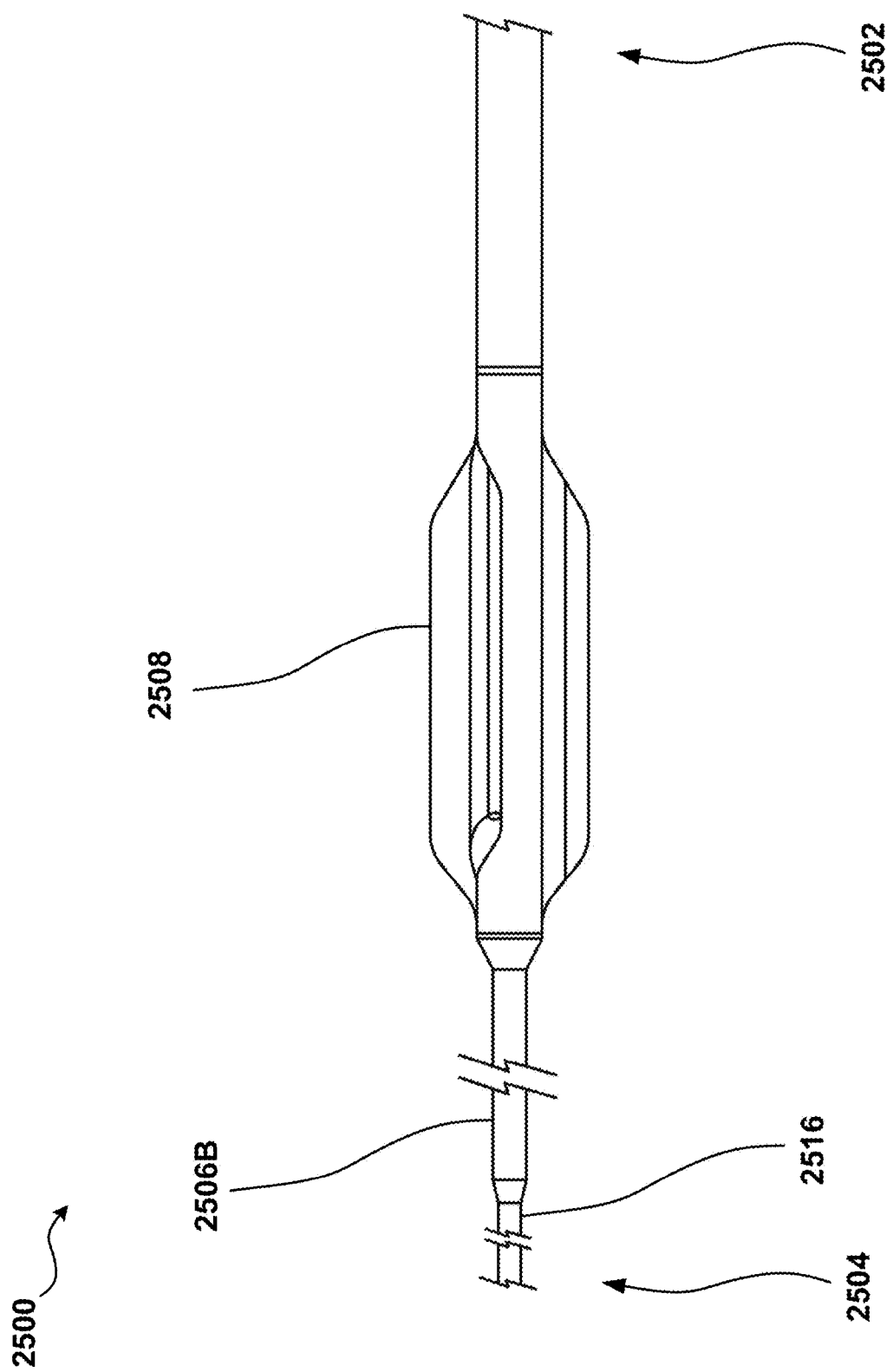

Device 2500 is configured to increase lateral stability of needle 214 while puncturing a tissue, such as the FO. Balloon 2508 has an expanded state (FIG. 49) and a relaxed state with a thin profile (FIG. 52). The relaxed state defines a delivery configuration for device 2500 and permits device 2500 to be guided into the right atrium of a patient's heart such that distal end 2504 of device 2500 can be positioned within a subject's superior vena cava. In some embodiments, balloon 2508 in a relaxed state can be folded over end effector 2511, stylus 2512, and sheath 2510, wherein the folded configuration (or delivery configuration) is maintained during insertion and advancement of device 2500 to a right atrium (similar to an intraortic balloon pump). Thus, device 2500 does not generally require a "sheath" catheter to be positioned over (i.e., cover) the assembly of a folded balloon 2508, end effector 2511, stylus 2512, and sheath 2510 during insertion or withdrawal. In some implementations, device 2500 can be provided with a casing or sleeve that slides over balloon 2508 in a relaxed state. In the expanded state, balloon 2508 is configured to be sufficiently rigid to enhance stability (e.g., lateral stability). In some embodiments, balloon 2508 is configured to selectively press against the wall of a right atrium adjacent to the FO to further enhance stability (e.g., lateral stability). Device 2500 thereby provides stability in the area immediately behind stylus 2512 by expanding to provide a larger clearance for FO access.

In some embodiments, balloon 2508 is configured to increase the stability and precision (i.e., steerability of stylus 2512) of puncturing tissue. For example, grommet 2507 can be placed at a point on balloon 2508, as described above, such that stylus 2512 protrudes through balloon 2508 by way of sheath 2510 at an angle with respect to a long axis of cannula 206 when balloon 2508 is in an expanded state. Thus, balloon 2508 functions similar to the GSA in embodiments described above. In some embodiments, the angle is between about 60 and 180 degrees. In some embodiments, the angle is between about 60 and 140 degrees. In some embodiments, the angle is between about 60 and 100 degrees. In some embodiments, the angle is between about 80 and 120 degrees. In some embodiments, the angle is approximately 90 degrees. In some embodiments, the angle is approximately 80 degrees (e.g., see FIG. 59A). In some embodiments, the angle is approximately 110 degrees. In some embodiments, stylus 2512 can protrude approximately 3-4 cm from balloon 2508, such that the protruding portion of stylus 2512 is generally straight.

Balloon 2508 can be further configured to affect the angle of stylus 2512 when inflated. For example, balloon 2508 may have a generally spherical-like shape, while in other implementations balloon 2508 has an elliptical-like shape. Still further, balloon 2508 may be generally symmetric or asymmetric (see FIG. 53A). For example, an asymmetric balloon 2508 may have an inflated radius that is larger at grommet 2507 than at a portion of balloon 2508 opposite grommet 2507. In another example, an asymmetric balloon 2508 may have an inflated radius that is different at grommet 2507 than at portions of balloon 2508 circumferentially adjacent to grommet 2507. From a cross-sectional view, cannula 2506 would thereby be non-centric with an inflated balloon 2508. Thus, grommet 2507 can be positioned at a point on balloon 2508 (having an inflated radius) that provides a preferred angle of stylus 2512 when balloon 2508 is in an expanded state to increase stability and steerability of stylus 2512.

In some implementations, balloon 2508 can be shaped to allow blood flow around balloon 2508. For example, balloon 2508 may have a plurality of lobes, such as longitudinally-oriented (or axially-oriented) lobes (see FIG. 53B). In an expanded state, lobes on balloon 2508 provide lateral stability by positioning stylus 2512 at a preferred angle, while a varied inflated radius of balloon 2508 permits blood to flow around portions of balloon 2508 (e.g., if balloon 2508 were to become wedged in either the superior or inferior vena cava). Furthermore, lobes on balloon 2508 may have lateral aspects to further increase lateral stability of stylus 2512. For example, the plurality of lobes may form spiral-like or helical shapes or patterns.

In some implementations, balloon 2508 may be positioned adjacent to cannula 2506. As shown in FIG. 53C, sheath 2510 can be cradled within a groove in cannula 2506 with balloon 208 folded around sheath 210. Inflating balloon 2508 pushes sheath 2510 away from cannula 2506, thereby positioning stylus 2512 within at a desired angle. In some implementations, the angle can be adjusted by varying the amount of inflation in balloon 2508.

Figure 54A:
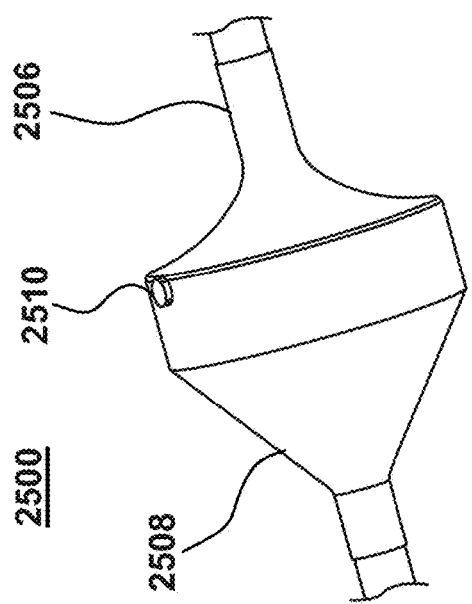
FIGS. 54A-54C illustrate various implementations of the septum puncture device 2500.
Figure 54B:
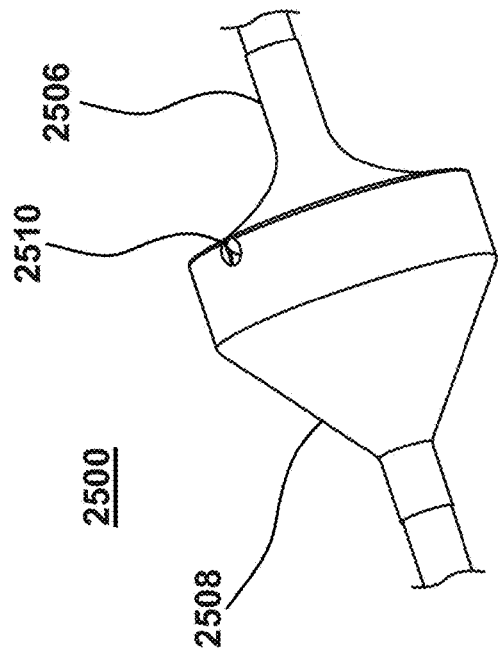
Figure 54C:
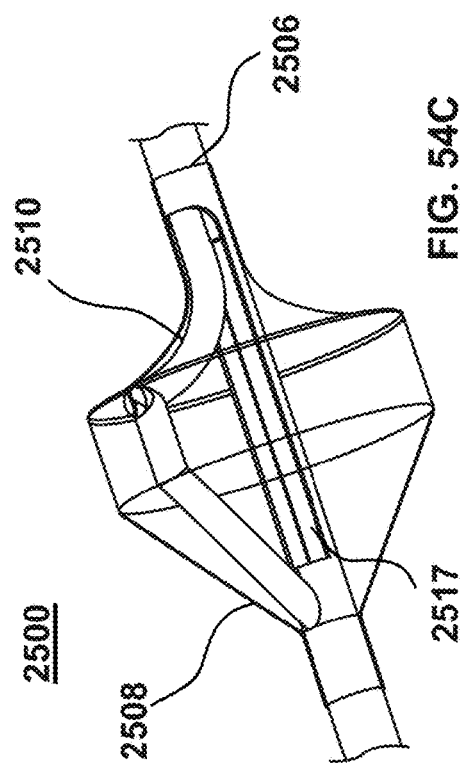
Figure 55:
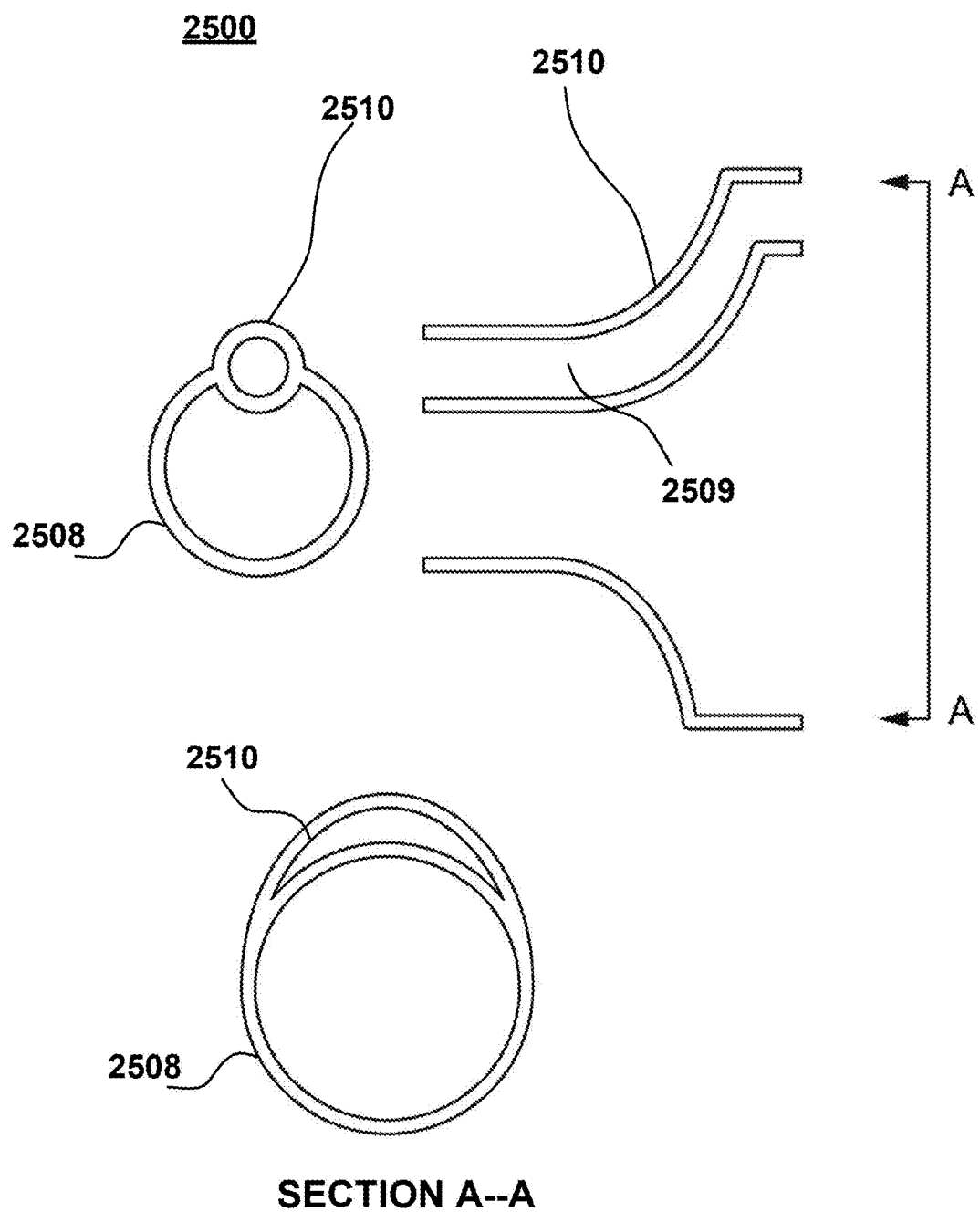
FIG. 55 illustrates a sheath of the septum puncture device 2500.

In some implementations, balloon 2508 may be shaped to have a concave or convex surface. For example, FIGS. 54A-54C depict a device 2500 having a balloon 2508 with a concave proximal surface. Sheath 2510 can be attached to the concave proximal surface and curve accordingly, thereby being configured to direct stylus 2512 outward in a lateral direction. In some implementations, sheath 2510 can be external or partially external to balloon 2508. For example, FIG. 55 depicts a cross-sectional view of a sheath 2510 that is partially embedded within an exterior surface of balloon 2508. It should be understood that sheath 2510 can have any desired cross-sectional shape, including but not limited to the oval-like and arcuate cross-sections depicted in FIG. 55.

Figure 56:
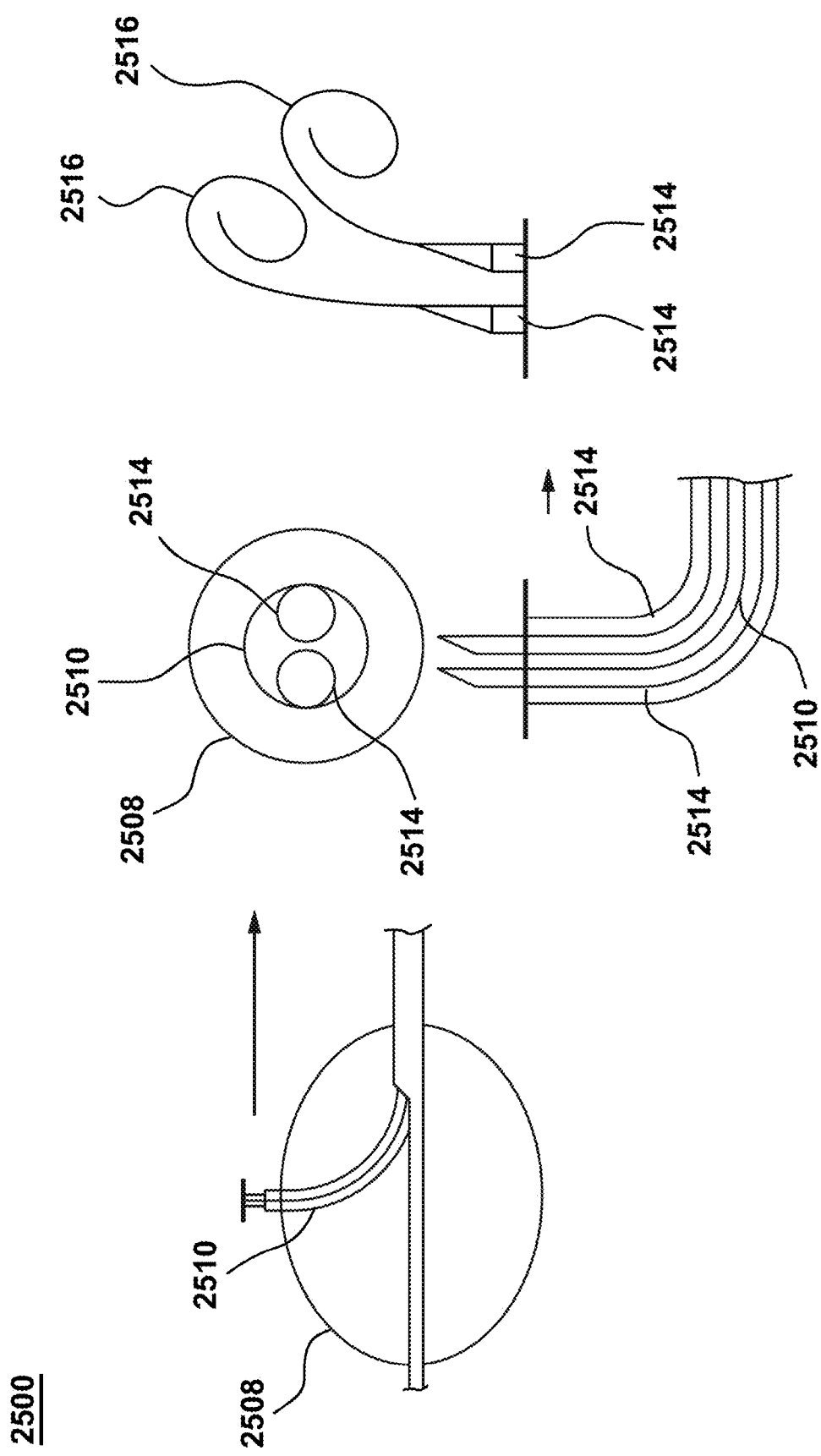
FIG. 56 illustrates various implementations of the septum puncture device 2500.

In various implementations, device 2500 can further comprise one or more modifications to enhance its performance. For example, device 2500 can be modified to include additional sheaths 2510, styluses 2512, needles 2514, and guidewires 2516, similar to the embodiments illustrated in FIGS. 19-23 and described above. As shown in FIG. 56, the additional sheaths 2510, styluses 2512, needles 2514, and guidewires 2516 can be secured to balloon 2508 to provide separate puncture sites. In this way, stylus 2512 can be used to allow separate punctures to perform different procedures or perform different steps of a procedure, such a first needle 2514 for a first procedure or step and a second needle 2514 for a second procedure or step, etc. Each needle 2514 can be positioned relative to each other on the FO (e.g., by positioning stylus 2512 within the right atrium, rotating stylus 2512, and adjusting the angle of stylus 2512) to preferably position each of the needles 2514 on the FO for each respective procedure or step of the procedure that they are being used. Thus, device 2500 can be configured to have multiple extendable elements in close proximity to allow simultaneous punctures.

In another example, device 2500 can comprise one or more corrugations or radiopaque, echo-bright, or sonically opaque markers. The markers enable the position of device 2500 to be monitored via fluoroscopy or echocardiography, and can be placed at or near structures of interest, including but not limited to at least a portion of cannula 2506, stylus 2512, end effector 2511, balloon 2508, or the like.

The various components of the embodiments described herein can be constructed using any suitable method. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the devices may be made using 3-dimensional ("3D") printing or other additive manufacturing techniques. Further, it should be understood that any descriptions applicable to one embodiment of the present invention are equally applicable to all embodiments described elsewhere herein.

Figure 57:
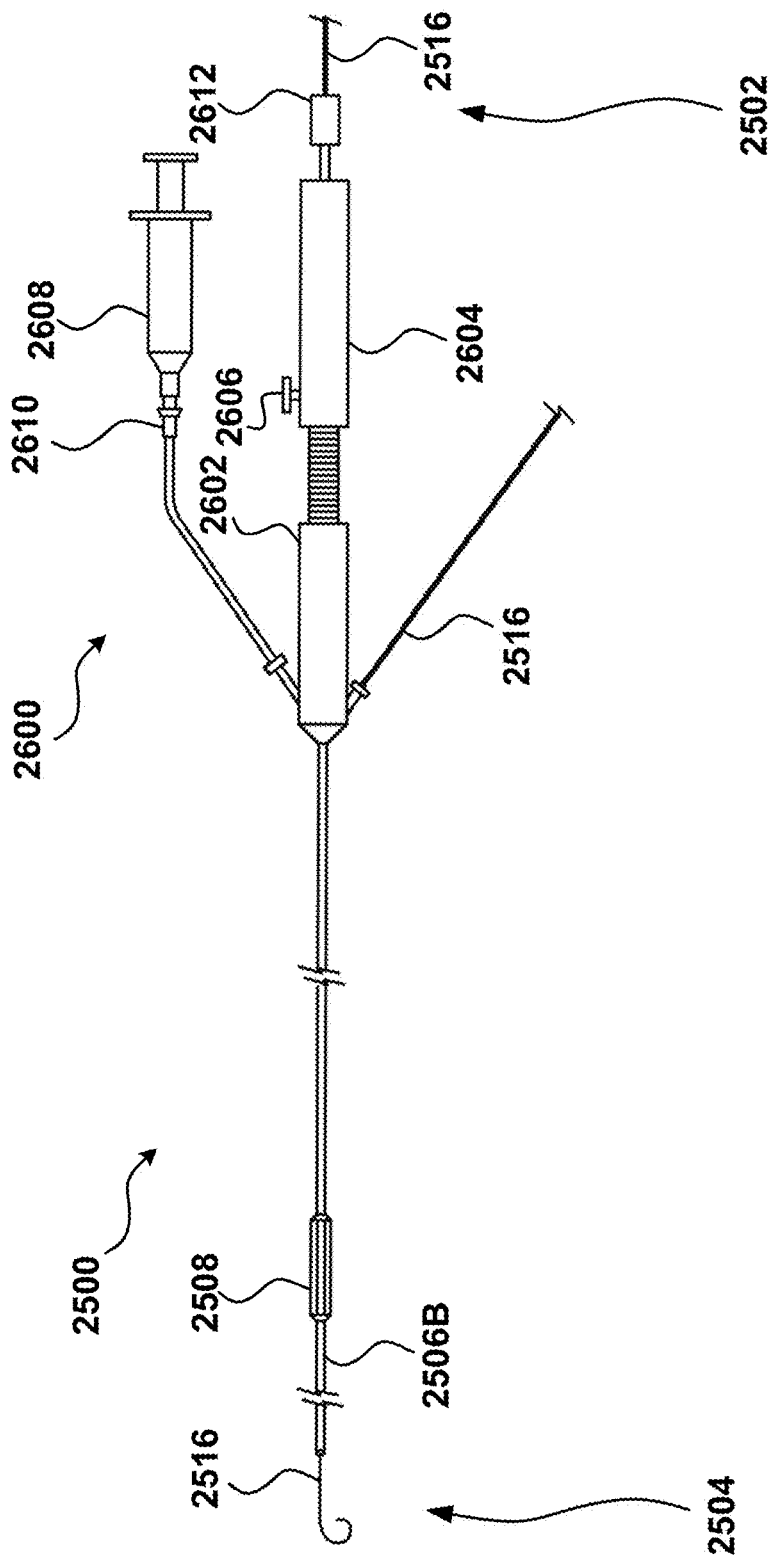
FIGS. 57 and 58 illustrate a handle assembly 2680, according to an embodiment.
Figure 58:
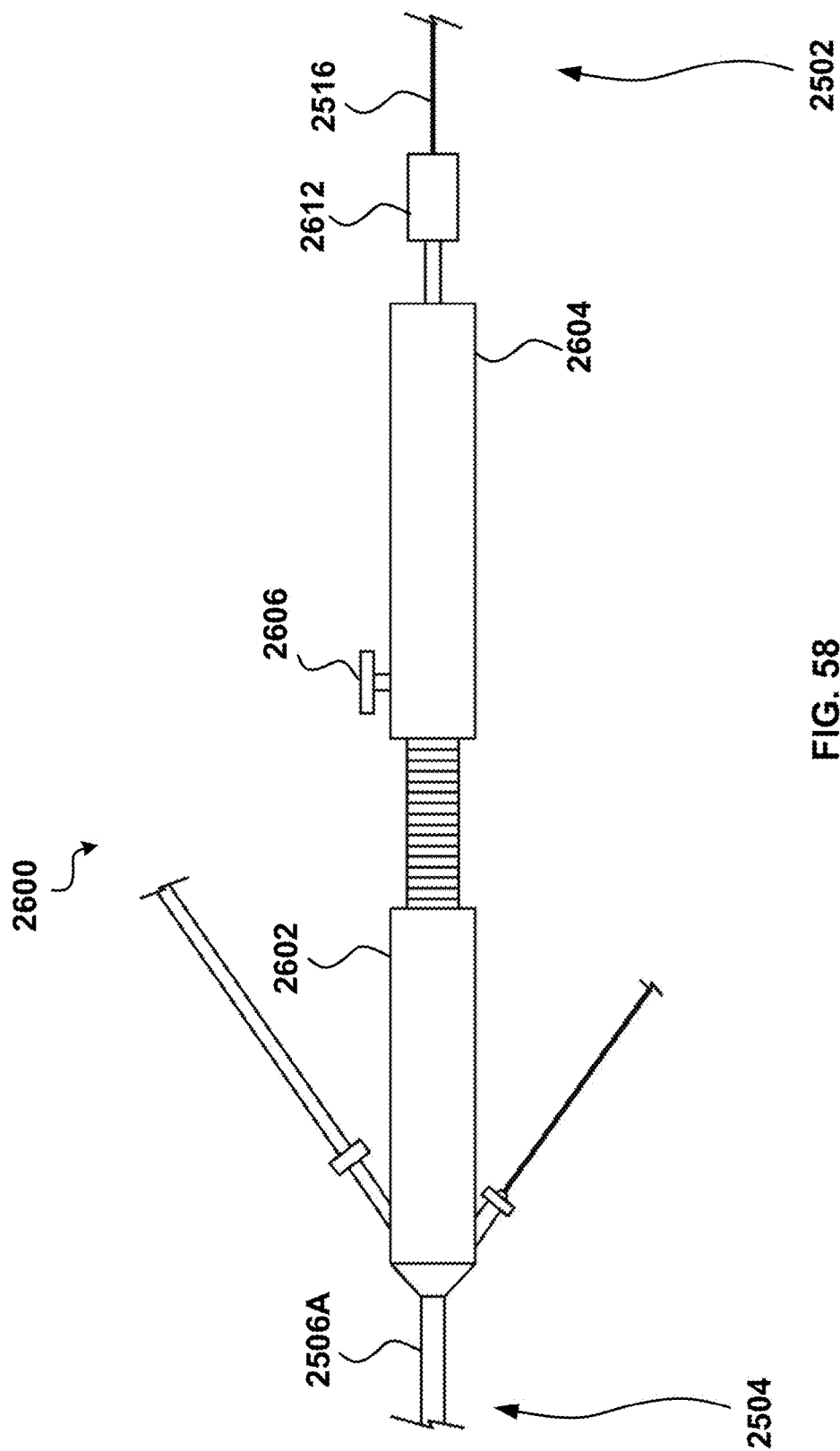

The septum puncture devices described herein can be used in conjunction with any suitable handle adapted to the components of the devices. Referring now to FIG. 57, an exemplary handle assembly 2680 is depicted. Handle assembly 2600 comprises main shaft handle 2602 engaged to a side catheter handle 304 by a side catheter deflection knob 2606. Knob 2606 can be tightened to secure handle 2604 to handle 2602 and loosened to permit handle 2604 to be actuated relative to handle 2602. Handle assembly 2680 further comprises a plurality of lumens connected to openings, the lumens and openings sized to receive guidewires and needles. Handle 2602 comprises a lumen and opening connected to a balloon inflation syringe 2608. A valve or stopcock 2610 is provided at the engagement between handle 2602 and syringe 2608. Handle assembly 2680 further comprises a needle tube handle 2612 and a needle safety tab 2614.

While handle assembly 2680 is connectable to any septum puncture device described herein, it is now described in relation to device 2500 by example. Handle 2602 is connectable to a proximal end of a cannula of a septum puncture device, such as cannula 2506, to manipulate, rotate, advance, and withdraw the cannula. Handle 2604 is connectable to a proximal end of a stylus of a septum puncture device, such as stylus 2512, to manipulate, rotate, advance, and withdraw the stylus. A venous guidewire 2516 inserted into the distal opening of device 2500 is configured to exit handle assembly 2680 through a side opening on handle 2602. Syringe 2608 is fluidly connected to inflation lumen 2509 to inflate and deflate balloon 2508, wherein stopcock 2610 can be actuated to maintain or release the inflated state of balloon 2508. Needle 2514 is connected at a proximal end to handle 2612, wherein needle safety tab 2614 can be clipped onto the proximal end of needle 2514 between handle 2604 and handle 2612 to prevent inadvertent extension of needle 2514. An atrial guidewire 2516 residing within needle 2514 can extend proximally from handle 2612. In various embodiments, handle assembly 2680 further comprises one or more actuatable knobs or screws connectable to the cannula, styluses, needles, and guidewires, such that extension and retraction of the components may be achieved with precision. In some embodiments, handle assembly 2600 can include components configured to further steer the components, such as pull cables.

Referring now to FIG. 58 and FIGS. 59A-59D, the operation of device 2500 using handle assembly 2680 is described. In FIG. 59A, balloon 2508 is inflated to an expanded state using syringe 2608 and is maintained in an expanded state by closing stopcock 2610. The inflation of balloon 2508 angles sheath 2510 away from cannula 2506, such as by an angle of 80 degrees relative to a long axis of cannula 2506. In FIG. 59B, knob 2606 is loosened to advance handle 604 towards handle 2602 and extend stylus 2512 out of sheath 2510, exposing end effector 2511. Stylus 2512 can be extended by any desired length, such as about 3-4 cm, and held in place by tightening knob 2606. In FIG. 59C, device 2500 is positioned adjacent to an atrial septum such that end effector 2511 presses against and tents the FO. In FIG. 59D, needle safety tab 2614 is removed to allow handle 2612 to be advanced toward handle 304 and extend needle 2514 out of stylus 2512 to pierce the FO. Needle 2514 can be extended by any desired length, such as about 4-10 mm. Atrial guidewire 2516 can then be advanced in a distal direction to pass through needle 2514, the FO, and into the left atrium.

Another embodiment of a device 2700 is shown in FIGS. 60A to 60D. Device 2700 has a plurality of slits 2775 positioned near its distal end uniformly distributed around the body, defining therebetween a plurality of arms 2776. Compressing device 2700 on either side of the plurality of slits 2775 expands the arms 2776 outwards, exposing stylet catheter section 2778, which may have a rigid construction, formed by either a hard plastic or a metal, and permits at least the distal end 2771 of cannula 2774 to advance proximally over catheter section 2778 to achieve expansion of arms 2776. In certain embodiments, the distal end 2771 of cannula 2774 is manipulated using one or more pull cables running through the length of device 2700. For example, the one or more pull cables can be equally retracted to expand each arm 2776 uniformly and to form equally sized openings between each arm 2776. In another example, the one or more pull cables can be selectively retracted, such that pull cables subjected to more tension cause greater expansion in the arms 2776 closest to those pull cables, varying the geometry of the opening between each arm 2776. Expanded arms 2776 provide clearance for the extension of stylet 80 out of catheter section 78, and also for the extension of hollow needle 82 out of stylet 80 and any desired guidewires out of hollow needle 2782.

Figure 60B:
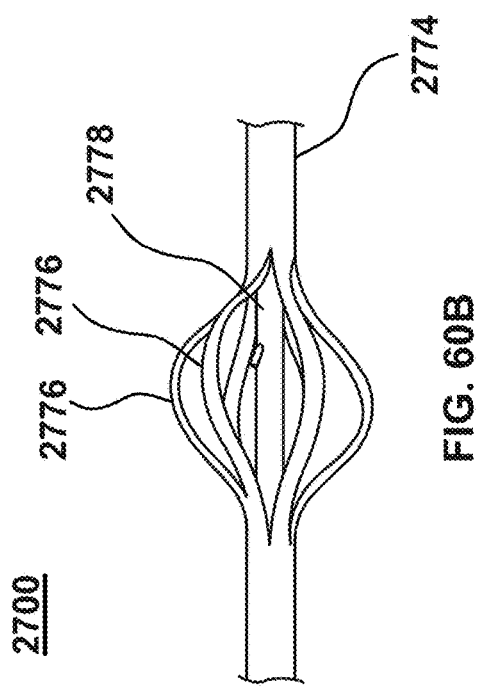
FIGS. 60A-60D illustrate a portion of a septum puncture device 2700, according to an embodiment.
Figure 60D:
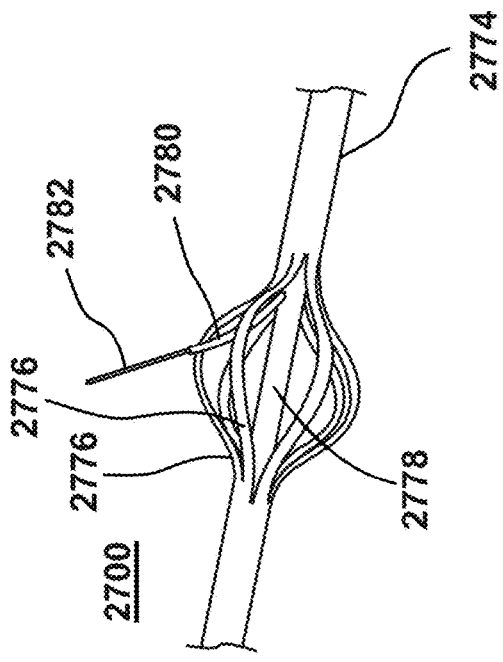
Figure 60A:
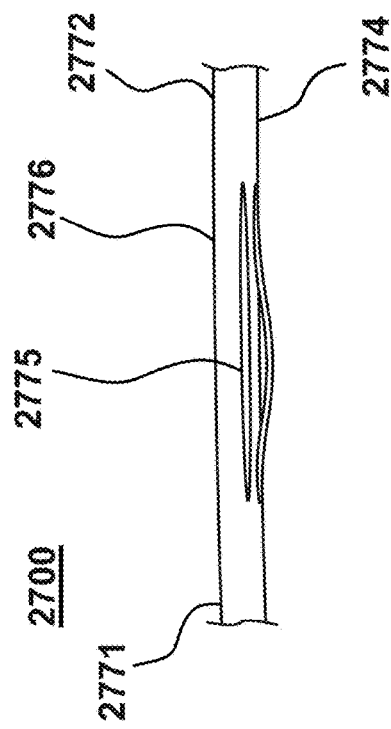
Figure 60C:
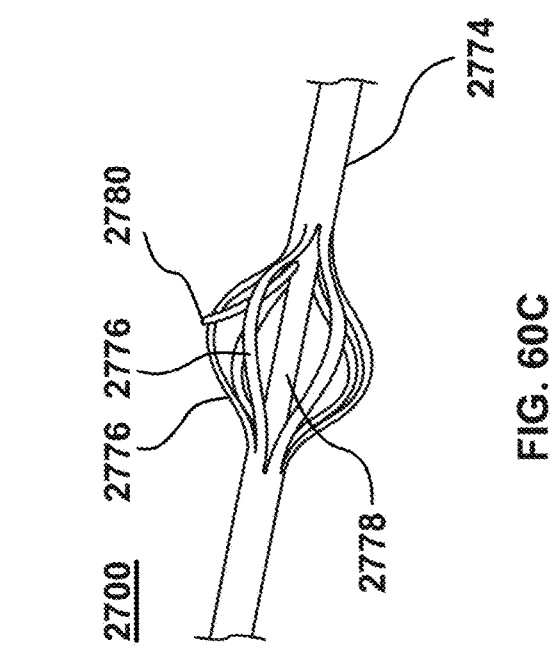

A device 2700 has a relaxed state with a thin profile (or delivery configuration, shown in FIG. 60A) and an expanded state (or deployed configuration, shown in FIG. 60B). The relaxed state permits device 2700 to be guided into the right atrium of a patient's heart such that the distal end of device 2700 rests in the patient's super vena cava. In the expanded state, the plurality of arms 2776 are configured to selectively press against the wall of the right atrium adjacent to the FO to enhance stability (e.g., lateral stability). Device 2700 thereby provides at least two stable platforms for septum puncture using stylet 2780: the plurality of arms 2776 pressing directly against the heart tissue, and the catheter section 2778 suspended between the plurality of arms 2776. Selective retraction of pull cables in device 2700 to non-uniformly expand device 2700 can be desirable in certain situations. For example, device 2770 can be expanded such that the arms 2776 adjacent to stylet 2780 are greatly expanded to provide a larger clearance for FO access, while the arms 2776 behind stylet 2780 can be expanded to a lesser degree to increase stability in the area immediately behind stylet 2780.

Figure 61A:
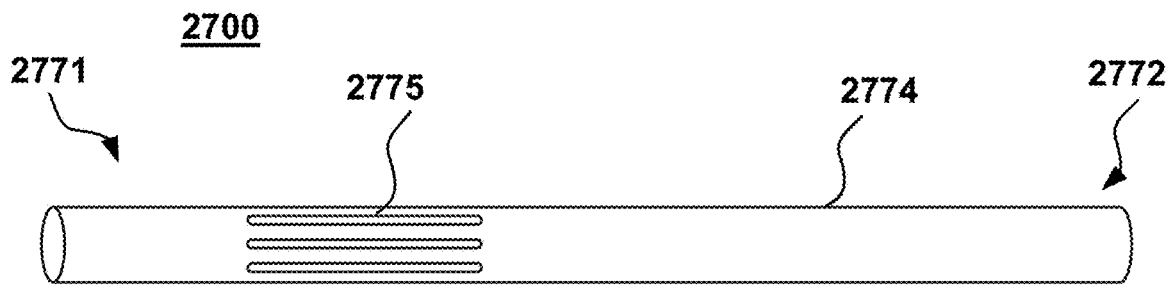
FIGS. 61A-62B illustrate various implementations of the septum puncture device 2700.
Figure 61B:
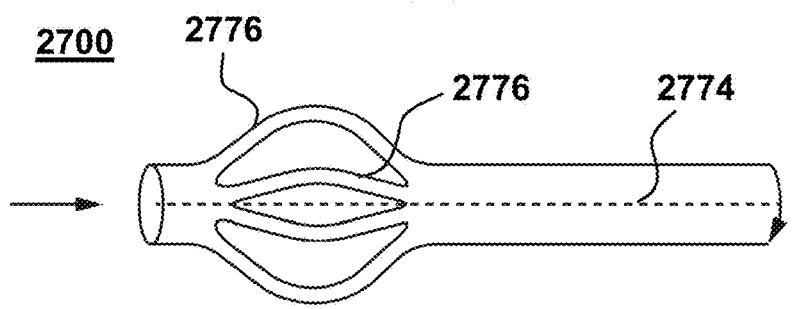
Figure 61C:
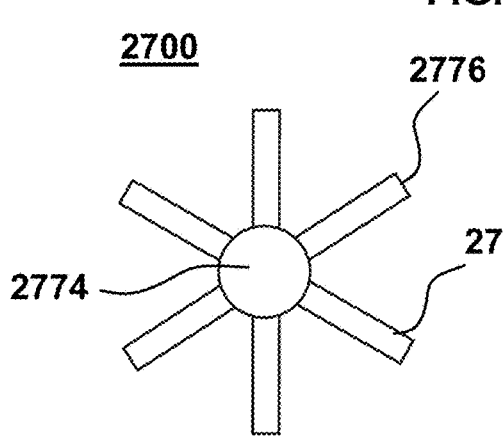
Figure 61D:
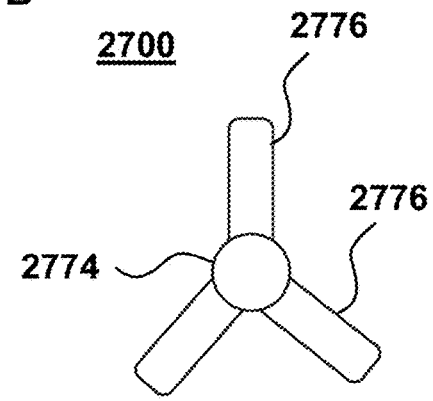
Figure 61E:
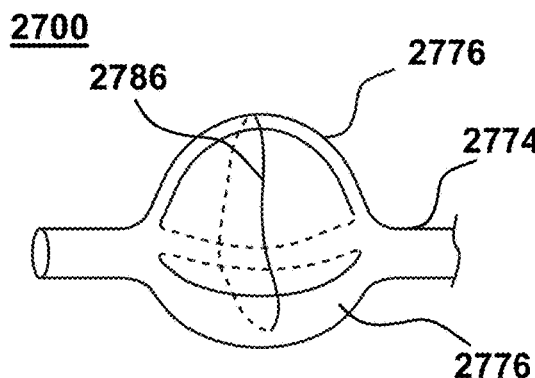
Figure 61F:
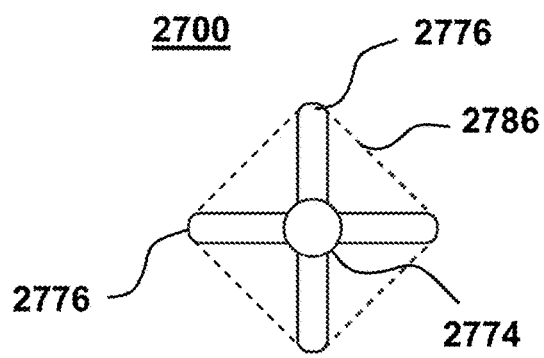
Figure 61G:
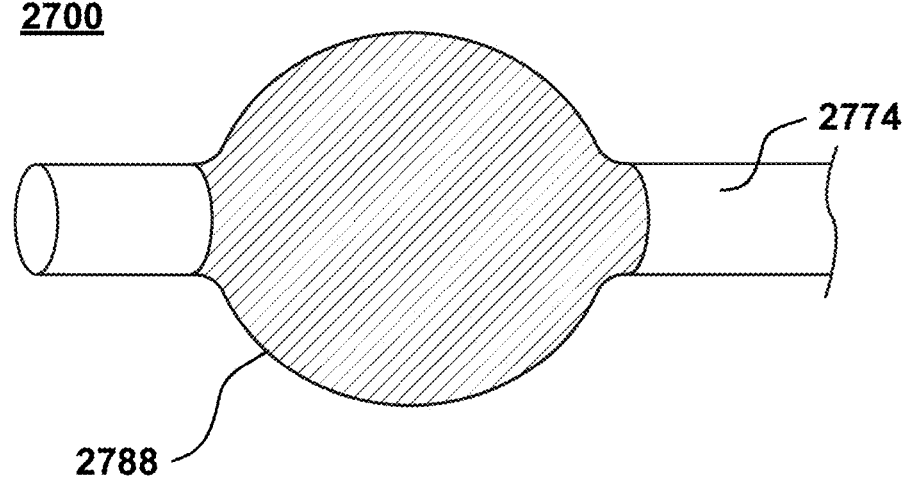
Figure 61H:
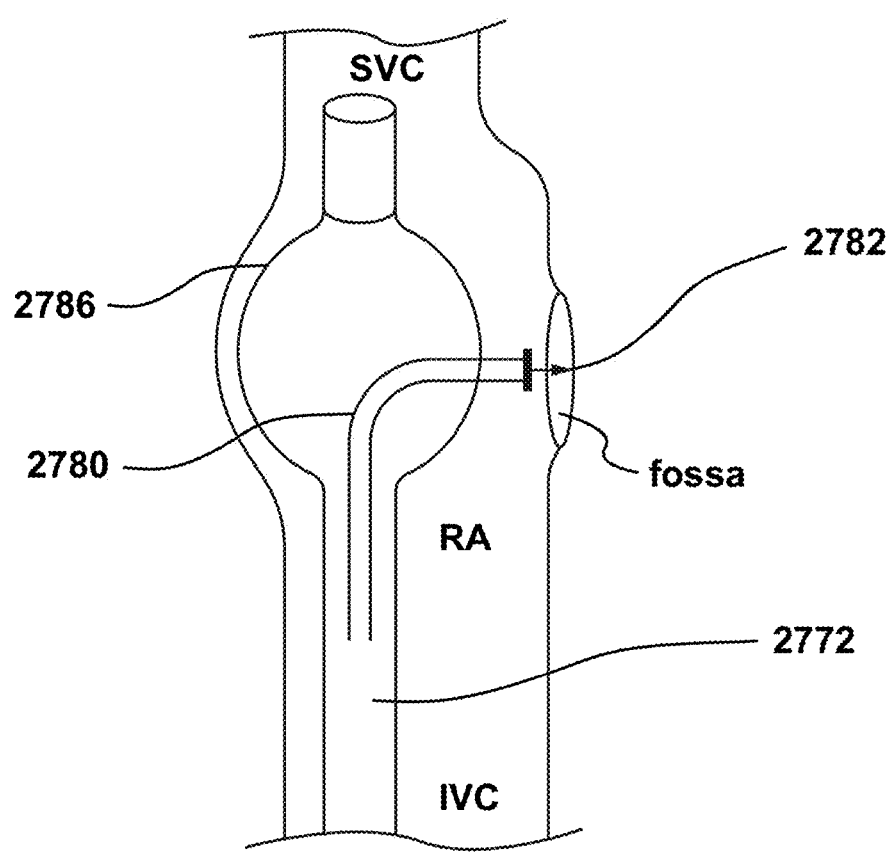

Referring now to FIGS. 61A-61H, further implementations of various configurations of device 2700 are depicted. While exemplary devices 2700 are depicted with three and six arms 2776, it should be understood that device 2700 can have any suitable number of arms 2776, such as between about three and ten arms. In certain embodiments, the plurality of arms 2776 can each be linked by one or more bands 2786, as shown in FIGS. 61E and 61F. By linking each arm 2776 to its adjacent arm 2776, band 2786 increases the stability of device 2700 by mitigating lateral motion of each arm 2776 and prevents injury from excessive expansion of arms 2776. In certain embodiments, the plurality of arms 2776 can be encased in covering 2788, as shown in FIGS. 61G and 61H. Covering 2788 is elastic and can be waterproof to smoothly guide device 2700 in a relaxed state and to provide a greater surface area in an expanded state that spreads out pressure and decrease trauma. Covering 2788 also provides the same benefits of band 86, in that covering 88 mitigates lateral motion and excessive expansion of arms 76 to improve stability. In FIG. 61H, stylet 2780 and needle 2782 are depicted as capable of piercing through covering 2788 to access and puncture the FO.

Figure 62A:
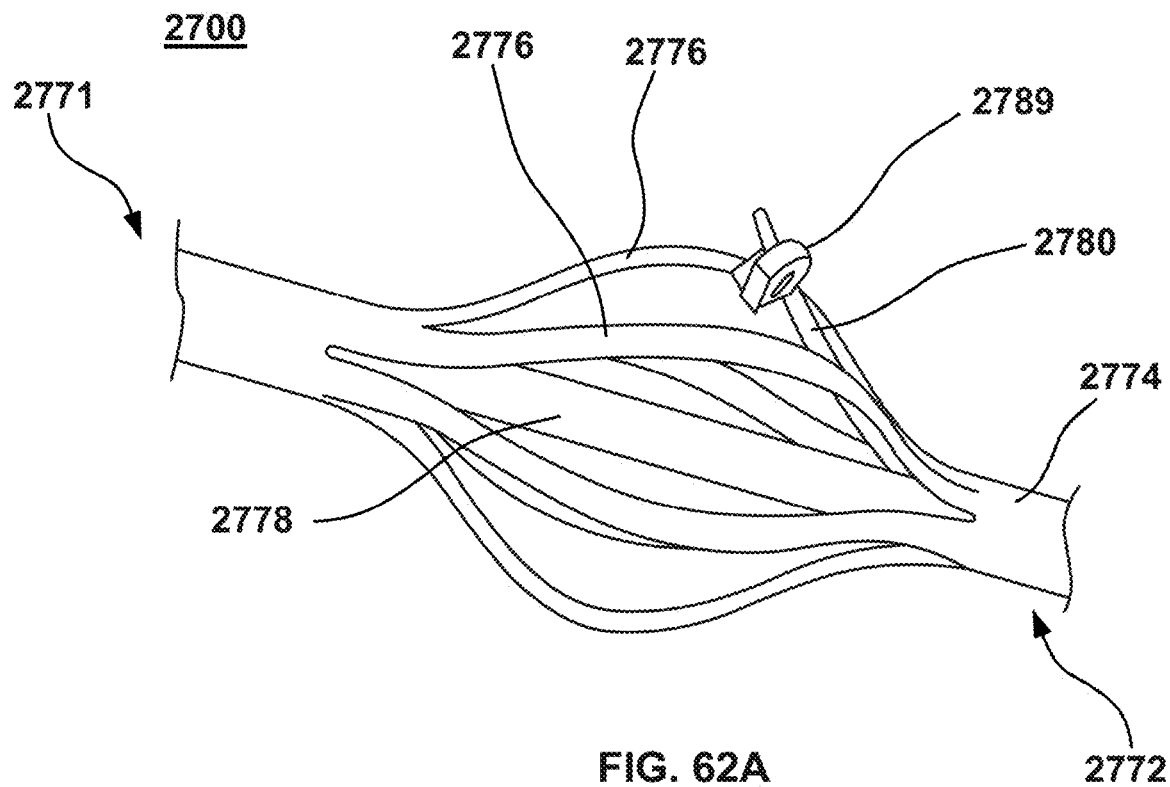
Figure 62B:
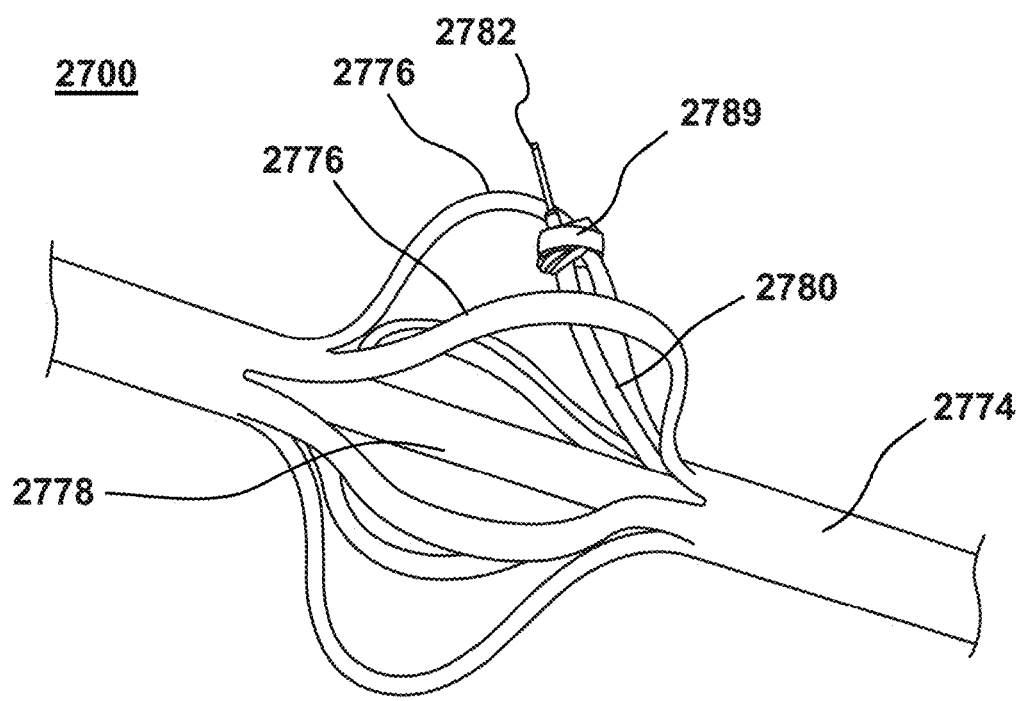

Referring now to FIGS. 62A and 62B, an exemplary implementation of device 2700 is depicted having loop guide 2789. Loop guide 2789 provides additional stability by linking an extended stylus 2780 to an expanded arm 2776. In some embodiments, loop guide 2789 is attached to the distal end of stylus 2780, such that after expanding the plurality of arms 2776, stylus 2780 can be extended along an expanded arm 2776 as loop guide 2789 slides over the expanded arm 2776. In other embodiments, loop guide 2789 is welded to both the distal end of stylus 2780 and to an expanded arm 2776, such that the expanding action of arm 2776 simultaneously extends stylus 2780 and curves stylus 2780 towards a FO.

Figure 63A:
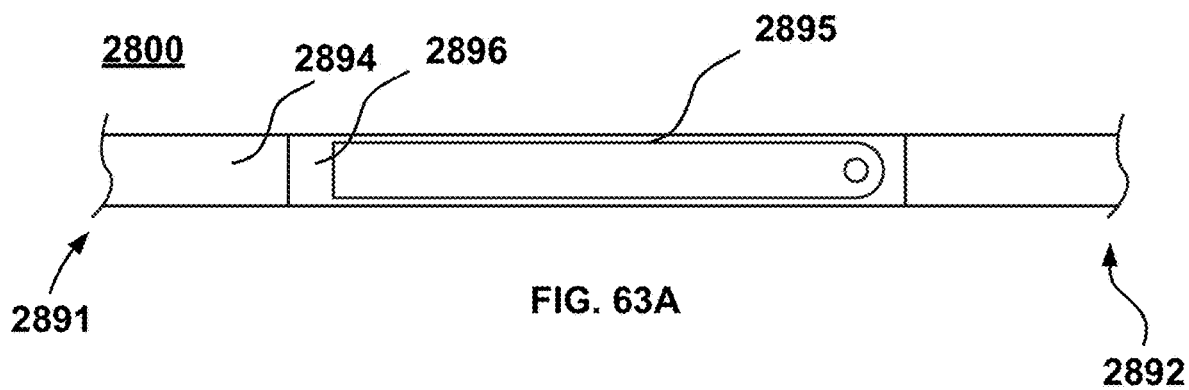
FIGS. 63A-63C illustrate a portion of a septum puncture device 2800, according to an embodiment.
Figure 63B:
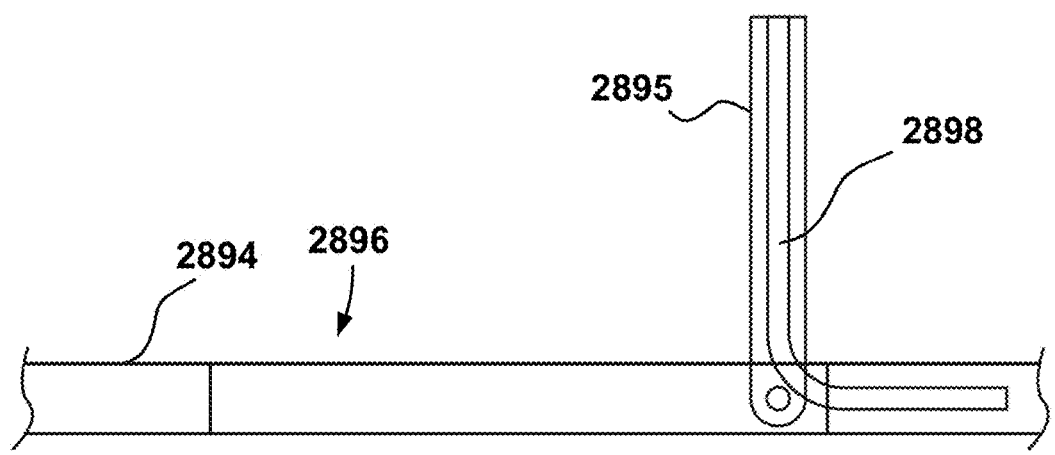
Figure 63C:
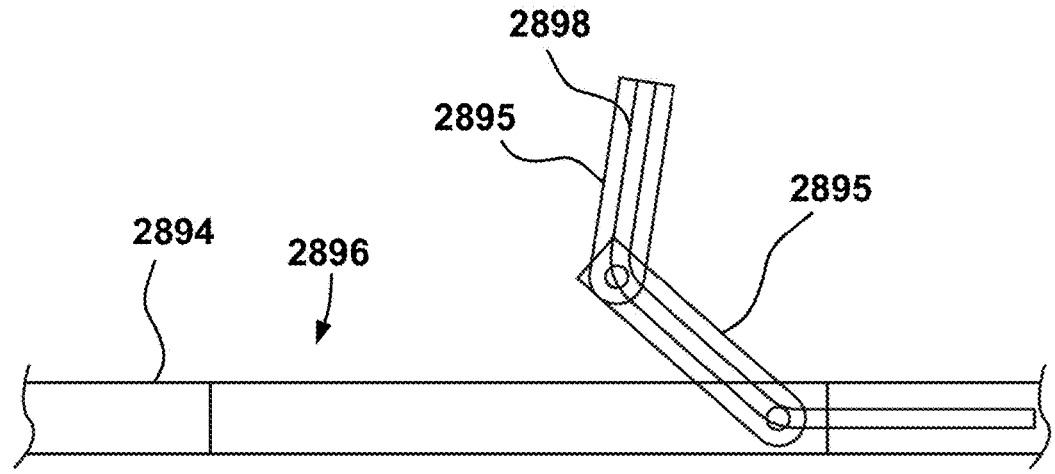

Referring now to FIGS. 63A-63C, an exemplary hinged septum puncture device 90 is depicted. Device 2800 has a distal end 2891, a proximal end 2892, and a cannula 2894 running throughout. Device 2800 has a hinged arm 2895 near its distal end 2891, the hinged arm 2895 resting within cannula 2894 adjacent to window 2896. Hinged arm 2895 is attached to the distal end of stylus 2898, such that rotating hinged arm 2895 out of window 2896 extends stylus 2898 out of cannula 2894 to face towards a FO. While exemplary embodiments of device 2800 are shown with one and two points of articulation in FIGS. 63B and 63C, respectively, it should be understood that hinged arm 2895 can have any suitable number of points of articulation, such as between about one and ten. Hinged arm 2895 can be rotated using any suitable means, including but not limited to one or more pull cables, one or more servomotors, one or more hydraulic pistons, or the like.

Figure 65A:
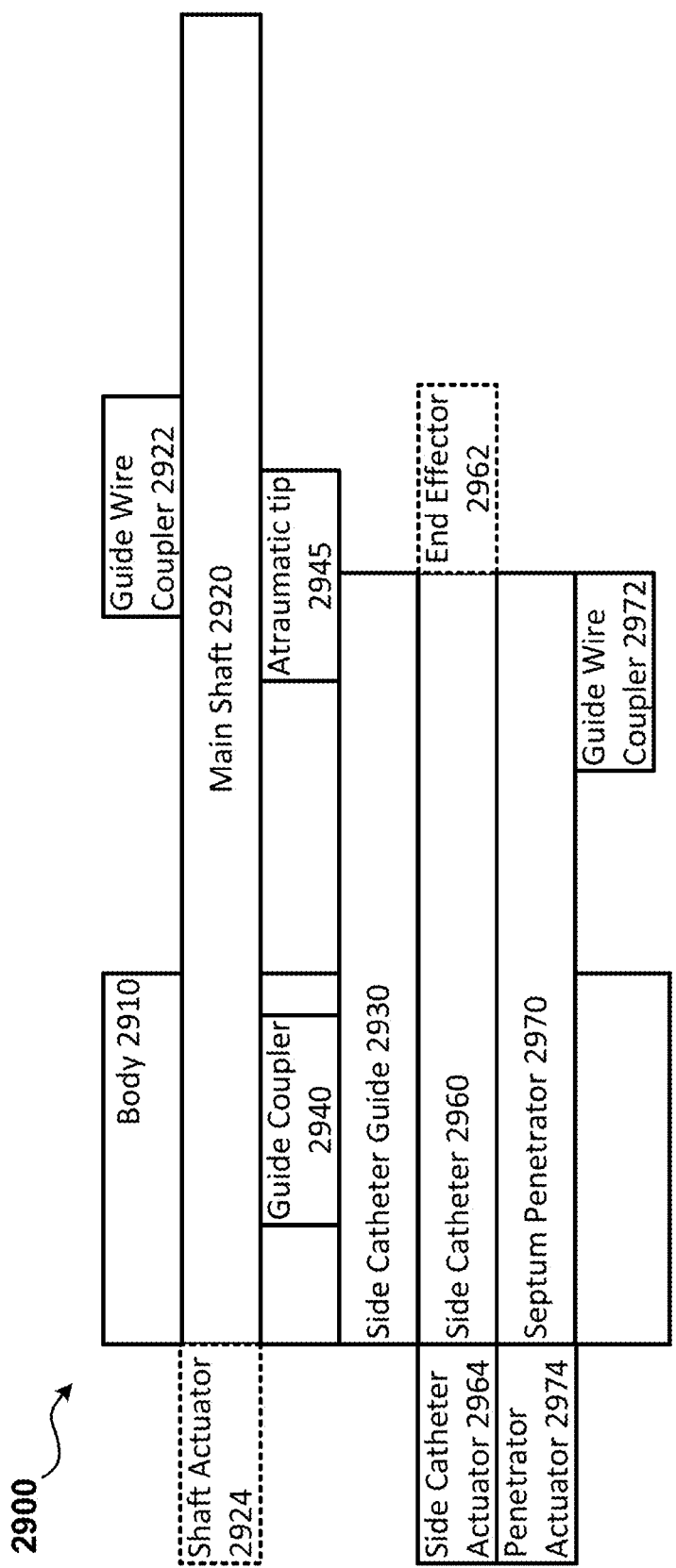
FIG. 65A is a schematic illustration of a septum puncture device, disposed in a delivery configuration, according to an embodiment.

Moreover, in general, devices such a catheters introduced into the vasculature of a patient carry a risk of inadvertent trauma to the patient's vascular wall and/or associate tissues, organs, etc. A sharp edge of a device, for example, could lacerate a vascular wall. In the context of this disclosure, a main shaft (e.g., main shaft 120), and/or a side catheter guide (e.g., side catheter guide 130) of a septum puncture device could exert a traumatic force against a wall of a curved or tortuous vessel. This could be of particular concern, for example, when a relatively stiff main shaft is used (e.g., for purposes of providing stability between the IVC and SVC). Further, having a side catheter guide adjacent the main shaft may present additional similar risks. To address such risks, any suitable portions of the septum puncture devices described herein can have atraumatic designs. FIGS. 65A and 65B illustrate such a septum puncture device 2900, according to an embodiment. Similar to or the same as described with respect to the septum puncture devices described herein, the septum puncture device 2900 can be used to access a left side of the heart (e.g., left atrium) from the right side of the heart (e.g., right atrium) and to deliver a guidewire to the left side of the heart. The septum puncture device 2900 can be constructed the same as or similar to, and can function the same as or similar to, any of the septum puncture devices described herein (e.g., septum puncture device 100). Thus, portions of the septum puncture device 2900 are not described in further detail herein.

As shown in FIG. 65A, the septum puncture device 2900 includes a body 2910 coupled to a main shaft 2920, a side catheter guide 2930, a side catheter 2960 (with an optional end effector 2962 extending therefrom), a septum penetrator 2970, and an atraumatic tip 2945. The main shaft 2920 is coupled to the side catheter guide 2930 via a guide coupler 2940, the side catheter guide 2930 is coupled to the side catheter 2960, and the side catheter 2960 is coupled to the septum penetrator 2970, as shown in FIG. 65A. The side catheter guide 2930 is configured to define a pathway through or across which the side catheter 2960 can travel (e.g., be advanced and/or withdrawn). Said another way, and as described in further detail herein, the side catheter guide 2930 can be manipulated (e.g., actuated from a delivery state to a deployed state) to guide the side catheter 2960 in a desired direction (the actuated or deployed state of the side catheter guide 2930 is shown in FIG. 65B), e.g., towards the left atrium.

The atraumatic tip 2945 is configured to protect the patient from inadvertent trauma caused by a portion of the side catheter guide 2930, such as, for example, a distal end portion of the side catheter guide 2930, which during insertion is guided into the patient's vasculature by the main shaft 2920. The atraumatic tip 2945 can be formed of any suitable material and can have any suitable shape. In some implementations, the atraumatic tip 2945 can be mounted on and/or coupled to the main shaft 2920. In some implementations, for example, the atraumatic tip 2945 be a nosecone (e.g., a blunt nosecone) mounted on and/or coupled to the main shaft 2920, with a tapered leading edge and a radiused trailing edge (e.g., such that the atraumatic tip 2945 is void of sharp edges). In some implementations, the atraumatic tip 2945 can be asymmetrically mounted on or coupled to the main shaft 2920 such that the atraumatic tip 2945 protects a distal end portion of the side catheter guide 2930 while limiting an overall diameter, cross-sectional area, and/or profile of the main shaft 2920 and side catheter guide 2930.

In some implementations, the atraumatic tip 2945, the main shaft 2920, and/or the body 2910 can be monolithically formed, while in other implementations, the atraumatic tip 2945, the main shaft 2920, and/or the body 2910 can be formed separately and then coupled to one another. In some such implementations, for example, the body 2910 and the atraumatic tip 2945 can be monolithically formed. Further to this example, the body 2910 and the atraumatic tip 2945 can define a lumen through which the main shaft 2920 can be slidably disposed. Further, the body 2910 and atraumatic tip 2945 can be configured to extend distally relative to the main shaft 2920 as far as desired; for example, the body 2910 and the atraumatic tip 2945 can have a distal end terminating proximal to the distal end of the main shaft 2920, at the distal end of the main shaft 2920, or distal to the distal end of the main shaft 2920. Further, the monolithically formed body 2910 and atraumatic tip 2945 can define a lateral opening to allow for the side catheter guide 2930 to extend and/or laterally deflect (e.g., away from the septum) and a lateral opening to through which the distal end of the side catheter guide 2930, the side catheter 2960, the septum penetrator 2970, and/or the guide wire (e.g., to be delivered to the left atrium), can extend.

In some implementations, the main shaft 2920 and the atraumatic tip 2945 can be monolithically formed, and define a lumen through which the side catheter guide 2930 (and a guide wire, for example) can be disposed. In some such implementations, the main shaft 2920/atraumatic tip 2945 can include a guide coupler coupler (not shown) configured to facilitate coupling of the main shaft 2920/atraumatic tip 2945 to the guide coupler 2940. The guide coupler coupler can be any suitable mechanism or feature suitable to secure the guide coupler 2940 to the main shaft 2920/atraumatic tip 2945. As an example, the guide coupler coupler can be a plurality of lateral apertures, slots, or the like defined by the main shaft 2920/atraumatic tip 2945 and configured to receive a portion of the guide coupler 2940.

In some implementations, the atraumatic tip 2945 can have a distal end configured to be spaced distal to the guide coupler 2940, a proximal end extending towards the body 2910, and two lateral openings disposed between the distal end and the proximal end; one lateral opening configured to allow for the side catheter guide 2930 to extend and/or laterally deflect (e.g., away from the septum) and the other lateral opening configured to provide access through which the distal end of the side catheter guide 2930, the side catheter 2960, the septum penetrator 2970, and/or the guide wire (e.g., to be delivered to the left atrium), can extend.

As described in further detail herein in other embodiments, the guide coupler 2940 can couple the side catheter guide 2930 to the main shaft 2920 to minimize or prevent relative translational movement between the main shaft 2920 and the side catheter guide 2930, but to allow relative rotational movement between the main shaft 2920 and the side catheter guide 2930, as illustrated schematically in FIG. 65B. In this manner, the guide coupler 2940 can facilitate transition of the side catheter guide 2930 from a delivery configuration (e.g., parallel to or substantially parallel to the main shaft 2920), e.g., for insertion through the patient's vasculature and into the RA, to a deployed configuration such that a distal end of the side catheter guide 2930 is deflected angularly and/or laterally relative to the main shaft 2920, e.g., towards the patient's left atrium (e.g., the FO of the atrial septum).

The atraumatic tip 2945 can be configured to facilitate such transition of the side catheter guide 2930 into its deployed configuration. In some implementations, for example, the atraumatic tip 2945 can define one or more apertures, lateral openings, and/or slots through which the distal end portion of the side catheter guide 2930 can angularly and/or laterally deflect, and/or through which a portion of the side catheter guide 2930 that is proximal to the distal end portion of the side catheter guide 2930 can extend and/or deflect (e.g., the proximal portion being one a first side of a central axis of the shaft while the distal portion is on a second side of the central axis opposite the first side of the central axis. In this manner, the side catheter guide 2930 is shielded prior to deployment, and free to deflect and assume an increased profile during deployment.

In some implementations, the entire atraumatic tip 2945 can be disposed distal to the guide coupler 2940, while in some implementations, the atraumatic tip 2945 can extend across and proximally beyond the guide coupler 2940.

The atraumatic tip 2945 can be of any suitable size. For example, in some implementations, the atraumatic tip 2945 can have an outer diameter of about 14 F. As another example, in some implementations, the atraumatic tip 2945 can have a length in a range of about 1 mm to about 150 mm. In some implementations, the atraumatic tip 2945 can have a length of about 10-30 times its diameter; such a length could be, for example, 75 mm, 100 mm, 150 mm, or any value therebetween.

In some implementations, the atraumatic tip 2945 can include a radiopaque material and/or marker (e.g., a band and/or a groove) such that the atraumatic tip 2945 can be visualized when within the heart from outside the patient under any suitable imaging modality (e.g., fluoroscopy, echocardiography, etc.), to facilitate an operator in deploying the side catheter guide 2930 and/or the side catheter 2960.

Further as shown in FIG. 65A, the septum puncture device 2900 includes a guide wire coupler 2922 configured to couple the main shaft 2920 to a guide wire (not shown in FIG. 65A) to facilitate delivery of the septum puncture device 2900 into a patient (e.g., through the vasculature of the patient) and to the patient's heart, and a guide wire coupler 2972 configured to couple a guide wire (not shown in FIG. 65A) to the septum penetrator 2970, to facilitate delivery of that guide wire to the left side of the heart (e.g., the left atrium).

Further as shown in FIG. 65A, the septum puncture device 2900 optionally includes a shaft actuator 2924 operably coupled to the main shaft 2920 and configured to actuate the main shaft 2920 to advance or withdraw the main shaft 2920 relative to the body 2910. The septum puncture device 2900 further includes (1) a side catheter actuator 2964 operably coupled to and configured to actuate the side catheter 2960 to advance or withdraw the side catheter 2960, thereby transitioning the side catheter 2960 between a delivery configuration and a deployed configuration (the side catheter 2960 shown in an actuated or deployed configuration in FIG. 65B), and (2) a septum penetrator actuator (or "penetrator actuator") 2974 to actuate the septum penetrator 2970 to advance or withdraw the septum penetrator 2970, thereby transitioning the septum penetrator between a delivery configuration and a deployed configuration (the septum penetrator 2970 shown in an actuated or deployed configuration in FIG. 65B), as described in further detail herein.

Further as shown in FIG. 65A, the septum puncture device 2900 optionally includes an end effector 2962 coupled to and extending distally from the side catheter 2960. The end effector 2962 is configured to facilitate subsequent puncture through a target puncture location, such as, for example, the FO of the septum of the heart. The end effector 2962 can be configured, for example, to contact or tent the FO, as described in further detail herein. Such contact or tenting of the FO can, for example, reduce or minimize the force required to penetrate the FO and/or provide for improved force distribution to the FO. The end effector 2962 can be configured to prevent inadvertent puncturing of and/or damage to the FO with the end effector 2962.

Each of the main shaft 2920, the guide wire coupler 2922, the side catheter guide 2930, the guide coupler 140, the side catheter 2960, the septum penetrator 2970, and the guide wire coupler 2972 are translatable (e.g., distally advanceable and/or extendable, and proximally withdrawable and/or retractable) relative to the body 2910. The side catheter 2960 is translatable relative to the side catheter guide 2930, and the septum penetrator 2970 is translatable relative to the side catheter 2960, as described in further detail herein.

Figure 66A:
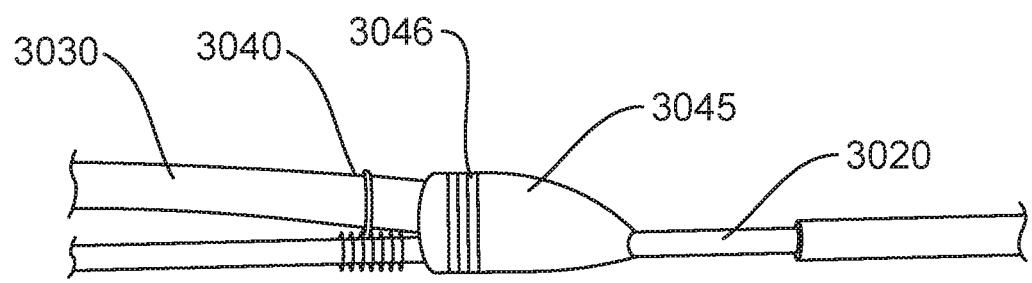
FIG. 66A illustrates a portion of a septum puncture device, disposed in a delivery configuration, according to an embodiment.
Figure 66B:
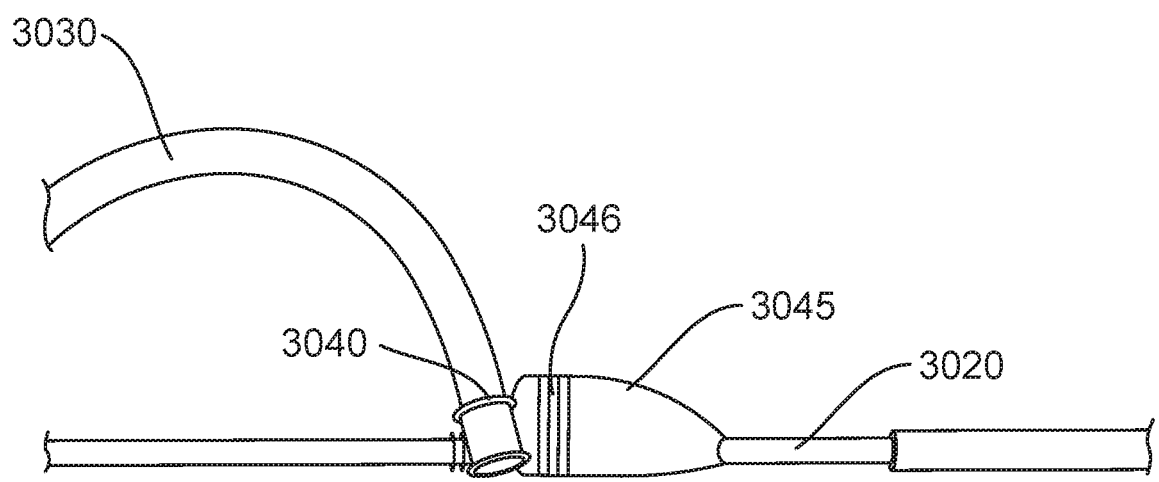
FIG. 66B illustrates a portion of the septum puncture device of FIG. 66A, disposed in a deployed configuration.

FIGS. 66A and 66B illustrate a portion of a septum puncture device 3000 in a delivery configuration and a deployed configuration, respectively, according to an embodiment.

Similar to other septum puncture devices described herein, the septum puncture device 3000 can be used to access a left side of the heart (e.g., left atrium) from the right side of the heart (e.g., right atrium) and to deliver a guidewire to the left side of the heart. The septum puncture device 3000 can be constructed the same as or similar to, and can function the same as or similar to, any of the septum puncture devices described herein. Thus, portions of the septum puncture device 3000 are not described in further detail herein.

In this embodiment, the septum puncture device 3000 includes a main shaft 3020 and a side catheter guide 3030 coupled to the main shaft 3020 via a guide coupler 3040, similar to as described in connection with other embodiments. The septum puncture device 3000 further includes an atraumatic tip 3045 coupled to and disposed about the main shaft 3020, and abutting a distal end portion of the side catheter guide 3030 when the side catheter guide 3030 is in a delivery configuration. As shown in FIG. 66A, the distal end of the side catheter guide 3030 is shielded or at least partially covered by the atraumatic tip 3045. In this manner, during insertion of the septum puncture device 3000 into the patient, with the side catheter guide 3030 in its delivery configuration, the atraumatic tip 3045 protects the patient's vasculature and associated anatomy from inadvertent trauma from the side catheter guide 3030. When deployed, as illustrated in FIG. 66B, the distal end of the side catheter guide 3030 is angularly deflected relative to the main shaft 3020, as described in other embodiments herein, such that a side catheter (not shown) can then be extended distally therethrough. Although in this embodiment the atraumatic tip 3045 abuts the distal end portion of the side catheter guide 3030 when the side catheter guide 3030 is in the delivery configuration, in other embodiments the atraumatic tip can be axially offset from the distal end portion of the side catheter guide such that the atraumatic tip is not in contact with the side catheter guide.

Further, in this embodiment, the atraumatic tip 3045 has an asymmetric shape such that during delivery, as shown in FIG. 66A, the atraumatic tip 3045 shields the entire distal end of the side catheter guide 3030, while limiting the overall footprint of the atraumatic tip 3045. More specifically, in this embodiment, the atraumatic tip 3045 reduces in cross-sectional area from its proximal end to its distal end.

Further, the atraumatic tip 3045 includes a radiopaque (e.g., fluoroscopic) marker band 3046 disposed circumferentially about an exterior surface of the atraumatic tip 3045. The atraumatic tip 3045 defines a grove on which the radiopaque marker band 3046 is disposed such that the band 3046 does not increase the overall profile, cross-sectional area, and/or diameter of the remaining portion of the atraumatic tip 3045.

Figure 67:
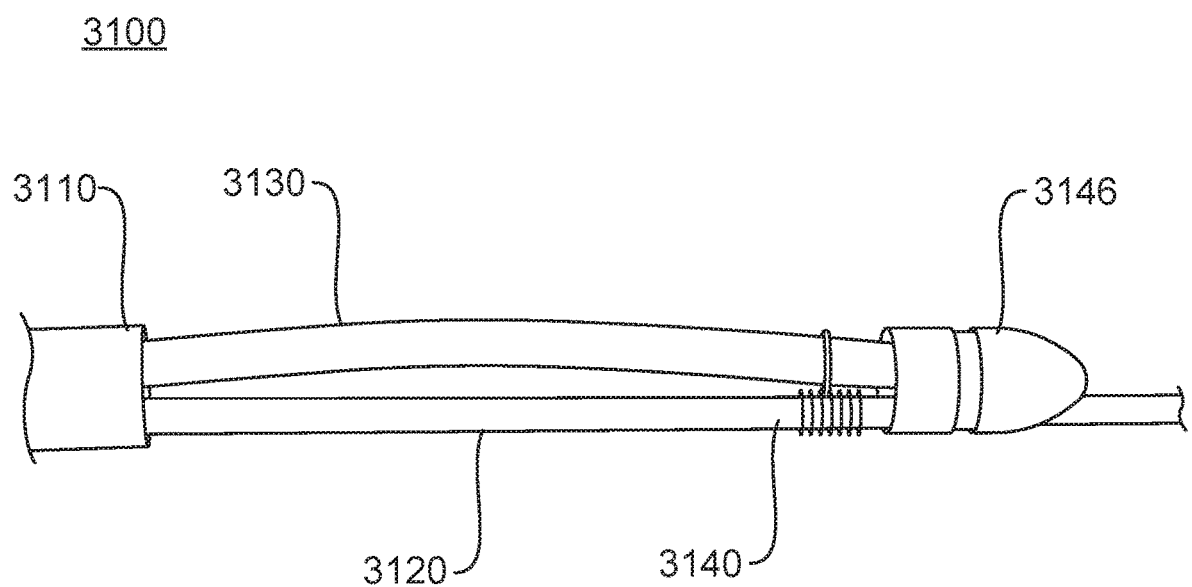
FIG. 67 illustrates a portion of a septum puncture device having an atraumatic tip, disposed in a delivery configuration, according to an embodiment.

In some embodiments, an atraumatic tip can define or include a slot or recess through which a side catheter guide can deflect. FIG. 67 illustrates a portion of a septum puncture device 3100 in a delivery configuration, according to such an embodiment.

Similar to other septum puncture devices described herein, the septum puncture device 3100 can be used to access a left side of the heart (e.g., left atrium) from the right side of the heart (e.g., right atrium) and to deliver a guidewire to the left side of the heart. The septum puncture device 3100 can be constructed the same as or similar to, and can function the same as or similar to, any of the septum puncture devices described herein. Thus, portions of the septum puncture device 3100 are not described in further detail herein.

In this embodiment, the septum puncture device 3100 includes a main shaft 3120 and a side catheter guide 3130 coupled to the main shaft 3120 via a guide coupler 3140 and extending distally from a body 3110, similar to as described in connection with other embodiments. The septum puncture device 3100 further includes an atraumatic tip 3145 coupled to and disposed about the main shaft 3120, and abutting a distal end portion of the side catheter guide 3130 when the side catheter guide 3130 is in a delivery configuration. Although in this embodiment the atraumatic tip 3145 abuts the distal end portion of the side catheter guide 3130 when the side catheter guide 3130 is in the delivery configuration, in other embodiments the atraumatic tip can be axially offset from the distal end portion of the side catheter guide such that the atraumatic tip is not in contact with the side catheter guide.

The atraumatic tip 3145 can be constructed the same as or similar to, and can function the same as or similar to, the atraumatic tip 3045, except the atraumatic tip 3145, as shown, includes a slot at its proximal end through which a distal end of the side catheter guide 3130 is disposed during delivery, and through and/or beyond which the distal end of the side catheter guide 3130 can extend when deployed.

Figure 68A:
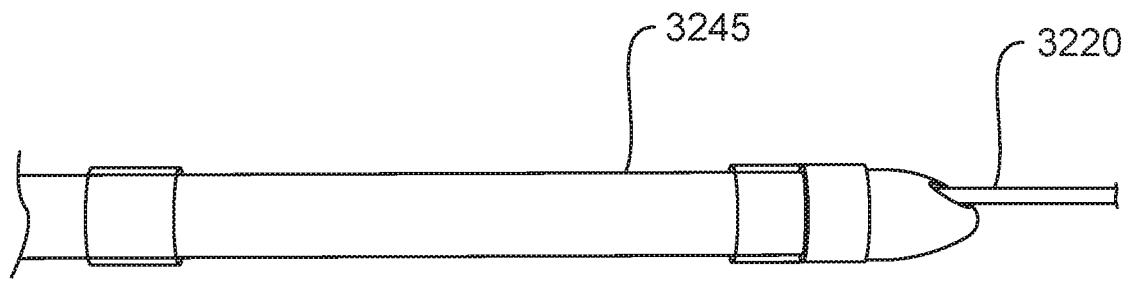
FIG. 68A illustrates a portion of a septum puncture device having an atraumatic tip, disposed in a delivery configuration, according to an embodiment.
Figure 68B:
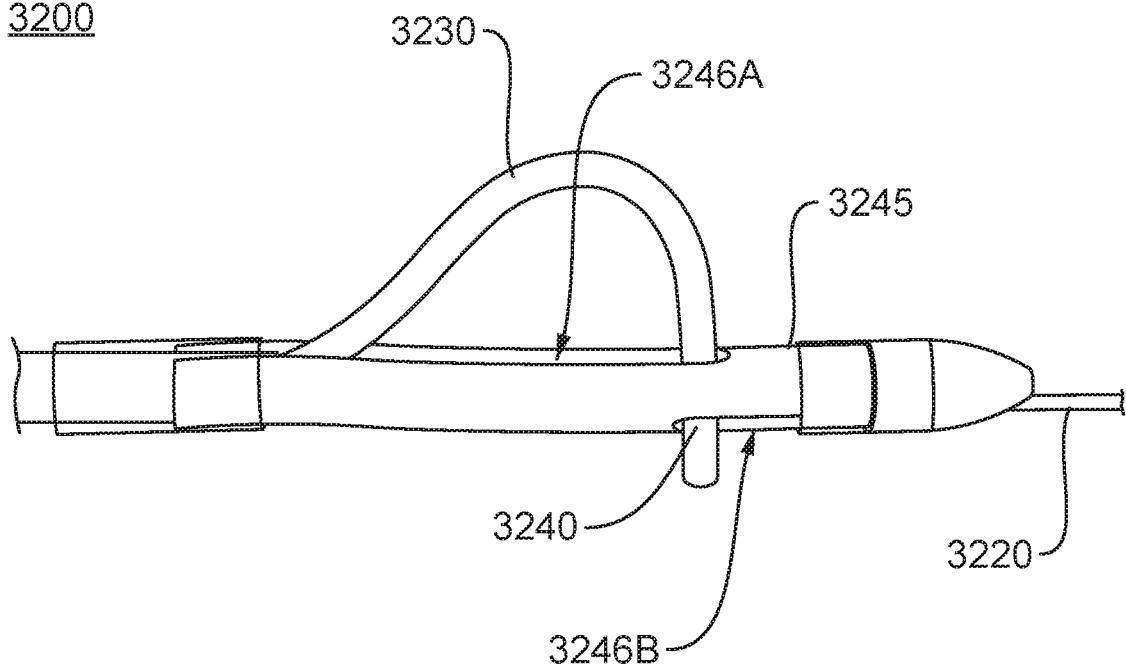
FIG. 68B illustrates a portion of the septum puncture device of FIG. 68A, disposed in a deployed configuration.

In some embodiments, an atraumatic tip can extend distally from a location proximal to the guide coupler, across the guide coupler, and distal to the distal end of the side catheter guide, and can define or include one or more slots or recesses through which the side catheter guide can be deployed and/or deflected. FIGS. 68A and 68B illustrate a portion of a septum puncture device 3200 in a delivery configuration and a deployed configuration, respectively, according to such an embodiment.

Similar to other septum puncture devices described herein, the septum puncture device 3200 can be used to access a left side of the heart (e.g., left atrium) from the right side of the heart (e.g., right atrium) and to deliver a guidewire to the left side of the heart. The septum puncture device 3200 can be constructed the same as or similar to, and can function the same as or similar to, any of the septum puncture devices described herein. Thus, portions of the septum puncture device 3200 are not described in further detail herein.

In this embodiment, the septum puncture device 3200 includes a main shaft 3220 and a side catheter guide 3230 coupled to the main shaft 3220 via a guide coupler 3240. The septum puncture device 3200 further includes an atraumatic tip 3245 coupled to and disposed about the main shaft 3220, and the side catheter guide 3230 when the side catheter guide 3230 is in its delivery configuration (FIG. 68A). As shown best in FIG. 68B, the atraumatic tip 3245 defines a first slot 3246A and a second slot 3256B (collectively referred to herein as "the slots 3246"). During delivery, the side catheter guide 3230 remains within the profile defined by the atraumatic tip 3245, such that the side catheter guide 3230 does not extend through and/or beyond the slots 3246, as shown in FIG. 68A. When deployed, as shown in FIG. 68B, the side catheter guide 3230 angularly deflects such that a distal end portion of the side catheter guide 3230 points in first direction (e.g., towards a septum), and a portion of the side catheter guide 3230 proximal the distal end portion and opposite a central axis of the main shaft 3220 when compared to the distal end portion, angularly and laterally deflects in a second direction different from the first direction. In this manner, the atraumatic tip 3245 covers and/or envelops the side catheter guide 3230 to shield the side catheter guide 3230 from inadvertent contact with and/or trauma to surrounding anatomy. Also, as shown, a distal end of the atraumatic tip 3245 is tapered (e.g., similar to a bullet nose or nose cone) so as to be atraumatic.

In various embodiments described herein, during deployment, a distal end portion of the side catheter guide laterally deflects relative to a central axis of the main shaft, such that the distal end of the side catheter guide is disposed laterally beyond an exterior surface of the main shaft (e.g., towards a septum). In some instances, it is desirable to minimize and/or avoid such lateral deflection, such that during deployment, the distal end of the side catheter guide angularly deflects such that the distal end of the side catheter guide does not extend beyond an exterior surface of the main shaft when viewed in side view, and/or does not extend beyond an exterior surface of the atraumatic tip when viewed in side view (e.g., in applicable embodiments in which the septum puncture device includes an atraumatic tip).

Figure 69A:
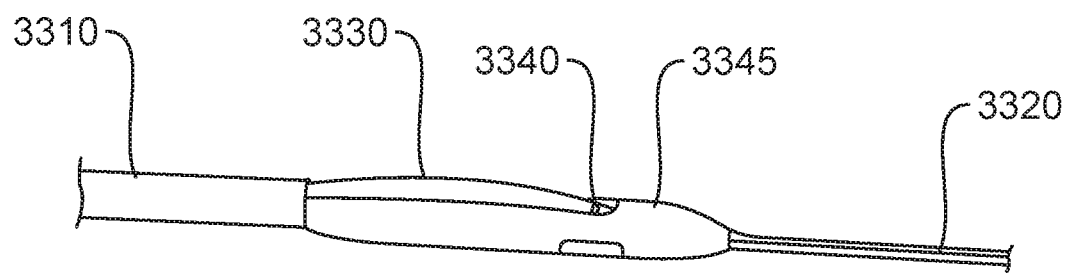
FIG. 69A illustrates a portion of a septum puncture device having an atraumatic tip, disposed in a delivery configuration, according to an embodiment.
Figure 69B:
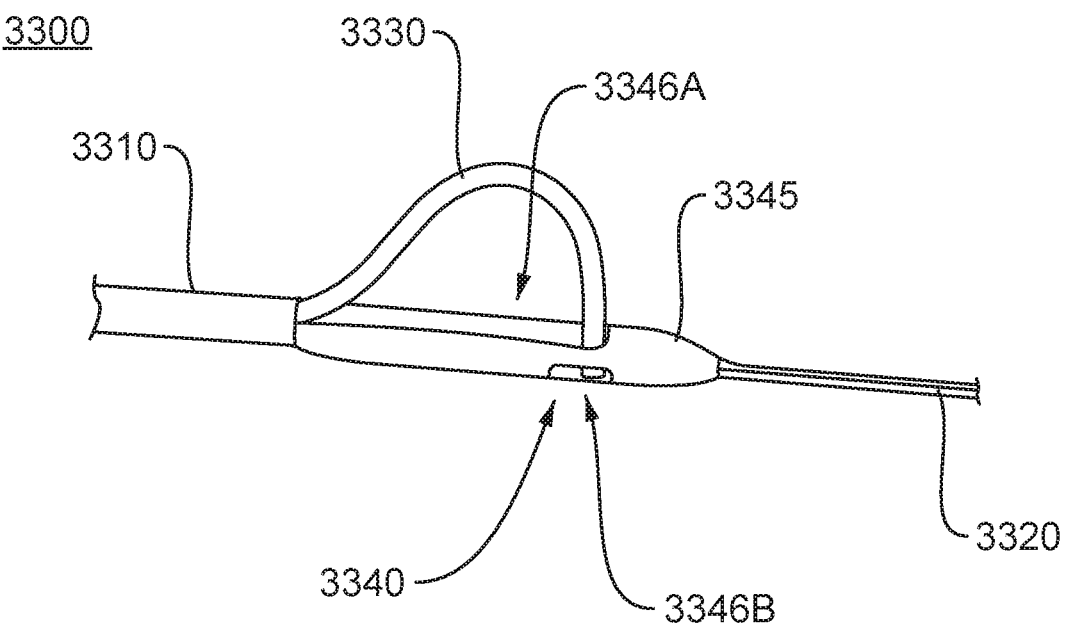
FIG. 69B illustrates a portion of the septum puncture device of FIG. 69A, disposed in a deployed configuration.

FIGS. 69A and 69B illustrate a portion of a septum puncture device 3300 in a delivery configuration and a deployed configuration, respectively, according to such an embodiment. Similar to other septum puncture devices described herein, the septum puncture device 3300 can be used to access a left side of the heart (e.g., left atrium) from the right side of the heart (e.g., right atrium) and to deliver a guidewire to the left side of the heart. The septum puncture device 3300 can be constructed the same as or similar to, and can function the same as or similar to, any of the septum puncture devices described herein. Thus, portions of the septum puncture device 3300 are not described in further detail herein.

In this embodiment, the septum puncture device 3300 includes a main shaft 3320 and a side catheter guide 3330 coupled to the main shaft 3320 via a guide coupler 3340. The septum puncture device 3300 further includes an atraumatic tip 3345 coupled to and disposed about the main shaft 3320, and the side catheter guide 3330 when the side catheter guide 3330 is in its delivery configuration (FIG. 69A). As shown best in FIG. 69B, the atraumatic tip 3345 defines a first slot 3346A and a second slot 3356B (collectively referred to herein as "the slots 3346").

In this embodiment, the guide coupler 3340 is disposed close to a distal end of the side catheter guide 3330 such that when the side catheter guide 3330 is deployed, its distal end deflects angularly, without any substantial lateral deflection, such that the distal end of the side catheter guide 3330 when deployed does not increase the collective cross-sectional area of the main shaft 3320 and the atraumatic tip 3345. Said another way, the distal end of the side catheter guide 3330, when deployed, extends a distance from the central axis of the main shaft that is less than or equal to the shortest distance of an exterior surface of the atraumatic tip to the central axis. Said another way, the distal end of the side catheter guide 3330, when deployed, does not extend laterally beyond the exterior surface of the atraumatic tip when viewed in side view.

Similarly, in any of the embodiments described herein, including, for example, embodiments described without an atraumatic tip, the guide coupler can be similarly disposed adjacent to the distal end of the side catheter guide such that the distal end of the side catheter guide, when deployed, angularly deflects without substantial lateral deflection. In this manner, for example, in some implementations, when deployed, the distal end of the side catheter guide may be disposed between the central axis of the main shaft and a line tangent the exterior surface of the main shaft when viewed in side view, such that deployment of the side catheter guide does not cause the distal end of the side catheter guide to increase the collective cross-sectional area of the side catheter guide and the main shaft. In some implementations, for example, the distal end of the side catheter guide, when deployed, is a distance from the central axis that is equal to or less than a radius of the main shaft (the radius being the radius of the main shaft at or adjacent to the guide coupler). In some implementations, for example, the distal end of the side catheter guide, when deployed, extends a lateral distance from the closest exterior surface of the main shaft of about less than the radius of the main shaft.

Although various atraumatic tips described herein are shown as a component and/or material that is formed separately and then coupled to the main shaft, in some embodiments, the functionality of an atraumatic tip (e.g., the atraumatic tip 3245) can be incorporated into and provided by the main shaft. FIGS. 70A-70E illustrate a portion of a septum puncture device, in various views, in a deployed configuration, according to such an embodiment.

Similar to other septum puncture devices described herein, the septum puncture device 3400 can be used to access a left side of the heart (e.g., left atrium) from the right side of the heart (e.g., right atrium) and to deliver a guidewire to the left side of the heart. The septum puncture device 3400 can be constructed the same as or similar to, and can function the same as or similar to, any of the septum puncture devices described herein. Thus, portions of the septum puncture device 3400 are not described in further detail herein.

Figure 70C:
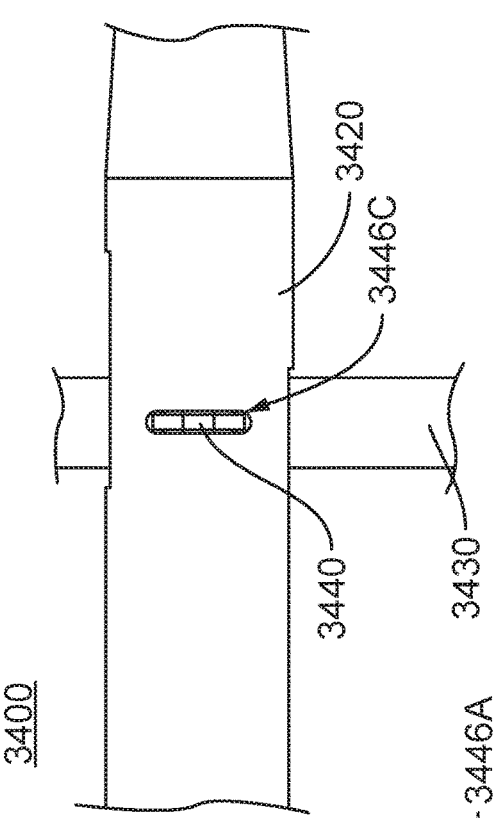
FIG. 70C illustrates a portion of the septum puncture device of FIG. 70A in side view.
Figure 70E:
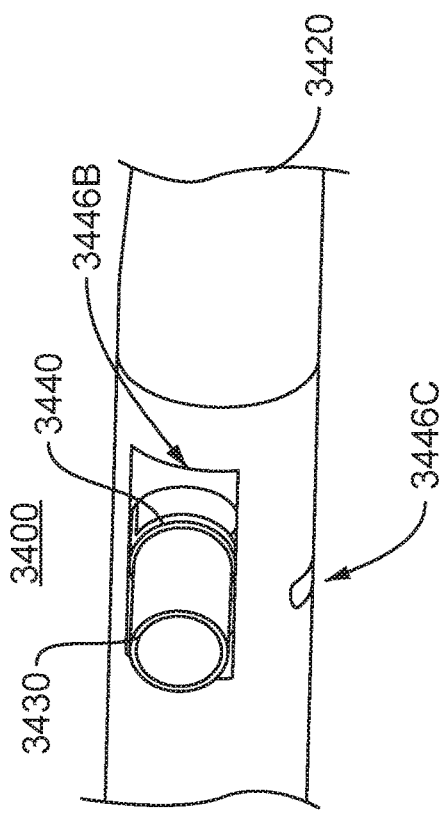
FIG. 70E illustrates a portion of the septum puncture device of FIG. 70A in bottom perspective view.
Figure 70D:
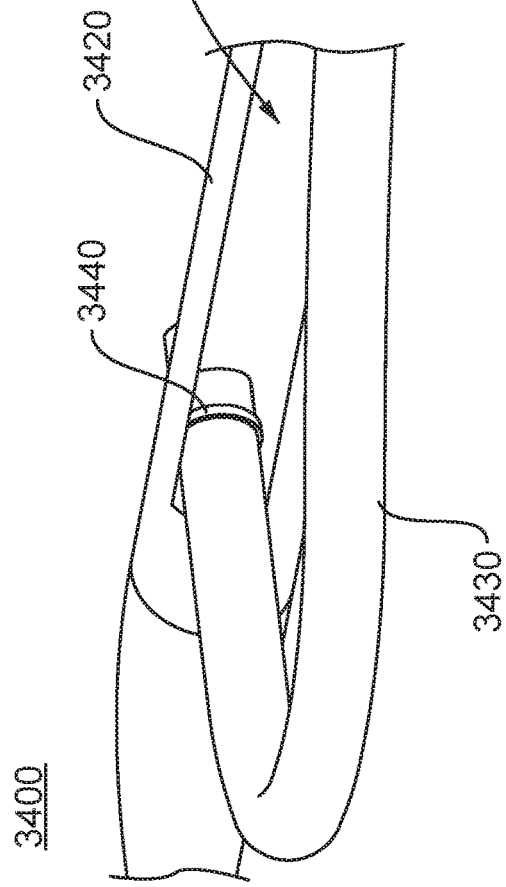
FIG. 70D illustrates a portion of the septum puncture device of FIG. 70A in top perspective view.

In this embodiment, the septum puncture device 3400 includes a main shaft 3420 and a side catheter guide 3430 coupled to the main shaft 3420 via a guide coupler 3440 (shown in FIGS. 70C-70E. A portion of the side catheter guide 3430 disposed proximal to the guide coupler 3420 is slidably disposed within a lumen defined by the main shaft 3420, and a portion of the side catheter guide 3430 disposed distal to the guide coupler is disposed within and deflectable relative to the lumen of the main shaft 3420. Slidably disposed within the side catheter guide 3430 is a side catheter 3460, and slidably disposed within the side catheter 3460 is a septum penetrator 3460 (as shown in FIGS. 70A and 70B). Although not shown in this embodiment, as can be the case in any of the embodiments described herein, in some implementations, the septum puncture device (e.g., including the septum puncture device 3400) can include an end effector (e.g., similar to or the same as in form and/or function as any of the end effectors described herein). As shown best in FIG. 70B, the main shaft 3420 defines a first slot 3446A and a second slot 3446B (both of which are in communication with the lumen of the main shaft 3420). During deployment, the side catheter guide 3430 can deflect and extend through and beyond the first slot 3446A and the second slot 3446B, similar to as described above with respect to the septum puncture device 3200 and the septum puncture device 3330.

The main shaft 3420 further includes a guide coupler coupler 3446C that is configured to promote coupling between the guide coupler 3440 and the main shaft 3420. In this embodiment, the guide coupler coupler 3446C is formed of two apertures defined within the main shaft 3420 and configured to receive a portion of the guide coupler 3446 (see e.g., FIG. 70C). In this manner, the side catheter guide 3430 can be secured to the main shaft 3420 via the guide coupler 3446, such that relative rotational movement between the main shaft 3420 and the side catheter guide 3420 is promoted, but relative translational movement between the same is limited or prevented.

Various embodiments described herein include a side catheter guide disposed adjacent and coupled to the main shaft via the guide coupler, however, it should be understand that any of these embodiments could be modified such that side catheter guide is disposed within a lumen defined by the main shaft (e.g., either through the guide wire coupler defined by or associated with the main shaft, or through a separate lumen defined by the main shaft). In such modified embodiments, the main shaft can define slots and/or apertures through which the side catheter guide can extend or traverse during deployment of the side catheter guide.

Various configurations and methods of using septum puncture devices for puncturing one or more holes through an atrial septum have been described herein. In some instances it may be desirable to verify that a puncture in fact was performed in the desired location, e.g., to verify communication with the left atrium, and verify an established communication lumen between the left atrium and outside the patient's body via the septum penetrator. For example, it may be desirable to identify an errant puncture (e.g., in an aorta or interatrial tissue) while the puncture is relatively small (e.g., before dilating the hole).

Once communication is established between the target region (e.g., the left atrium) and outside the patient via the lumen defined by the septum penetrator that has been extended into the left atrium, a variety of verification techniques can be used. For example, one or more of the following verification techniques can be used: measuring a pressure within the septum penetrator lumen, withdrawing a blood sample through the septum penetrator lumen, injecting through the septum penetrator lumen a contrast agent configured to be visible by an imaging modality such as fluoroscopy and/or echocardiography, and/or the like.

In some implementations in which verification is desired, there are multiple competing design goals. A first goal is clearly to provide a communication lumen from outside the patient to the target region (e.g., the left atrium). This goal can be accomplished, as described in various embodiments here, by providing a septum penetrator with a lumen defined therein. A second goal is to limit the cross-sectional area and/or overall profile of the septum penetrator and thereby the hole that it creates. This goal can be accomplished by closely matching the outer diameter of the guidewire to be inserted into the left atrium with the inner diameter of the septum penetrator such that no, or close to no, annular gap exists between the internal surface of the septum penetrator and the exterior surface of the guidewire. A third goal is to preload the guidewire so as to minimize the time period required for the guidewire to be inserted into left atrium following the puncture. Said another way, with the guidewire preloaded or disposed within the septum penetrator lumen before the septum penetrator lumen punctures the FO, the remaining distance needed for the guidewire to travel to reach the left atrium is less than if the guidewire were first introduced into the septum penetrator lumen after the septum penetrator punctures the FO.

With those goals in mind, in some embodiments, it is desirable to design a septum penetrator having a lumen of varying diameter such that an annular gap between the external surface of the guidewire and the internal surface of the septum penetrator can be provided while still preloading the guidewire and keeping the septum penetrator diameter to a minimum.

FIGS. 71A-71D are schematic illustrations of a portion of a septum penetrator of a septum puncture member 3500, according to such an embodiment. Similar to other septum puncture devices described herein, the septum puncture device 3500 can be used to access a left side of the heart (e.g., left atrium) from the right side of the heart (e.g., right atrium) and to deliver a guidewire to the left side of the heart. The septum puncture device 3500 can be constructed the same as or similar to, and can function the same as or similar to, any of the septum puncture devices described herein. Thus, portions of the septum puncture device 3500 are not described in further detail herein.

Figure 71A:
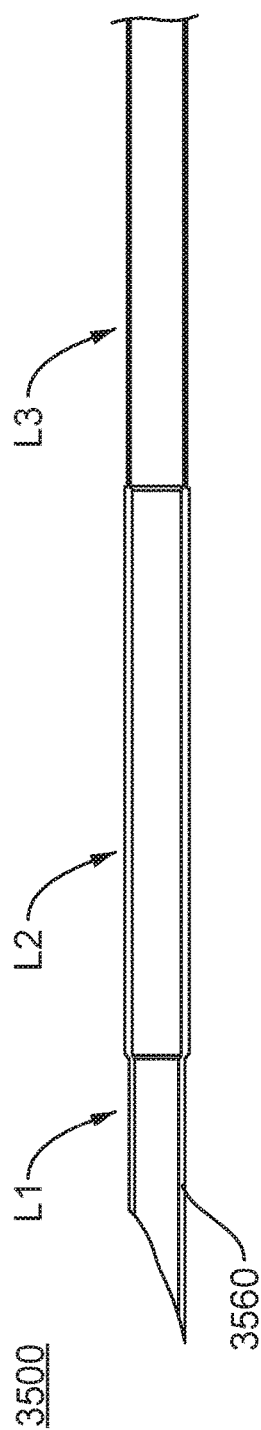
FIGS. 71A-71D illustrate a portion of a septum penetrator having a variable inner diameter, according to an embodiment.
Figure 71B:
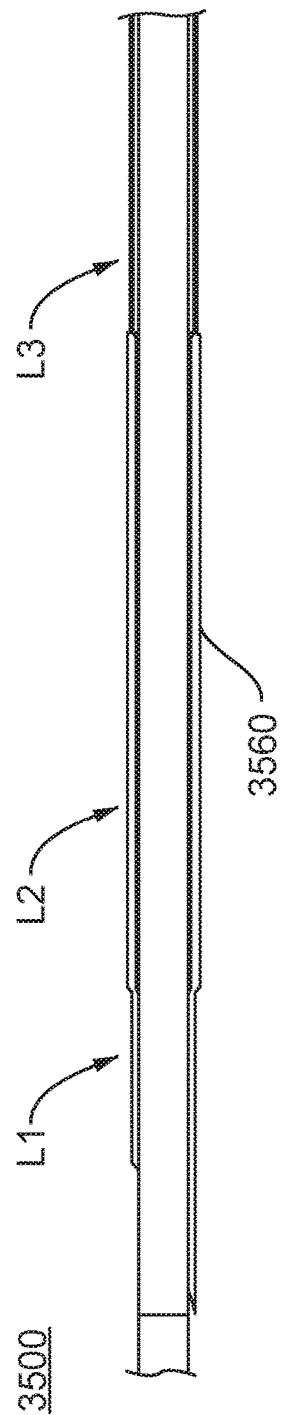

As shown in FIGS. 71A and 71B in cross-sectional side view and in side view in line form, respectively, the septum puncture member 3500 includes a septum penetrator 3560 that defines a lumen therethrough. In this embodiment, the septum penetrator 3560 is divided into three segments, including a first segment L1, a second segment L2, and a third segment L3. At the distal end of the septum penetrator 3560 is the sharp end portion of the septum penetrator 3560 that is configured to puncture the target tissue (e.g., the FO of the septum). This sharp end portion defines the first segment L1 with little to no annular gap between its inner diameter and the external diameter of the guidewire, while the sharp end portion has a wall thickness strong enough to maintain enough rigidity to suitably puncture the septum. The second segment L2 is disposed immediately proximal to the first segment L1 and has an inner diameter greater than the external diameter of the guidewire GW2 thereby providing an annular gap between its inner wall and an external surface of the guidewire GW2. Further, the second segment L2 is sufficiently flexible to assume a curved orientation as defined by the side catheter (not shown) within which it is slidably disposed when deflected with the side catheter guide (not shown). Further, the second segment L2 is configured to have a length sufficient to extend the entire curved distance. The third segment L3 is disposed immediately proximal to the second segment L2, and also has an inner diameter greater than the external diameter of the guidewire GW2, but does not necessarily have the same characteristics (e.g., flexibility, material, etc.) as the second segment L2. The third segment L3 has a length sufficient to extend proximally from the second segment L2, when the second segment L2 is disposed within the heart of the patient, to outside the patient (e.g., and coupled to a handle).

Figure 71C:
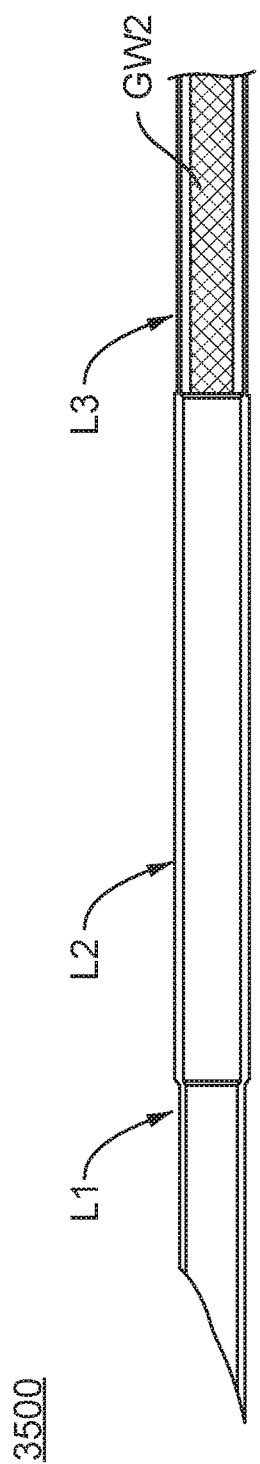
Figure 71D:
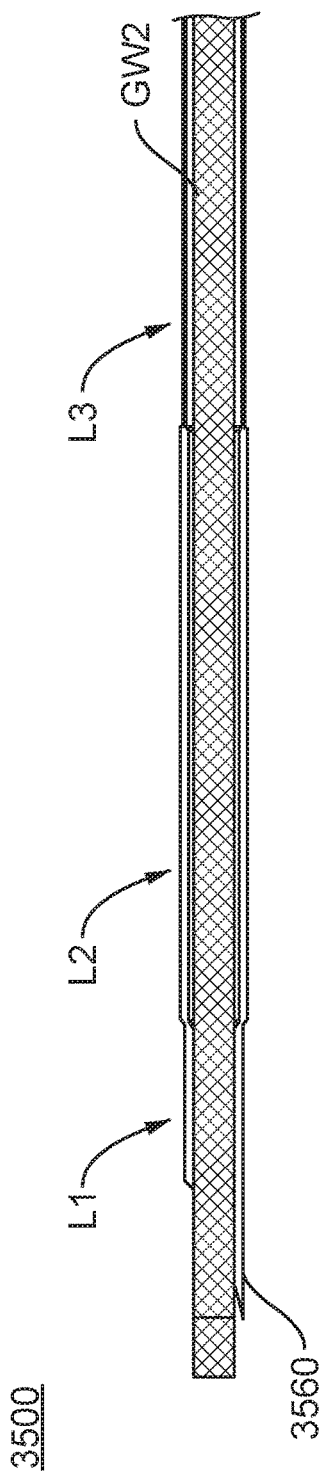

FIG. 71C illustrates in cross-sectional side view the septum penetrator 3560 having the guidewire GW2 preloaded in the third segment L3, with the distal end of the guidewire GW2 terminating within the third segment L3, and FIG. 71D illustrates in cross-sectional side view the septum penetrator 3560 with the guidewire GW2 extending distally relative to the preloaded position and distal to the septum penetrator 3560. As described in various embodiments, in use, with the guidewire GW2 delivered distally from the septum penetrator 3560 and into the left atrium, the septum penetrator 3560 can then be withdrawn proximally relative to the guidewire GW2, leaving the guidewire GW2 disposed within the left atrium. In the context of this embodiment, referring to FIG. 71C in which the distal end of the guidewire GW2 is disposed proximal to the first segment L1, the proximal end of the septum penetrator 3560 is in fluid communication with the distal end portion of the septum penetrator (e.g., the first segment L1 and the second segment L2) via its lumen, such that the verification techniques described herein can be employed using the lumen. For example, in some instances, a contrast agent can be introduced into the lumen of the septum penetrator 3560 at its proximal end (e.g., from outside the patient) and conveyed around the guidewire GW2 (i.e., within the annular gap defined between the inner surface of the septum penetrator 3560 and the exterior surface of the guidewire GW2), through and out of the distal end of the septum penetrator 3560, and into the left atrium, whereby the contrast agent can be viewed via fluoroscopy, and/or similar imaging modalities. After verification, the annular gap is no longer needed, and so the guidewire GW2 can then be extended distally relative to the septum penetrator 3560 and delivered to the left atrium.

Although the guidewire GW2 is shown preloaded into the third segment L3, but proximal to the second segment L2, in other implementations, the guidewire GW2 can be preloaded into the second segment L2, but proximal to the first segment L2, such that fluid communication is similarly provided from the first segment L1, proximally through the second segment L2 and the third segment L3, and further proximally through the septum penetrator 3560 and out the patient, e.g., and to a handle assembly (not shown).

Although the septum penetrator 3560 is shown and described as having three segments, in some embodiments, the septum penetrator 3560 can have any suitable number of segments (e.g., one segment, two segments, or more than three segments). For example, in some embodiments, the most-distal segment of the septum penetrator can have a first lumen having a first diameter, and a second segment proximal to the most-distal segment can have a second lumen having a second diameter greater than the first diameter. In this manner, similar to as described with respect to the septum penetrator 3560 and the guidewire GW2, a guidewire can be disposed within the second lumen and upstream the first lumen, thereby providing fluidic communication between the first lumen and the second lumen, and hence to outside the patient (e.g. via a handle assembly to which a proximal end portion of the septum penetrator is coupled).

In some embodiments, instead of or in addition to a septum penetrator having variable lumen diameters, the septum penetrator can include multiple distinct or partially distinct lumens. In such embodiments, for example, the septum penetrator can have two distinct lumens extending across the entire septum penetrator; one designated for the guidewire and the other designated for fluidic communication for purposes of verification, as described in further detail herein. As another example, the septum penetrator can have a single lumen extending proximally from its most-distal end, and then bifurcate into two lumens, one of which can be designated for the guidewire and the other of which can be designated for fluidic communication for purposes of verification. In this manner, in use, the guidewire can be preloaded within one of the bifurcated lumens when the septum penetrator punctures the septum, a verification technique can be employed via the other bifurcated lumen, and then the guidewire can be advanced distally into the single lumen and delivered distally from the septum penetrator and into the left atrium (or other target region).

Figure 72A:
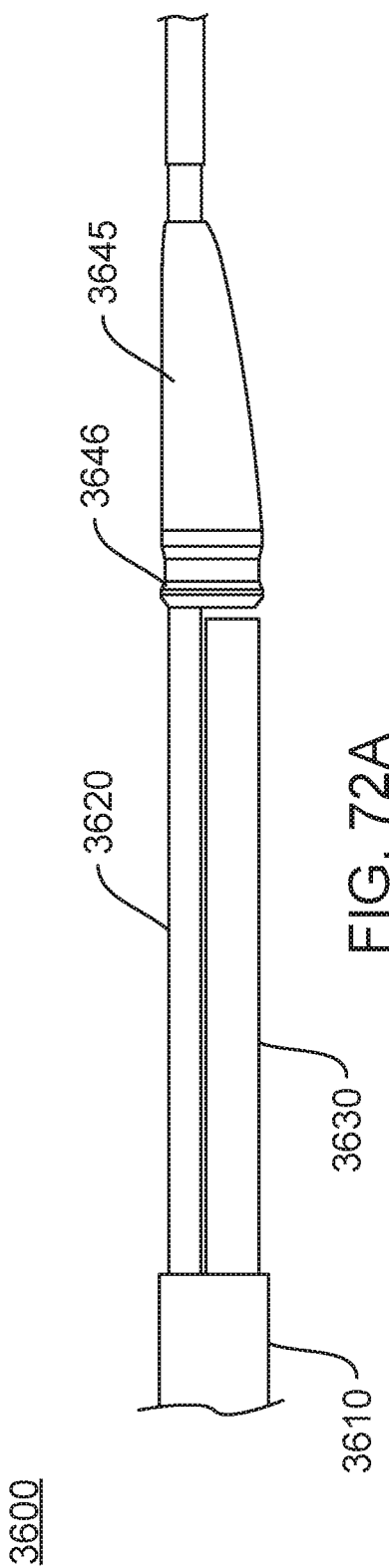
FIGS. 72A and 72B illustrate a portion of a septum puncture device having an atraumatic tip, disposed in a delivery configuration, in side view and perspective view, respectively, according to an embodiment.
Figure 72B:
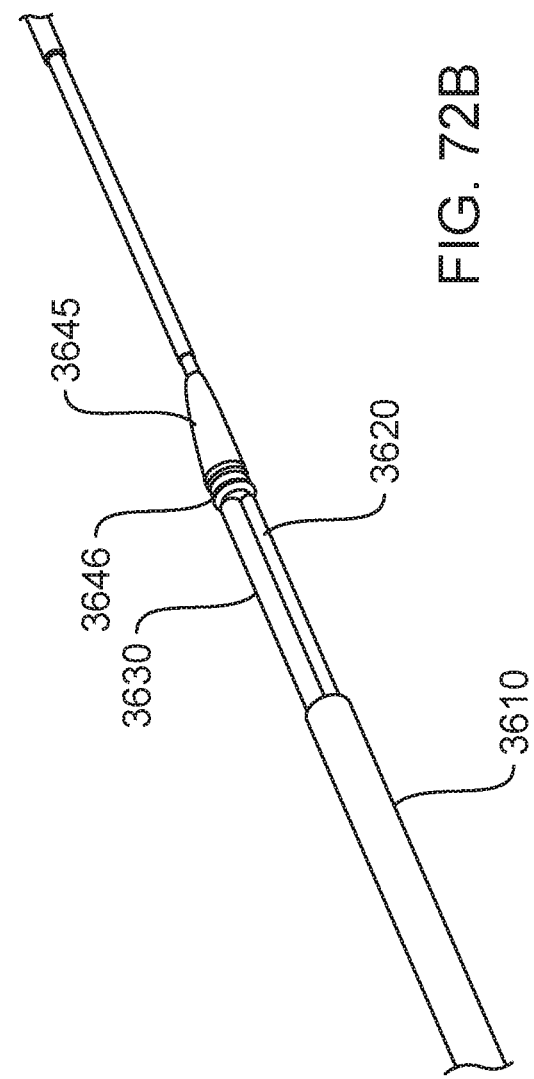

FIGS. 72A and 72B illustrate a portion of a septum puncture device 3600 in a delivery configuration in side view and perspective view, respectively, according to an embodiment.

Similar to other septum puncture devices described herein, the septum puncture device 3600 can be used to access a left side of the heart (e.g., left atrium) from the right side of the heart (e.g., right atrium) and to deliver a guidewire to the left side of the heart. The septum puncture device 3600 can be constructed the same as or similar to, and can function the same as or similar to, any of the septum puncture devices described herein. Thus, portions of the septum puncture device 3600 are not described in further detail herein.

In this embodiment, the septum puncture device 3600 includes a main shaft 3620 and a side catheter guide 3630 coupled to the main shaft 3620 via a guide coupler 3640, similar to as described in connection with other embodiments. The septum puncture device 3600 further includes an atraumatic tip 3645 coupled to and disposed about the main shaft 3620, and slightly axially offset from a distal end portion of the side catheter guide 3030 when the side catheter guide 3030 is in the delivery configuration. As shown in FIG. 72A, the distal end of the side catheter guide 3630 is shielded or at least partially covered by the atraumatic tip 3645. In this manner, during insertion of the septum puncture device 3600 into the patient, with the side catheter guide 3630 in its delivery configuration, the atraumatic tip 3645 protects the patient's vasculature and associated anatomy from inadvertent trauma from the side catheter guide 3630. When deployed (not shown), the distal end of the side catheter guide 3630 is angularly deflected relative to the main shaft 3620, as described in some embodiments herein, such that a side catheter (not shown) can then be extended distally therethrough. As shown, in this embodiment, the collective cross-sectional area of the main shaft 3620 and the side catheter guide 3630 is less than the cross-sectional area of the atraumatic tip 3645 at its proximal end (i.e., it's maximum cross-sectional area), such that the atraumatic tip 3645 shields the distal end portion of the side catheter guide 3630. Said another way, when viewed in front view, the side catheter guide 3645 is not visible, as its profile is smaller than the profile of the atraumatic tip 3645.

Further, in this embodiment, the atraumatic tip 3645 has an asymmetric shape such that during delivery, as shown in FIG. 72A, the atraumatic tip 3645 shields the entire distal end of the side catheter guide 3630, while limiting the overall footprint of the atraumatic tip 3645. More specifically, in this embodiment, the atraumatic tip 3645 reduces in cross-sectional area from its proximal end to its distal end.

Further, the atraumatic tip 3645 includes a radiopaque (e.g., fluoroscopic) marker band 3646 disposed circumferentially about an exterior surface of the atraumatic tip 3645. The atraumatic tip 3645 defines a grove on which the radiopaque marker band 3646 is disposed such that the band 3646 does not increase the overall profile, cross-sectional area, and/or diameter of the remaining portion of the atraumatic tip 3645.

In some embodiments, a needle can be aimed at a specific region of the FO for puncture. The FO can be divided into quadrants, for example, in which a puncture in each quadrant is advantageous for a specific procedure. The needle can thereby be aimed to puncture slightly superior, posterior, and 3.5 cm-4.5 cm above the mitral valve for a MitraClip device, or to puncture posterior and slightly inferior within the FO for typical left atrial appendage occlusion devices. After successful puncture and insertion of a guidewire, the septum puncture device can be completely removed to make way for any suitable instrument or device to be guided into the left atrium of the heart to perform a desired procedure, such as atrial fibrillation ablation, left atrial appendage closure, and valve replacements.

Various embodiments described herein include a side catheter guide configured to transition from a delivery configuration to a deployed configuration in response to a distal force applied to a portion of the side catheter guide that is disposed proximal to the guide coupler (e.g., a distal force applied at the handle). In some implementations of such embodiments described herein, instead of or in addition to such distal force, a proximal force can be applied to the main shaft (e.g., proximal the guide coupler) to cause similar deployment of the side catheter guide. Said another way, deployment of the side catheter guide can be accomplished merely by relative movement between the main shaft and the side catheter guide, which can include a proximal force applied to the main shaft and/or a distal force applied to the side catheter guide.

In various embodiments described herein, a side catheter guide is deflected such that a distal end portion of the side catheter guide angularly and/or laterally deflects about 90 degrees relative to a central axis of a main shaft to which the side catheter guide is coupled. In any of the embodiments described herein, in some implementations, such deflection can be greater than or less than 90 degrees. In such implementations, the deflection may be less than less than about 90 degrees, such as, for example, about 15 degrees, about 30 degrees, about 45 degrees, about 60 degrees, about 75 degrees, or any degrees therebetween. In some implementations, the deflection may be about 75 degrees to about 85 degrees, e.g., about 80 degrees. In even further implementations, the deflection may be greater than about 90 degrees, such as, for example, about 95 degrees, about 105 degrees, about 110 degrees, about 115 degrees, about 120 degrees, about 135 degrees, or any degrees therebetween. In yet further implementations, the deflection may be from about 50 degrees to about 90 degrees.

In various embodiments described herein, a side catheter guide is deflected such that a distal end portion of the side catheter guide angularly and/or laterally deflects relative to a central axis of the a main shaft to which the side catheter guide is coupled (and/or relative to a target tissue, such as an atrial septum). In any of the embodiments described herein, in some implementations, deflection of the side catheter guide can be operator-selectable, meaning that an operator of the septum puncture device can select a particular amount or angle of deflection from among multiple available amounts or angles of deflection. In such implementations, for example, a side catheter guide can be configured to deflect a first amount or angle and a different, second amount or angle, such that an operator can selectively deflect the side catheter guide as desired (e.g., based on a particular patient's anatomy, and/or the particular procedure(s) being performed). In this manner, a septum puncture device can have multiple deployed configurations, each having varying amounts/angles of deflection.

Further, in some embodiments, the deflection selected by the operator can be subsequently fixed and/or temporarily locked in place, such that the selected deflection remains during subsequent steps, such as, for example, distal extension of a side catheter and/or puncture member, and subsequent puncture of the target tissue. Such fixation can be employed in any suitable manner. As an example, a proximal end portion of the side catheter guide can be slidably fixed (e.g., to a body and/or a handle assembly).

Figure 64:
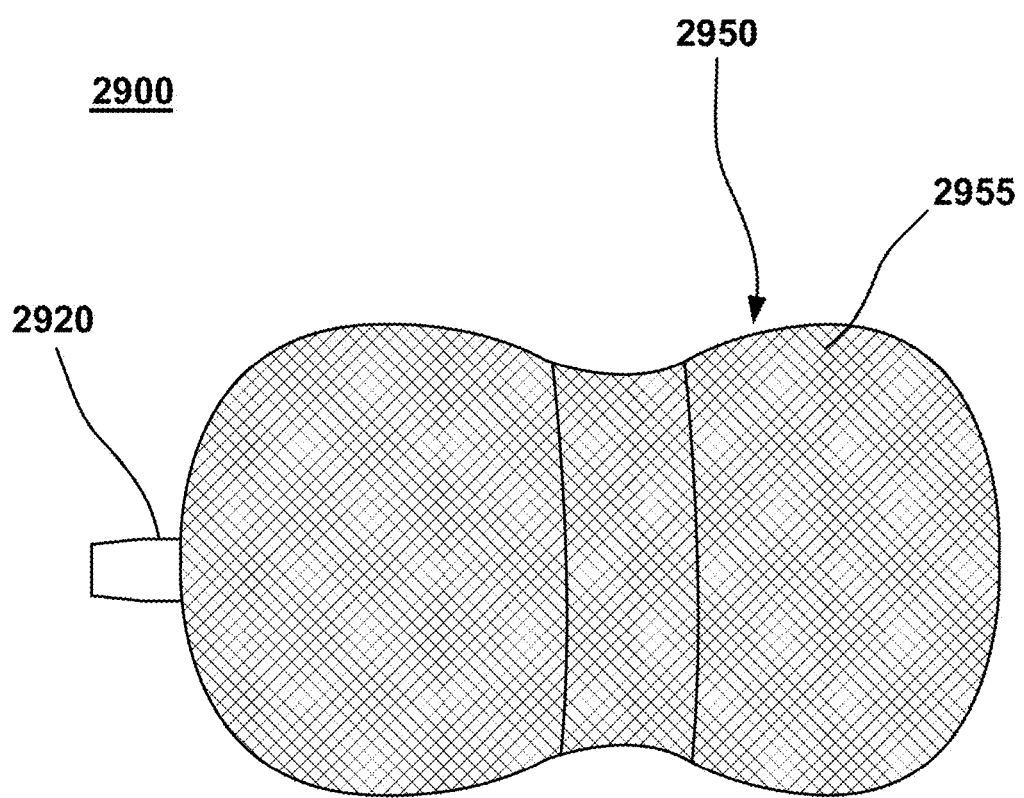
FIG. 64 illustrates a portion of a septum puncture device 2900 having a balloon covered in mesh, according to an embodiment.

Various embodiments described herein include a GSA or balloon configured to transition between a delivery configuration and a deployed configuration. In some implementations of any of the embodiments described herein, one or more GSAs or balloons can be covered partially or completely with a mesh made from any suitable material (e.g., nylon, polymer, etc.). The mesh, coupled to a balloon, for example, can facilitate a preferred, predefined shape of the balloon when inflated, or can facilitate the step or steps of inflating the balloon by, e.g., providing additional stability. An example illustrate of a mesh covering a balloon is illustrated in FIG. 64 which shows a GSA 2950 covered with a mesh GSA 2955, both of which are disposed circumferentially about a main shaft 2920. In some embodiments, the mesh can be used for securing (slidably or fixedly) the balloon(s) to a side catheter guide or a side catheter.

Although various embodiments described herein focus on using a puncture device to puncture a septum of a heart, the functionality provided by various puncture devices described herein can be desirable in other procedures and in other parts of a patient. For example, many procedures exist in which it would be desirable to be able to provide a stable, precise, safe, and repeatable lateral puncture. In some instances, for example, any of the puncture devices described herein could be used to facilitate a tricuspid annuloplasty. The puncture device, for example, could be arrange such that a central axis of its main shaft is parallel to a plane of the tricuspid valve, and so the puncture device could provide lateral or perpendicular access to the annulus of the tricuspid, e.g., to deliver sutures, screws, or other anchoring devices for purposes of a tricuspid annuloplasty.

As another example, the puncture devices described herein could provide a access and a direct vector to a coronary sinus of a heart, to, e.g., insert or deliver a wire, a catheter, a mitral valve repair device, pacemaker leads, etc. into the coronary sinus.

As another example, the puncture devices described herein could be used for delivering therapeutic repair or replacement devices to a mitral valve within a heart. If, for example, a side catheter guide or a side catheter disclosed herein were extended further, and beyond about 90 degrees, the side catheter could be directed into the LA and towards the mitral valve. In some instances, the natural trajectory of the side catheter in some of the embodiments described herein would be angled or directed towards the mitral valve if extended or advanced a suitable distance. For example, as the side catheter assumes its laterally deflected shape or orientation, it may be curved or possess an arc, such that further advancement relative to the main shaft results in the side catheter advancing along such a curvature or arc such that the distal end of the side catheter turns or is further laterally deflected towards the mitral valve. Said another way, in some instances, advancement of the side catheter from its delivery configuration to an advanced/deployed configuration can include the distal end of the side catheter being laterally deflected up to about 180 degrees.

As another example, the puncture devices described herein could incorporate an intracardiac echo catheter to enable accelerate transseptal puncture.

As another example, the puncture devices described herein could be used in connection with cardiac arrest. In such instances, for example, one or more puncture devices could be used in combination with a broad, curved catheter, to enable a guide wire to be directed or delivered from the femoral vein, across the FO, through the mitral valve and out the left ventricular outflow tract ("LVOT")/aortic valve. In some embodiments a balloon/flow-directed catheter would be advanced across the FO, into the LA, across the mitral valve and then across the LVOT/aortic valve; the balloon, for example, would serve to "flow direct" the catheter out the LVOT and across the aortic valve into the aorta. Once in position, the wire could be used as a track for a small catheter that could provide extracorporeal membrane oxygenation ("ECMO") and oxygen to the brain. A distal end of the catheter in the aorta would be the outflow, and more proximal ports (e.g., in the RA or the IVC) would be the inflow to the pump.

As another example, the puncture devices described herein could be used in an aorta to facilitate delivery of branch vessel stents, to deliver coils to branch vessels, or to deliver a screen for cerebral embolic protection to the head vessel.

Detailed embodiments of the present disclosure have been disclosed herein or purposes of describing and illustrating claimed structures and methods that can be embodied in various forms, and are not intended to be exhaustive in any way, or limited to the disclosed embodiments. Many modifications and variations will be apparent without departing from the scope of the disclosed embodiments. The terminology used herein was chosen to best explain the principles of the one or more embodiments, practical applications, or technical improvements over current technologies, or to enable understanding of the embodiments disclosed herein. As described, details of well-known features and techniques can be omitted to avoid unnecessarily obscuring the embodiments of the present disclosure.

References in the specification to "one embodiment," "an embodiment," "an example embodiment," or the like, indicate that the embodiment described can include one or more particular features, structures, or characteristics, but it shall be understood that such particular features, structures, or characteristics may or may not be common to each and every disclosed embodiment disclosed herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

Parameters, dimensions, materials, and configurations described herein are meant to be examples and that the actual parameters, dimensions, materials, and/or configurations will depend upon the specific application or applications for which the inventive teachings is/are used. It is, therefore, to be understood that the foregoing embodiments are presented by way of example only and that, within the scope of the appended claims and equivalents thereto; and that embodiments can be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

As you herein, the phrase "and/or" should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" phrase, whether related or unrelated to those elements specifically identified. Thus, as a non-limiting example, a reference to "A and/or B", when used in conjunction with open-ended language such as "comprising" or "including" can refer, in one embodiment, to A only (optionally including elements other than B); in another embodiment, to B only (optionally including elements other than A); in yet another embodiment, to both A and B (optionally including other elements); etc.

As used herein, the term, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein, the terms "about" and/or "approximately" when used in conjunction with values and/or ranges generally refer to those values and/or ranges near to a recited value and/or range. In some instances, the terms "about" and "approximately" may mean within ±10% of the recited value. For example, in some instances, "approximately a diameter of an instrument" may mean within ±10% of the diameter of the instrument. The terms "about" and "approximately" may be used interchangeably. Similarly, the term "substantially" when used in conjunction with physical and/or geometric feature(s), structure(s), characteristic(s), relationship(s), etc. is intended to convey that the feature(s), structure(s), characteristic(s), relationship(s), etc. so defined is/are nominally the feature(s), structure(s), characteristic(s), relationship(s), etc. As one example, a first quantity that is described as being "substantially equal" to a second quantity is intended to convey that, although equality may be desirable, some variance can occur. Such variance can result from manufacturing tolerances, limitations, approximations, and/or other practical considerations. Thus, the term "substantially."

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments described herein.

The specific configurations of the various components can also be varied. For example, the size and specific shape of the various components can be different from the embodiments shown, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

The invention claimed is:

1. An apparatus, comprising:
a shaft;
a guide coupled and angularly deflectable relative to the shaft via a guide coupler, the guide configured to be transitioned between a delivery configuration and a deployed configuration in which a distal end of the guide points away from a centerline of the shaft when transitioned from its delivery configuration to its deployed configuration, the guide defining a lumen;
an elongate member slidably disposable within the lumen of the guide and configured to extend distally relative to the distal end of the guide, the elongate member defining a lumen;
a puncture member slidably disposable within the lumen of the elongate member and configured to extend distally relative to a distal end of the elongate member, the puncture member being configured to puncture tissue of a patient; and
an atraumatic member defining a lumen there through, a first lateral opening, and a second lateral opening, at least a portion of the shaft and the guide being disposed within the lumen of the atraumatic member, a portion of the guide that is disposed proximal to the guide coupler is configured to extend through the first lateral opening when the guide transitions from the delivery configuration to the deployed configuration,
the elongate member configured to extend distally through the second lateral opening when the guide is in the deployed configuration.

2. The apparatus of claim 1, wherein the elongate member has an atraumatic distal end.

3. The apparatus of claim 1, wherein the guide coupler is spaced proximally from a distal end of the shaft.

4. The apparatus of claim 1, wherein the guide is configured to be transitioned between its delivery configuration and its deployed configuration in response to relative movement between (1) a portion of the guide disposed proximal to the guide coupler and (2) the shaft.

5. The apparatus of claim 1, wherein the elongate member is a side catheter, and the guide is a side catheter guide.

6. The apparatus of claim 1, wherein the elongate member has an atraumatic distal end with a cross-sectional area greater than a cross-sectional area of a portion of the elongate member proximal to the atraumatic distal end.

* * * * *